United States Patent
Klein et al.

(10) Patent No.: US 12,000,064 B2
(45) Date of Patent: Jun. 4, 2024

(54) UNIVERSAL REPORTER CELL ASSAY FOR SPECIFICITY TEST OF NOVEL ANTIGEN BINDING MOIETIES

(71) Applicant: Hoffmann-La Roche Inc., Little Falls, NJ (US)

(72) Inventors: Christian Klein, Schlieren (CH); Ekkehard Moessner, Schlieren (CH); Lydia Jasmin Hanisch, Schlieren (CH); Wei Xu, Schlieren (CH); Camille Loise Sophie Delon, Schlieren (CH); Diana Darowski, Schlieren (CH); Christian Jost, Schlieren (CH); Vesna Pulko, Schlieren (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 457 days.

(21) Appl. No.: 16/906,778

(22) Filed: Jun. 19, 2020

(65) Prior Publication Data
US 2020/0316128 A1    Oct. 8, 2020

Related U.S. Application Data

(63) Continuation of application No. PCT/EP2018/086038, filed on Dec. 20, 2018.

(30) Foreign Application Priority Data

Dec. 21, 2017  (EP) .................................... 17209201

(51) Int. Cl.
*C40B 30/04*     (2006.01)
*A61K 35/17*     (2015.01)
(Continued)

(52) U.S. Cl.
CPC .............. *C40B 30/04* (2013.01); *A61K 35/17* (2013.01); *C07K 14/70539* (2013.01);
(Continued)

(58) Field of Classification Search
None
See application file for complete search history.

(56) References Cited

U.S. PATENT DOCUMENTS

2020/0318105 A1    10/2020   Klein et al.

FOREIGN PATENT DOCUMENTS

| CN | 104271158 A | 1/2015 |
| CN | 107428839 A | 12/2017 |

(Continued)

OTHER PUBLICATIONS

Brower, V., "The CAR T-Cell Race" The Scientist (Article Dated: Mar. 31, 2015), (Apr. 1, 2015) https://www.the-scientist.com/?articles.view/articleNo/42462/title/The-CAR-T-Cell-Race/.

(Continued)

*Primary Examiner* — Christian C Boesen
(74) *Attorney, Agent, or Firm* — Lawrence S. Graham

(57) ABSTRACT

The present invention generally relates to specificity assays using cell cultures, in particular to chimeric antigen receptor (CAR) expressing reporter T (CAR-T) cell assays to test novel antigen binding moieties in different formats. Furthermore, the present invention relates to the use of CAR-T cells, transfected/transduced with an engineered chimeric antigen receptor (CAR) comprising a target antigen binding moiety capable of specific binding to a recognition domain of an antigen binding molecule. The invention also relates to methods and kits for specificity testing of a candidate antigen binding moiety and/or nucleic acid molecules and vectors expressing engineered CARs.

13 Claims, 31 Drawing Sheets

Specification includes a Sequence Listing.

(51) Int. Cl.
  *C07K 14/74* (2006.01)
  *C07K 16/18* (2006.01)
  *C07K 16/28* (2006.01)
  *C07K 16/30* (2006.01)
  *G01N 33/50* (2006.01)
  *G01N 33/574* (2006.01)

(52) U.S. Cl.
  CPC .......... *C07K 16/18* (2013.01); *C07K 16/2887* (2013.01); *C07K 16/30* (2013.01); *C07K 16/3007* (2013.01); *G01N 33/505* (2013.01); *G01N 33/574* (2013.01); *C07K 2317/52* (2013.01)

(56) References Cited

FOREIGN PATENT DOCUMENTS

| WO | 2012/109659 A1 | 8/2012 |
|---|---|---|
| WO | 2012/130831 A1 | 10/2012 |
| WO | 2012/135854 A2 | 10/2012 |
| WO | 2013/132044 A1 | 9/2013 |
| WO | 2014/131694 A1 | 9/2014 |
| WO | 2016/014535 A1 | 1/2016 |
| WO | 2016/028896 A1 | 2/2016 |
| WO | 2016/079177 A1 | 5/2016 |
| WO | 2016/149109 A1 | 9/2016 |
| WO | 2016/164731 A2 | 10/2016 |
| WO | 2017/072210 A1 | 5/2017 |

OTHER PUBLICATIONS

"International Search Report—PCT/EP2018/086038":pp. 1-7 (dated Feb. 12, 2019).

Wang, Z., et al., "New development in CAR-T cell therapy" J Hematol Oncol 10(53):1-11 (Feb. 21, 2017).

Xia, A et al., "Chimeric-antigen receptor T (CAR-T) cell therapy for solid tumors: challenges and opportunities" Oncotarget 8(52):90521-90531 (Oct. 27, 2017).

Quintero-Hernandez, V et al., "The change of the scFv into the Fab format improves the stability and in vivo toxin neutralization capacity of recombinant antibodies" Molecular Immunology 44(6):1307-1305 (Feb. 1, 2007).

Anonymous, "scFv/Fab Construction—Antibody Fragments Expression" DetaiBio, URL:http://www.detaibio.com/en/scFv-Fab-constmction.html [retrieved on Oct. 16, 2023], pp. 1-7, pp. 1-7 (Retrieved from Internet Oct. 16, 2023).

Chmielewski, M. et al., "TRUCKs: the fourth generation of CARs" Expert Opin Biol 15(8):1145-1154 (May 18, 2015).

Smith, A J. et al., "Chimeric antigen receptor (CAR) T cell therapy for malignant cancers: Summary and perspective" J Cell Immunother 2(2):59-68 (Nov. 1, 2016).

International Preliminary Report on Patentability for PCT/EP2018/086038, pp. 1-7 ( Jun. 23, 2020).

Fab Format

ATM = anchoring transmembrane domain
CSD = co-stimulatory signaling domain
SSD = stimulatory signaling domain scFv Format

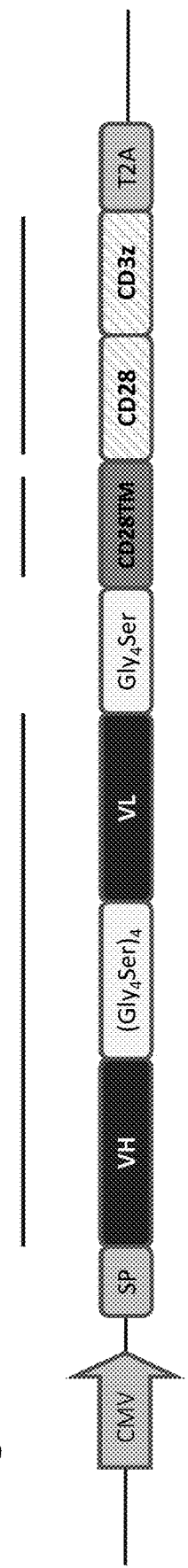
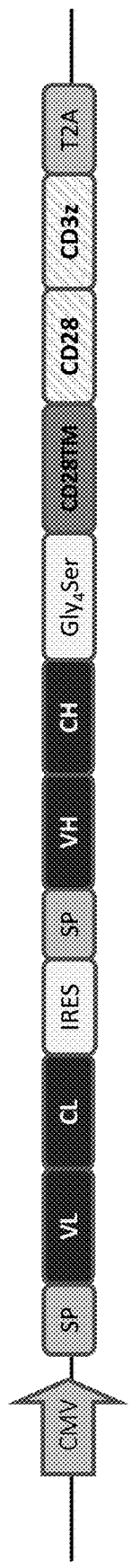
Figure 2A
Figure 2B
CMV = Cytomegalovirus promotor
SP = Signal peptide
VH = variable heavy chain
VL = variable light chain
TM = transmembrane domain
IRES = internal ribosomal entry site

UNIVERSAL REPORTER CELL ASSAY FOR SPECIFICITY TEST OF NOVEL ANTIGEN BINDING MOIETIES

CROSS-REFERENCE TO RELATED APPLICATIONS

This application is a continuation of International Application No. PCT/EP2018/086038, filed Dec. 20, 2018, which claims benefit to European Patent Application No. 17209201.7, filed Dec. 21, 2017; all of which are hereby expressly incorporated by reference in their entirety as though fully set forth herein.

SEQUENCE LISTING

This application contains a Sequence Listing that has been submitted via EFS-Web and is hereby expressly incorporated by reference in its entirety. Said ASCII copy, created on Jun. 8, 2020, is named P34477-US_Sequence_Listing.txt and is 181,735 bytes in size.

FIELD OF THE INVENTION

The present invention generally relates to specificity assays using cell cultures, in particular to chimeric antigen receptor (CAR) expressing reporter T (CAR-T) cell assays to test novel antigen binding moieties in different formats. Furthermore, the present invention relates to the use of CAR-T cells, transfected/transduced with an engineered chimeric antigen receptor (CAR) comprising a target antigen binding moiety capable of specific binding to a recognition domain of an antigen binding molecule. The invention also relates to methods and kits for specificity testing of a candidate antigen binding moiety and/or nucleic acid molecules and vectors expressing engineered CARs.

BACKGROUND

Chemotherapy is until now still one of the most commonly used treatments for cancer.

Additionally, antibody based therapies have evolved over the last 15 years and represent now a valuable combination or alternative to chemotherapeutic approaches in the treatment of hematological malignancies and solid tumors. Unlike chemotherapy, antibody therapies target specific antigens on cancer cells thus allowing a more site-directed treatment thereby reducing the side effects on healthy tissue. In the process of developing an antibody-based therapeutic reagent, various assays are required to identify the best candidates to bring into clinical trials and eventually to the market. In a first early preclinical phase, the antibodies have to be generated and analyzed for their target-specificity, as well as their affinity to the target.

Binding properties can be analyzed using various protein-protein interaction assays, such as FRET-based methods, Surface Plasmon Resonance (SPR) or fluorescence-activated cell sorting (FACS). However, available assay formats might not always reproduce the in vivo situation comprehensively and integrative. For example targeting of cancer cells with therapeutic antibodies binding to cell surface receptors can have impacts on multiple levels, e.g., intracellular signaling via the binding and cross-linking of surface molecules as well as marking the tumor cells to engage immune cells. Furthermore, the recognition cascade from antigen binding to establishing of an effector function, e.g., T cell cytotoxicity, requires a well-orchestrated sequence of cell surface interactions, wherein binding affinity of an antigen binding moiety is one among several factors. Plain protein-protein affinity interaction assays may therefore not result with the complete picture, although these assays are a very valuable tool for early candidate development.

Conclusively, there remains a need to develop binding assays which do more closely mimic the situation in vivo in a more comprehensive setup minimizing non-specific effects on target-antibody binding as far as possible. Furthermore, designing combination assays which allow assessment of binding and functionality at an early state in the development process of an antibody therapeutic molecule would be of great benefit.

The inventors of the present invention developed a novel assay which is applicable to a wide variety of different cancer cell types to assess binding of antibodies to their target. The innovative assay includes modified T-cells as reporter cells combining straight-forward readout with a comprehensive and inclusive result.

Furthermore, the present invention provides assays which combine the assessment of binding and functionality of antibodies and antibody-like constructs (e.g., ligands). The novel assay is useful for example for screening or characterization purposes of therapeutic antibody drug candidates, i.e., in high-throughput formats.

This new assay represents a valuable tool for early and late stage screening and characterization of antibody binding to the native target and assessing functionality which will allow identifying the best binders at an early stage in the development of the drug candidate.

SUMMARY OF THE INVENTION

The present invention generally relates to a method for selecting novel antigen binding moieties, particularly in the drug development process, and combines the assessment of binding to a target antigen, e.g., on a tumor cell, with the activation of T cells in response to the antibody-target binding. Provided is a method for assessing the specificity of an antigen binding moiety comprising the steps of:
a) providing an antigen binding molecule comprising an antigen binding domain and a recognition domain, wherein the antigen binding domain comprises the antigen binding moiety, wherein the antigen binding moiety is specific for a target antigen;
b) contacting the antigen binding molecule with a target cell comprising the target antigen on the surface, particularly wherein the target cell is a cancer cell;
c) contacting the antigen binding molecule with a chimeric antigen receptor (CAR) expressing reporter T (CAR-T) cell wherein the reporter CAR-T cell comprises:
  i. a CAR capable of specific binding to the recognition domain wherein the antigen binding moiety is operationally coupled to a response element;
  ii. a reporter gene under the control of the response element; and
d) determining T cell activation by determining the expression of the reporter gene to establish the specificity of the antigen binding moiety.

In one embodiment, the recognition domain is an immunoglobulin domain.

In one embodiment, the recognition domain is an Fc domain.

In one embodiment, the Fc domain is human Fc domain, particularly a human IgG1 Fc domain.

In one embodiment, the Fc domain is a mutated Fc domain, wherein the mutated Fc domain comprises at least one amino acid substitution compared to the non-mutated parent Fc domain, wherein the CAR is capable of specific binding to the mutated Fc domain but not capable of specific binding to the non-mutated parent Fc domain.

In one embodiment, the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

In one embodiment, the mutated Fc domain comprises the amino acid mutation P329G according to EU numbering.

In one embodiment, the mutated Fc domain comprises at least one amino acid mutation at a position selected from the group consisting of I253, H310 and H435 according to EU numbering, in particular the amino acid mutations I253A, H310A and H435A ("AAA").

In one embodiment, the antigen binding moiety is a Fab fragment, in particular a Fab fragment deriving from a phage display library screening.

In one embodiment, the CAR comprises at least one intracellular stimulatory signaling and/or co-stimulatory signaling domain.

In one embodiment, binding of the antigen binding moiety to the target antigen and binding of the reporter CAR-T cell to the antigen binding molecule comprising the antigen binding moiety leads to activation of the intracellular signaling and/or co-signaling domain.

In one embodiment, activation of the intracellular signaling and/or co-signaling domain leads to activation of the response element.

In one embodiment, the response element controls the expression of the reporter gene.

In one embodiment, activation of the response element leads to expression of the reporter gene.

In one embodiment, the response element is part of the NFAT pathway, the NF-κB pathway or the AP-1 pathway.

In one embodiment, the reporter gene is coding for a luminescent protein, in particular a fluorescent protein.

In one embodiment, the reporter gene is coding for green fluorescent protein (GFP) or luciferase.

In one embodiment, the target antigen is a cell surface receptor.

In one embodiment, the target antigen is selected from the group consisting of CD20, CEA, HER2, TYRP, EGFR, MCSP, STEAP1, WT1 and FolR1.

In one embodiment, the target antigen is a peptide bound to a molecule of the human major histocompatibility complex (MHC).

In one embodiment, the antigen binding moiety is a T cell receptor like (TCRL) antigen binding moiety.

In one embodiment, the method additionally comprises the step of:
e) comparing the expression of the reporter gene to a reference.

In one embodiment, the reference is expression of the reporter gene in absence of the target cell.

In one embodiment, the expression of the reporter gene in the presence of the target cell is at least 2×, 3×, 4×, 5×, 10×, 100×, 1000×, or 10000×, higher compared to the expression of the reporter gene in absence of the target cell.

In one embodiment, the method additionally comprises the step of:
f) selecting the novel antigen binding moiety if the expression of the reporter gene in the presence of the target cell in relation to the expression of the reporter gene in absence of the target cell is higher than a predefined threshold value.

In one embodiment, the threshold value is 2, 3, 4, 5, 10, 100, 1000, or 10000.

In one embodiment, high level of expression of the reporter gene in the presence of the target cell and low level of expression of the reporter gene in the absence of the target cell is indicative for high specificity of the antigen binding moiety. In one embodiment, high level of expression of the reporter gene in the presence of the target cell and low level of expression of the reporter gene in the absence of the target cell is indicative for high specificity of a T cell bispecific (TCB) antibody comprising the antigen binding moiety.

In one embodiment, the method is an in vitro method

In one embodiment, provided is a method for generating a TCB antibody, wherein the TCB antibody format comprises a first antigen binding moiety specific for a target antigen and a second antigen binding moiety capable of specific binding to a T cell activating receptor, wherein the first antigen binding moiety is selected according to the methods as described herein.

In one embodiment, the T cell activating receptor is CD3.

SHORT DESCRIPTION OF THE FIGURES

FIG. 1A-1B depicts the architecture of exemplary CARs used according to the invention. FIG. 1A shows the architecture of the anti-P329G-scFv-CD28ATD-CD28CSD-CD3zS SD format and anti-P329G-ds-scFv-CD28ATD-CD28CSD-CD3zSSD format. Depicted is the extracellular domain comprising an antigen binding moiety capable of specific binding to a mutated Fc domain comprising the P329G mutation. The antigen binding moiety consists of a variable heavy and a variable light chain. Both are connected by a $(Gly_4Ser)_4$ linker. Attached to the variable light chain, a $Gly_4Ser$ linker connects the antigen recognition domain with the CD28 transmembrane domain (TM) which is fused to the intracellular co-stimulatory signaling domain (CSD) of CD28 which in turn is fused to the stimulatory signaling domain (SSD) of CD3z.

FIG. 1B shows the architecture of the anti-P329G-Fab-CD28ATD-CD28CSD-CD3zSSD and anti-P329G-ds-Fab-CD28ATD-CD28CSD-CD3zS SD format. Depicted is the extracellular domain comprising an antigen binding moiety capable of specific binding to a mutated Fc domain comprising the P329G mutation. The antigen binding moiety consists of an Ig heavy chain fragment and an Ig light chain. Attached to the heavy chain, a $Gly_4Ser$ linker connects the antigen recognition domain with the CD28 transmembrane domain which is fused to the intracellular co-stimulatory signaling domain of CD28 which in turn is fused to the stimulatory signaling domain of CD3z.

FIG. 2A-2B depicts a schematic representation illustrating the modular composition of exemplary expression constructs encoding CARs used according to the invention.

FIG. 2A depicts a P392G-targeted scFv format.

FIG. 2B depicts a P392G-targeted Fab format.

Figure 1B:
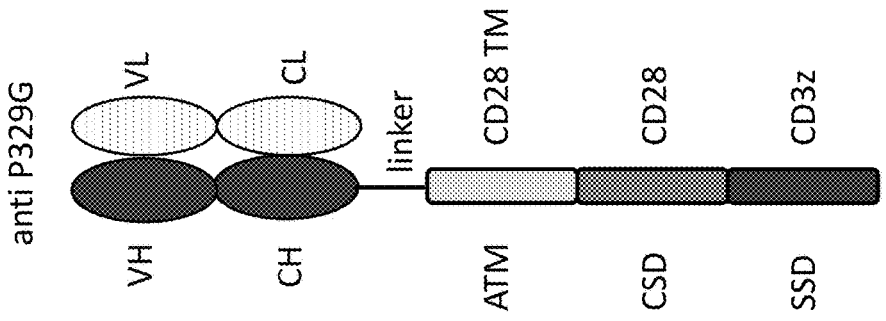
Figure 1A:
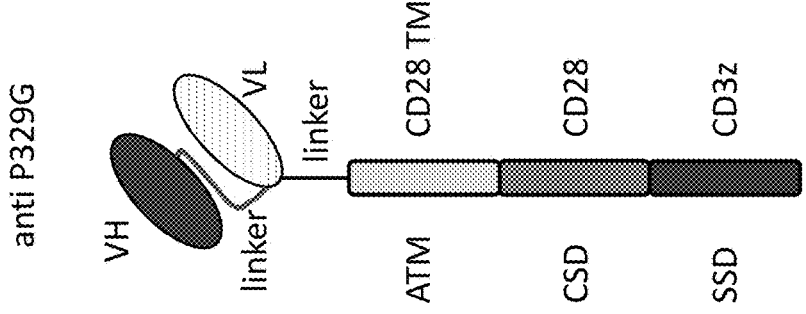
Figure 3:
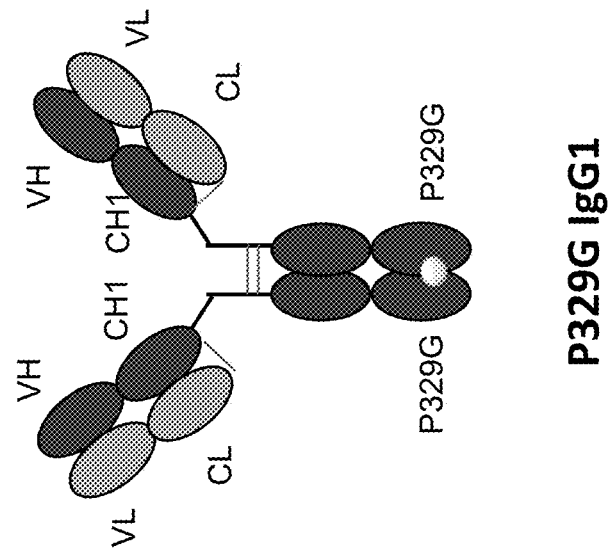
FIG. 3 depicts an exemplary IgG1 molecule harboring the P329G mutation in the Fc domain which is recognized by an anti-P329G CAR used according to the invention.
Figure 4:
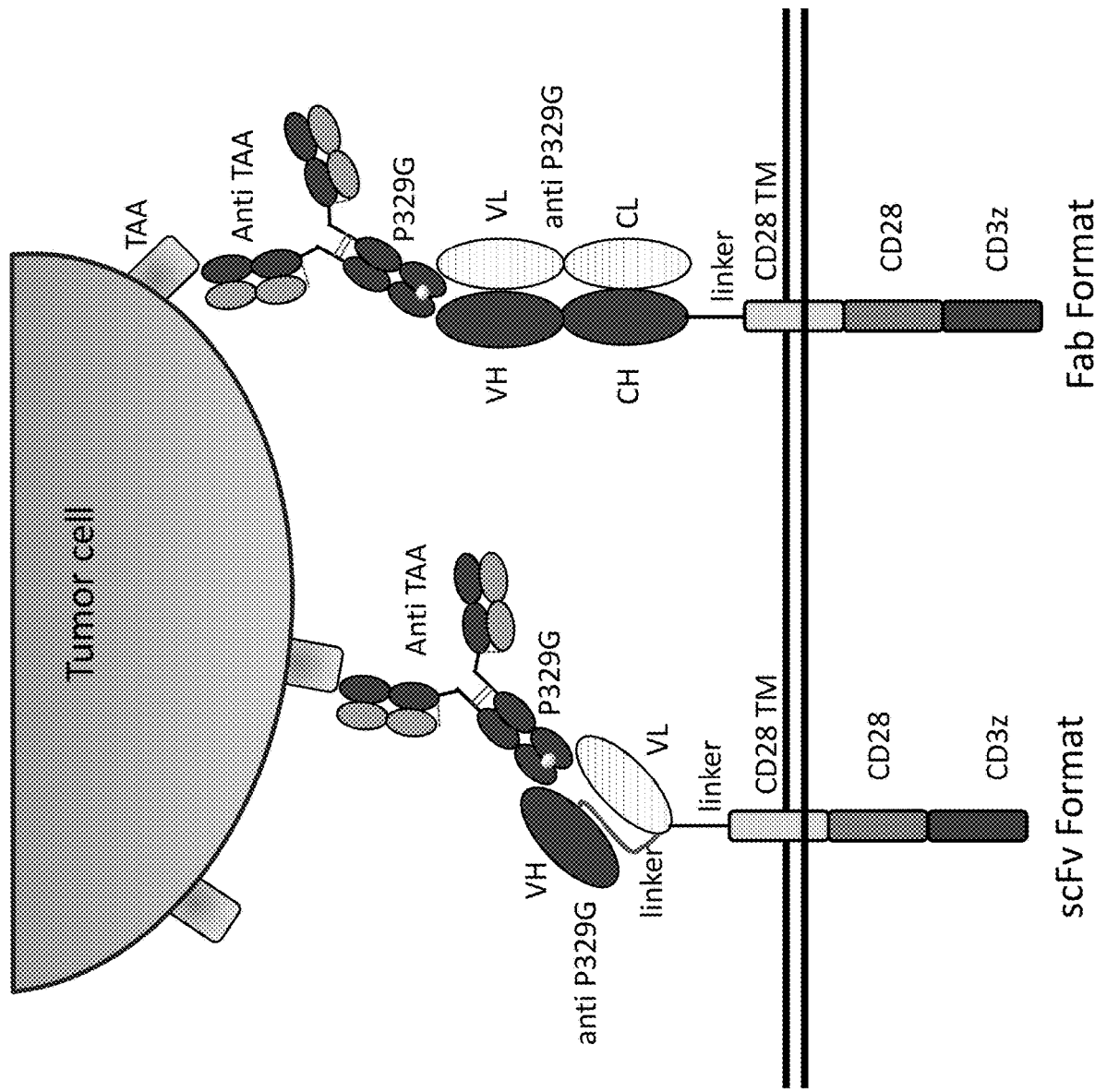
FIG. 4 depicts a schematic representation of a tumor associated antigen (TAA) bound IgG harboring the P329G mutation. This antibody can in turn be recognized by an anti-P329G CAR expressing T cell, whereby the T cell gets activated.
Figure 5:
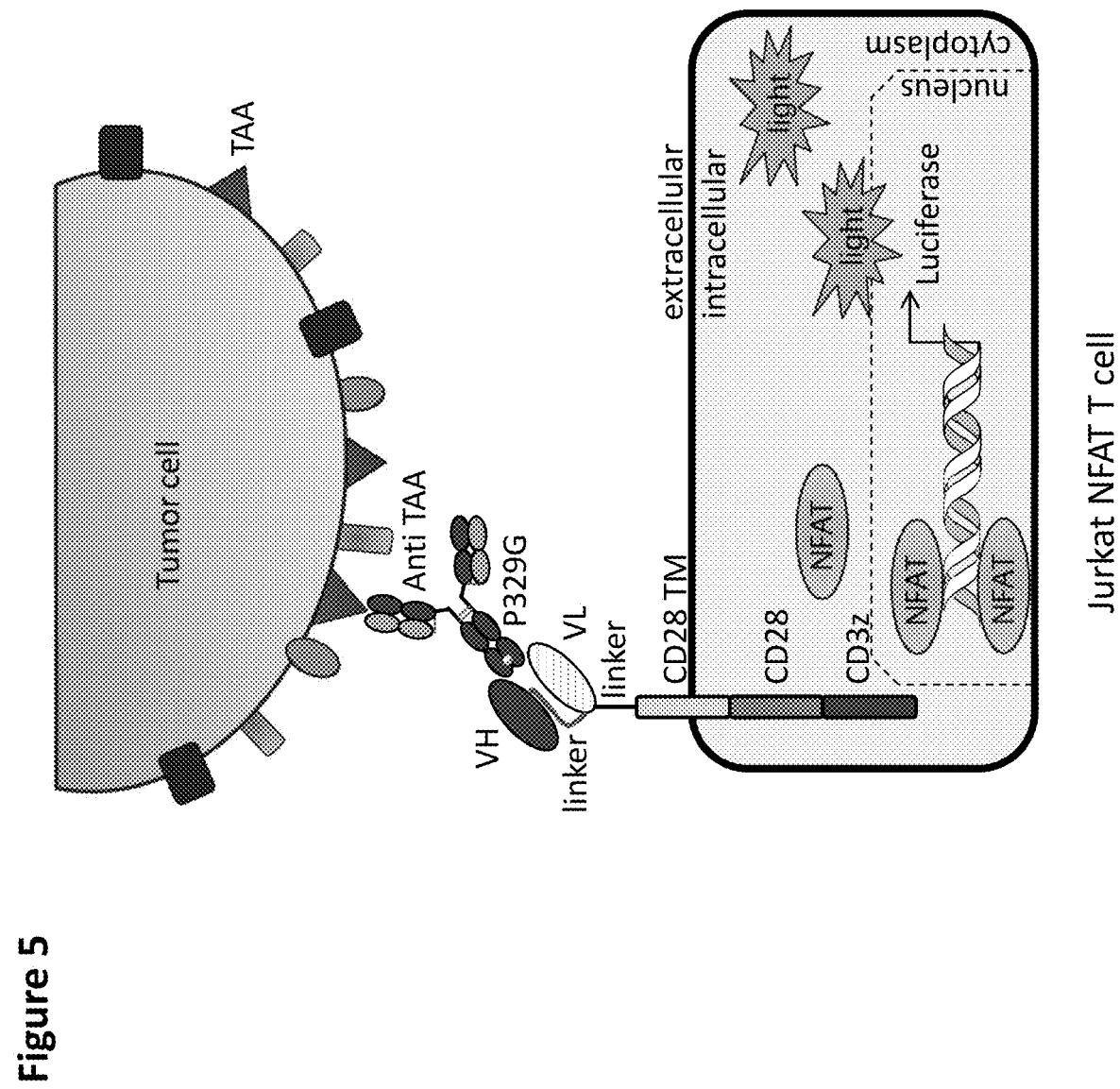

FIG. 5 shows a schematic representation of a Jurkat NFAT reporter CAR-T cell assay. TAA bound IgG harboring the P329G mutation can be recognized by the anti-P329G CAR expressing Jurkat NFAT reporter T cell. This recognition leads to the activation of the cell which can be detected by measuring luminescence (cps).

Figure 6A:
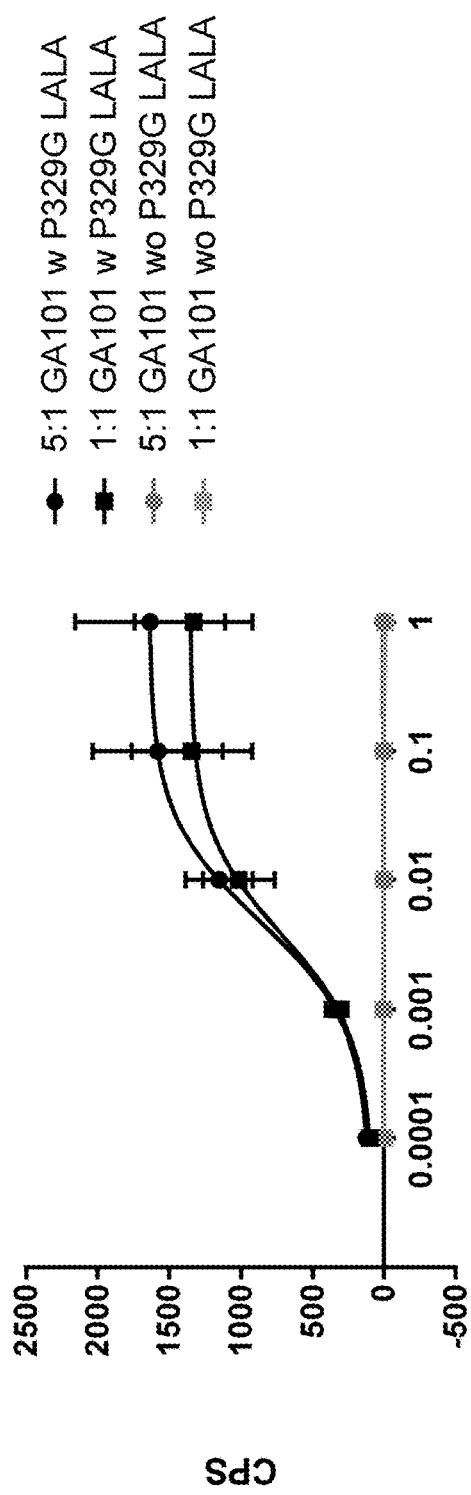
Figure 6B:
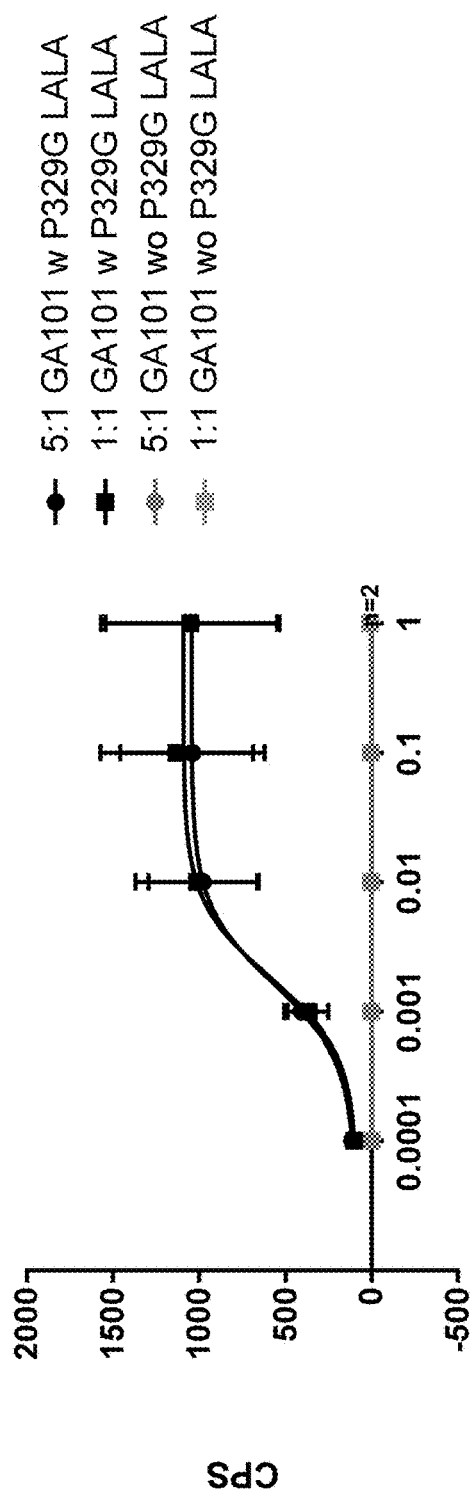

FIG. 6A-6B depicts a Jurkat NFAT reporter CAR-T cell reporter assay using CD20 expressing SUDHDL4 tumor cells as target cells. An anti-CD20 IgG antibody (GA101) harboring the P329G mutation was used, which on one hand recognizes the tumor associated antigen and on the other hand is recognized by the Jurkat NFAT reporter CAR-T cells.

FIG. 6A is a graph showing a sorted pool of anti-P329G-ds-Fab-CD28ATD-CD28CSD-CD3zSSD expressing Jurkat NFAT reporter CAR-T cell was used as reporter cells.

FIG. 6B is a graph showing a sorted pool of anti-P329G-ds-scFv-CD28ATD-CD28CSD-CD3zSSD expressing Jurkat NFAT reporter CAR-T cells was used as reporter cells.

FIG. 7A-7D depicts a Jurkat NFAT reporter CAR-T cell assay using CD20 tumor cells as target cells. An anti-CD20 IgG antibody (GA101) harboring the P329G mutation was used which recognizes the tumor associated antigen and is recognized by the Jurkat NFAT reporter CAR-T cells used according to the invention.

Figure 7A:
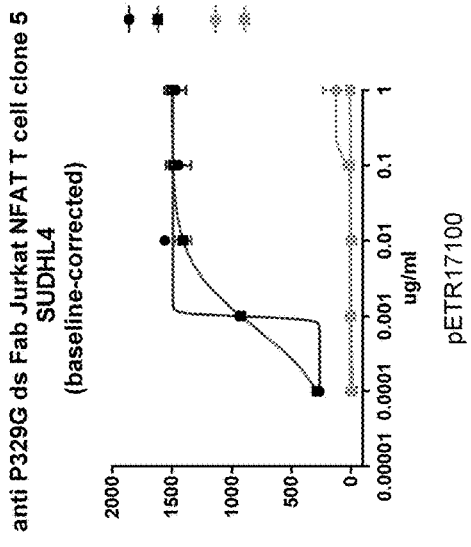

FIG. 7A shows the single clone 5 of anti-P329G-ds-Fab-CD28ATD-CD28CSD-CD3zSSD expressing Jurkat NFAT reporter CAR-T cells was used as reporter cells and WSUDLCL2 cells as tumor cells.

Figure 7C:
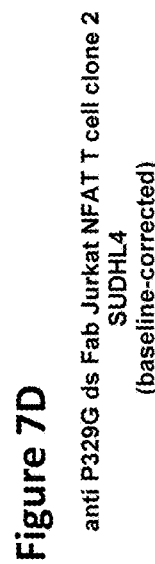
Figure 7C:
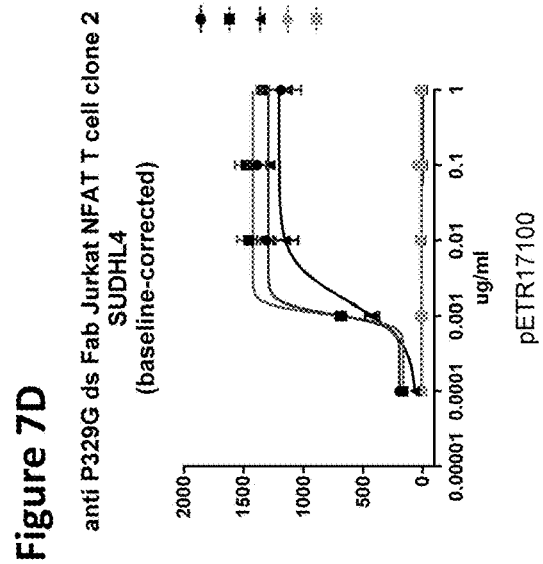
Figure 7B:
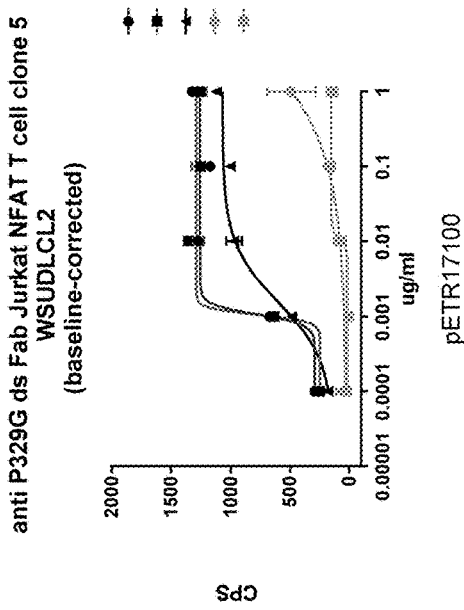

FIG. 7B shows the single clone 2 of anti-P329G-ds-Fab-CD28ATD-CD28CSD-CD3zSSD expressing Jurkat NFAT reporter CAR-T cells was used as reporter cells and WSUDLCL2 cells as tumor cells.

FIG. 7C shows the single clone 5 of anti-P329G-ds-Fab-CD28ATD-CD28CSD-CD3zSSD expressing Jurkat NFAT reporter CAR-T cells was used as reporter cells and SUDHL4 cells as tumor cells.

Figure 7D:
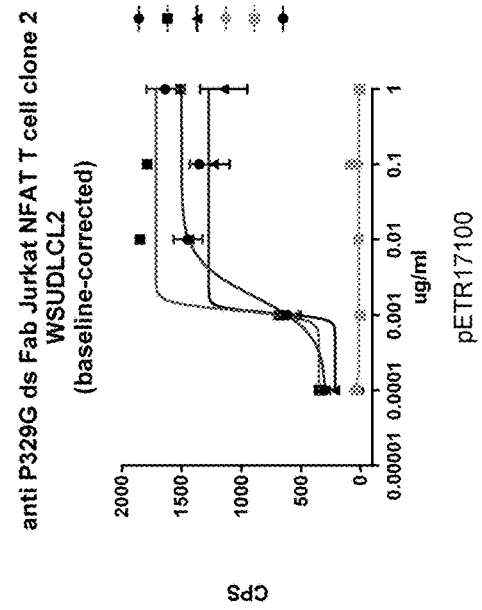

FIG. 7D shows the single clone 2 of anti-P329G-ds-Fab-CD28ATD-CD28CSD-CD3zSSD expressing Jurkat NFAT reporter CAR-T cells was used as reporter cells and SUDHL4 as tumor cells.

FIG. 8A-8D depicts a Jurkat NFAT reporter CAR-T cell assay performed using adherent FAP expressing NIH/3T3-huFAP cl 19 tumor cells as target cells. The anti-FAP IgG antibody clone 4B9 harboring the P329G mutation was used which the tumor associated antigen and is recognized by the Jurkat NFAT reporter CAR-T cells. IgG DP47/vk3 harboring P329G mutation was included as isotype control.

Figure 8A:
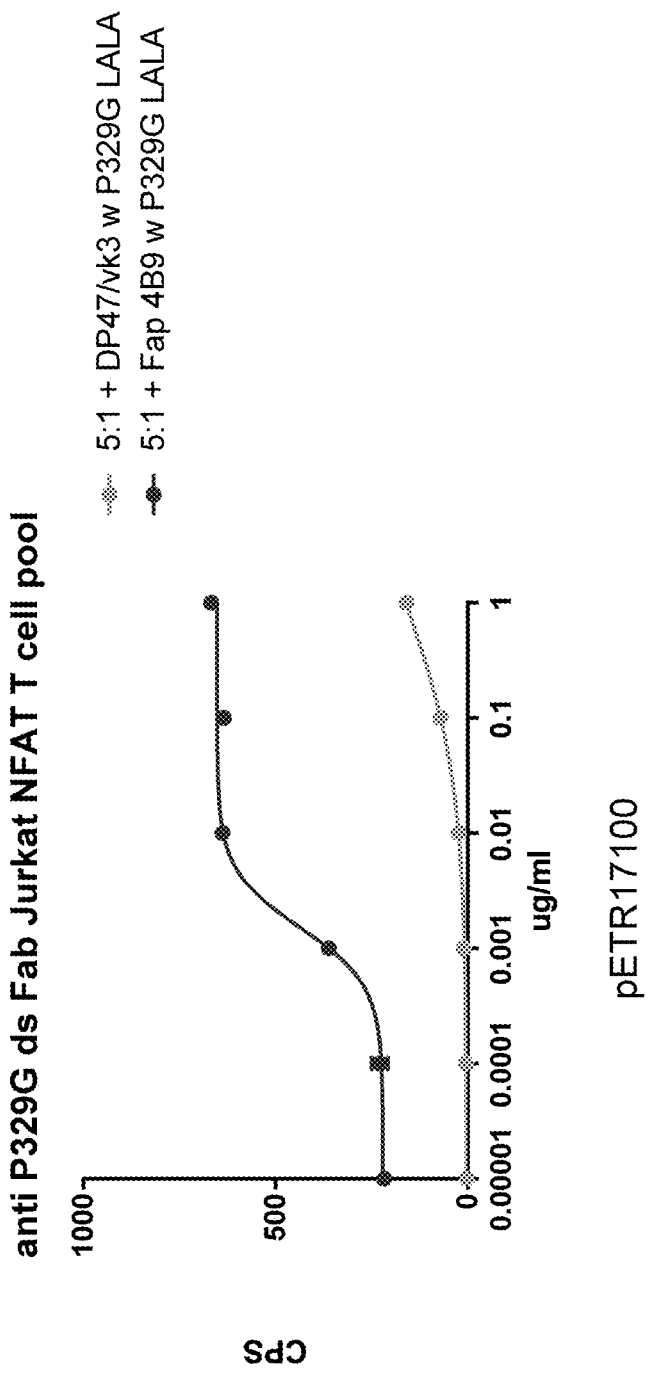

FIG. 8A a sorted pool of anti-P329G-ds-Fab-CD28ATD-CD28CSD-CD3zSSD expressing Jurkat NFAT reporter CAR-T cells was used as reporter cells.

Figure 8B:
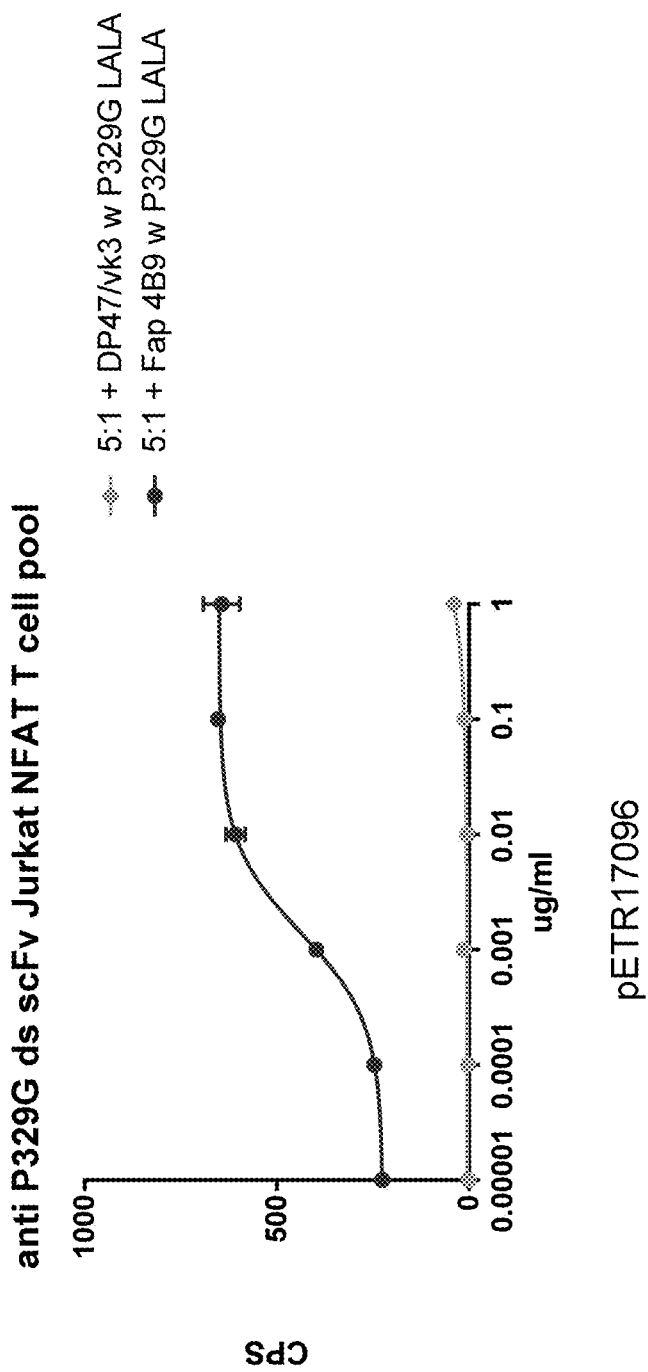

FIG. 8B a sorted pool of anti-P329G-ds-scFv-CD28ATD-CD28CSD-CD3zSSD expressing Jurkat NFAT reporter CAR-T cells was used as reporter cells.

Figure 8C:
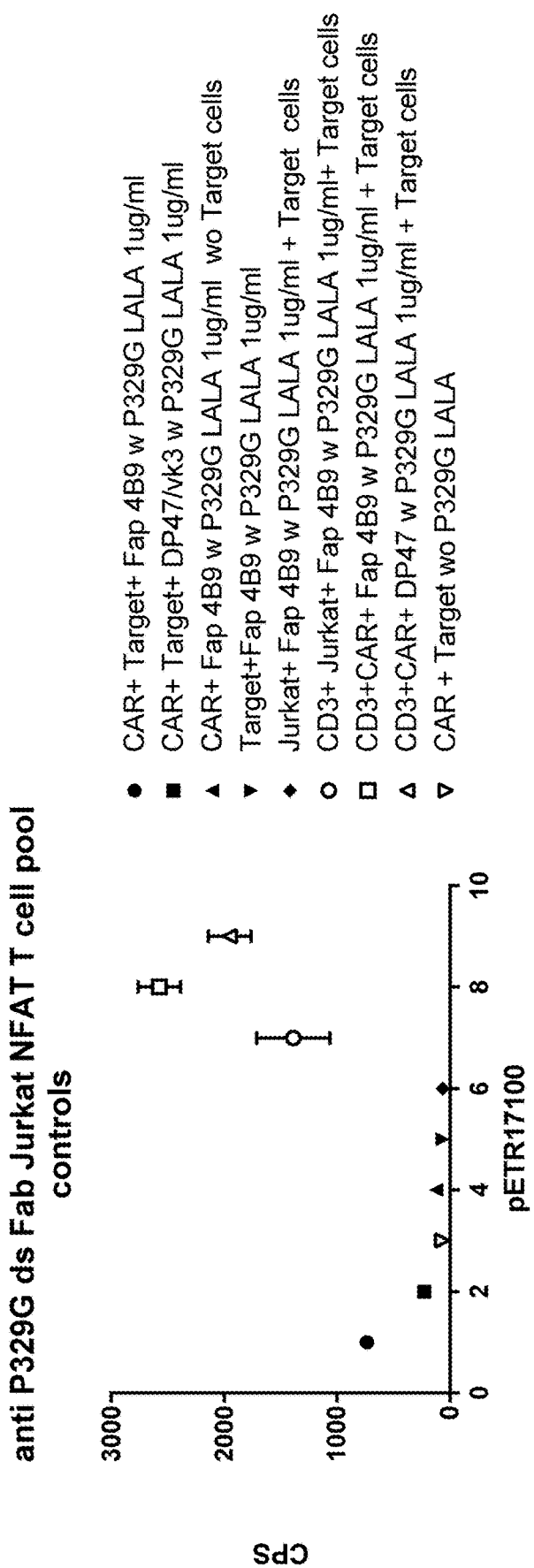

FIG. 8C a sorted pool of anti-P329G-ds-Fab-CD28ATD-CD28CSD-CD3zSSD expressing Jurkat NFAT reporter CAR-T cells was used as reporter cells.

Figure 8D:
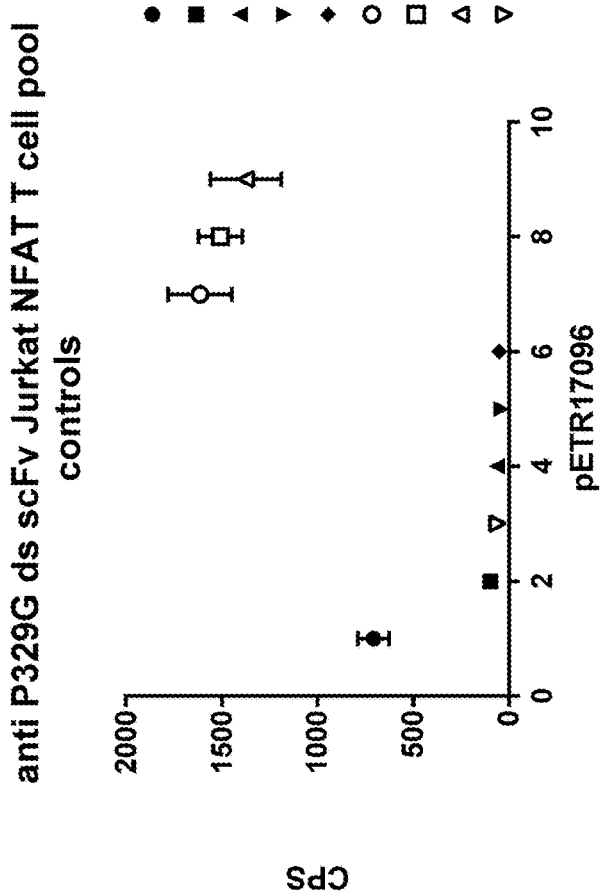

FIG. 8D a sorted pool of anti-P329G-ds-scFv-CD28ATD-CD28CSD-CD3zSSD expressing Jurkat NFAT reporter CAR-T cells was used as reporter cells FIG. 9A-9D depicts a Jurkat NFAT reporter CAR-T cell assay using adherent CEA expressing MKN45 tumor cells as target cells. Either the anti-CEA IgG clone A5B7 or the anti-CEA IgG clone T84 LCHA both harboring the P329G mutation were used which recognize the tumor associated antigen and are recognized by the Jurkat NFAT reporter CAR-T cells. Further IgG DP47/vk3 harboring the P329G mutation was included as isotype control.

Figure 9A:
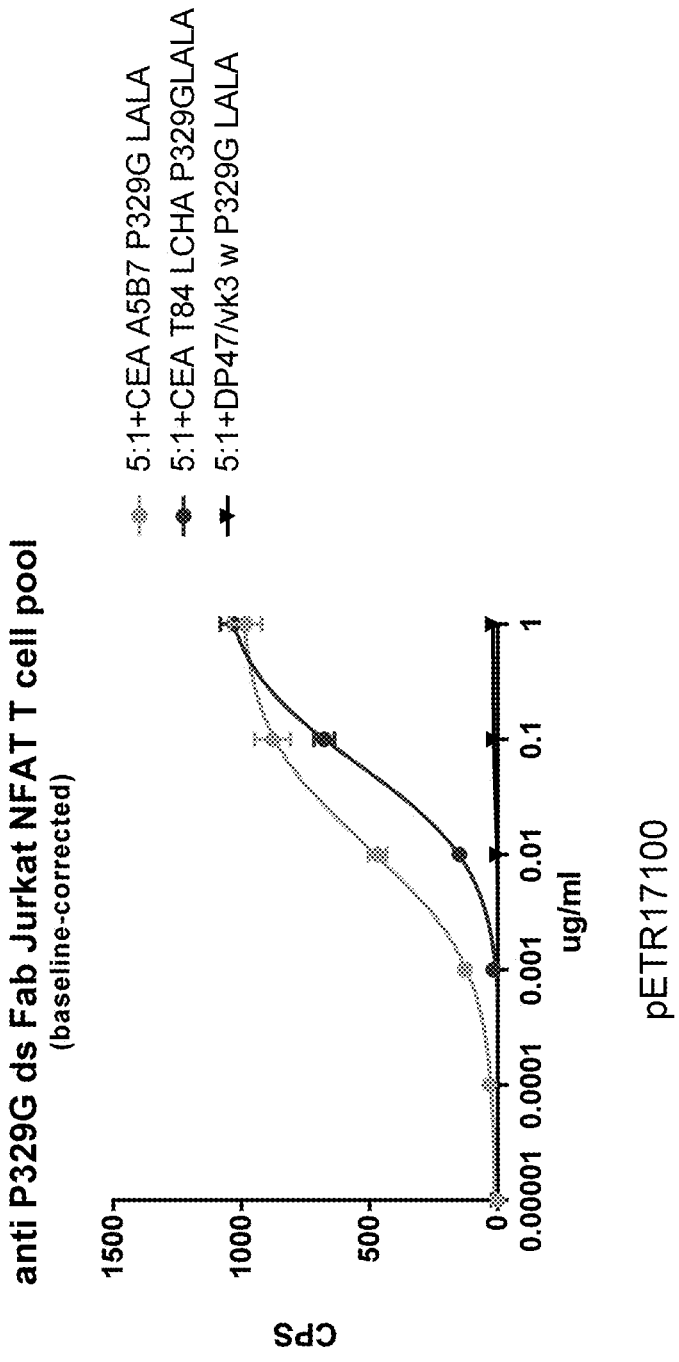
Figure 9B:
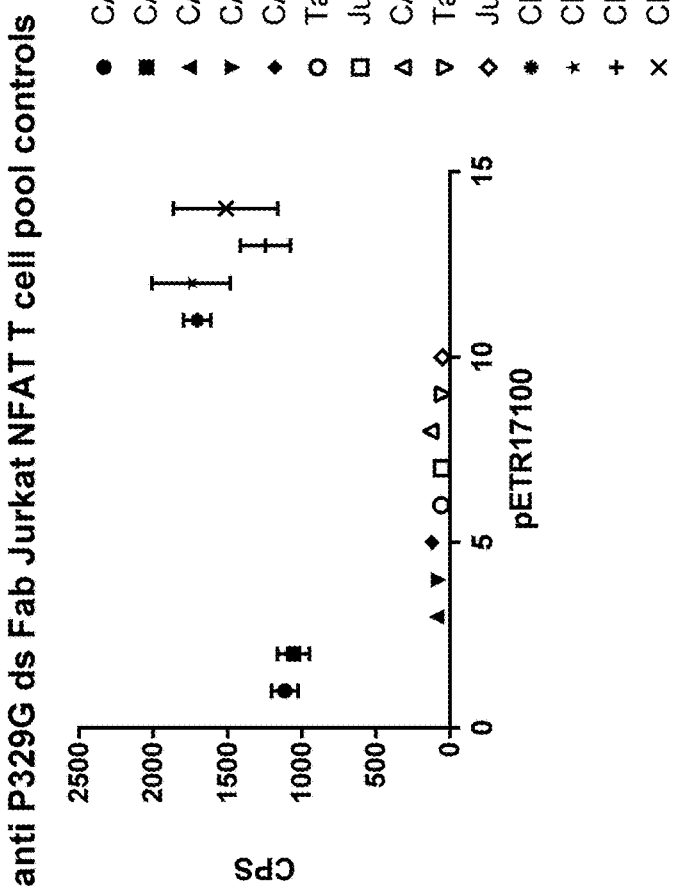

FIG. 9A and in FIG. 9B a sorted pool of anti-P329G-ds-Fab-CD28ATD-CD28CSD-CD3zSSD expressing NFAT T cells was used as reporter cells.

Figure 9C:
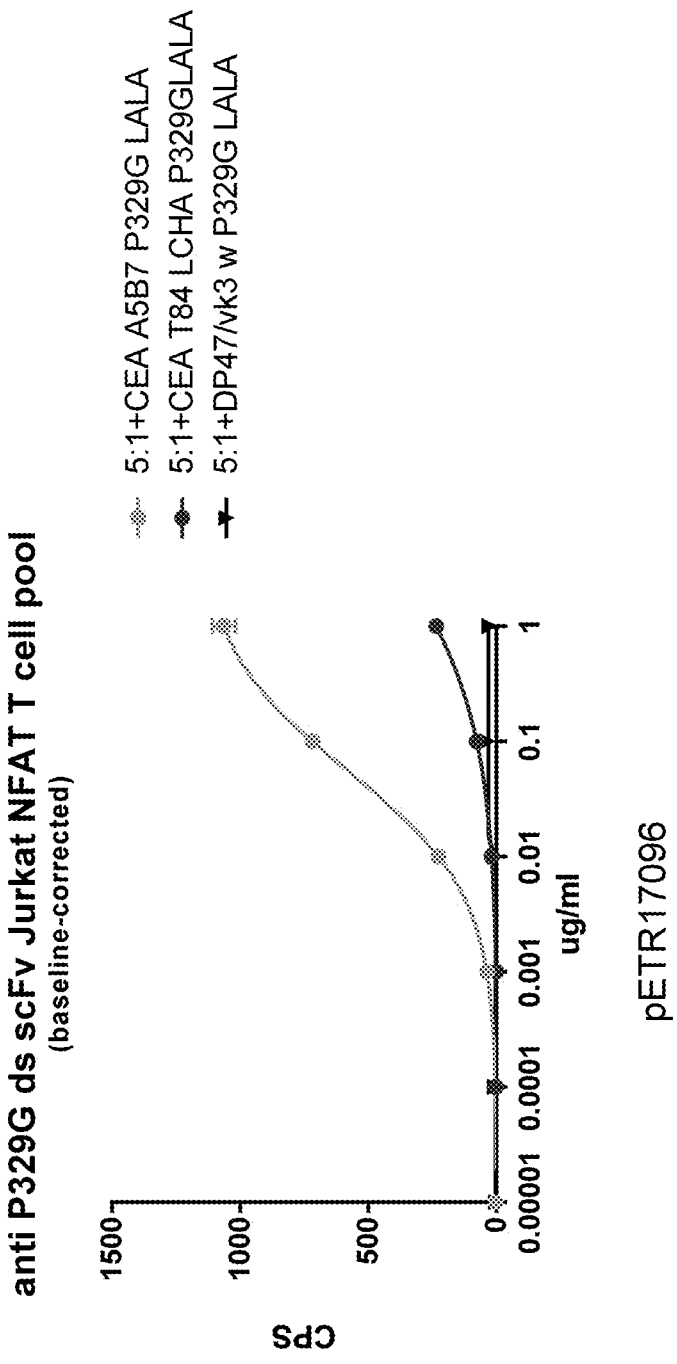
Figure 9D:
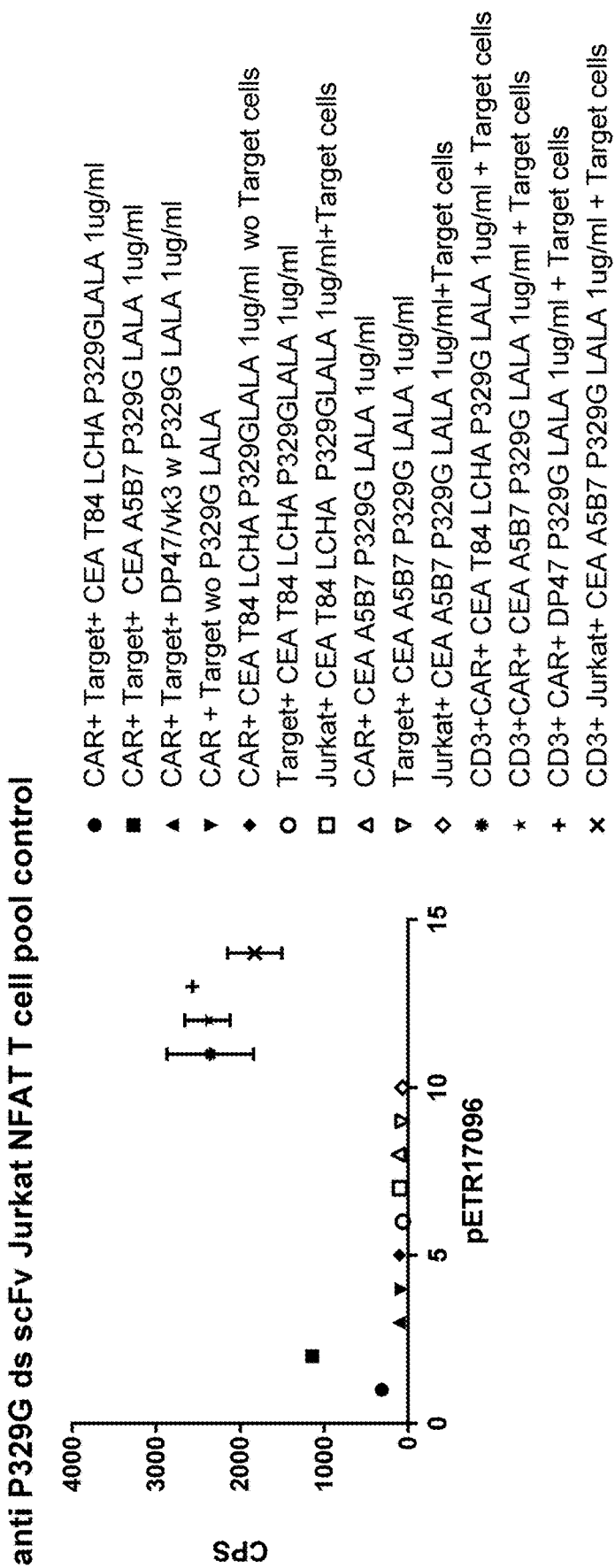

FIG. 9C and in FIG. 9D a sorted pool of anti-P329G-ds-scFv-CD28ATD-CD28CSD-CD3zSSD expressing NFAT T cells was used as reporter cells.

FIG. 10A-10D depicts a Jurkat NFAT reporter CAR-T cell assay using adherent CEA expressing MKN45 tumor cells as target cells. Either the anti-CEA clone CH1A1A 98 99 or the anti-CEA IgG clone hMN14 IgG both harboring the P329G mutation were used which recognize the tumor associated antigen and are recognized by the Jurkat NFAT reporter CAR-T cells. Further IgG DP47/vk3 harboring P329G mutation was included as isotype control.

Figure 10A:
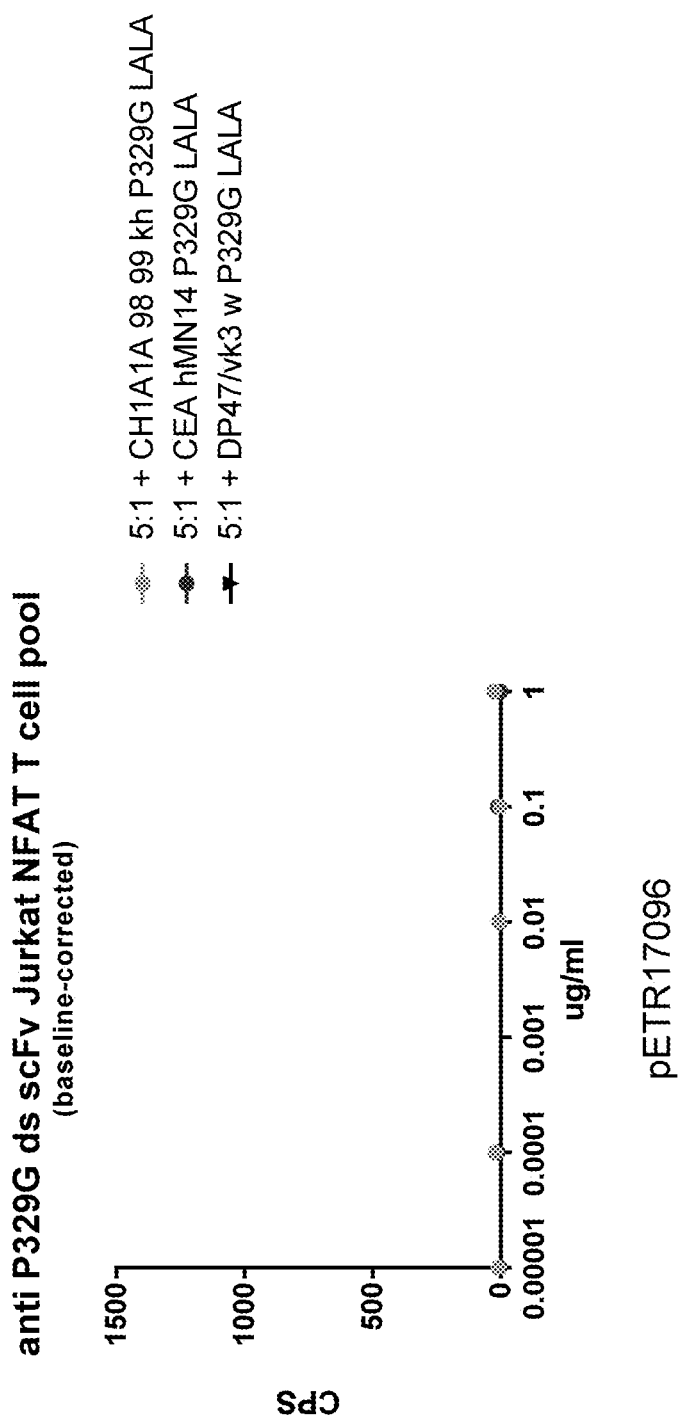
Figure 10B:
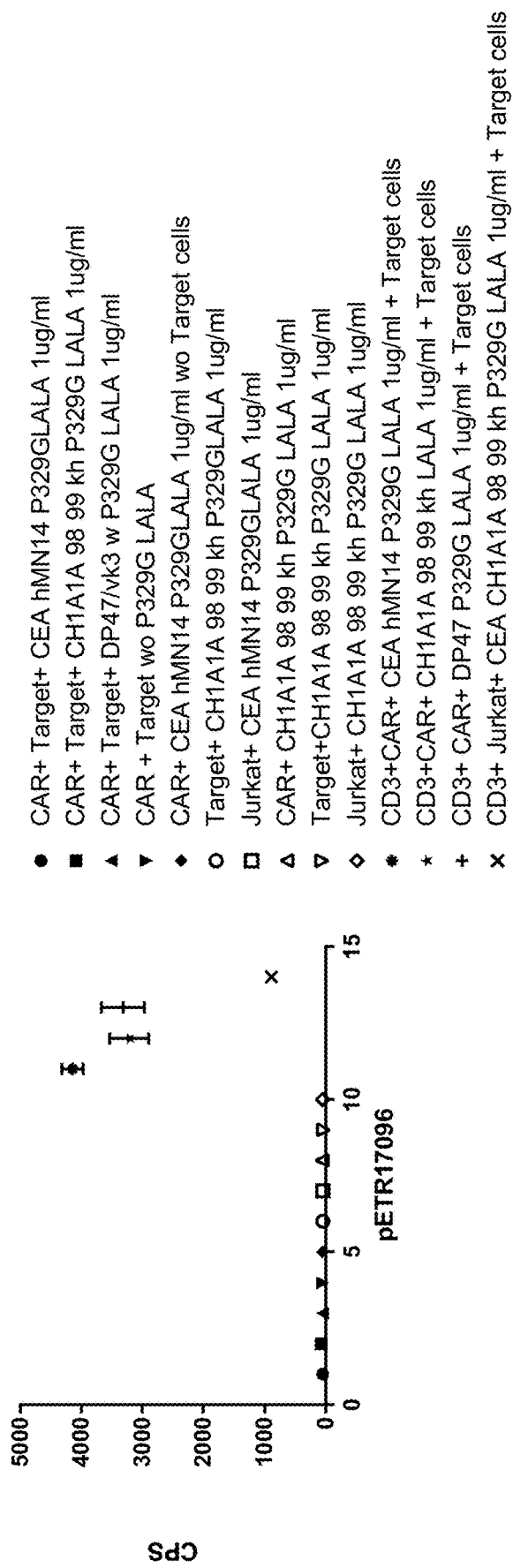

FIG. 10A and in FIG. 10B a sorted pool of anti-P329G-ds-scFv-CD28ATD-CD28CSD-CD3zSSD expressing NFAT T cells was used as reporter cells.

Figure 10C:
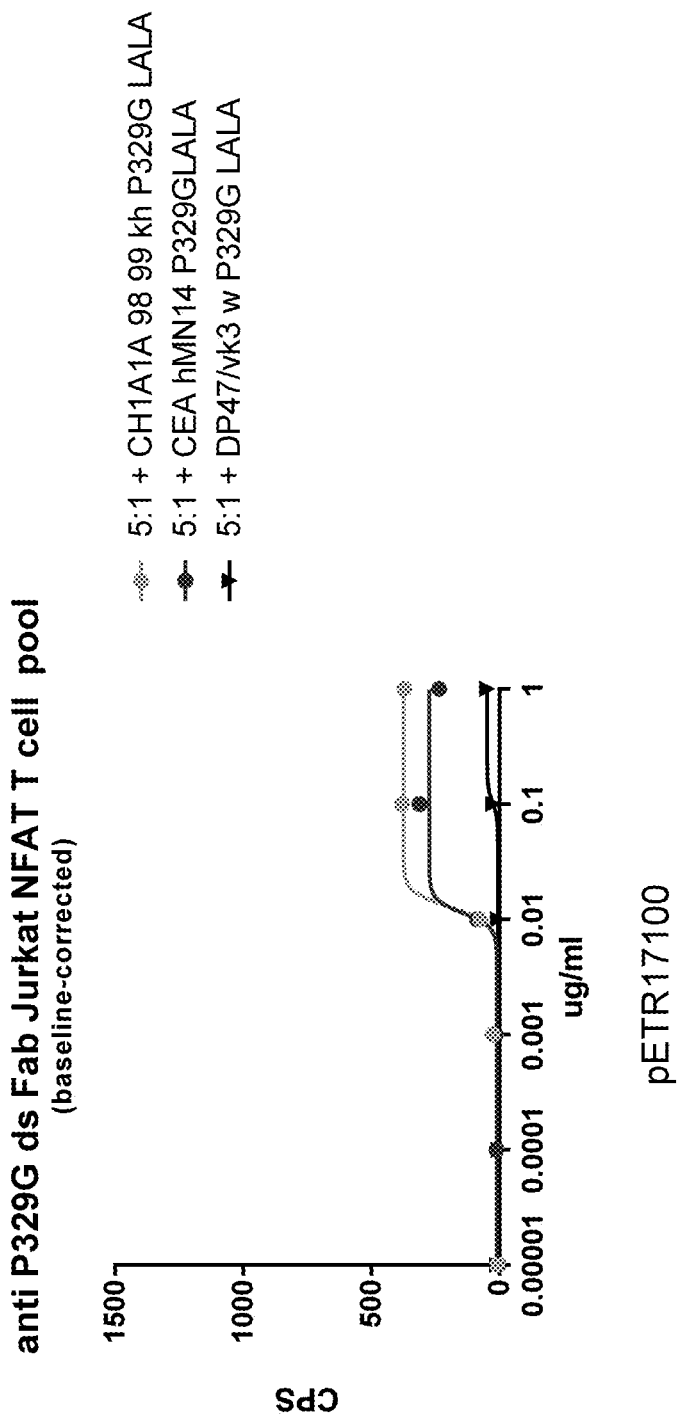
Figure 10D:
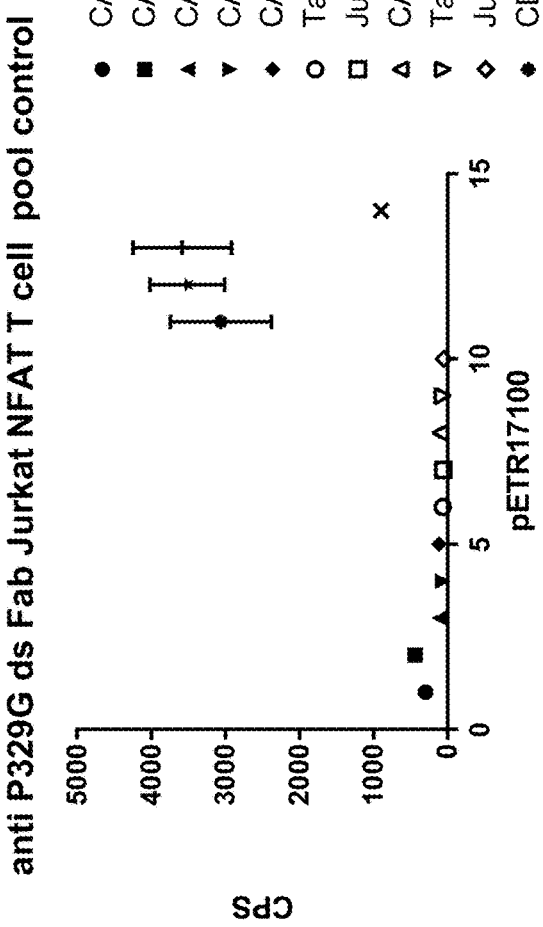

FIG. 10C and in FIG. 10D a sorted pool of anti-P329G-ds-Fab-CD28ATD-CD28CSD-CD3zSSD expressing NFAT T cells was used as reporter cells.

FIG. 11A-11D depicts a Jurkat NFAT reporter CAR-T cell assay using adherent TNC expressing CT26TNC cl 19 tumor cells as target cells. The anti-TNC IgG clone A2B10 harboring the P329G mutation was used as IgG antibody which recognizes the tumor associated antigen and is recognized by the Jurkat NFAT reporter CAR-T cells. Further IgG DP47/vk3 harboring P329G mutation was included as isotype control.

Figure 11A:
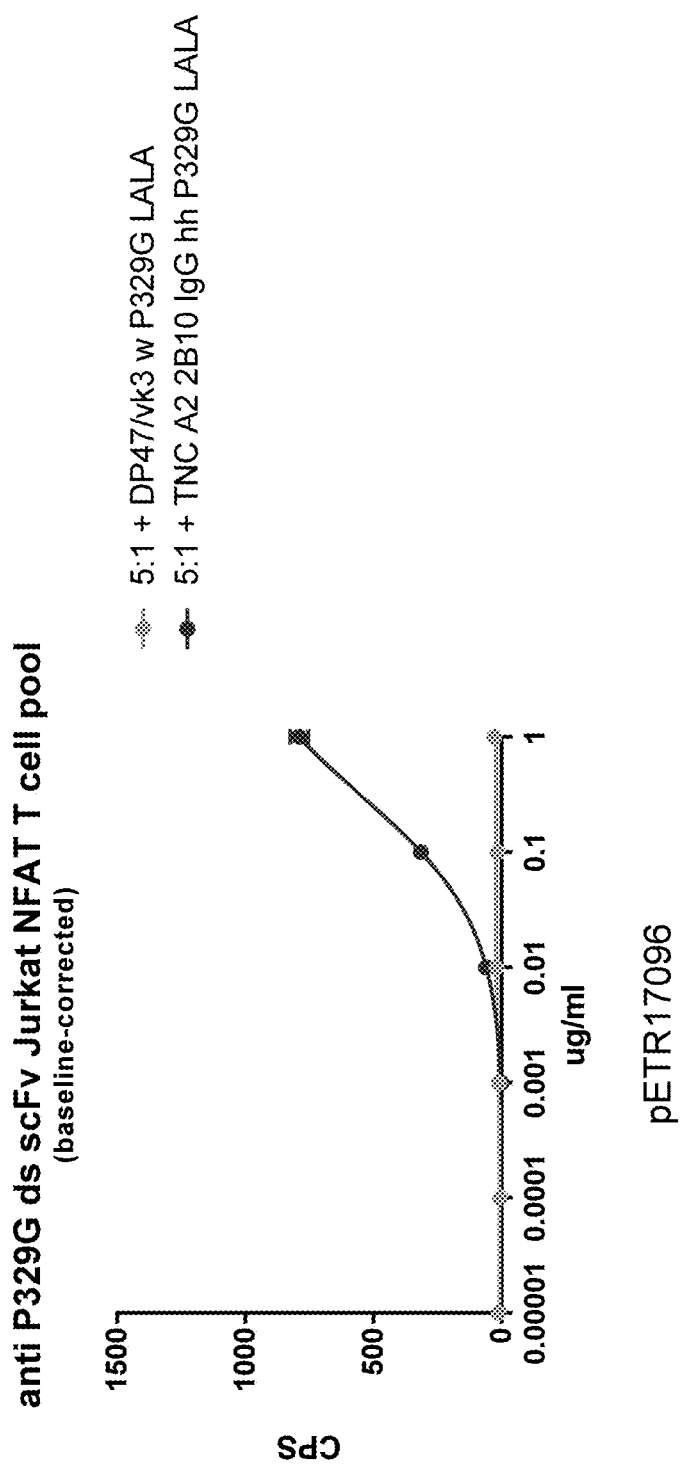
Figure 11B:
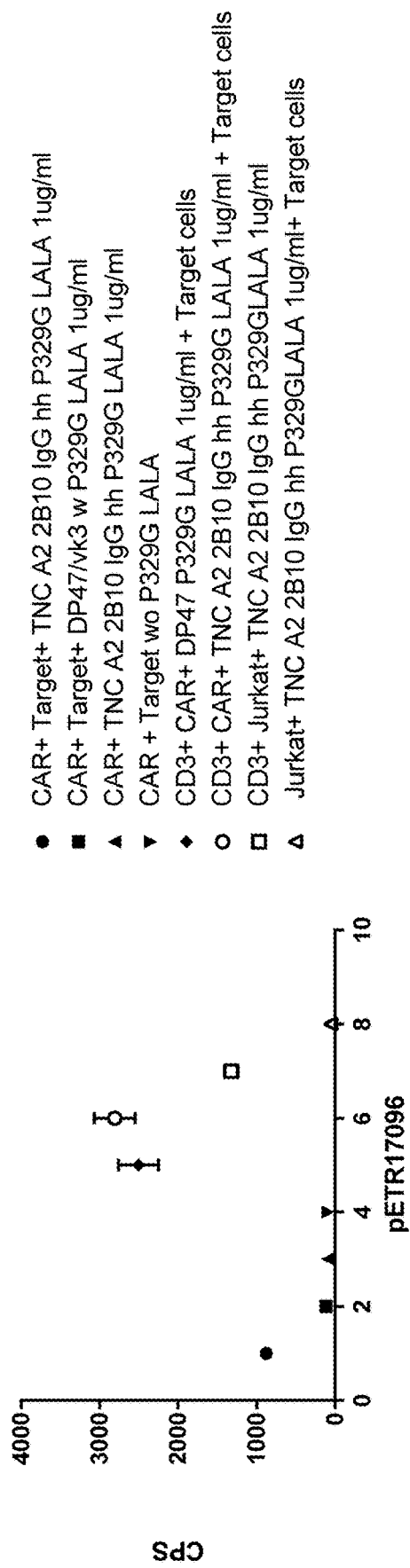

FIG. 11A and in FIG. 11B a sorted pool of anti-P329G-ds-scFv-CD28ATD-CD28CSD-CD3zSSD expressing NFAT T cells was used as reporter cells.

Figure 11C:
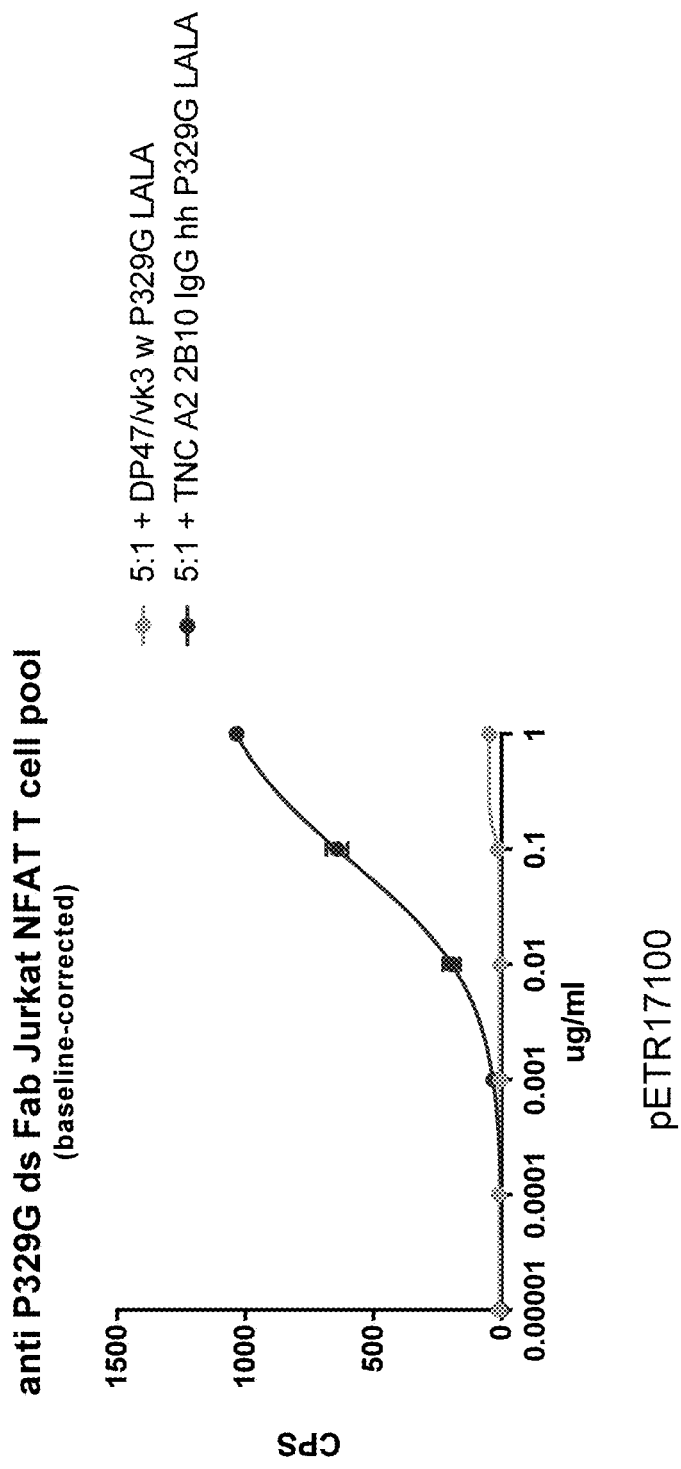
Figure 11D:

FIG. 11C and in FIG. 11D a sorted pool of anti-P329G-ds-Fab-CD28ATD-CD28CSD-CD3zSSD expressing NFAT T cells was used as reporter cells.

Figure 12A:
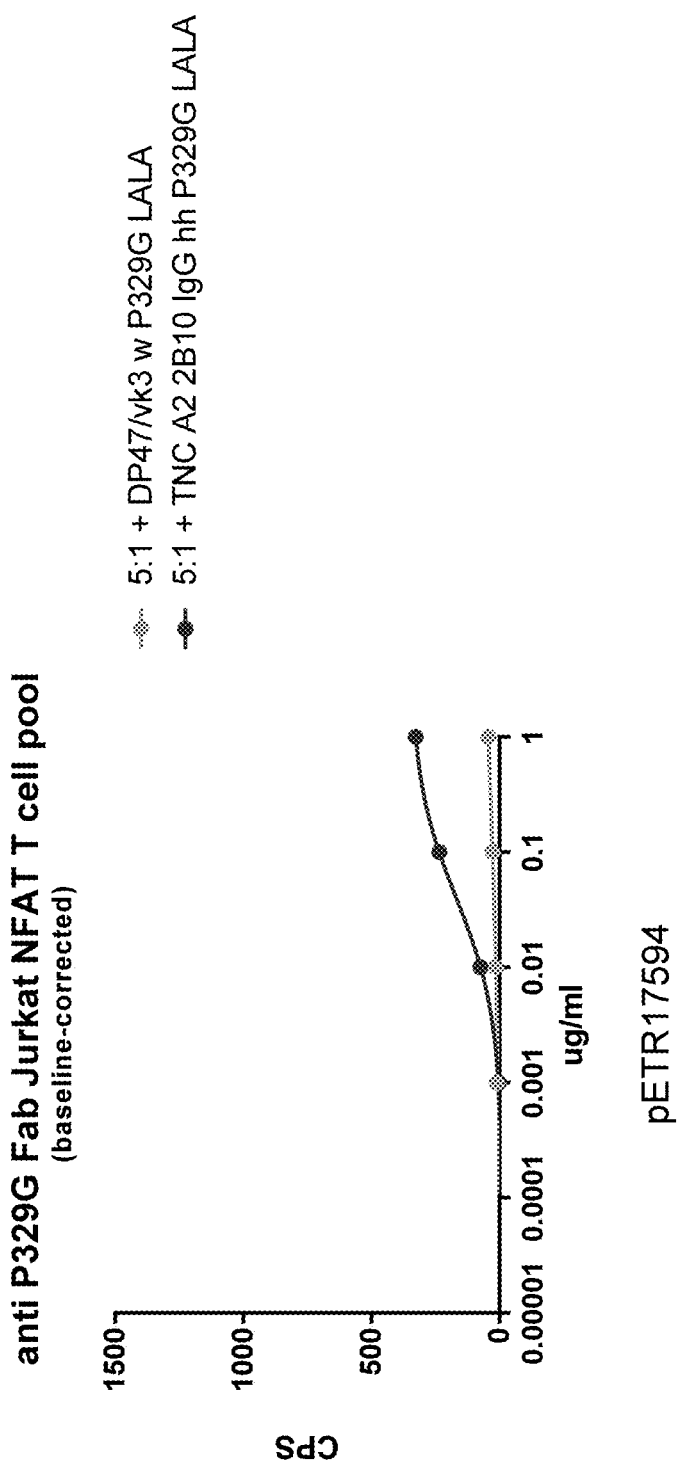
Figure 12B:

FIG. 12A and FIG. 12B depict a Jurkat NFAT reporter CAR-T cell assay using adherent TNC expressing CT26TNC cl 19 tumor cells as target cells. The anti-TNC IgG clone A2B10 harboring the P329G mutation was used which recognizes the tumor associated antigen and is recognized by the Jurkat NFAT reporter CAR-T cells. Further IgG DP47/vk3 harboring P329G mutation was included as isotype control. A sorted pool of anti-P329G-Fab-CD28ATD-CD28CSD-CD3zSSD expressing Jurkat NFAT reporter CAR-T cells was used as reporter cells.

Figure 13A:
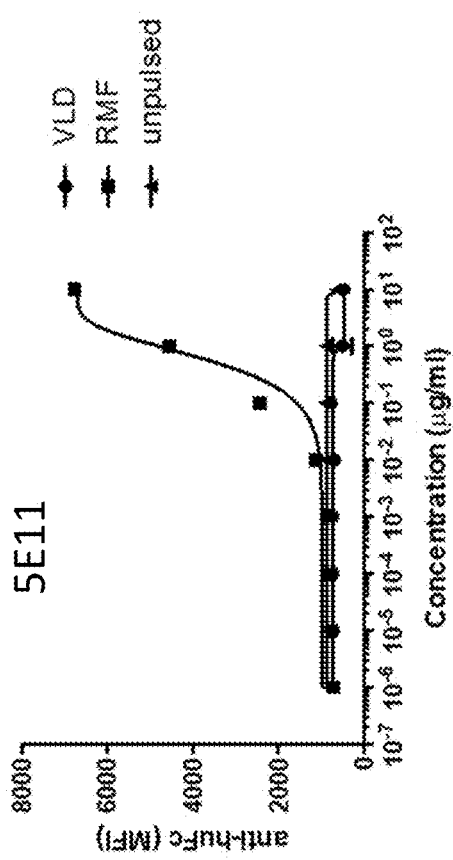
Figure 13B:
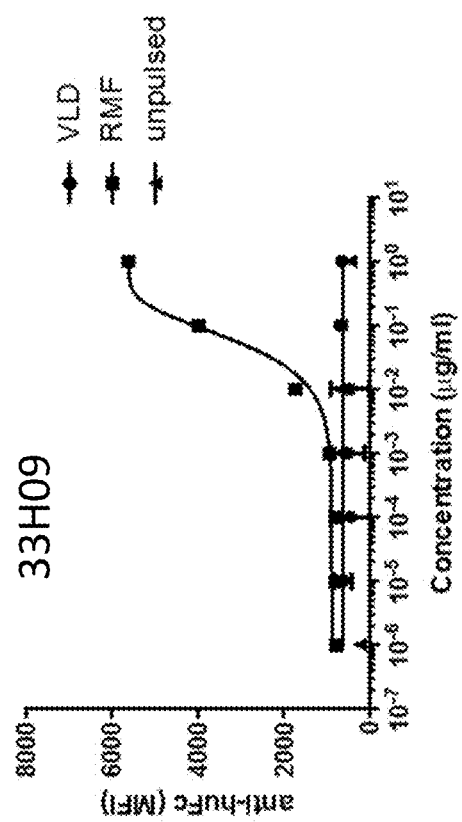
Figure 14A:
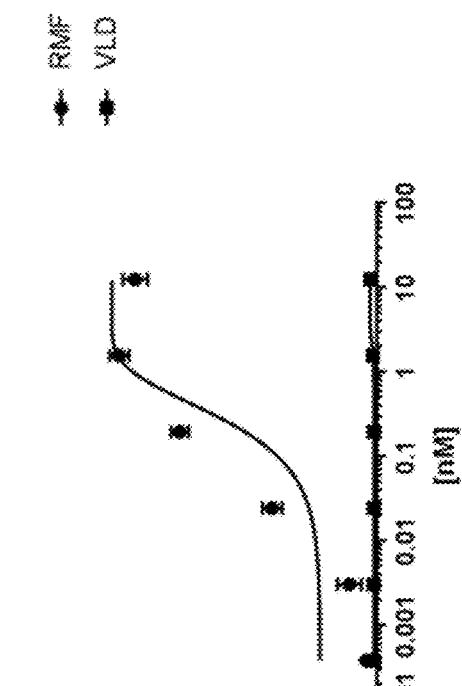
Figure 14B:
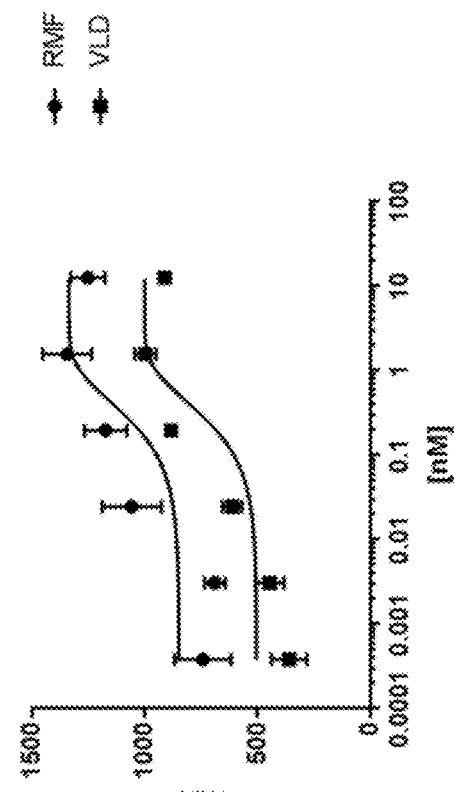
Figure 14C:
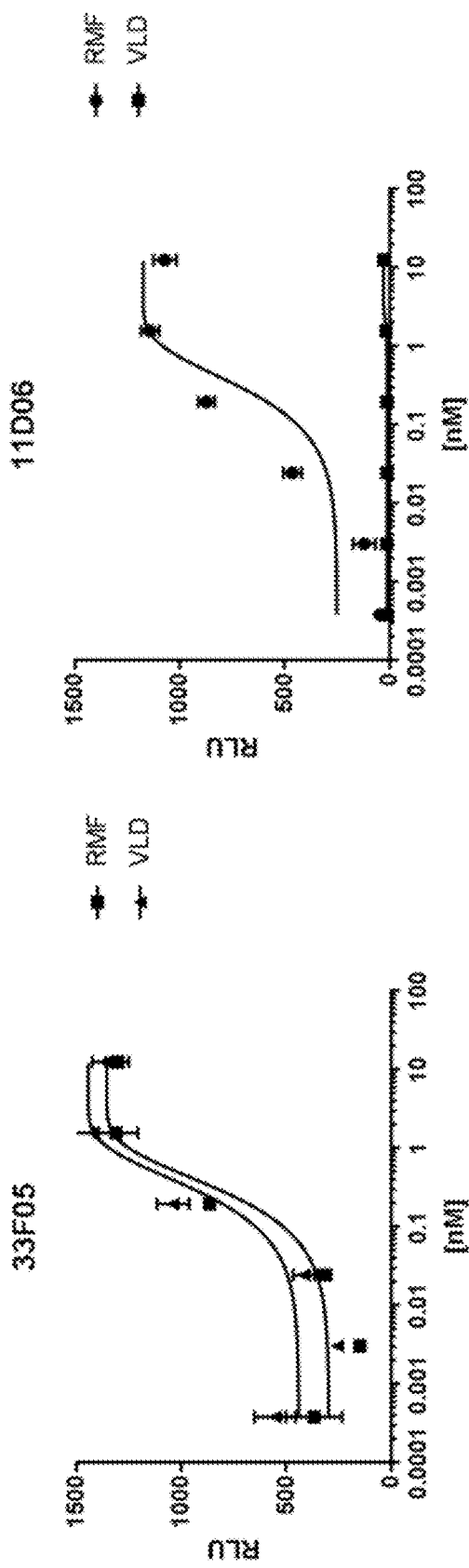
Figure 14D:
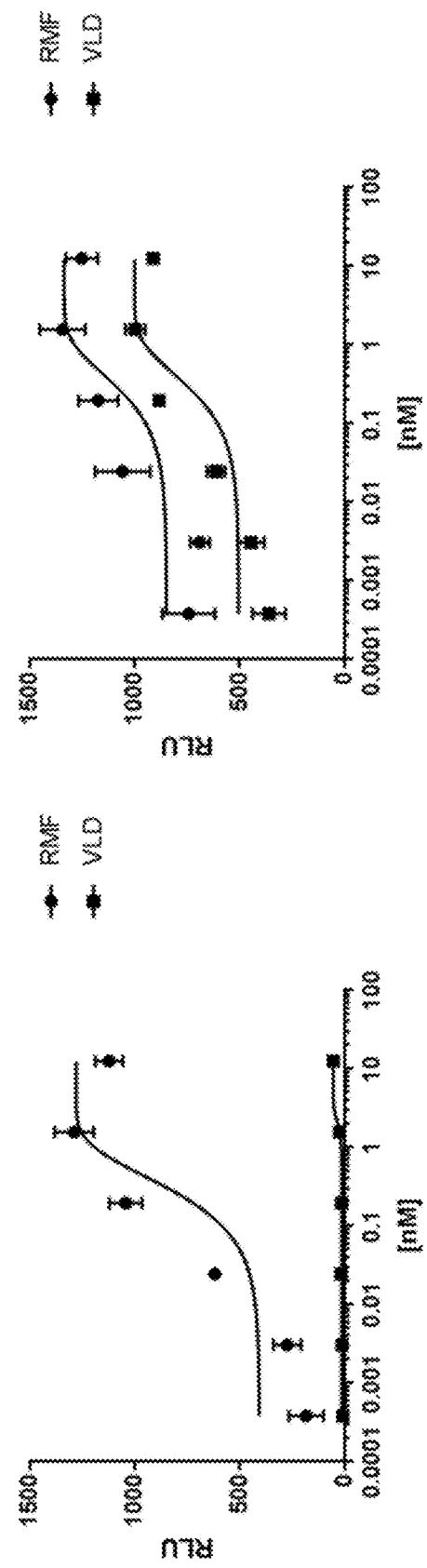
Figure 15A:
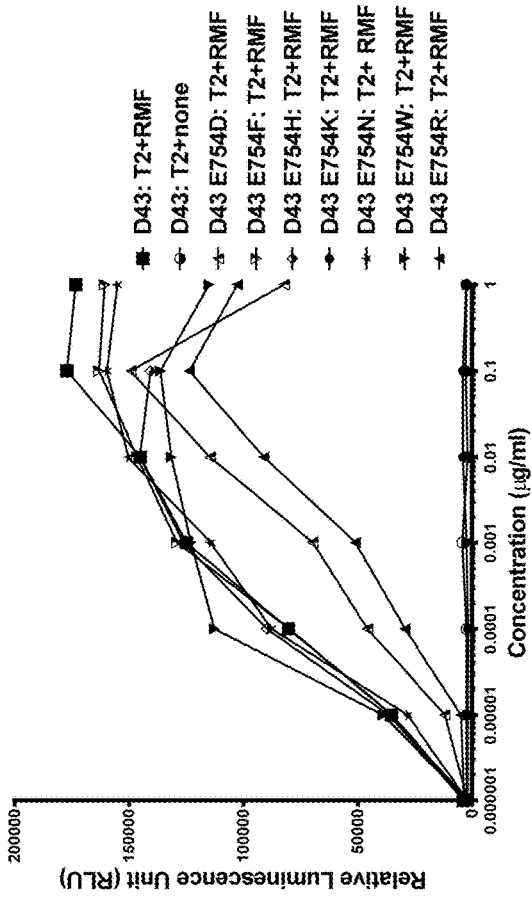
Figure 15B:
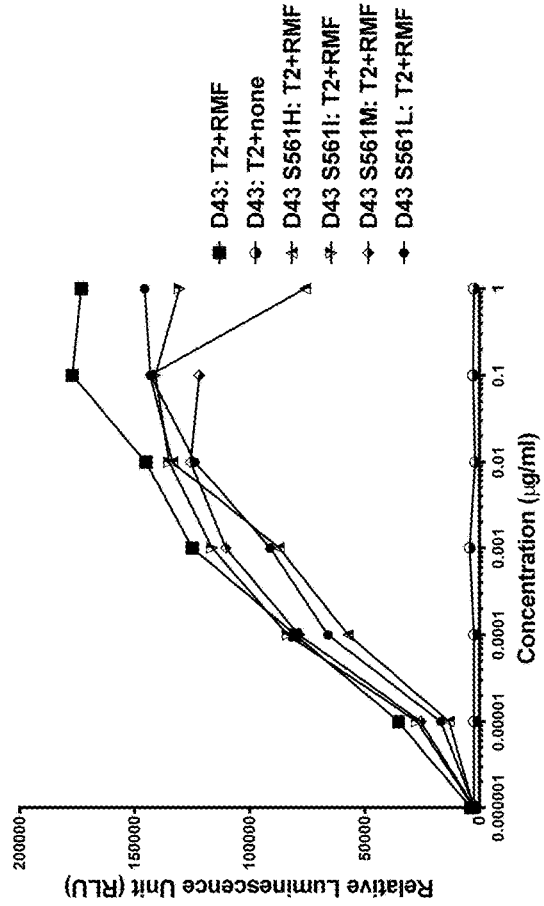
Figure 15C:
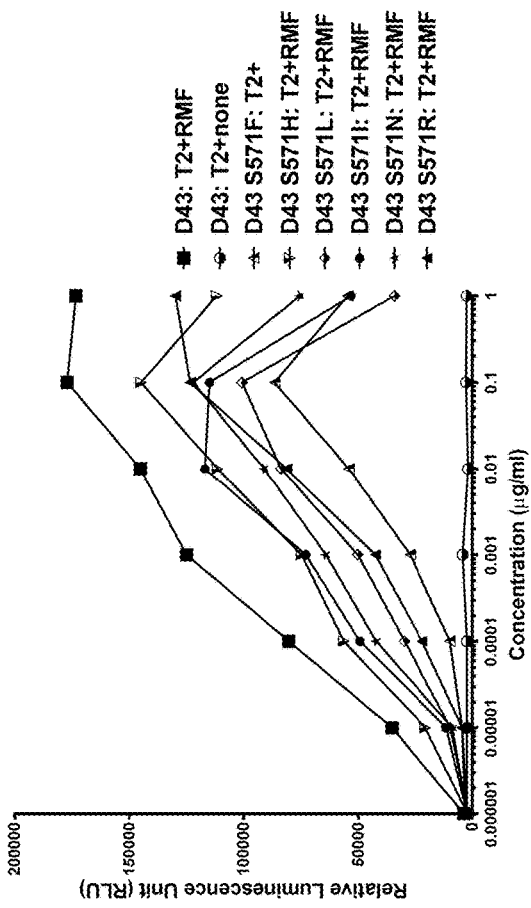
Figure 15D:
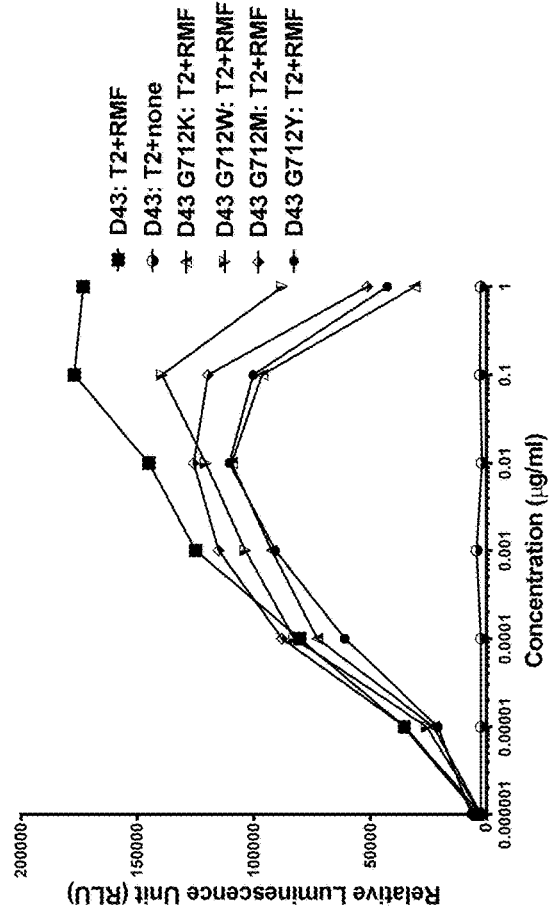
Figure 15E:
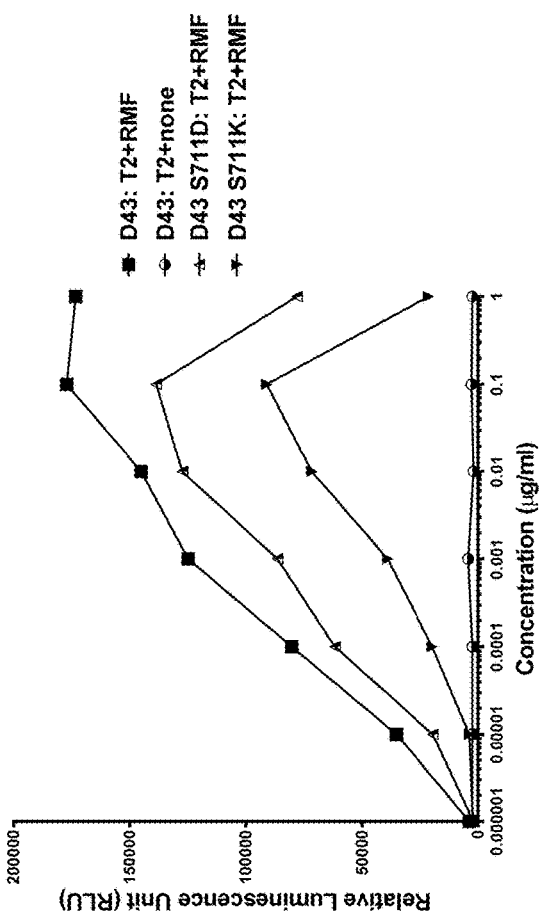
Figure 15F:
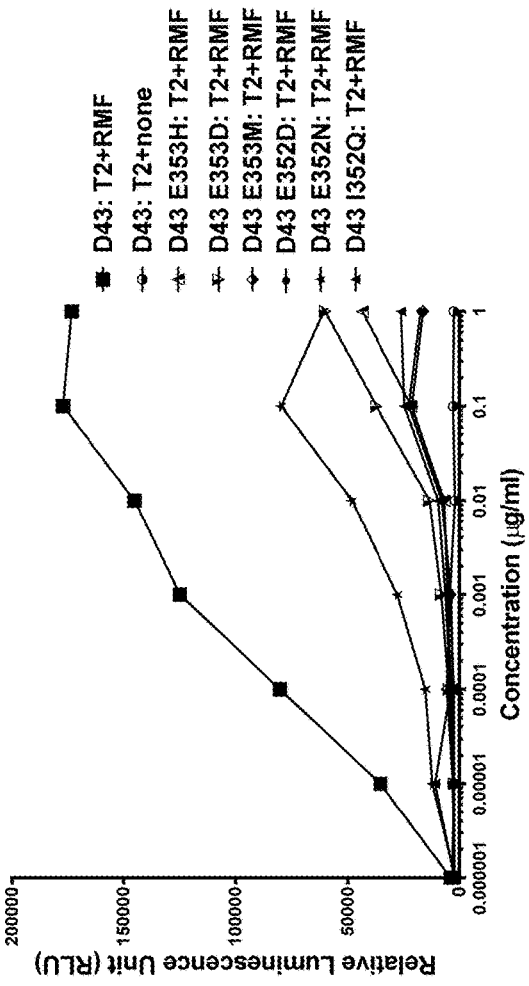

FIG. 13A and FIG. 13B depict assessment of specificity of WT1/HLA-binders 5E11 and 33H09 by FACS with T2 cells pulsed with RMF-peptide or VLD-peptide.

FIG. 14A to FIG. 14D depict activation of CAR-NFAT-signaling in Jurkat NFAT reporter CAR-T cells by HLA-A2/WT1-peptide-binding PGLALA IgG variants to RMF- or VLD-peptide-pulsed T2 cells. As reporter cells, a sorted pool of Anti-P329G-ds-Fab-CD28ATD-CD28CSD-CD3zSSD expressing Jurkat NFAT reporter CAR-T cells were used. Each subfigure represents dilutions of the particular binder (FIG. 14A 33F05, FIG. 14B 11D06, FIG. 14C 33H09 and FIG. 14D 5E11). Comparison of signals on RMF-peptide (target) vs. VLD-peptide (off-target) helps to assess specificity of activation.

FIG. 15A to FIG. 15F depict binding of HLA-A2/WT1 D43 PGLALA IgG variants to RMF peptide-pulsed T2 cells. Each subfigure represents group of variants of single aa (E754, S561, S571, G712, G711, E353 and I352) comparing to original D43 PGLALA IgG. Values in graphs' y-axes indicate relative luminescence detection of luciferase in Jurkat NFAT reporter CAR-T cells recognizing PGLALA.

Figure 16:
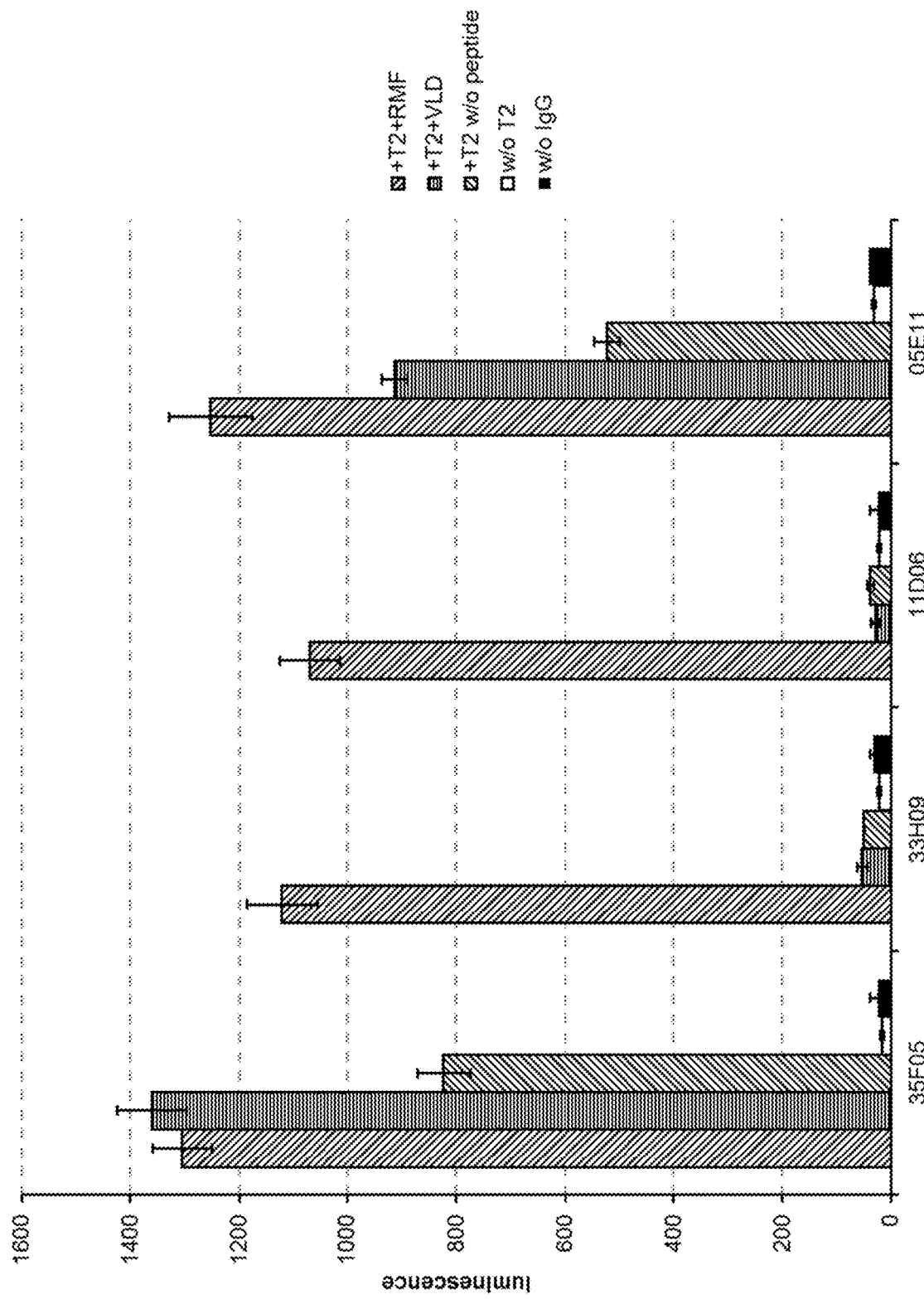

FIG. 16 depicts activation of CAR-NFAT-signaling in Jurkat NFAT reporter CAR-T cells to assess the specificity of selected WT1/HLA-A2-binders 33F05, 33H09, 11D06 and 5E11 upon incubation with T2 cells pulsed with RMF-peptide or VLD-peptide. Negative controls using Jurkat NFAT reporter CAR-T cells with unpulsed T2 cells, without T2 cells or without IgG are included. Activation (luciferase signal from Jurkat NFAT reporter CAR-T cells) was measured afterwards by adding luciferase substrate and measuring luminescence.

DETAILED DESCRIPTION

Definitions

Terms are used herein as generally used in the art, unless otherwise defined in the following. An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity ("ADCC") is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been mutated. For example the reduction in ADCC mediated by an antibody comprising in its Fc domain an amino acid mutation that reduces ADCC, is relative to the ADCC mediated by the same antibody without this amino acid mutation in the Fc domain. Suitable assays to measure ADCC are well known in the art (see e.g., PCT publication no. WO 2006/082515 or PCT publication no. WO 2012/130831).

An "effective amount" of an agent (e.g., an antibody) refers to the amount that is necessary to result in a physiological change in the cell or tissue to which it is administered.

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen and/or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art, including those described herein. A preferred method for measuring affinity is Surface Plasmon Resonance (SPR) and a preferred temperature for the measurement is 25° C.

The term "amino acid" ("aa") refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor. Amino acid sequence deletions and insertions include amino- and/or carboxy-terminal deletions and insertions of amino acids. Particular amino acid mutations are amino acid substitutions. For the purpose of altering e.g., the binding characteristics of an Fc region, non-conservative amino acid substitutions, i.e., replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

The term "antibody" herein is used in the broadest sense and encompasses various antibody structures, including but not limited to monoclonal antibodies, polyclonal antibodies, and antibody fragments so long as they exhibit the desired antigen-binding activity. Accordingly, in the context of the present invention, the term antibody relates to full immunoglobulin molecules as well as to parts of such immunoglobulin molecules. Furthermore, the term relates, as discussed herein, to modified and/or altered antibody molecules, in particular to mutated antibody molecules. The term also relates to recombinantly or synthetically generated/synthesized antibodies. In the context of the present invention the term antibody is used interchangeably with the term immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g., scFv), and single-domain antibodies. For a review of certain antibody fragments, see Hudson et al., Nat Med 9, 129-134 (2003). For a review of scFv fragments, see e.g., Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody (Domantis, Inc., Waltham, Mass.; see e.g., U.S. Pat. No. 6,248,516 B1). Antibody fragments can be made by various techniques, including but not limited to proteolytic digestion of an intact antibody as well as production by recombinant host cells (e.g., E. coli or phage), as described herein.

As used herein, the term "antigen binding molecule" and the abbreviation "ABM" refers in its broadest sense to a molecule that specifically binds an antigenic determinant. Examples of ABMs are antibodies/immunoglobulins and derivatives, e.g., fragments, thereof. Furthermore, the term relates, as discussed herein, to modified and/or altered ABMs, in particular to mutated antibody molecules. The term also relates to recombinantly or synthetically generated/synthesized antibodies. In the context of the present invention the ABM is preferably an antibody or fragment thereof.

As used herein, the term "antigen binding moiety" refers to a polypeptide molecule that specifically binds to an antigenic determinant. In one embodiment, an antigen binding moiety is able to direct the entity to which it is attached (e.g., an immunoglobulin or a CAR) to a target site, for example to a specific type of tumor cell or tumor stroma bearing the antigenic determinant or to an immunoglobulin binding to the antigenic determinant on a tumor cell. In another embodiment an antigen binding moiety is able to activate signaling through its target antigen, for example signaling is activated upon binding of an antigenic determinant to a CAR on a T cell. In the context of the present invention, antigen binding moieties may be included in antibodies and fragments thereof as well as in antigen binding receptors (e.g., CARs) and fragments thereof as further defined herein. Antigen binding moieties include an antigen binding domain, e.g., comprising an immunoglobulin heavy chain variable region and an immunoglobulin light chain variable region. A "candidate antigen binding moiety" or "CABM" is an antigen binding moiety which is assessed according to the methods as described herein.

In the context of the present invention the term "antigen binding receptor" relates to an antigen binding molecule comprising an anchoring transmembrane domain and an extracellular domain comprising at least one antigen binding moiety. An antigen binding receptor (e.g., a CAR) can be made of polypeptide parts from different sources. Accordingly, it may be also understood as a "fusion protein" and/or a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. In the context of the present invention a CAR (chimeric antigen receptor) is understood to be an antigen binding receptor comprising an extracellular portion comprising an antigen binding moiety fused by a spacer sequence to an anchoring transmembrane domain which is itself fused to the intracellular signaling domains of CD3z and CD28.

An "antigen binding site" refers to the site, i.e., one or more amino acid residues, of an antigen binding molecule which provides interaction with the antigen. For example, the antigen binding site of an antibody or a CAR comprises amino acid residues from the complementarity determining regions (CDRs). A native immunoglobulin molecule typically has two antigen binding sites, a Fab or a scFv molecule typically has a single antigen binding site.

The term "antigen binding domain" refers to the part of an antibody or an antigen binding receptor (e.g., a CAR) that comprises the area which specifically binds to and is complementary to part or all of an antigen. An antigen binding domain may be provided by, for example, one or more immunoglobulin variable domains (also called variable regions). Particularly, an antigen binding domain comprises an immunoglobulin light chain variable region (VL) and an immunoglobulin heavy chain variable region (VH).

The term "variable region" or "variable domain" refers to the domain of an immunoglobulin heavy or light chain that is involved in binding the antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, $6^{th}$ ed., W.H. Freeman and Co, page 91 (2007). A single VH or VL domain is usually sufficient to confer antigen-binding specificity.

The term "ATD" as used herein refers to "anchoring transmembrane domain" which defines a polypeptide stretch capable of integrating in (the) cellular membrane(s) of a cell. The ATD can be fused to further extracellular and/or intracellular polypeptide domains wherein these extracellular and/or intracellular polypeptide domains will be confined to the cell membrane as well. In the context of the antigen binding receptors as used in the present invention the ATD confers membrane attachment and confinement of the antigen binding receptor, e.g., a CAR used according to the present invention.

The term "binding to" as used in the context of the antigen binding receptors (e.g., CARs) used according to the present invention defines a binding (interaction) of an "antigen-interaction-site" and an antigen with each other. The term "antigen-interaction-site" defines a motif of a polypeptide which shows the capacity of specific interaction with a specific antigen or a specific group of antigens (i.e., mutated Fc domains). Said binding/interaction is also understood to define a "specific recognition". The term "specifically recognizing" means in accordance with this invention that the antigen binding receptor is capable of specifically interacting with and/or binding to the recognition domain, i.e., a modified molecule as defined herein whereas the non-modified molecule is not recognized. The antigen binding moiety of an antigen binding receptor (e.g., a CAR) can recognize, interact and/or bind to different epitopes on the same molecule. This term relates to the specificity of the antigen binding receptor, i.e., to its ability to discriminate between the specific regions of a modified molecule, i.e., a mutated Fc domain, as defined herein. The specific interaction of the antigen-interaction-site with its specific antigen may result in an initiation of a signal, e.g., due to the induction of a change of the conformation of the polypeptide comprising the antigen, an oligomerization of the polypeptide comprising the antigen, an oligomerization of the antigen binding receptor, etc. Thus, a specific motif in the amino acid sequence of the antigen-interaction-site and the antigen bind to each other as a result of their primary, secondary or tertiary structure as well as the result of secondary modifications of said structure. Accordingly, the term binding to does not only relate to a linear epitope but may also relate to a conformational epitope, a structural epitope or a discontinuous epitope consisting of two regions of the target molecules or parts thereof. In the context of this invention, a conformational epitope is defined by two or more discrete amino acid sequences separated in the primary sequence which comes together on the surface of the molecule when the polypeptide folds to the native protein (Sela, Science 166 (1969), 1365 and Laver, Cell 61 (1990), 553-536). Moreover, the term "binding to" is interchangeably used in the context of the present invention with the term "interacting with". The ability of the antigen binding moiety (e.g., a Fab or scFv domain) of a CAR or an antibody to bind to a specific target antigenic determinant can be measured either through an enzyme-linked immunosorbent assay (ELISA) or other techniques familiar to one of skill in the art, e.g., surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the target antigen as measured, in particular by SPR. In certain embodiments, an antigen binding moiety that binds to the target antigen, has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). The term "specific binding" as used in accordance with the present invention means that the molecules used in the invention do not or do not essentially cross-react with (poly-) peptides of similar structures, i.e., with a non-mutated parent Fc domain. Accordingly, the antigen binding receptor (e.g., the CAR) used according to the invention specifically binds to/interacts with a recognition domain, e.g., an Fc domain, preferably a mutated Fc domain. Cross-reactivity of a panel of constructs under investigation may be tested, for example, by assessing binding of a panel of antigen binding moieties under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the recognition domain of interest, e.g., an Fc domain as well as to parent non-mutated Fc domain. Only those constructs (i.e., Fab fragments, scFvs and the like) that bind to the domain of interest but do not or do not essentially bind to structurally closely related domain, e.g., a non-mutated parent Fc domain, are considered specific for the recognition domain of interest and selected for further studies in accordance with the method provided herein. These methods may comprise, inter alia, binding studies, blocking and competition studies with structurally and/or functionally closely related domains. The binding studies also comprise FACS analysis, surface plasmon resonance (SPR, e.g., with BIAcore®), analytical ultracentrifugation, isothermal titration calorimetry, fluorescence anisotropy, fluorescence spectroscopy or by radiolabeled ligand binding assays.

The term "CDR" as employed herein relates to "complementary determining region", which is well known in the art. The CDRs are parts of immunoglobulins or antigen binding receptors that determine the specificity of said molecules and make contact with a specific ligand. The CDRs are the most variable part of the molecule and contribute to the antigen binding diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in "Kabat" (Sequences of Proteins of Immunological Interest", 5th edit. NIH Publication no. 91-3242 U.S. Department of Health and Human Services (1991); Chothia J. Mol. Biol. 196 (1987), 901-917) or "Chothia" (Nature 342 (1989), 877-883).

The term "CD3z" refers to T-cell surface glycoprotein CD3 zeta chain, also known as "T-cell receptor T3 zeta chain" and "CD247".

The term "chimeric antigen receptor" or "chimeric receptor" or "CAR" refers to an antigen binding receptor constituted of an extracellular portion of an antigen binding moiety (e.g., a scFv or a Fab) fused by a spacer sequence to intracellular signaling domains (e.g., of CD3z and CD28). The term "CAR" is understood in its broadest form and comprises antigen binding receptors constituted of an extracellular portion comprising an antigen binding moiety fused to CD3z and fragment thereof and to CD28 and fragments thereof, optionally through one or several peptide linkers.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ϑ, γ, and µ, respectively.

By a "crossover Fab molecule" (also termed "crossFab" or "crossover Fab fragment") is meant a Fab molecule wherein either the variable regions or the constant regions of the Fab heavy and light chain are exchanged, i.e., the crossFab fragment comprises a peptide chain composed of the light chain variable region and the heavy chain constant region, and a peptide chain composed of the heavy chain variable region and the light chain constant region. For clarity, in a crossFab fragment wherein the variable regions of the Fab light chain and the Fab heavy chain are exchanged, the peptide chain comprising the heavy chain constant region is referred to herein as the heavy chain of the crossover Fab molecule. Conversely, in a crossFab fragment wherein the constant regions of the Fab light chain and the Fab heavy chain are exchanged, the peptide chain comprising the heavy chain variable region is referred to herein as the heavy chain of the crossFab fragment. Accordingly, a crossFab fragment comprises a heavy or light chain composed of the heavy chain variable and the light chain constant regions (VH-CL), and a heavy or light chain composed of the light chain variable and the heavy chain constant regions (VL-CH1). In contrast thereto, by a "Fab" or "conventional Fab molecule" is meant a Fab molecule in its natural format, i.e., comprising a heavy chain composed of the heavy chain variable and constant regions (VH-CH1), and a light chain composed of the light chain variable and constant regions (VL-CL).

The term "CSD" as used herein refers to co-stimulatory signaling domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the terms "engineer", "engineered", "engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

A "Fab molecule" refers to a protein consisting of the VH and CH1 domain of the heavy chain (the "Fab heavy chain") and the VL and CL domain of the light chain (the "Fab light chain") of an antigen binding molecule.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the "EU numbering" system, also called the EU index, as described in Kabat et al., Sequences of Proteins of Immunological Interest, 5th Ed. Public Health Service, National Institutes of Health, Bethesda, Md., 1991. A subunit of an Fc domain as used herein refers to one of the two polypeptides forming the dimeric Fc domain, i.e., a polypeptide comprising C-terminal constant regions of an immunoglobulin heavy chain, capable of stable self-association. For example, a subunit of an IgG Fc domain comprises an IgG CH2 and an IgG CH3 constant domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g., IgG 1 and IgG2), IgM, IgA, IgD, and IgE.) The full length antibodies used according to the invention can be from a single species e.g., human, or they can be chimerized or humanized antibodies. In some embodiments, the full length antibodies used according to the invention, i.e., an antibody comprising a mutated Fc domain, comprise two antigen binding sites each formed by a pair of VH and VL, which both specifically bind to the same antigen. In further embodiments, the full length antibodies used according to the invention comprise two antigen binding sites each formed by a pair of VH and VL, wherein the two antigen binding sites bind to different antigens, e.g., wherein the antibodies are bispecific. The C-terminus of the heavy or light chain of said full length antibody denotes the last amino acid at the C-terminus of said heavy or light chain. By "fused" is meant that the components (e.g., a Fab and a transmembrane domain) are linked by peptide bonds, either directly or via one or more peptide linkers.

The terms "host cell", "host cell line" and "host cell culture" are used interchangeably and refer to cells into which exogenous nucleic acid has been introduced, including the progeny of such cells. Host cells include "transformants" and "transformed cells" which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate an antibody used according to the present invention. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody and/or an antigen binding receptor or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of Kabat numbering to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antigen binding moiety variable region are according to the Kabat numbering system. The polypeptide sequences of the sequence listing are not numbered according to the Kabat numbering system. However, it is well within the ordinary skill of one in the art to convert the numbering of the sequences of the Sequence Listing to Kabat numbering.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

By "isolated nucleic acid" molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed below for polypeptides (e.g., ALIGN-2).

By an "isolated polypeptide" or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "nucleic acid molecule" relates to the sequence of bases comprising purine- and pyrimidine bases which are comprised by polynucleotides, whereby said bases represent the primary structure of a nucleic acid molecule. Herein, the term nucleic acid molecule includes DNA, cDNA, genomic DNA, RNA, synthetic forms of DNA and mixed polymers comprising two or more of these molecules. In addition, the term nucleic acid molecule includes both, sense and antisense strands. Moreover, the herein described nucleic acid molecule may contain non-natural or derivatized nucleotide bases, as will be readily appreciated by those skilled in the art. As used herein "NFAT" refers to the "nuclear factor of activated T-cells" and is a family of transcription factors which is expressed in most immune cells. Activation of transcription factors of the NFAT family is dependent on calcium signaling. As an example, T cell activation through the T cell synapse results in calcium influx. Increased intracellular calcium levels activate the calcium-sensitive phosphatase, calcineurin, which rapidly dephosphorylates the serine-rich region (SRR) and SP-repeats in the amino termini of NFAT proteins. This results in a conformational change that exposes a nuclear localization signal promoting NFAT nuclear import and activation of target genes.

As used herein "NFAT pathway" refers to the stimuli that lead to modulation of activity of member of the NFAT family of transcription factors. NFAT DNA elements are known to the art and are herein also referred to as "response element of the NFAT pathway". Hence, a "receptor of the NFAT pathway" refers to a receptor which can trigger the modulation of activity of NFAT. Examples of a "receptor of the NFAT pathway" are e.g., T cell receptor and B cell receptor.

As used herein "NF-κB" refers to the "nuclear factor kappa-light-chain-enhancer of activated B cells" and is a transcription factor which is implicated in the regulation of many genes that code for mediators of apoptosis, viral replication, tumorigenesis, various autoimmune diseases and inflammatory responses. NFκB is present in almost all eukaryotic cells. Generally, it is located in the cytosol in an inactive state, since it forms a complex with inhibitory kappa B (IκB) proteins. Through the binding of ligands to integral membrane receptors (also referred to as "receptors of the NF-κB pathway", the IκB kinase (IKK) is activated. IKK is an enzyme complex which consists of two kinases and a regulatory subunit. This complex phosphorylates the IκB proteins, which leads to ubiquitination and therefore degradation of those proteins by the proteasome. Finally, the free NFκB is in an active state, translocates to the nucleus and binds to the κB DNA elements and induces transcription of target genes.

As used herein "NF-κB pathway" refers to the stimuli that lead to modulation of activity of NF-κB. For example activation of the Toll-like receptor signaling, TNF receptor signaling, T cell receptor and B cell receptor signaling through either binding of a ligand or an antibody result in activation of NF-κB. Subsequently, phosphorylated NF-κB dimers bind to κB DNA elements and induce transcription of target genes. κB DNA elements are known in the art and herein also referred to as "response element of the NF-κB pathway". Hence, a "receptor of the NF-κB pathway" refers to a receptor which can trigger the modulation of activity of NF-κB. Examples of a "receptor of the NF-κB pathway" are Toll-like receptors, TNF receptors, T cell receptor and B cell receptor.

As used herein "AP-1" refers to the "activator protein 1" and is a transcription factor which is involved a number of cellular processes including differentiation, proliferation, and apoptosis. AP-1 functions are dependent on the specific Fos and Jun subunits contributing to AP-1 dimers. AP-1 binds to a palindromic DNA motif (5'-TGA G/C TCA-3') to regulate gene expression.

The term "pharmaceutical composition" refers to a preparation which is in such form as to permit the biological activity of an active ingredient contained therein to be effective, and which contains no additional components which are unacceptably toxic to a subject to which the formulation would be administered. A pharmaceutical composition usually comprises one or more pharmaceutically acceptable carrier(s).

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative. As used herein, the term "polypeptide" refers to a molecule composed of monomers (amino acids) linearly linked by amide bonds (also known as peptide bonds). The term polypeptide refers to any chain of two or more amino acids, and does not refer to a specific length of the product. Thus, peptides, dipeptides, tripeptides, oligopeptides, protein, amino acid chain, or any other term used to refer to a chain of two or more amino acids, are included within the definition of polypeptide, and the term polypeptide may be used instead of, or interchangeably with any of these terms. The term polypeptide is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term nucleic acid molecule refers to any one or more nucleic acid segments, e.g., DNA or RNA fragments, present in a polynucleotide.

The term "protein with intrinsic fluorescence" refers to a protein capable of forming a highly fluorescent, intrinsic chromophore either through the cyclization and oxidation of internal amino acids within the protein or via the enzymatic addition of a fluorescent co-factor. The term "protein with intrinsic fluorescence" includes wild-type fluorescent proteins and mutants that exhibit altered spectral or physical properties. The term does not include proteins that exhibit weak fluorescence by virtue only of the fluorescence contribution of non-modified tyrosine, tryptophan, histidine and phenylalanine groups within the protein. Proteins with intrinsic fluorescence are known in the art, e.g., green fluorescent protein (GFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Ormo et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) and can be measured e.g., by live cell imaging (e.g., Incucyte) or fluorescent spectrophotometry.

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e., complete abolishment of the interaction. Conversely, "increased binding" refers to an increase in binding affinity for the respective interaction.

The term "regulatory sequence" refers to DNA sequences, which are necessary to effect the expression of coding sequences to which they are ligated. The nature of such control sequences differs depending upon the organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

As used herein, a "reporter gene" means a gene whose expression can be assayed. In one preferred embodiment a "reporter gene" is a gene that encodes a protein the production and detection of which is used as a surrogate to detect indirectly the activity of the antibody or ligand to be tested. The reporter protein is the protein encoded by the reporter gene. Preferably, the reporter gene encodes an enzyme whose catalytic activity can be detected by a simple assay method or a protein with a property such as intrinsic fluorescence or luminescence so that expression of the reporter gene can be detected in a simple and rapid assay requiring minimal sample preparation. Non-limiting examples of enzymes whose catalytic activity can be detected are Luciferase, beta Galactosidase, Alkaline Phosphatase. Luciferase is a monomeric enzyme with a molecular weight (MW) of 61 kDa. It acts as a catalysator and is able to convert D-luciferin in the presence of Adenosine triphosphate (ATP) and Mg2+ to luciferyl adenylate. In addition, pyrophosphate (PPi) and adenosine monophosphate (AMP) are generated as byproducts. The intermediate luciferyl adenylate is then oxidized to oxyluciferin, carbon dioxide ($CO_2$) and light. Oxyluciferin is a bioluminescent product which can be quantitatively measured in a luminometer by the light released from the reaction. Luciferase reporter assays are commercially available and known in the art, e.g., Luciferase 1000 Assay System and ONE-Glo™ Luciferase Assay System.

A "response element" refers to a specific transcription factor binding element, or cis acting element which can be activated or silenced on binding of a certain transcription factor. In one embodiment the response element is a cis-acting enhancer element located upstream of a minimal promotor (e.g., a TATA box promotor) which drives expression of the reporter gene upon transcription factor binding.

As used herein, the term "single-chain" refers to a molecule comprising amino acid monomers linearly linked by peptide bonds. In certain embodiments, one of the antigen binding moieties is a scFv fragment, i.e., a VH domain and a VL domain connected by a peptide linker. In certain embodiments, one of the antigen binding moieties is a single-chain Fab molecule, i.e., a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule. The term "SSD" as used herein refers to stimulatory signaling domain.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "target antigenic determinant" is synonymous with "target antigen", "target epitope" and "target cell antigen" and refers to a site (e.g., a contiguous stretch of amino acids or a conformational configuration made up of different regions of non-contiguous amino acids) on a polypeptide macromolecule to which an antibody binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g., CD20, CEA, FAP, TNC) can be any native form of the proteins from any vertebrate source, including mammals such as primates (e.g., humans) and rodents (e.g., mice and rats), unless otherwise indicated. In a particular embodiment the target antigen is a human protein. Where reference is made to a specific target protein herein, the term encompasses the "full-length", unprocessed target protein as well as any form of the target protein that results from processing in the target cell. The term also encompasses naturally occurring variants of the target protein, e.g., splice variants or allelic variants. Exemplary human target proteins useful as antigens include, but are not limited to: CD20, CEA, FAP, TNC, MSLN, FolR1, HER1 and HER2.

Antibodies comprising a mutated Fc domain may have one, two, three or more binding domains and may be monospecific, bispecific or multispecific. The antibodies can be full length from a single species, or be chimerized or humanized. For an antibody with more than two antigen binding domains, some binding domains may be identical and/or have the same specificity.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art described herein.

In accordance with this invention, the term "T cell receptor" or "TCR" is commonly known in the art. In particular, herein the term "T cell receptor" refers to any T cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subjected to be treated. In this context, suitable T cell receptors which fulfill the above mentioned three criteria are known in the art such as receptors recognizing NY-ESO-1 (for sequence information(s) see, e.g., PCT/GB2005/001924) and/or HER2neu (for sequence information(s) see WO-A1 2011/0280894). Major histocompatibility complex (MHC) class I molecules present peptides from endogenous antigens to CD8+ cytotoxic T cells, and therefore, MHC-peptide complexes are a suitable target for immunotherapeutic approaches. The MHC-peptide complexes can be targeted by recombinant T-cell receptors (TCRs). However, most TCRs may have affinities which are too low immunotherapy whereas high affinity binding moieties with TCR specific would be beneficial. Towards this end, high-affinity soluble antibody molecules with TCR-like specificity can be generated, e.g., by generating phage display libraries (e.g., combinatorial libraries) and screening such libraries as further described herein. These soluble antigen binding moieties e.g., scFv or Fab, with TCR-like specificity herein are referred to as "T cell receptor like antigen binding moieties" or "TCRL antigen binding moieties".

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode antigen binding receptors of the invention or fragments thereof.

In this context, provided herein are methods, particularly in vitro methods, for selecting novel antigen binding moieties for further development according to their specificity, in particular in relation to activation of reporter cells (e.g., T cells) upon contact to a target cell. In the herein described methods and assays, the antigen binding moiety mediates the contact between a target cell, in particular a cancer cell, and a reporter cell, in particular a T cell. In this context, the methods as described herein are useful to select a candidate antigen binding moiety (CABM) with superior specificity. Accordingly, in one embodiment, provided is a method for assessing the specificity of an antigen binding moiety comprising the steps of:

a) providing an antigen binding molecule comprising an antigen binding domain and a recognition domain, wherein the antigen binding domain comprises the antigen binding moiety, wherein the antigen binding moiety is specific for a target antigen;

b) contacting the antigen binding molecule with a target cell comprising the target antigen on the surface, particulary wherein the target cell is a cancer cell;

c) contacting the antigen binding molecule with a chimeric antigen receptor (CAR) expressing reporter T (CAR-T) cell wherein the reporter CAR-T cell comprises:

i) a CAR capable of specific binding to the recognition domain wherein the antigen binding moiety is operationally coupled to a response element;

ii) a reporter gene under the control of the response element; and d) determining T cell activation by determining the expression of the reporter gene to establish the specificity of the antigen binding moiety.

In this context further described and used for the methods as described herein are antigen binding receptors (e.g., CARs) capable of specific binding to the recognition domain of the ABM comprising a candidate antigen binding moiety. The recognition domain can be any polypeptide domain capable of stable folding into a protein domain which can be recognized by an antigen binding moiety. In certain embodiments, the recognition domain is an immunoglobulin domain. Immunoglobulins typically comprise variable and constant domain capable of stable folding wherein the variable domains confer the specificity of the immunoglobulin molecule towards a target antigen. Accordingly, the variable domains are the parts of an immunoglobulin with the highest degree of sequence variance. On the other hand, the constant domains are parts of minimal variance among immunoglobulins of the same class and, therefore, can be used in the context of this invention as recognition domain for the assay formats of the present invention.

The present invention further describes the transduction and use of T cells, such as CD8+ T cells, CD4+ T cells, CD3+ T cells, γδT cells or natural killer (NK) T cells and imortalized cell lines, e.g., Jurkat cells, with a CAR as described herein and their targeted recruitment by an antigen binding molecule, e.g., a candidate therapeutic antibody, comprising a recognition domain, preferably an Fc domain, e.g., a mutated Fc domain as herein described. In one embodiment, the antibody is capable of specific binding to a tumor-specific antigen that is naturally occurring on the surface of a tumor cell.

The approach of the present invention bears significant advantages over conventional binding assays, as the T cell based in vitro method as described herein, without being bound by theory, more closely resembles the in vivo situation encountered for or with, e.g., therapeutic antibodies engaging T cells (e.g., T cell bispecific antibodies).

Accordingly, the invention provides a versatile screening platform wherein antibodies, in particular IgG type antibodies comprising an antigen binding moiety, may be used to mark or label target cells (e.g., tumor cells) as a guidance for immune cells (e.g., T cells), in particular wherein T cells are specifically targeted toward the tumor cells by the antibody comprising the antigen binding moiety. After binding of the CAR to the recognition domain and binding of the antigen binding moiety comprising the antigen binding moiety to the target antigen on the surface of a tumor cell, the reporter T cell becomes activated wherein the activation can be measured, e.g., by read-out of a fluorescent or luminescent signal. The platform is flexible and specific by allowing the use of diverse newly developed antigen binding moieties or co-application of multiple antibodies with different antigen specificity but comprising the same recognition domain.

According to the present invention, the ABM comprises an antigen binding domain and a recognition domain. The recognition domain can be specifically recognized by the antigen binding moiety capable of specific binding to the recognition domain. In a preferred embodiment, the recognition domain is a fragment crystalizable (Fc) region. In specific embodiments, the recognition domain is an IgG1 or an IgG4 Fc domain. In one embodiment, the recognition domain is a human IgG1 Fc domain. In further embodiments, the recognition domain is a mutated Fc domain, e.g., comprising a mutation at a position selected from the group consisting of L234, L235, I253, H310, P331, P329 and H435 according to EU numbering. In such embodiments, the antigen binding moiety as provided herein is capable of specific binding to the mutated Fc domain but not capable of specific binding to the parent non-mutated Fc domain, thereby, discriminating between mutated and non-mutated Fc domain.

In the context of the present invention, the CAR comprises an extracellular domain that does not naturally occur in or on T cells. Thus, the CAR is capable of providing tailored binding specificity to the recognition domain, e.g., an Fc domain of a therapeutic antibody format used for screening according to the invention. Cells, e.g., T cells, transduced with a CAR and used according to the invention become capable of specific binding to the recognition domain. Specificity for the recognition domain is provided by the antigen binding moiety of the extracellular domain of the CAR.

Accordingly, the present invention also relates to the use of CARs comprising an extracellular domain comprising at least one antigen binding moiety capable of specific binding to a mutated Fc domain, wherein the at least one antigen binding moiety is not capable of specific binding to the parent non-mutated Fc domain. In such embodiments, the CAR is capable of specific binding to the mutated Fc domain of an antigen binding molecule, e.g., an antibody. In a preferred embodiment, the mutated Fc domain comprises at least one amino acid substitution compared to the non-mutated parent Fc domain. In some embodiments, Fc receptor binding by the mutated Fc domain is reduced compared to Fc receptor binding by the non-mutated Fc domain.

Accordingly, the CAR is capable of specific binding to a mutated Fc domain but not capable of specific binding to the non-mutated parent Fc domain, wherein the mutated Fc domain comprises at least one amino acid substitution compared to the non-mutated parent Fc domain. Antigen binding moieties capable of specific binding to a recognition domain, e.g., a mutated Fc domain, may be generated by immunization of e.g., a mammalian immune system. Such methods are known in the art and e.g., are described in Burns in Methods in Molecular Biology 295:1-12 (2005). Alternatively, antigen binding moieties of desired activity may be isolated by screening combinatorial libraries for antibodies with the desired activity or activities. Methods for screening combinatorial libraries are reviewed, e.g., in Lerner et al. in Nature Reviews 16:498-508 (2016). For example, a variety of methods are known in the art for generating phage display libraries and screening such libraries for antigen binding moieties possessing the desired binding characteristics. Such methods are reviewed, e.g., in Frenzel et al. in mAbs 8:1177-1194 (2016); Bazan et al. in Human Vaccines and Immunotherapeutics 8:1817-1828 (2012) and Zhao et al. in Critical Reviews in Biotechnology 36:276-289 (2016) as well as in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992) and in Marks and Bradbury in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). In certain phage display methods, repertoires of VH and VL genes are separately cloned by polymerase chain reaction (PCR) and recombined randomly in phage libraries, which can then be screened for antigen-binding phage as described in Winter et al. in Annual Review of Immunology 12: 433-455 (1994). Phage typically display antibody fragments, either as single-chain Fv (scFv) fragments or as Fab fragments. Libraries from immunized sources provide high-affinity antigen binding moieties to the immunogen without the requirement of constructing hybridomas. Alternatively, the naive repertoire can be cloned (e.g., from human) to provide a single source of antigen binding moieties to a wide range of non-self and also self antigens without any immunization as described by Griffiths et al. in EMBO Journal 12:

725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in Journal of Molecular Biology 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. and 2009/0002360. Further examples of methods known in the art for screening combinatorial libraries for antigen binding moieties with a desired activity or activities include ribosome and mRNA display, as well as methods for antibody display and selection on bacteria, mammalian cells, insect cells or yeast cells. Methods for yeast surface display are reviewed, e.g., in Scholler et al. in Methods in Molecular Biology 503:135-56 (2012) and in Cherf et al. in Methods in Molecular biology 1319:155-175 (2015) as well as in the Zhao et al. in Methods in Molecular Biology 889:73-84 (2012). Methods for ribosome display are described, e.g., in He et al. in Nucleic Acids Research 25:5132-5134 (1997) and in Hanes et al. in PNAS 94:4937-4942 (1997).

In one aspect of the invention, provided herein is the use of CARs comprising at least one antigen binding moiety capable of specific binding to a mutated Fc domain. Transduced cells, e.g., T cells, expressing such a CAR are capable of specific binding to the mutated Fc domain of an antigen binding molecule, i.e., of a therapeutic antibody. The Fc domain confers to antigen binding molecules, e.g., therapeutic antibodies, favorable pharmacokinetic properties, including a long serum half-life which contributes to good accumulation in the target tissue and a favorable tissue-blood distribution ratio. At the same time it may, however, lead to undesirable targeting of therapeutic antibodies to cells expressing Fc receptors rather than to the preferred antigen-bearing cells. Moreover, the co-activation of Fc receptor signaling pathways may lead to cytokine release which, results in excessive activation of cytokine receptors and severe side effects upon systemic administration of therapeutic antibodies. Activation of (Fc receptor-bearing) immune cells other than T cells may even reduce efficacy of therapeutic antibodies due to the potential destruction of immune cells. Accordingly, antibody formats known in the art may be engineered or mutated to exhibit reduced binding affinity to an Fc receptor and/or reduced effector function, as compared to, e.g., a native $IgG_1$ Fc domain. The present invention inter alia provided a straight-forward screening platform to assess specificity of novel antigen binding moieties in a therapeutically meaningful antigen binding molecule format. The methods according to the invention integrate relevant cellular and molecular components of activation cascades of known or potential effector cells in a high-throughput assay format.

In an illustrative embodiment of the present invention, as a proof of concept, provided is the use of CARs capable of specific binding to a mutated Fc domain comprising the amino acid mutation P329G and reporter cells (Jurkat NFAT reporter CAR-T cells) expressing said CARs. The P329G mutation reduces binding to Fcγ receptors and associated effector function. Accordingly, the mutated Fc domain comprising the P329G mutation binds to Fcγ receptors with reduced or abolished affinity compared to the non-mutated Fc domain.

However, antibodies with reduced with improved or diminished binding to Fc receptors (FcRs) and/or effector function comprising a mutated Fc domain are widely used in the art. Accordingly, herein described are CARs capable of specific binding to antibodies comprising a mutated Fc domain, such antibodies are herein also referred to as target antibodies. Accordingly, in one embodiment the CAR used in the present invention is capable of specific binding to a target antibody comprising a mutated Fc domain with reduced binding affinity to an Fc receptor and/or reduced effector function. Target antibodies with reduced effector function include those with mutation of one or more of Fc region residues 238, 265, 269, 270, 297, 327 and 329 (U.S. Pat. No. 6,737,056). Such Fc mutants include Fc mutants with mutations at two or more of amino acid positions 265, 269, 270, 297 and 327, including the so-called “DANA” Fc mutant with mutation of residues 265 and 297 to alanine (U.S. Pat. No. 7,332,581). In certain embodiments, a CAR is provided capable of specific binding to an antibody variant comprises an Fc region with one or more amino acid mutations which improve ADCC, e.g., mutations at positions 298, 333, and/or 334 of the Fc region (EU numbering of residues). In certain embodiments, a target antibody variant comprises an Fc region with one or more amino acid mutations, which reduce or diminish FcRn binding, e.g., mutations at positions 253, and/or 310, and/or 435 of the Fc region (EU numbering of residues). In certain embodiments, the target antibody variant comprises an Fc region with the amino acid mutations at positions 253, 310 and 435. In one embodiment the mutations are I253A, H310A and H435A in an Fc region derived from a human IgG1 Fc region. See e.g., Grevys, A., et al., J. Immunol. 194 (2015) 5497-5508.

In certain embodiments, a CAR is used capable of specific binding to an antibody variant comprising an Fc region with one or more amino acid mutations, which reduced or diminished FcRn binding, e.g., mutations at one of the positions 310 and/or, 433 and/or 436 of the Fc region (EU numbering of residues). In certain embodiments, the target antibody variant comprises an Fc region with the amino acid mutations at positions 310, 433 and 436. In one embodiment the mutations are H310A, H433A and Y436A in an Fc region derived from a human IgG1 Fc region. In certain embodiments, a target antibody variant comprises an Fc region with one or more amino acid mutations, which increased FcRn binding, e.g., mutations at positions 252 and/or, 254 and/or 256 of the Fc region (EU numbering of residues). In certain embodiments, the target antibody variant comprises an Fc region with the amino acid mutations at positions 252, 254, and 256. In one embodiment the mutations are M252Y, S254T and T256E in an Fc region derived from a human IgG1 Fc region. In certain embodiments, a CAR is used capable of specific binding to an antibody variant comprising an Fc region with amino acid mutations, which diminish FcγR binding, e.g., mutations at positions 234, 235 and 329 of the Fc region (EU numbering of residues). In one embodiment the mutations are L234A and L235A (LALA). In certain embodiments, the target antibody variant further comprises D265A and/or P329G in an Fc region derived from a human IgG1 Fc region. In one embodiment the mutation is P329G (“PG”) in an Fc region derived from a human IgG1 Fc region. In another embodiment, the mutations are I253A, H310A and H435A (“AAA”) in an Fc region derived from a human IgG1 Fc region.

In one embodiment the CAR is capable of specific binding to a mutated Fc domain composed of a first and a second subunit capable of stable association. In one embodiment the Fc domain is an IgG, specifically an $IgG_1$ or $IgG_4$, Fc domain. In one embodiment the Fc domain is a human Fc domain. In one embodiment the mutated Fc domain exhibits reduced binding affinity to an Fc receptor and/or reduced effector function, as compared to a native IgG₁ Fc domain. In one embodiment the Fc domain comprises one or more amino acid mutations that reduce binding to an Fc receptor and/or effector function.

In one preferred embodiment the one or more amino acid mutation is at one or more position selected from the group of L234, L235, and P329 (Kabat numbering). In one particular embodiment each subunit of the Fc domain comprises three amino acid mutations that reduce binding to an activating Fc receptor and/or effector function wherein said amino acid mutations are L234A, L235A and P329G. In one particular embodiment the Fc receptor is an Fcγ receptor. In one embodiment the effector function is antibody-dependent cell-mediated cytotoxicity (ADCC).

In particular embodiments, the CARs comprise an extracellular domain comprising at least one antigen binding moiety capable of specific binding to a mutated Fc domain, wherein the at least one antigen binding moiety is not capable of specific binding to the parent non-mutated Fc domain, wherein the mutated Fc domain comprises at least one amino acid substitution selected from the group consisting of L234, L235, I253, H310, P331, P329 and H435, in particular wherein the amino acid mutation is L234A, L235A, I253A, N297A, H310A, P329G and/or H435A compared to the non-mutated parent Fc domain. In one embodiment, Fc receptor binding by the mutated Fc domain is reduced compared to Fc receptor binding by the non-mutated Fc domain. In one preferred embodiment, the amino acid mutation is P329G wherein binding to Fcγ receptor is reduced as measured by SPR at 25° C. In a further embodiment, the amino acid mutations are I253A, H310A and H435A wherein binding to the neonatal Fc receptor (FcRn) is reduced as measured by SPR at 25° C.

In a particular embodiment, the mutated Fc domain comprises the P329G mutation. The mutated Fc domain comprising the P329G mutation binds to Fcγ receptors with reduced or abolished affinity compared to the non-mutated Fc domain.

In one embodiment the CAR capable of specific binding to an Fc domain comprising the P329G mutation comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO:1, SEQ ID NO:2 and SEQ ID NO:3 and at least one light chain CDR selected from the group of SEQ ID NO:4, SEQ ID NO:5 and SEQ ID NO:6.

In one embodiment the CAR capable of specific binding to an Fc domain comprising the P329G mutation comprises the heavy chain complementarity determining regions (CDRs) of SEQ ID NO:1, SEQ ID NO:2 and SEQ ID NO:3 and the light chain CDRs of SEQ ID NO:4, SEQ ID NO:5 and SEQ ID NO:6.

In one preferred embodiment the CAR capable of specific binding to an Fc domain comprising the P329G mutation comprises a heavy chain variable region comprising:
(a) a heavy chain complementarity determining region (CDR H) 1 amino acid sequence of RYWMN (SEQ ID NO:1);
(b) a CDR H2 amino acid sequence of EITPDSSTI-NYTPSLKD (SEQ ID NO:2);
(c) a CDR H3 amino acid sequence of PYDYGAWFAS (SEQ ID NO:3);
and a light chain variable region comprising:
(d) a light chain (CDR L)1 amino acid sequence of RSSTGAVTTSNYAN (SEQ ID NO:4);
(e) a CDR L2 amino acid sequence of GTNKRAP (SEQ ID NO:5); and
(f) a CDR L3 amino acid sequence of ALWYSNHWV (SEQ ID NO:6).

In one embodiment the CAR capable of specific binding to an Fc domain comprising the P329G mutation comprises a heavy chain variable region (VH) comprising an amino acid sequence that is at least about 95%, 96%, 97%, 98%, 99% or 100% identical to an amino acid sequence selected from SEQ ID NO:8 and SEQ ID NO:32 and a light chain variable region (VL) comprising an amino acid sequence that is at least about 95%, 96%, 97%, 98%, 99% or 100% identical to an amino acid sequence selected from SEQ ID NO:9 and SEQ ID NO:33.

In one embodiment the CAR capable of specific binding to an Fc domain comprising the P329G mutation comprises a heavy chain variable region (VH) comprising an amino acid sequence selected from SEQ ID NO:8 and SEQ ID NO:32, and a light chain variable region (VL) comprising an amino acid sequence selected from SEQ ID NO:9 and SEQ ID NO:33.

In one embodiment the CAR capable of specific binding to an Fc domain comprising the P329G mutation comprises a heavy chain variable region (VH) comprising the amino acid sequence of SEQ ID NO:32 and a light chain variable region (VL) comprising the amino acid sequence of SEQ ID NO:33.

In one preferred embodiment the CAR capable of specific binding to an Fc domain comprising the P329G mutation comprises a heavy chain variable region (VH) comprising the amino acid sequence of SEQ ID NO:8 and a light chain variable region (VL) comprising the amino acid sequence of SEQ ID NO:9.

In one embodiment, the at least one antigen binding moiety is a scFv, a Fab, a crossFab or a scFab fragment. In one embodiment the CAR capable of specific binding to an Fc domain comprising the P329G mutation comprises a Fab fragment. In a preferred embodiment the CAR capable of specific binding to an Fc domain comprising the P329G mutation comprises a Fab fragment comprising a heavy chain of SEQ ID NO:40 and a light chain of SEQ ID NO:41.

In one embodiment the CAR capable of specific binding to an Fc domain comprising the P329G mutation comprises a scFv fragment which is a polypeptide consisting of an heavy chain variable domain (VH), an light chain variable domain (VL) and a linker, wherein said variable domains and said linker have one of the following configurations in N-terminal to C-terminal direction: a) VH-linker-VL or b) VL-linker-VH. In a preferred embodiment, the scFv fragment has the configuration VH-linker-VL.

In a preferred embodiment the CAR capable of specific binding to an Fc domain comprising the P329G mutation comprises an scFv fragment comprising the amino acid sequence of SEQ ID NO:10.

In an alternative particular embodiment, the mutated Fc domain comprises the I253A, H310A and H435A ("AAA") mutations. The AAA mutations reduce binding to the neonatal Fc receptor (FcRn). Accordingly, the mutated Fc domain comprising the AAA mutations binds to FcRn with reduced or abolished affinity compared to the non-mutated Fc domain.

In one embodiment the CAR capable of specific binding to an Fc domain comprising the I253A, H310A and H435A mutations comprises at least one heavy chain complementarity determining region (CDR) comprising an amino acid sequence that is at least about 95%, 96%, 97%, 98%, 99% or 100% identical to an amino acid sequence selected from the group consisting of SEQ ID NO:53, SEQ ID NO:54 and SEQ ID NO:55 and at least one light chain CDR selected from the group of SEQ ID NO:56, SEQ ID NO:57 and SEQ ID NO:58.

In one embodiment the CAR capable of specific binding to an Fc domain comprising the P329G mutation comprises the heavy chain complementarity determining regions (CDRs) of SEQ ID NO:53, SEQ ID NO:54 and SEQ ID NO:55 and the light chain CDRs of SEQ ID NO:56, SEQ ID NO:57 and SEQ ID NO:58.

In a preferred embodiment the CAR capable of specific binding to an Fc domain comprising the I253A, H310A and H435A mutations comprises a heavy chain variable region comprising:
(a) a heavy chain complementarity determining region (CDR H) 1 amino acid sequence of SYGMS (SEQ ID NO:53);
(b) a CDR H2 amino acid sequence of SSGGSY (SEQ ID NO:54);
(c) a CDR H3 amino acid sequence of LGMITTG-YAMDY (SEQ ID NO:55); and a light chain variable region comprising:
(d) a light chain (CDR L)1 amino acid sequence of RSSQTIVHSTGHTYLE (SEQ ID NO:56);
(e) a CDR L2 amino acid sequence of KVSNRFS (SEQ ID NO:57); and
(f) a CDR L3 amino acid sequence of FQGSHVPYT (SEQ ID NO:58).

In one embodiment the CAR capable of specific binding to an Fc domain comprising the I253A, H310A and H435A mutations comprises a heavy chain variable region (VH) comprising an amino acid sequence that is at least about 95%, 96%, 97%, 98%, 99% or 100% identical to the amino acid sequence of SEQ ID NO:61 and a light chain variable region (VL) comprising an amino acid sequence that is at least about 95%, 96%, 97%, 98%, 99% or 100% identical to the amino acid sequence selected of SEQ ID NO:62.

In one embodiment the CAR capable of specific binding to an Fc domain comprising the I253A, H310A and H435A mutations comprises a heavy chain variable region (VH) comprising the amino acid sequence of SEQ ID NO:61, and a light chain variable region (VL) comprising the amino acid sequence of SEQ ID NO:62.

In one embodiment, the at least one antigen binding moiety is a scFv, a Fab, a crossFab or a scFab fragment. In one embodiment the CAR capable of specific binding to an Fc domain comprising the I253A, H310A and H435A mutations comprises a Fab fragment. In a particular embodiment the extracellular domain of the antigen binding receptor comprises an antigen binding moiety capable of specific binding to an Fc domain comprising the I253A, H310A and H435A mutations, wherein the Fab fragment comprises a heavy chain of SEQ ID NO:64 and a light chain of SEQ ID NO:65.

In one embodiment the CAR capable of specific binding to an Fc domain comprising the I253A, H310A and H435A mutations comprises a scFv fragment. In a particular embodiment the CAR capable of specific binding to an Fc domain comprising the I253A, H310A and H435A mutations comprises the amino acid sequence of SEQ ID NO:60.

In further embodiments according to the invention the antigen binding moiety comprised in the extracellular domain is a single chain Fab fragment or scFab.

Fab and scFab fragments are stabilized via the natural disulfide bond between the CL domain and the CH1 domain. Antigen binding moieties comprising a heavy chain variable domain (VH) and a light chain variable domain (VL), such as the Fab, crossFab, scFv and scFab fragments as described herein might be further stabilized by introducing interchain disulfide bridges between the VH and the VL domain. Accordingly, in one embodiment, the Fab fragment(s), the crossFab fragment(s), the scFv fragment(s) and/or the scFab fragment(s) comprised in the antigen binding receptors according to the invention might be further stabilized by generation of interchain disulfide bonds via insertion of cysteine residues (e.g., position 44 in the variable heavy chain and position 100 in the variable light chain according to Kabat numbering). Such stabilized antigen binding moieties are referred to by the term "ds" within the appended examples and Figures.

In an illustrative embodiment of the present invention, as a proof of concept, CARs are provided comprising extracellular domain comprising at least one antigen binding moiety, wherein the at least one antigen binding moiety is capable of specific binding to a mutated Fc domain but not capable of specific binding to the non-mutated parent Fc domain, wherein the mutated Fc domain comprises at least one amino acid substitution compared to the non-mutated parent Fc. In certain embodiment, at least one of the antigen binding moieties is a conventional Fab fragment, i.e., a Fab molecule consisting of a Fab light chain and a Fab heavy chain. A particular advantage of this antigen binding receptor formats is the straight-forward integration of a library derived antigen binding moiety without changing the format, e.g., a Fab antigen binder deriving from screening a phage display library can be included in the Fab and/or crossFab format as described herein. Accordingly, antigen binding moieties deriving form Fab displaying phage libraries can be included in an antigen binding receptor of the present invention without changing the format to e.g., a scFv format which might affect the binding properties of the library derived binder negatively. In a preferred embodiment, the antigen binding moiety is a Fab fragment, in particular a Fab fragment deriving from a phage display library screening.

In further embodiments, at least one of the antigen binding moieties is a crossFab fragment, i.e., a Fab molecule consisting of a Fab light chain and a Fab heavy chain, wherein either the variable regions or the constant regions of the Fab heavy and light chain are exchanged.

In further embodiments, at least one of the antigen binding moieties is a scFv fragment. In a particular such embodiment, the C-terminus of the variable heavy chain (VH) is connected to the N-terminus of the variable light chain (VL) in the scFv molecule, optionally through a peptide linker.

In certain embodiments, the CARs as used herein comprise an extracellular domain comprising an antigen binding moiety capable of specific binding to the recognition domain, an anchoring transmembrane domain and at least one intracellular signaling and/or at least one co-stimulatory signaling domain. The anchoring transmembrane domain of the CAR may be characterized by not having a cleavage site for mammalian proteases. Proteases refer to proteolytic enzymes that are able to hydrolyze the amino acid sequence of a transmembrane domain comprising a cleavage site for the protease. The term proteases include both endopeptidases and exopeptidases. In the context of the present invention any anchoring transmembrane domain of a transmembrane protein as laid down among others by the CD-nomenclature may be used to generate a CAR suitable according to the invention, which activate T cells, upon binding to a recognition domain, e.g., a mutated Fc domain, as defined herein.

Accordingly, in the context of the present invention, the anchoring transmembrane domain may comprise part of a murine/mouse or preferably of a human transmembrane domain. An example for such an anchoring transmembrane domain is a transmembrane domain of CD28, for example, having the amino acid sequence as shown herein in SEQ ID NO:11 (as encoded by the DNA sequence shown in SEQ ID NO:24). In the context of the present invention, the transmembrane domain of the CAR may comprise/consist of an amino acid sequence as shown in SEQ ID NO:11 (as encoded by the DNA sequence shown in SEQ ID NO:24).

In an illustrative embodiment of the present invention, as a proof of concept, a CAR is used which comprises an antigen binding moiety comprising an amino acid sequence of SEQ ID NO:10 (as encoded by the DNA sequence shown in SEQ ID NO:22), and a fragment/polypeptide part of CD28 (the Uniprot Entry number of the human CD28 is P10747 (with the version number 173 and version 1 of the sequence)) as shown herein as SEQ ID NO:71 (as encoded by the DNA sequence shown in SEQ ID NO:70). Alternatively, any protein having a transmembrane domain, as provided among others by the CD nomenclature, may be used as an anchoring transmembrane domain of the antigen binding receptor protein of the invention. As described above, the herein described antigen binding receptor may comprise the anchoring transmembrane domain of CD28 which is located at amino acids 153 to 179, 154 to 179, 155 to 179, 156 to 179, 157 to 179, 158 to 179, 159 to 179, 160 to 179, 161 to 179, 162 to 179, 163 to 179, 164 to 179, 165 to 179, 166 to 179, 167 to 179, 168 to 179, 169 to 179, 170 to 179, 171 to 179, 172 to 179, 173 to 179, 174 to 179, 175 to 179, 176 to 179, 177 to 179 or 178 to 179 of the human full length CD28 protein as shown in SEQ ID NO:71 (as encoded by the cDNA shown in SEQ ID NO:70). Accordingly, in context of the present invention the anchoring transmembrane domain may comprise or consist of an amino acid sequence as shown in SEQ ID NO:11 (as encoded by the DNA sequence shown in SEQ ID NO:24).

As described herein, the CAR used according to the invention comprises at least one stimulatory signaling and/or co-stimulatory signaling domain. The stimulatory signaling and/or co-stimulatory signaling domain transduce the binding of the antigen binding molecule comprising the antigen binding moiety to an intracellular signal in the reporter CAR-T cell. Accordingly, the herein described CAR preferably comprises a stimulatory signaling domain, which provides T cell activation. In a preferred embodiment, binding of the antigen binding moiety to the target antigen and binding of the reporter CAR-T cell to the antigen binding molecule comprising the antigen binding moiety leads to activation of the intracellular signaling and/or co-signaling domain. In certain embodiments, the herein described CAR comprises a stimulatory signaling domain which is a fragment/polypeptide part of murine/mouse or human CD3z (the UniProt Entry of the human CD3z is P20963 (version number 177 with sequence number 2; the UniProt Entry of the murine/mouse CD3z is P24161 (primary citable accession number) or Q9D3G3 (secondary citable accession number) with the version number 143 and the sequence number 1)), FCGR3A (the UniProt Entry of the human FCGR3A is P08637 (version number 178 with sequence number 2)), or NKG2D (the UniProt Entry of the human NKG2D is P26718 (version number 151 with sequence number 1); the UniProt Entry of the murine/mouse NKG2D is O54709 (version number 132 with sequence number 2)). Thus, the stimulatory signaling domain which is comprised in the herein described CAR may be a fragment/ polypeptide part of the full length of CD3z, FCGR3A or NKG2D. The amino acid sequence of the murine/mouse full length of CD3z is shown herein as SEQ ID NO68 (murine/mouse as encoded by the DNA sequence shown in SEQ ID NO:69). The amino acid sequence of the human full length CD3z is shown herein as SEQ ID NO:66 (human as encoded by the DNA sequence shown in SEQ ID NO:67). The CAR used according to the present invention may comprise fragments of CD3z, FCGR3A or NKG2D as stimulatory domain, provided that at least one signaling domain is comprised. In particular, any part/fragment of CD3z, FCGR3A, or NKG2D is suitable as stimulatory domain as long as at least one signaling motive is comprised. However, more preferably, the CAR comprises polypeptides which are derived from human origin. Preferably, the CAR comprises the amino acid sequence as shown herein as SEQ ID NOs:66 (CD3z) (human as encoded by the DNA sequences shown in SEQ ID NOs:67 (CD3z)). For example, the fragment/polypeptide part of the human CD3z which may be comprised in the CAR used according to the present invention may comprise or consist of the amino acid sequence shown in SEQ ID NO:7 (as encoded by the DNA sequence shown in SEQ ID NO:19). Accordingly, in one embodiment the CAR comprises the sequence as shown in SEQ ID NO:7 or a sequence which has up to 1, 2, 3, 4, 5, 6, 7, 8, 9, 10, 11, 12, 13, 14, 15, 16, 17, 18, 19, 20, 21, 22, 23, 23, 24, 25, 26, 27, 28, 29 or 30 substitutions, deletions or insertions in comparison to SEQ ID NO:7 and which is characterized by having a stimulatory signaling activity. Specific configurations of CARs comprising a stimulatory signaling domain are provided herein below and in the Examples and Figures. The stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

The herein described CAR preferably comprises at least one co-stimulatory signaling domain which provides additional activity to the reporter CAR-T cell. The herein described CAR may comprise a co-stimulatory signaling domain which is a fragment/polypeptide part of murine/mouse or human CD28 (the UniProt Entry of the human CD28 is P10747 (version number 173 with sequence number 1); the UniProt Entry of the murine/mouse CD28 is P31041 (version number 134 with sequence number 2)), CD137 (the UniProt Entry of the human CD137 is Q07011 (version number 145 with sequence number 1); the UniProt Entry of murine/mouse CD137 is P20334 (version number 139 with sequence number 1)), OX40 (the UniProt Entry of the human OX40 is P23510 (version number 138 with sequence number 1); the UniProt Entry of murine/mouse OX40 is P43488 (version number 119 with sequence number 1)), ICOS (the UniProt Entry of the human ICOS is Q9Y6W8 (version number 126 with sequence number 1)); the UniProt Entry of the murine/mouse ICOS is Q9WV40 (primary citable accession number) or Q9JL17 (secondary citable accession number) with the version number 102 and sequence version 2)), CD27 (the UniProt Entry of the human CD27 is P26842 (version number 160 with sequence number 2); the Uniprot Entry of the murine/mouse CD27 is P41272 (version number 137 with sequence version 1)), 4-1-BB (the UniProt Entry of the murine/mouse 4-1-BB is P20334 (version number 140 with sequence version 1); the UniProt Entry of the human 4-1-BB is Q07011 (version number 146 with sequence version)), DAP10 (the UniProt Entry of the human DAP10 is Q9UBJ5 (version number 25 with sequence number 1); the UniProt entry of the murine/ mouse DAP10 is Q9QUJ0 (primary citable accession number) or Q9R1E7 (secondary citable accession number) with the version number 101 and the sequence number 1)) or DAP12 (the UniProt Entry of the human DAP12 is O43914 (version number 146 and the sequence number 1); the UniProt entry of the murine/mouse DAP12 is O054885 (primary citable accession number) or Q9R1E7 (secondary citable accession number) with the version number 123 and the sequence number 1). In certain embodiments of the present invention the CAR used according to the present invention may comprise one or more, i.e., 1, 2, 3, 4, 5, 6 or 7 of the herein defined co-stimulatory signaling domains. Accordingly, in the context of the present invention, the CAR may comprise a fragment/polypeptide part of a murine/mouse or preferably of a human CD28 as first co-stimulatory signaling domain and the second co-stimulatory signaling domain is selected from the group consisting of the murine/mouse or preferably of the human CD27, CD28, CD137, OX40, ICOS, DAP10 and DAP12, or fragments thereof. Preferably, the CAR comprises a co-stimulatory signaling domain which is derived from a human origin. Thus, more preferably, the co-stimulatory signaling domain(s) which is (are) comprised in the CAR used according to the present invention may comprise or consist of the amino acid sequence as shown in SEQ ID NO:12 (as encoded by the DNA sequence shown in SEQ ID NO:25).

Thus, the co-stimulatory signaling domain which may be optionally comprised in the herein described CAR is a fragment/polypeptide part of the full length CD27, CD28, CD137, OX40, ICOS, DAP10 and DAP12. The amino acid sequence of the murine/mouse full length CD28 is shown herein as SEQ ID NO:73 (murine/mouse as encoded by the DNA sequences shown in SEQ ID NO:72). However, because human sequences are most preferred in the context of the present invention, the co-stimulatory signaling domain which may be optionally comprised in the herein described CAR protein is a fragment/polypeptide part of the human full length CD27, CD28, CD137, OX40, ICOS, DAP10 or DAP12. The amino acid sequence of the human full length CD28 is shown herein as SEQ ID NO:71 (human as encoded by the DNA sequence shown in SEQ ID NO:70).

In one preferred embodiment, the CAR comprises CD28 or a fragment thereof as co-stimulatory signaling domain. The herein described CAR may comprise a fragment of CD28 as co-stimulatory signaling domain, provided that at least one signaling domain of CD28 is comprised. In particular, any part/fragment of CD28 is suitable for the CAR as described herein as long as at least one of the signaling motives of CD28 is comprised. For example, the CD28 polypeptide which is comprised in the CAR used according to the present invention may comprise or consist of the amino acid sequence shown in SEQ ID NO:12 (as encoded by the DNA sequence shown in SEQ ID NO:25). In the present invention the intracellular domain of CD28, which functions as a co-stimulatory signaling domain, may comprise a sequence derived from the intracellular domain of the CD28 polypeptide having the sequence(s) YMNM (SEQ ID NO:74) and/or PYAP (SEQ ID NO:75). Preferably, the CAR comprises polypeptides which are derived from human origin. For example, the fragment/polypeptide part of the human CD28 which may be comprised in the CAR may comprise or consist of the amino acid sequence shown in SEQ ID NO:12 (as encoded by the DNA sequence shown in SEQ ID NO:25). Accordingly, in one embodiment, the CAR comprises the sequence as shown in SEQ ID NO:12 or a sequence which has up to 1, 2, 3, 4, 5, 6, 7, 8, 9 or 10 substitutions, deletions or insertions in comparison to SEQ ID NO:12 and which is characterized by having a co-stimulatory signaling activity. Specific configurations of CARs comprising a co-stimulatory signaling domain (CSD) are provided herein below and in the Examples and Figures. The co-stimulatory signaling activity can be determined; e.g., by enhanced cytokine release, as measured by ELISA (IL-2, IFNγ, TNFα), enhanced proliferative activity (as measured by enhanced cell numbers), or enhanced lytic activity as measured by LDH release assays.

As mentioned above, in an embodiment of the present invention, the co-stimulatory signaling domain of the CAR may be derived from the human CD28 gene (Uni Prot Entry No: P10747 (accession number with the entry version: 173 and version 1 of the sequence)) and provides CD28 activity, defined as cytokine production, proliferation and lytic activity of the transduced cell described herein, like a transduced T cell. CD28 activity can be measured by release of cytokines by ELISA or flow cytometry of cytokines such as interferon-gamma (IFN-γ) or interleukin 2 (IL-2), proliferation of T cells measured e.g., by ki67-measurement, cell quantification by flow cytometry, or lytic activity as assessed by real time impedance measurement of the target cell (by using e.g., an ICELLligence instrument as described e.g., in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Düwell et al., Cell Death Differ. 21(12) (2014), 1825-1837, Erratum in: Cell Death Differ. 21(12) (2014), 161). The co-stimulatory signaling domains PYAP and YMNM are beneficial for the function of the CD28 polypeptide and the functional effects enumerated above. The amino acid sequence of the YMNM domain is shown in SEQ ID NO:74; the amino acid sequence of the PYAP domain is shown in SEQ ID NO:75. Accordingly, in the antigen binding receptor of the present invention, the CD28 polypeptide preferably comprises a sequence derived from intracellular domain of a CD28 polypeptide having the sequences YMNM (SEQ ID NO:74) and/or PYAP (SEQ ID NO:75). These signaling motives may, be present at any site within the intracellular domain of the described CARs.

Moreover, the herein described CAR may comprise at least one linker (or "spacer"). A linker is usually a peptide having a length of up to 20 amino acids. Accordingly, in the context of the present invention the linker may have a length of 1, 2, 3, 4, 5, 6, 7, 8, 9, 10, 11, 12, 13, 14, 15, 16, 17, 18, 19 or 20 amino acids. For example, the herein described CAR may comprise a linker between the extracellular domain comprising at least one antigen binding moiety capable of specific binding to the recognition domain, the anchoring transmembrane domain, the co-stimulatory signaling domain and/or the stimulatory signaling domain. Such linkers have the advantage that they increase the probability that the different polypeptides of the CAR (i.e., the extracellular domain comprising at least one antigen binding moiety capable of specific binding to the recognition domain, the anchoring transmembrane domain, the co-stimulatory signaling domain and/or the stimulatory signaling domain) fold independently and behave as expected. Thus, in the context of the present invention, the extracellular domain comprising at least one antigen binding moiety capable of specific binding to the recognition domain, the anchoring transmembrane domain that does not have a cleavage site for mammalian proteases, the co-stimulatory signaling domain and the stimulatory signaling domain may be comprised in a single-chain multi-functional polypeptide. A single-chain fusion construct e.g., may consist of (a)

polypeptide(s) comprising (an) extracellular domain(s) comprising at least one antigen binding moiety capable of specific binding to a mutated Fc domain, (an) anchoring transmembrane domain(s), (a) co-stimulatory signaling domain(s) and/or (a) stimulatory signaling domain(s). In alternative embodiments, the CAR comprises an antigen binding moiety which is not a single chain fusion construct, i.e., the antigen binding moiety is a Fab or a crossFab fragment. In such embodiments the CAR is not a single chain fusion construct comprising only one polypeptide chain. Preferably such constructs will comprise a single chain heavy chain fusion polypeptide combined with an immunoglobulin light chain as described herein, e.g., heavy chain fusion polypeptide comprises (an) immunoglobulin heavy chain(s), (an) anchoring transmembrane domain(s), (a) co-stimulatory signaling domain(s) and/or (a) stimulatory signaling domain(s) and is combined with (an) immunoglobulin light chain(s). Accordingly, the antigen binding moiety, the anchoring transmembrane domain, the co-stimulatory signaling domain and the stimulatory signaling domain may be connected by one or more identical or different peptide linker as described herein. For example, in the herein described CAR the linker between the extracellular domain comprising at least one antigen binding moiety capable of specific binding to the recognition domain and the anchoring transmembrane domain may comprise or consist of the amino and amino acid sequence as shown in SEQ ID NO:17. Accordingly, the anchoring transmembrane domain, the co-stimulatory signaling domain and/or the stimulatory domain may be connected to each other by peptide linkers or alternatively, by direct fusion of the domains.

In some embodiments, the antigen binding moiety comprised in the extracellular domain is a single-chain variable fragment (scFv) which is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. For example, in the herein described CAR the linker may have the amino and amino acid sequence as shown in SEQ ID NO:16. The scFv antigen binding moiety as described herein retains the specificity of the original antibody, despite removal of the constant regions and the introduction of the linker. scFv antibodies are, e.g., described in Houston, J. S., Methods in Enzymol. 203 (1991) 46-96).

In some embodiments the antigen binding moiety comprised in the extracellular domain is a single chain Fab fragment or scFab which is a polypeptide consisting of an heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain.

In some embodiments the antigen binding moiety comprised in the extracellular domain is a crossover single chain Fab fragment which is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids.

The herein described CAR or parts thereof may comprise a signal peptide. Such a signal peptide will bring the protein to the surface of the T cell membrane. For example, in the herein described antigen binding receptor the signal peptide may have the amino and amino acid sequence as shown in SEQ ID NO:76 (as encoded by the DNA sequence shown in SEQ ID NO:77).

The components of the CARs as described herein can be fused to each other in a variety of configurations to generate T cell activating CARs.

In some embodiments, the CAR comprises an extracellular domain composed of a heavy chain variable domain (VH) and a light chain variable domain (VL) connected to an anchoring transmembrane domain. In some embodiments, the VH domain is fused at the C-terminus to the N-terminus of the VL domain, optionally through a peptide linker. In other embodiments, the CAR further comprises a stimulatory signaling domain and/or a co-stimulatory signaling domain. In a specific such embodiment, the CAR essentially consists of a VH domain and a VL domain, an anchoring transmembrane domain, and optionally a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain.

Optionally, the CAR further comprises a co-stimulatory signaling domain. In one such specific embodiment, the antigen binding receptor essentially consists of a VH domain and a VL domain, an anchoring transmembrane domain, a stimulatory signaling domain and a co-stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the stimulatory signaling domain, wherein the stimulatory signaling domain is fused at the C-terminus to the N-terminus of the co-stimulatory signaling domain. In an alternative embodiment, the co-stimulatory signaling domain is connected to the anchoring transmembrane domain instead of the stimulatory signaling domain. In a preferred embodiment, the CAR essentially consists of a VH domain and a VL domain, an anchoring transmembrane domain, a co-stimulatory signaling domain and a stimulatory signaling domain connected by one or more peptide linkers, wherein the VH domain is fused at the C-terminus to the N-terminus of the VL domain, and the VL domain is fused at the C-terminus to the N-terminus of the anchoring transmembrane domain, wherein the anchoring transmembrane domain is fused at the C-terminus to the N-terminus of the co-stimulatory signaling domain, wherein the co-stimulatory signaling domain is fused at the C-terminus to the N-terminus of the stimulatory signaling domain.

In preferred embodiments, one of the binding moieties is a Fab fragment or a crossFab fragment. In one preferred embodiment, the antigen binding moiety is fused at the C-terminus of the Fab or crossFab heavy chain to the N-terminus of the anchoring transmembrane domain, optionally through a peptide linker. In an alternative embodiment, the antigen binding moiety is fused at the C-terminus of the Fab or crossFab light chain to the N-terminus of the anchoring transmembrane domain, optionally through a peptide linker. In other embodiments, the CAR further comprises a stimulatory signaling domain and/or a co-stimulatory signaling domain. In a specific such embodiment, the CAR essentially consists of a Fab or crossFab fragment, an anchoring transmembrane domain, and optionally a stimulatory signaling domain connected by one or more peptide linkers, wherein the Fab or crossFab fragment is fused at the C-terminus of the heavy or light chain to the N-terminus of the anchoring transmembrane domain, wherein the anchoring transmembrane domain is fused at the C-terminus to the N-terminus of the stimulatory signaling domain. Preferably, the CAR further comprises a co-stimulatory signaling domain. In one such embodiment, the CAR essentially consists of a Fab or crossFab fragment, an anchoring transmembrane domain, a stimulatory signaling domain and a co-stimulatory signaling domain connected by one or more peptide linkers, wherein the Fab or crossFab fragment is fused at the C-terminus of the heavy or light chain to the N-terminus of the anchoring transmembrane domain, wherein the stimulatory signaling domain is fused at the C-terminus to the N-terminus of the co-stimulatory signaling domain. In a preferred embodiment, the co-stimulatory signaling domain is connected to the anchoring transmembrane domain instead of the stimulatory signaling domain. In a most preferred embodiment, the CAR essentially consists of a Fab or crossFab fragment, an anchoring transmembrane domain, a co-stimulatory signaling domain and a stimulatory signaling domain, wherein the Fab or crossFab fragment is fused at the C-terminus of the heavy chain to the N-terminus of the anchoring transmembrane domain through a peptide linker, wherein the anchoring transmembrane domain is fused at the C-terminus to the N-terminus of the co-stimulatory signaling domain, wherein the co-stimulatory signaling domain is fused at the C-terminus to N-terminus of the stimulatory signaling domain.

The antigen binding moiety, the anchoring transmembrane domain and the stimulatory signaling and/or co-stimulatory signaling domains may be fused to each other directly or through one or more peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers, wherein "n" is generally a number between 1 and 10, typically between 2 and 4. A preferred peptide linker for connecting the antigen binding moiety and the anchoring transmembrane moiety is GGGGS ($G_4S$) according to SEQ ID NO 17. An exemplary peptide linker suitable for connecting variable heavy chain (VH) and the variable light chain (VL) is GGGSGGGSGGGSGGGS ($G_4S)_4$ according to SEQ ID NO 16.

Additionally, linkers may comprise (a portion of) an immunoglobulin hinge region. Particularly where an antigen binding moiety is fused to the N-terminus of an anchoring transmembrane domain, it may be fused via an immunoglobulin hinge region or a portion thereof, with or without an additional peptide linker.

As described herein, the CARs used according to the present invention comprise an extracellular domain comprising at least one antigen binding moiety. A CAR with a single antigen binding moiety capable of specific binding to a recognition domain is useful and preferred, particularly in cases where high expression of the antigen binding receptor is needed. In such cases, the presence of more than one antigen binding moiety specific for the target cell antigen may limit the expression efficiency of the antigen binding receptor. In other cases, however, it will be advantageous to have a CAR comprising two or more antigen binding moieties specific for a target cell antigen, for example to optimize targeting to the target site or to allow crosslinking of target cell antigens.

In certain embodiments the CAR comprises a polypeptide wherein the Fab light chain variable region of the antigen binding moiety shares a carboxy-terminal peptide bond with the Fab heavy chain constant region of the antigen binding moiety (i.e., the antigen binding moiety comprises a cross-Fab heavy chain, wherein the heavy chain variable region is replaced by a light chain variable region), which in turn shares a carboxy-terminal peptide bond with the anchoring transmembrane domain ($VL_{(1)}$-$CH1_{(1)}$-ATD). In some embodiments the CAR further comprises a polypeptide wherein the Fab heavy chain variable region of the first antigen binding moiety shares a carboxy-terminal peptide bond with the Fab light chain constant region of the first antigen binding moiety ($VH_{(1)}$-$CL_{(1)}$). In certain embodiments the polypeptides are covalently linked, e.g., by a disulfide bond. In alternative embodiments the CAR comprises a polypeptide wherein the Fab heavy chain variable region of the antigen binding moiety shares a carboxy-terminal peptide bond with the Fab light chain constant region of the antigen binding moiety (i.e., the antigen binding moiety comprises a crossFab heavy chain, wherein the heavy chain constant region is replaced by a light chain constant region), which in turn shares a carboxy-terminal peptide bond with an anchoring transmembrane domain ($VH_{(1)}$-$CL_{(1)}$-ATD). In some embodiments the CAR further comprises a polypeptide wherein the Fab light chain variable region of the antigen binding moiety shares a carboxy-terminal peptide bond with the Fab heavy chain constant region of the antigen binding moiety ($VL_{(1)}$-$CH1_{(1)}$) In certain embodiments the polypeptides are covalently linked, e.g., by a disulfide bond.

In the context of the methods according to the invention, contacting the ABM with a target cell comprising the target antigen on the surface and contacting the ABM with the CAR comprising an antigen binding moiety capable of specific binding to the recognition domain leads to expression of the reporter gene as described herein. Accordingly, in one embodiment, activation of the intracellular signaling and/or co-signaling domain as described herein leads to activation of a response element as herein described. In a preferred embodiment, the response element controls the expression of the reporter gene. In one embodiment, upon or after binding of the antigen binding moiety to the target antigen, the CAR binds to the recognition domain, e.g., the mutated Fc domain, wherein the response element activates the expression of a reporter gene as described herein. In a preferred embodiment, activation of the response element leads to expression of the reporter gene. Accordingly, the reporter gene in the reporter cells (e.g., the reporter CAR-T cell) is expressed upon binding of the antigen binding moiety to the target antigen and binding of the CAR to the recognition domain of the antibody comprising the candidate antigen binding moiety. In one embodiment, the expression of the reporter gene is indicative for binding of the antigen binding moiety to the target antigen. In this context, the binding of the antibody to the CAR elicits a cellular response which results in a modulation of the activity of the response element, either directly or through a cascade of cell signaling. The response element is a DNA element which can be silenced or activated by transcription factors or the like. Response elements are known in the art and are commercially available, e.g., in reporter vectors. Usually the response element comprises DNA repeat elements and is a cis-acting enhancer element located upstream of a minimal promotor which drives expression of a reporter gene upon transcription factor binding.

Binding of the CAR to the recognition domain, e.g., the mutated Fc domain, activates the response element. In one embodiment the response element is a nuclear response element located in the nucleus of the cell. In another embodiment said response element is located on a plasmid in the reporter cell. In one embodiment the assay comprises the preliminary step of transfection of the reporter cells, e.g., a CAR-T cell, with an expression vector comprising the DNA sequence coding for the reporter gene under the control of the response element. Additionally, the reporter cells can be transfected with an expression vector comprising the DNA sequence coding for the CAR. The reporter cells can be transfected with an expression vector comprising all elements of the signaling cascade or with different vectors individually expressing the different components. In one embodiment, the reporter cells comprise the DNA sequence coding for the reporter gene under the control of the response element, and the DNA sequence coding for the antigen binding receptor.

Accordingly, as described herein, the CAR is functionally linked to a response element. In one embodiment, the response element controls the expression of the reporter gene. In one embodiment the part of the NFAT pathway, the NF-κB pathway or the AP-1 pathway, preferably, the NFAT pathway.

In one embodiment the reporter gene is selected from a gene coding for a fluorescent protein or a gene coding for an enzyme whose catalytic activity can be detected. In one embodiment, the reporter gene is coding for a luminescent protein, in particular for a fluorescent protein. In one embodiment, the reporter gene is coding for green fluorescent protein (GFP) or luciferase. In further embodiments the fluorescent protein is selected from the group consisting of green fluorescent protein (GFP), yellow fluorescent protein (YFP), red fluorescent protein (RFP), Blue fluorescent protein (BFP, Heim et al. 1994, 1996), a cyan fluorescent variant known as CFP (Heim et al. 1996; Tsien 1998); a yellow fluorescent variant known as YFP (Oruro et al. 1996; Wachter et al. 1998); a violet-excitable green fluorescent variant known as Sapphire (Tsien 1998; Zapata-Hommer et al. 2003); and a cyan-excitable green fluorescing variant known as enhanced green fluorescent protein or EGFP (Yang et al. 1996) enhanced green fluorescent protein (EGFP) and can be measured e.g., by live cell imaging (e.g., Incucyte) or fluorescent spectrophotometry. In one embodiment the enzyme whose catalytic activity can be detected is selected from the group consisting of luciferase, beta Galactosidase and Alkaline Phosphatase. In one embodiment the reporter gene is encoding for GFP. In a preferred embodiment the reporter gene is encoding for luciferase. The activity of luciferase can be detected by commercially available assays, e.g., by Luciferase 1000 Assay System (or ONE-Glo™ Luciferase Assay System (both Promega). The Luciferase 1000 Assay System contains coenzyme A (CoA) besides luciferin as a substrate, resulting in a strong light intensity lasting for at least one minute. For assaying the intracellular luciferase, it is necessary to lyse the cells prior to detection. The light which is produced as a by-product of the reaction is collected by the luminometer from the entire visible spectrum. In the examples shown herein the signal was proportional to the amount of produced luciferase and therefore proportional to the strength of the activation of the NFAT promotor. In another embodiment a Luciferase assay is used wherein the luciferase is secreted from the cells. Hence the assay can be performed without lysis of the cells.

As described herein, the expression of the reporter gene can be directly correlated with the binding of the antigen binding moiety to be tested and the resulting activation of the T cell, e.g., the reporter CAR-T cell. For example when using a gene encoding for a fluorescent protein or a gene encoding for luciferase as a reporter gene, the amount of light detected from the cells correlates directly with the target antigen binding and specificity of the antigen binding moiety to be tested. In one embodiment the antigen binding molecule comprising the antigen binding moiety is applied in different concentrations and the half maximal effective concentration (EC50) of reporter gene activation is determined. EC50 refers to the concentration of the antibody or ligand at which the antibody or ligand activates or inhibits the reporter gene halfway between the baseline and maximum after a specified exposure time. The EC50 of the dose response curve therefore represents the concentration of the antigen binding moiety where 50% of its maximal activating or inhibitory effect on the target antigen is observed.

In one embodiment, the target antigen is a cell surface receptor. In one embodiment, the target antigen is selected from the group consisting of CD20, CEA, HER2, TYRP, EGFR, MCSP, STEAP1, WT1 and FolR1. However, the target antigen is not limited to proteins located on the cell surface but may also derive from polypeptides or proteins which are temporarily or permanently located intracellularly. In such cases, the target antigen deriving from an intracellular polypeptide or protein can be presented on the cell surface by one or seveal molecules of the major histocompatibility complex (MHC). In one embodiment, the target antigen is a peptide bound to a molecule of the MHC. In one embodiment, the MHC is a human MHC. In one embodiment, the peptide bound to a molecule of the MHC has an overall length of between 8 and 100, preferably between 8 and 30, and more preferred between 8 and 16 amino acids. In one embodiment, the target antigen derives from a protein which is exclusively or mainly expressed in tumor tissue. In one embodiment, the protein is an intracellular protein and the peptide is generated by the MHC-I or MHC-II pathway and presented by a MHC class I or MHC class II complex. In one embodiment, the peptide is generated by the MHC-I pathway and presented by a MHC class I complex. In one embodiment, the antigen binding moiety is a T cell receptor like (TCRL) antigen binding moiety. The TCRL antigen binding moiety is capable of specific binding to a peptide antigen which is exclusively or mainly expressed in tumor tissue, wherein the peptide antigen is bound to a molecule of the MHC located on the surface of a cell, particularly a cancer cell. In this context, the methods of the present invention are suitable to assess specificity of established or novel TCRL antigen binding moieties in a high-throughput assay format.

The binding of the antigen binding moiety to the target antigen can be determined qualitatively or qualitatively, i.e., by the presence or absence of the expression of the reporter gene; with the absence of any fluorescence or luminescense being indicative of no binding. For quantitative measurement of binding and activation the amount of reporter gene activation can be compared to a reference. Accordingly, the method as described herein may additionally comprise the step of comparing the level of expression of the reporter gene to a reference. A suitable reference usually comprises a negative control which is substantially identical to the referenced assay omitting one essential component of the assay or method. For the methods of the invention the omitted component may be, e.g., omitting addition of the ABM or omitting the target cell. Alternatively, a reporter CAR-T cell comprising an antigen binding moiety not capable of binding to the recognition domain of the ABM can be used. In a preferred embodiment, the reference is expression of the reporter gene in absence of the target cell. In specific embodiments, the expression of the reporter gene is at least 2×, 3×, 4×, 5×, 10×, 100×, 1000×, or 10000×, higher compared to the expression of the reporter gene in absence of the target cell. Alternatively, the absence of reporter gene expression can be defined by a certain threshold, i.e., after deduction of a background signal. The background signal is usually determined by performing the assay with all reagents but the ABM to be tested or in absence of the target cells. A novel antigen binding moiety can, e.g., be selected according to the method of the invention by defining a threshold for baseline activation of the reporter gene expression and selecting the novel antigen binding moiety if the level of expression of the reporter gene in the presence of the target cell in relation to the expression of the reporter gene in absence of the target cell is higher than a predefined threshold value. Accordingly, the method as described herein may additionally comprise the step of selecting the novel antigen binding moiety if the level of expression of the reporter gene in the presence of the target cell in relation to the expression of the reporter gene in absence of the target cell is higher than a predefined threshold value. In specific embodiments, the threshold value is 2, 3, 4, 5, 10, 100, 1000, or 10000.

The novel assay as described herein is robust, suitable for use in high-throughput format and efficient in terms of hands-on time needed to accomplish the assay. Furthermore, the assay of the present invention tolerates the presence of dead cells in the sample to be analyzed. This is in contrast to cell assays wherein the binding and functionality of an antibody is determined by measuring cell viability or cell death, e.g., a killing assay.

One further advantage of the new assay described herein is that no washing steps are required. The antibodies to be tested and the reporter cells can be added to the target cells, e.g., tumor cells, in either order or at the same time. In one embodiment, the antibody is diluted in cell culture medium and the tumor sample is added to the cell culture medium containing the diluted antibody in a suitable cell culture format, e.g., in a well of a 24 well plate or in a well of a 96 well plate. Preferably the testing medium is a medium that provides conditions for cells to be viable for up to 48 hours. Suitable media are for example Jurkat medium, as outlined in the examples. In one embodiment the assay is performed in a microtiter plate. In one embodiment the microtiter plate is suitable for high throughput screening. The assay of the present invention can be performed in any format that allows for rapid preparation, processing, and analysis of multiple reactions. This can be, for example, in multi-well assay plates (e.g., 24 wells, 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting fluorescent and/or luminescent signals.

In one embodiment about 100000 to about 1000000 reporter CAR-T cells per well of a 24-well plate are provided in step c). In a preferred embodiment about 300000 to about 700000 cells or about 400000 to about 600000 reporter CAR-T cells per well of a 24-well plate are provided. In one embodiment about 500000 reporter CAR-T cells per well of a 24-well plate are provided in step c). In one embodiment about 10000 to about 100000 reporter CAR-T per well of a 96-well plate are provided in step c). In a preferred embodiment about 30000 to about 70000 reporter CAR-T or about 40000 to about 60000 reporter CAR-T per well of a 96-well plate are provided. In one embodiment about 50000 reporter CAR-T per well of a 96-well plate are provided in step c). In one embodiment about 3000 to about 30000 reporter CAR-T cells per well of a 384-well plate are provided in step c). In a preferred embodiment about 5000 to about 15000 cells or about 8000 to about 12000 reporter CAR-T cells per well of a 384-well plate are provided. In one embodiment about 10000 reporter CAR-T cells per well of a 384-well plate are provided in step c). In one embodiment about 200000 to about 2000000 reporter CAR-T per ml of cell culture medium are provided in step c). In a preferred embodiment about 600000 to about 1400000 reporter CAR-T or about 800000 to about 1200000 reporter CAR-T per ml of cell culture medium are provided. In one embodiment about 1000000 reporter CAR-T per ml of cell culture medium are provided in step c).

In one embodiment the ABM is provided in step b) to achieve a final concentration of about 0.001 µg/ml to 10 µg/ml. In further embodiments the ABM is provided in step b) to achieve a final concentration of about 0.05 µg/ml to about 2 µg/ml or about 0.1 µg/ml to about 1 µg/ml. In further embodiments the ABM is provided in step b) to achieve a final concentration of about 0.5 µg/ml. In one embodiment the ABM is provided in step b) to achieve a final concentration of about 1 nM to about 1000 nM. In further embodiments the ABM is provided in step b) to achieve a final concentration of about 5 nM to about 200 nM or about 10 nM to about 100 nM. In further embodiments the ABM is provided in step b) to achieve a final concentration of about 50 nM. The ABM can be diluted in cell culture medium, e.g., in Jurkat medium as described in the example section. The ABM diluted to the final concentration as described herein is added to the tumor sample before or after adding the reporter cells. In one embodiment, the ABM diluted to the final concentration as described herein is added to the tumor sample before adding the reporter cells. In one embodiment, the tumor samples are provided in cell culture inserts. In one embodiment, the tumor samples are embedded in Matrigel.

In certain embodiments methods of the invention can be used to assess specificity of a novel antigen binding moiety to be included in a T cell bispecific (TCB) format. The methods according to the present invention are particularly suitable to assess and select novel antigen binding moieties for TCBs because the methods of the present invention measure T cell activation. It is a drawback of assays known to the art (e.g., binding assays) that the measured affinity does not always reflect the specificity in the TCB format. TCBs are highly potent molecules able to mediate T cell activation and killing already through binding affinities in the micromolar range. TCBs comprising a novel target antigen binding moietys therefore need to be highly selective to avoid unspecific reactivity, e.g, killing of target cells or alloreactivity. The methods as described in the present invention satisfy the high demands of such formats since the assay is based on T cell activation and a comparable mechanism of action. Accordingly, provided is a method as described herein, wherein high level of expression of the reporter gene in the presence of the target cell and low level of expression of the reporter gene in the absence of the target cell is indicative for high specificity of the antigen binding moiety, in particular when the antigen binding moiety is transferred into a T cell bispecific (TCB) antibody format. Furthermore, provided is a method for generating a TCB antibody, wherein the TCB antibody format comprises a first antigen binding moiety specific for a target antigen and a second antigen binding moiety capable of specific binding to a T cell activating receptor, wherein the first antigen binding moiety is selected according to the method as described herein, i.e., the first antigen binding moiety is assayed and selected as candidate antigen binding moiety in the method of the present invention. In preferred embodiments, the T cell activating receptor is CD3.

In one such embodiment the TCB antibody comprises
(a) a first antigen binding moiety which is a Fab molecule capable of specific binding to a target cell antigen;
(b) a second antigen binding moiety which is a Fab molecule capable of specific binding to CD3.

In one specific embodiment the TCB antibody comprises
(a) a first antigen binding moiety which is a Fab molecule capable of specific binding to a target cell antigen;
(b) a second antigen binding moiety which is a Fab molecule capable of specific binding to CD3, and which comprises the heavy chain complementarity determining regions (CDRs) of SEQ ID NO:104, SEQ ID NO:105 and SEQ ID NO:106 and the light chain CDRs of SEQ ID NO:107, SEQ ID NO:108, SEQ ID NO:109.

A TCB antibody with a single antigen binding moiety capable of specific binding to a target cell antigen is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have a bispecific antibody comprising two or more antigen binding moieties specific for a target cell antigen, for example to optimize targeting to the target site.

Accordingly, in certain embodiments, the TCB antibody comprises a third antigen binding moiety capable of specific binding to a target cell antigen. In further embodiments, the third antigen binding moiety is a conventional Fab molecule, or a crossover Fab molecule wherein either the variable or the constant regions of the Fab light chain and the Fab heavy chain are exchanged. In one embodiment, the third antigen binding moiety is capable of specific binding to the same target cell antigen as the first antigen binding moiety. In a particular embodiment, the second antigen binding moiety is capable of specific binding to CD3, and the first and third antigen binding moieties are capable of specific binding to a target cell antigen. In a particular embodiment, the first and the third antigen binding moiety are identical (i.e., they comprise the same amino acid sequences) and are selected according to the method as described herein.

A further aspect of the present disclosure are transduced T cells, i.e., reporter CAR-T cells, capable of expressing a CAR as described herein. The CAR relates to a molecule which is naturally not comprised in and/or on the surface of T cells and which is not (endogenously) expressed in or on normal (non-transduced) T cells. Thus, the CAR as described herein in and/or on T cells is artificially introduced into T cells. Accordingly, the CAR as described herein which is artificially introduced and subsequently presented in and/or on the surface of said T cells, e.g., reporter CAR-T cells, comprises domains comprising one or more antigen binding moiety accessible (in vitro or in vivo) to (Ig-derived) immunoglobulins, preferably antibodies, in particular to the Fc domain of the antibodies. In the context of the present invention, these artificially introduced molecules are presented in and/or on the surface of said T cells after transduction as described herein below. Accordingly, after transduction, T cells according to the disclosure can be activated by immunoglobulins, preferably (therapeutic) antibodies comprising specific mutations in the Fc domain as described herein.

The disclosure also relates to transduced T cells expressing a CAR encoded by (a) nucleic acid molecule(s) encoding the CAR as described herein. Accordingly, in the context of the present invention, the transduced cell may comprise a nucleic acid molecule encoding the CAR as described herein.

In the context of the present invention, the term "transduced T cell" relates to a genetically modified T cell (i.e., a T cell wherein a nucleic acid molecule has been introduced deliberately). In particular, the nucleic acid molecule encoding the CAR as described herein can be stably integrated into the genome of the T cell by using a retroviral or lentiviral transduction. This extracellular domain of the CAR may comprise the complete extracellular domain of an antigen binding moiety as described herein but also parts thereof. The minimal size required being the antigen binding site of the antigen binding moiety in the CAR. The extracellular portion of the CAR (i.e., the extracellular domain of the antigen binding receptor can be detected on the cell surface, while the intracellular portion (i.e., the co-stimulatory signaling domain(s) and the stimulatory signaling domain) are not detectable on the cell surface. The detection of the extracellular domain of the CAR can be carried out by using an antibody which specifically binds to this extracellular domain or by the recognition domain, e.g., the mutated Fc domain, which the extracellular domain is capable to bind. The extracellular domain can be detected using these antibodies or recognition domains by flow cytometry or microscopy.

The transduced cells may be any immune cell. These include but are not limited to B-cells, T cells, Natural Killer (NK) cells, Natural Killer (NK) T cells, γδ T cells, innate lymphoid cells, macrophages, monocytes, dendritic cells, or neutrophils and immortalized cell lines thereof. Preferentially, said immune cell would be a lymphocyte, preferentially a NK or T cells. The said T cells include CD4 T cells and CD8 T cells. Triggering of the CAR on the surface of the leukocyte will render the cell responsive against a target cell in conjunction with an antibody, e.g., a therapeutic antibody, comprising the recognition domain, e.g., a mutated Fc domain, irrespective of the lineage the cell originated from. Activation will happen irrespective of the stimulatory signaling domain or co-stimulatory signaling domain chosen for the CAR and is not dependent on the exogenous supply of additional cytokines.

The transduced cell may be co-transduced with further nucleic acid molecules, e.g., with a nucleic acid molecule encoding a response element as described herein.

Specifically, the present disclosure relates to a method for the production of a reporter CAR-T cell expressing one or more CAR and one or more response elements and reporter genes, comprising the steps of transducing a T cell with one or several vectors as described herein and culturing the transduced T cell under conditions allowing the expressing of the antigen binding receptor in or on said transduced cell.

Methods for transducing cells (e.g., T cells) are known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e., a vector which is not a viral vector).

The transduced T cell/T cells is/are preferably grown under controlled conditions, outside of their natural environment. In particular, the term "culturing" means that cells (e.g., the transduced cell(s)) which are in vitro. Culturing cells is a laboratory technique of keeping cells alive which are separated from their original tissue source. Herein, the transduced cell used according to the present invention is cultured under conditions allowing the expression of the CAR in or on said transduced cells. Conditions which allow the expression or a transgene (i.e., of the CAR and/or reporter gene) are commonly known in the art.

A further aspect of the present disclosure are nucleic acids and vectors encoding one or several CARs used according to the present invention. The nucleic acid molecules may be under the control of regulatory sequences. For example, promoters, transcriptional enhancers and/or sequences which allow for induced expression of the CARs may be employed. In the context of the present invention, the nucleic acid molecules are expressed under the control of constitutive or inducible promoter. Suitable promoters are e.g., the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACTSC promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24). Herein the term vector relates to a circular or linear nucleic acid molecule which can autonomously replicate in a cell (i.e., in a transduced cell) into which it has been introduced. Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322, pGA18 and pGBT9. Typical expression vectors include pTRE, pCAL-n-EK, pESP-1, pOP13CAT.

In the context of the present invention the vector can be polycistronic. Such regulatory sequences (control elements) are known to the skilled person and may include a promoter, a splice cassette, translation initiation codon, translation and insertion site for introducing an insert into the vector(s). In the context of the present invention, said nucleic acid molecule(s) is (are) operatively linked to said expression control sequences allowing expression in eukaryotic or prokaryotic cells. It is envisaged that said vector(s) is (are) an expression vector(s) comprising the nucleic acid molecule(s) encoding the CAR as defined herein. Operably linked refers to a juxtaposition wherein the components so described are in a relationship permitting them to function in their intended manner. A control sequence operably linked to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector(s) is (are) an expression vector(s). An expression vector is a construct that can be used to transform a selected cell and provides for expression of a coding sequence in the selected cell. An expression vector(s) can for instance be cloning (a) vector(s), (a) binary vector(s) or (a) integrating vector(s). Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in E. coli, and examples of regulatory elements permitting expression in eukaryotic host cells are the AOX1 or GAL1 promoter in yeast or the CMV-, SV40, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences encoding signal peptides capable of directing the polypeptide to a cellular compartment or secreting it into the medium may be added to the coding sequence of the recited nucleic acid sequence and are well known in the art; see also, e.g., appended Examples.

The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a CAR including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (In-vitrogene), pEF-DHFR, pEF-ADA or pEF-neo (Raum et al. Cancer Immunol Immunother 50 (2001), 141-150) or pSPORT1 (GIBCO BRL).

The described nucleic acid molecule(s) or vector(s) which is (are) introduced in the T cell or its precursor cell may either integrate into the genome of the cell or it may be maintained extrachromosomally.

Exemplary Embodiments

1. A method for assessing the specificity of an antigen binding moiety comprising the steps of:
   a) providing an antigen binding molecule comprising an antigen binding domain and a recognition domain, wherein the antigen binding domain comprises the antigen binding moiety, wherein the antigen binding moiety is specific for a target antigen;
   b) contacting the antigen binding molecule with a target cell comprising the target antigen on the surface, particularly wherein the target cell is a cancer cell;
   c) contacting the antigen binding molecule with a chimeric antigen receptor (CAR) expressing reporter T (CAR-T) cell wherein the reporter CAR-T cell comprises:
      i. a CAR capable of specific binding to the recognition domain wherein the CAR is operationally coupled to a response element;
      ii. a reporter gene under the control of the response element; and
   d) determining T cell activation by determining the expression of the reporter gene to establish the specificity of the antigen binding moiety.
2. The method of embodiment 1, wherein the recognition domain is an immunoglobulin domain.
3. The method of any one of embodiments 1 or 2, wherein the recognition domain is an Fc domain.
4. The method of embodiment 3, wherein the Fc domain is a human Fc domain, particularly a human IgG1 Fc domain.
5. The method of any one of embodiment 3 or 4, wherein the Fc domain is a mutated Fc domain, wherein the mutated Fc domain comprises at least one amino acid substitution compared to the non-mutated parent Fc domain, wherein the CAR is capable of specific binding to the mutated Fc domain but not capable of specific binding to the non-mutated parent Fc domain.
6. The method of embodiment 5, wherein the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.
7. The method of any one of embodiment 5 or 6, wherein the mutated Fc domain comprises the amino acid mutation P329G according to EU numbering.
8. The method of any one of embodiment 5 to 7, wherein the mutated Fc domain comprises at least one amino acid mutation at a position selected from the group consisting of I253, H310 and H435 according to EU numbering, in particular the amino acid mutations I253A, H310A and H435A ("AAA").
9. The method of any one of embodiments 1 to 8, wherein the antigen binding moiety is a Fab fragment, in particular a Fab fragment deriving from a phage display library screening.
10. The method of any one of embodiments 1 to 9, wherein the CAR comprises at least one intracellular stimulatory signaling and/or co-stimulatory signaling domain.
11. The method of embodiment 10, wherein binding of the antigen binding moiety to the target antigen and binding of the reporter CAR-T cell to the antigen binding molecule comprising the antigen binding moiety leads to activation of the intracellular signaling and/or co-signaling domain.
12. The method of any one of embodiments 10 or 11, wherein activation of the intracellular signaling and/or co-signaling domain leads to activation of the response element.
13. The method according to any one of embodiments 1 to 12, wherein the response element controls the expression of the reporter gene.
14. The method according to any one of embodiments 1 to 13, wherein activation of the response element leads to expression of the reporter gene.
15. The method according to any one of embodiments 1 to 14, wherein the response element is part of the NFAT pathway, the NF-κB pathway or the AP-1 pathway.
16. The method according to any one of embodiments 1 to 15, wherein the reporter gene is coding for a luminescent protein, in particular for a fluorescent protein.
17. The method according to any one of embodiments 1 to 16, wherein the reporter gene is coding for green fluorescent protein (GFP) or luciferase.
18. The method according to any one of embodiments 1 to 17, wherein the target antigen is a cell surface receptor.
19. The method according to any one of embodiments 1 to 18, wherein the target antigen is selected from the group consisting of CD20, CEA, HER2, TYRP, EGFR, MCSP, STEAP1, WT1 and FolR1, or a fragment thereof.
20. The method according to any one of embodiments 1 to 19, wherein the target antigen is a peptide bound to a molecule of the human major histocompatibility complex (MHC).
21. The method according to embodiment 20, wherein the antigen binding moiety is a T cell receptor like (TCRL) antigen binding moiety.
22. The method according to any one of embodiments 1 to 21, additionally comprising the step of:
   e) comparing the expression of the reporter gene to a reference.
23. The method according to embodiment 22, wherein the reference is expression of the reporter gene in absence of the target cell.
24. The method according to embodiment 23, wherein the expression of the reporter gene in the presence of the target cell is at least 2×, 3×, 4×, 5×, 10×, 100×, 1000×, or 10000×, higher compared to the expression of the reporter gene in absence of the target cell.
25. The method according to embodiment 22, additionally comprising the step of:
   f) selecting the antigen binding moiety if the expression of the reporter gene in the presence of the target cell in relation to the expression of the reporter gene in absence of the target cell is higher than a predefined threshold value.
26. The method according to embodiment 25, wherein the threshold value is 2, 3, 4, 5, 10, 100, 1000, or 10000.
27. The method according to any one of embodiments 1 to 26, wherein high level of expression of the reporter gene in the presence of the target cell and low level of expression of the reporter gene in the absence of the target cell is indicative for high specificity of the antigen binding moiety.

28. The method according to any one of embodiments 1 to 27, wherein high level of expression of the reporter gene in the presence of the target cell and low level of expression of the reporter gene in the absence of the target cell is indicative for high specificity of a T cell bispecific (TCB) antibody comprising the antigen binding moiety.

29. The method according to any one of embodiment 1 to 28, wherein the method is an in vitro method.

30. A method for generating a TCB antibody, wherein the TCB antibody comprises a first antigen binding moiety specific for a target antigen and a second antigen binding moiety capable of specific binding to a T cell activating receptor, wherein the first antigen binding moiety is selected according to the method of any one of embodiments 1 to 29.

31. The method of embodiment 30, wherein the T cell activating receptor is CD3.

32. The methods as hereinbefore described.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g., by SDS-PAGE and size exclusion chromatography (SEC).

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Antibody Production

The Pro329Gly, Leu234Ala and Leu235Ala mutations were introduced in the constant region to abrogate binding to Fc gamma receptors according to the method described in International Patent Appl. Publ. No. WO2012/130831A1. Accordingly, the I253A, H310A and H435A ("AAA") mutations were introduced in the constant region to abrogate binding to FcRn. The respective antibodies were produced by co-transfecting HEK293-EBNA cells with the mammalian expression vectors using polyethylenimine. The cells were transfected with the corresponding expression vectors for heavy and light chains in a 1:1 ratio Lentiviral Transduction of Jurkat NFAT CAR-T Cells To produce lentiviral vectors, respective DNA sequences for the correct assembly of the antigen binding receptor were cloned in frame in a lentiviral polynucleotide vector under a constitutively active human cytomegalovirus immediate early promoter (CMV). The retroviral vector contained a woodchuck hepatitis virus posttranscriptional regulatory element (WPRE), a central polypurine tract (cPPT) element, a pUC origin of replication and a gene encoding for antibiotic resistance facilitating the propagation and selection in bacteria.

To produce functional virus particles, Lipofectamine LTX™ based transfection was performed using 60-70% confluent Hek293T cells (ATCC CRL3216) and CAR containing vectors as well as pCMV-VSV-G:pRSV-REV: pCgpV transfer vectors at 3:1:1:1 ratio. After 48 h supernatant was collected, centrifuge for 5 minutes at 250 g to remove cell debris and filtrated through 0.45 or 0.22 μm polyethersulfon filter. Concentrated virus particles (Lenti-x-Concentrator, Takara) were used to transduce Jurkat NFAT cells (Signosis). Positive transduced cells were sorted as pool or single clones using FACS-ARIA sorter (BD Bioscience). After cell expansion to appropriate density Jurkat NFAT reporter CAR-T cells were used for experiments.

Example 1

Described herein is a Jurkat NFAT reporter CAR-T cell assay using CD20 expressing SUDHDL4 tumor cells as target cells and a sorted pool of Anti-P329G-ds-Fab-CD28ATD-CD28CSD-CD3zSSD expressing Jurkat NFAT reporter CAR-T cells (FIG. 6A) or a pool of Anti-P329G-ds-scFv-CD28ATD-CD28CSD-CD3zS SD expressing Jurkat NFAT reporter CAR-T cells (FIG. 6B) as reporter cells. GA101 IgG with P329G LALA mutation was used as IgG, which on one hand recognizes the tumor antigen and on the other hand is recognized by the transduced Jurkat NFAT reporter CAR-T cells. As positive control a 96 well plate (Cellstar Greiner-bio-one, CAT-No. 655185) was coated with 10 µg/ml CD3 antibody (from Biolegend®) in phosphate buffered saline (PBS) either for 4° C. over night or for at least 1 h at 37° C. The CD3 coated wells were washed twice with PBS, after the final washing step PBS was fully removed. Reporter cells or Jurkat NFAT wild type cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the reporter cells, to $1 \times 10^6$ viable cells/ml in growth medium. Target cells and reporter cells were plated in either 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon co-cultivation of target and reporter cells in a ratio 5:1 (dots) or 1:1 (squares) for 20 h the graphs show a dose-dependent activation of Anti-P329G-ds-Fab-CD28ATD-CD28CSD-CD3zSSD expressing Jurkat NFAT reporter CAR-T cells as well as Anti-P329G-ds-scFv-CD28ATD-CD28CSD-CD3zSSD expressing Jurkat NFAT reporter CAR-T cells when GA101 IgG with P329G LALA mutation was used as antibody (FIGS. 6A and B, depicted in black). If the GA101 IgG without P329G LALA mutation (FIGS. 6A and B, depicted in grey) was used, no activation of the transduced Jurkat NFAT reporter CAR-T cells was detectable. Each point represents the mean value of biological duplicates, each performed as technical duplicate. All values are depicted as baseline corrected. Standard deviation is indicated by error bars.

Example 2

Described herein is a Jurkat NFAT reporter CAR-T cell assay using CD20 expressing SUDHDL4 (FIGS. 7C and 7D) or WSUDLCL2 (FIGS. 7A and 7B) tumor cells as target cells and single clone Jurkat NFAT cells expressing Anti-P329G-ds-Fab-CD28ATD-CD28CSD-CD3zSSD as reporter cells. GA101 IgG with P329G LALA mutation was used as IgG which on one hand recognizes the tumor antigen and on the other hand is recognized by the Jurkat NFAT reporter CAR-T cells. Reporter cells or Jurkat NFAT wild type cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the reporter cells, to $1 \times 10^6$ viable cells/ml in growth medium. Target cells and reporter cells were plated in either 10:1, 5:1 or 1:1 E:T ratio (110.000 cells per well in total) in triplicates in a 96-well suspension culture plate (Greiner-bio one). As a next step a serial dilution of GA101 with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

Upon co-cultivation of target and reporter cells in a ratio 10:1 (dots), 5:1 (squares) or 1:1 (triangles) for 20 h the graphs show a GA101 IgG with P329G LALA dose-dependent activation of Anti-P329G-ds-Fab-CD28ATD-CD28CSD-CD3zSSD expressing Jurkat NFAT reporter CAR-T cells (FIG. 7A-D, depicted in black). If the GA101 IgG without P329G LALA mutation (FIG. 7A-D, depicted in grey) was used, then only little activation of the transduced Jurkat NFAT reporter CAR-T cells was detectable at the highest antibody concentration of 1 µg/ml. Each point represents the mean value of technical duplicate. All values are depicted as baseline corrected. Standard deviation is indicated by error bars.

Example 3

Described herein is a Jurkat NFAT reporter CAR-T cell assay performed using adherent FAP expressing NIH/3T3-huFAP cl 19 tumor cells as target cells. As reporter cells a sorted pool of Anti-P329G-ds-Fab-CD28ATD-CD28CSD-CD3zSSD expressing Jurkat NFAT reporter CAR-T cells (FIG. 8A) or Anti-P329G-ds-scFv-CD28ATD-CD28CSD-CD3zSSD expressing Jurkat NFAT reporter CAR-T cells (FIG. 8C) were used. FAP 4B9 IgG with P329G LALA mutation was used as IgG which on one hand recognizes the tumor antigen and on the other hand is recognized by the Jurkat NFAT reporter CAR-T cells. IgG DP47/vk3 harboring P329G LALA mutation was included as isotype control. As positive control wells of a 96 well plate (Greiner-bio-one, CAT-No. 655185) were coated with 10 µg/ml CD3 antibody (from Biolegend®) in phosphate buffered saline (PBS) for at least 1 h at 37° C. The CD3 coated wells were washed twice with PBS, after the final washing step PBS was fully removed. Adherent NIH/3T3-huFAP cl 19 target cells were washed once with PBS and detached using Trypsin. Detached cells were resuspended in DMEM+4.5 g LD-Glucose+L-Glutamine+25 mM HEPES+10% FCS and 1% Glutamax. Reporter cells or Jurkat NFAT wild type T cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium). Target cells expressing the antigen of interest, were counted and checked for their viability as well. The cell number was adjusted, analog as described for the reporter cells, to $1\times10^6$ viable cells/ml in growth medium. Target cells and reporter cells were plated in 5:1 E:T ratio (110.000 cells per well in total) in triplicates in a 96-well suspension culture plate (Greiner-bio one). As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml, in a final volume of 200 ul per well, a 50 µl aliquot of the different dilutions was pipetted to the respective wells. The 96-well plate was centrifuged for 2 min at 190 g and RT. Sealed with Parafilm®, the plate was incubated at 37° C. and 5% $CO_2$ in a humidity atmosphere. After 20 h incubation the content of each well was mixed by pipetting up and down 10 times using a multichannel pipette. 100 µl cell suspension was transferred to a new white flat clear bottom 96-well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time.

FIGS. 8B and 8D, represent data of Anti-P329G-ds-Fab-CD28ATD-CD28CSD-CD3zSSD expressing Jurkat NFAT reporter CAR-T cells (FIG. 8D) or Anti-P329G-ds-scFv-CD28ATD-CD28CSD-CD3zSSD expressing Jurkat NFAT reporter CAR-T cells (FIG. 8B) both co-cultivated with target cells and 1 µg/ml of FAP 4B9 antibody compared to different control conditions.

Upon incubation with 1 µg/ml FAP 4B9 P329G LALA, Jurkat NFAT reporter CAR-T cells (FIGS. 8B and 8D black triangle) as well as target cells only (FIGS. 8B and 8D upside down black triangle) do not show any detectable luminescence signal.

Also Jurkat NFAT reporter CAR-T cells show no luminescence signal upon co-cultivation with target cells and 1 µg/ml of FAP 4B9 antibody (FIG. 8B and FIG. 8D black diamond). Whereas CD3 dependent activation of Jurkat NFAT cells co-cultivated with target cells and 1 µg/ml of FAP 4B9 antibody proofs their functionality through a detectable luminescence signal (withe dots).

CD3 dependent activation of Anti-P329G-ds-Fab-CD28ATD-CD28CSD-CD3zSSD expressing Jurkat NFAT reporter CAR-T cells (FIG. 8B white squares) and activation of Anti-P329G-ds-scFv-CD28ATD-CD28CSD-CD3zS SD expressing Jurkat NFAT reporter CAR-T cells (FIG. 8D depicted in white squares) co-cultivated with target cells and 1 µg/ml of FAP 4B9 antibody shows the highest luminescence signals of all, since it combines the CAR mediated activation with CD3 mediated activation. CD3 mediated luminescence signal is also visible when CARs are incubated with target cells and 1 µg/ml of DP47/vk3 antibody (FIG. 8B and FIG. 8D upside down white triangles). Each point represents the mean value of technical triplicates. All values are depicted as baseline corrected. Standard deviation is indicated by error bars.

Example 4

Described herein is a Jurkat NFAT reporter CAR-T cell assay using adherent CEA expressing MKN45 tumor cells as target cells. As reporter cells a sorted pool of Anti-P329G-ds-Fab-CD28ATD-CD28CSD-CD3zSSD expressing Jurkat NFAT reporter CAR-T cells (FIG. 9A) or Anti-P329G-ds-scFv-CD28ATD-CD28CSD-CD3zSSD expressing Jurkat NFAT reporter CAR-T cells (FIG. 9C) were used. Either CEA A5B7 IgG or CEA T84 LCHA IgG both with P329G LALA mutation were used. Further IgG DP47/vk3 harboring P329G LALA mutation was included as isotype control.

As positive control wells of a 96 well plate (Greiner-bioone, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent MKN45 target cells were washed once with PBS and detached using Trypsin. Detached cells were resuspended in DMEM+4.5 g LD-Glucose+L-Glutamine +25 mM HEPES+10% FCS and 1% Glutamax.

Reporter cells or Jurkat NFAT wild type cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the reporter cells, to $1\times10^6$ viable cells/ml in RPMI-1640+10% FCS+1% Glutamax.

Target cells and reporter cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and reporter cells in a ratio 5:1 (FIGS. 9A and C, dots) for 20 h the graphs show a dose-dependent activation of Anti-P329G-ds-Fab-CD28ATD-CD28CSD-CD3zSSD expressing Jurkat NFAT reporter CAR-T cells as well Anti-P329G-ds-scFv-CD28ATD-CD28CSD-CD3zSSD expressing Jurkat NFAT reporter CAR-T cells when CEA A5B7 with P329G LALA mutation was used as antibody (FIGS. 9A and C grey dots). The use of CEA T84 LCHA with P329G LALA mutation showed only for Anti-P329G-ds-Fab-CD28ATD-CD28CSD-CD3zSSD expressing Jurkat NFAT reporter CAR-T cells a dose dependent activation (FIG. 9A black dots). Whereas, when using the antibody with P329G LALA mutation an activation of Anti-P329G-ds-scFv-CD28ATD-CD28CSD-CD3zSSD expressing Jurkat NFAT reporter CAR-T cells was detectable only at the highest antibody concentration of 1 μg/ml.

If the control antibody DP47/vk3 IgG with P329G LALA mutation (FIGS. 9A and C, black triangles) was used, no activation of Anti-P329G-ds-scFv-CD28ATD-CD28CSD-CD3zSSD Jurkat NFAT reporter CAR-T cells or Anti-P329G-ds-Fab-CD28ATD-CD28CSD-CD3zSSD expressing Jurkat NFAT reporter CAR-T cells was detectable. Each point represents the mean value of technical triplicates. Standard deviation is indicated by error bars.

FIGS. 9B and 9D, represent data of Anti-P329G-ds-Fab-CD28ATD-CD28CSD-CD3zSSD expressing Jurkat NFAT reporter CAR-T cells (FIG. 9B) or Anti-P329G-ds-scFv-CD28ATD-CD28CSD-CD3zSSD expressing Jurkat NFAT reporter CAR-T cells (FIG. 9D) both co-cultivated with target cells and 1 μg/ml of CEA T8 LCHA P329G LALA or CEA A5B7 P329G LALA antibody compared to different control conditions.

Upon incubation with 1 μg/ml CEA T8 LCHA P329G LALA, Jurkat NFAT CAR T cells alone (FIGS. 9B and 9D black diamond) as well as target cells alone (FIGS. 9B and 9D white circle) do not show any detectable luminescence signal.

Also Jurkat NFAT reporter CAR-T cells do not show a detectable luminescence signal upon co-cultivation with target cells and 1 μg/ml IgG (FIG. 9B and FIG. 9D white square and white diamond). Whereas CD3 dependent activation of Jurkat NFAT reporter CAR-T cells co-cultivated with target cells and 1 μg/ml IgG proofs their functionality through a detectable luminescence signal (FIGS. 9B and D grey cross).

CD3 dependent activation of Anti-P329G-ds-Fab-CD28ATD-CD28C SD-CD3zS SD Jurkat NFAT reporter CAR-T cells (FIG. 9B black star and grey star) and activation of Anti-P329G-ds-scFv-CD28ATD-CD28CSD-CD3zSSD expressing NFAT T cells (FIG. 9D black star and grey star) co-cultivated with target cells and 1 μg/ml IgG show the highest luminescence signals of all, since CAR mediated activation and CD3 mediated activation is combined. CD3 mediated luminescence signal is also visible when CARs are incubated with target cells and 1 μg/ml of DP47/vk3 antibody (FIG. 9B and FIG. 9D, grey plus). Each point represents the mean value of technical triplicates. Standard deviation is indicated by error bars.

Example 5

Described herein is a Jurkat NFAT reporter CAR-T cell reporter using adherent CEA expressing MKN45 tumor cells as target cells. As reporter cells, a sorted pool of Anti-P329G-ds-Fab-CD28ATD-CD28CSD-CD3zSSD expressing Jukat NFAT T cells (FIG. 10C) or Anti-P329G-ds-scFv-CD28ATD-CD28CSD-CD3zSSD expressing Jurkat NFAT reporter CAR-T cells (FIG. 10A) were used. Either CH1A1A 98 99 or CEA hMN14 IgG both with P329G LALA mutation were used. Further IgG DP47/vk3 harboring P329G LALA mutation was included as isotype control.

As positive control wells of a 96-well plate (Greiner-bio-one, CAT-No. 655185) were coated with 10 μg/ml CD3 antibody (from Biolegend®) in phosphate buffered saline (PBS) for 1 h at 37° C. The CD3 coated wells were washed twice with PBS, after the final washing step, PBS was fully removed.

Adherent MKN45 target cells were washed once with PBS and detached using Trypsin. Detached cells were resuspended in DMEM+4.5 g LD-Glucose+L-Glutamine +25 mM HEPES+10% FCS and 1% Glutamax.

Reporter cells or Jurkat NFAT wild type cells were counted and checked for their viability using Cedex HiRes. The cell number was adjusted to $1\times10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the reporter cells, to $1\times10^6$ viable cells/ml in RPMI-1640+10% FCS+1% Glutamax.

Target cells and reporter cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 μg/ml to 0.0001 μg/ml in a final volume of 200 ul per well, a 50 μl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 μl cell suspension was transferred to a new white flat clear bottom 96-well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon 20 h co-cultivation of target cells and Anti-P329G-ds-scFv-CD28ATD-CD28CSD-CD3zSSD expressing Jurkat NFAT reporter CAR-T cells in a ratio 5:1 (FIG. 10A black and grey dots) no activation is detectable, when the CEA hMN14 antibody or the CH1A1A 98 99 antibody was used as (FIGS. 9A and B, grey dots). Anti-P329G-ds-Fab-CD28ATD-CD28CSD-CD3zSSD expressing Jurkat NFAT reporter CAR-T cells show little activation at 0.1 and 1 μg/ml of both CEA hMN14 antibody or the CH1A1A 98 99 antibodies (FIG. 10C black and grey dots).

If the control antibody DP47/vk3 IgG with P329G LALA mutation (FIGS. 10A and C, black triangles) was used, neither the activation of Anti-P329G-ds-scFv-CD28ATD-CD28CSD-CD3zSSD expressing Jurkat NFAT reporter CAR-T cells nor Anti-P329G-ds-Fab-CD28ATD-CD28CSD-CD3zSSD expressing Jurkat NFAT reporter CAR-T cells was detectable. Each point represents the mean value of technical triplicates. All values are depicted as baseline corrected. Standard deviation is indicated by error bars.

FIGS. 10B and 10D, represent data of Anti-P329G-ds-Fab-CD28ATD-CD28CSD-CD3zSSD expressing Jurkat NFAT reporter CAR-T cells (Figure D) or Anti-P329G-ds-scFv-CD28ATD-CD28CSD-CD3zSSD expressing NFAT T cells (FIG. 9D) both co-cultivated with target cells and 1 μg/ml of CEA hMN14 antibody or the CH1A1A 98 99 antibody compared to different control conditions.

All performed control experiments do not show any detectable luminescence signal, except those were CD3 was used as an activation stimulus. Each point represents the mean value of technical triplicates. Standard deviation is indicated by error bars.

Example 6

Described herein is a Jurkat NFAT reporter CAR-T cell assay using adherent TNC expressing CT26TNC cl 19 tumor cells as target cells. As reporter cells, a sorted pool of Anti-P329G-ds-Fab-CD28ATD-CD28CSD-CD3zSSD expressing Jurkat NFAT reporter CAR-T cells (FIG. 11C) or Anti-P329G-ds-scFv-CD28ATD-CD28CSD-CD3zSSD expressing Jurkat NFAT reporter CAR-T cells (FIG. 11A) were used. TNCA2B10 with P329G LALA mutation was used as IgG. Further IgG DP47/vk3 harboring P329G LALA mutation was included as isotype control.

As positive control wells of a 96 well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+ 15 µg/ml Puromycin.

Reporter cells or Jurkat NFAT wild type T cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the reporter cells, to $1 \times 10^6$ viable cells/ml in RPMI-1640+10% FCS+1% Glutamax.

Target cells and reporter cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and reporter cells in a ratio 5:1 (FIGS. 11A and C black dots) for 20 h the graphs show a dose-dependent activation of Anti-P329G-ds-Fab-CD28ATD-CD28CSD-CD3zSSD expressing Jurkat NFAT reporter CAR-T cells as well as of Anti-P329G-ds-scFv-CD28ATD-CD28CSD-CD3zS SD expressing Jurkat NFAT reporter CAR-T cells when TNC A2B10 with P329G LALA mutation was used as antibody. If the control antibody DP47/vk3 IgG with P329G LALA mutation (FIGS. 11A and C black dots) was used, neither the activation of Anti-P329G-ds-scFv-CD28ATD-CD28CSD-CD3zS SD expressing Jurkat NFAT reporter CAR-T cells nor Anti-P329G-ds-Fab-CD28ATD-CD28CSD-CD3zSSD expressing Jurkat NFAT reporter CAR-T cells was detectable. Each point represents the mean value of technical triplicates. All values are depicted as baseline corrected. Standard deviation is indicated by error bars.

FIGS. 11B and 11D, represent data of Anti-P329G-ds-Fab-CD28ATD-CD28CSD-CD3zSSD expressing Jurkat NFAT reporter CAR-T cells (FIG. 11 D) or Anti-P329G-ds-scFv-CD28ATD-CD28CSD-CD3zSSD expressing Jurkat NFAT reporter CAR-T cells (FIG. 11B) both co-cultivated with target cells and 1 µg/ml of TNC A2B10 compared to different control conditions.

Jurkat NFAT reporter CAR-T cells do not show any detectable luminescence signal upon co-cultivation with target cells and 1 µg/ml IgG (FIG. 11B and FIG. 11D white triangle). Whereas CD3 dependent activation of Jurkat NFAT cells co-cultivated with target cells and 1 µg/ml IgG proofs their functionality through a detectable luminescence signal (FIG. 11B and FIG. 11D white square).

CD3 dependent activation of Anti-P329G-ds-Fab-CD28ATD-CD28C SD-CD3zSSD expressing Jurkat NFAT reporter CAR-T cells (FIG. 11B white circle) and activation of Anti-P329G-ds-scFv-CD28ATD-CD28CSD-CD3zS SD expressing Jurkat NFAT reporter CAR-T cells (FIG. 11D white circle) co-cultivated with target cells and 1 µg/ml IgG show the highest luminescence signals of all, since CAR mediated activation and CD3 mediated activation is combined. CD3 mediated luminescence signal is also visible when CARs are incubated with target cells and 1 µg/ml of DP47/vk3 antibody (FIGS. 11B and FIG. 11D, black diamond). Each point represents the mean value of technical triplicates. Standard deviation is indicated by error bars.

Example 7

Described herein is a Jurkat NFAT reporter CAR-T cell assay using adherent TNC expressing CT26TNC cl 19 tumor cells as target cells. As reporter cells, a sorted pool of Anti-P329G-Fab-CD28ATD-CD28CSD-CD3zSSD expressing Jurkat NFAT reporter CAR-T cells (FIG. 12A) was used. TNCA2B10 with P329G LALA mutation was used as IgG. Further IgG DP47/vk3 harboring P329G LALA mutation was included as isotype control.

As positive control wells of a 96-well plate (Greiner-bio-one, CAT-No. 655185) were coated with 10 µg/ml CD3 antibody (from Biolegend®) in phosphate buffered saline (PBS) for 1 h at 37° C. The CD3 coated wells were washed twice with PBS, after the final washing step, PBS was fully removed.

Adherent CT26TNC cl 19 target cells were washed once with PBS and detached using Trypsin. Detached cells were resuspended in RPMI-1630+10% FCS and 1% Glutamax+ 15 µg/ml Puromycin.

Reporter cells or Jurkat NFAT wild type cells were counted and checked for their viability using Cedex HiRes. The cell number was adjusted to $1 \times 10^6$ viable cells/ml. Therefore an appropriate aliquot of the cell suspension was pelleted at 210 g for 5 min at room temperature (RT) and resuspended in fresh RPMI-160+10% FCS+1% Glutamax (growth medium).

Target cells expressing the antigen of interest, were counted and checked for their viability as well. The cell number was adjusted, analog as described for the reporter cells, to $1 \times 10^6$ viable cells/ml in RPMI-1640+10% FCS+1% Glutamax.

Target cells and reporter cells were plated in 5:1 E:T ratio (110.000 cells per well in total) in triplicates in a 96-well suspension culture plate (Greiner-bio one).

As a next step a serial dilution of an antibody with P329G LALA mutation, targeting the antigen of interest, was prepared in growth medium using a 2 ml deep well plate (Axygen®). To obtain final concentrations ranging from 1 µg/ml to 0.0001 µg/ml in a final volume of 200 ul per well, a 50 µl aliquot of the different dilutions was pipetted to the respective wells. The 96 well plate was centrifuged for 2 min at 190 g and RT. Sealed with Parafilm®, the plate was incubated at 37° C. and 5% $CO_2$ in a humidity atmosphere.

After 20 h incubation the content of each well was mixed by pipetting up and down 10 times using a multichannel pipette. 100 µl cell suspension was transferred to a new white flat clear bottom 96 well plate (Greiner-bio-one) and 100 ul ONE-Glo™ Luciferase Assay (Promega) was added. After 15 min incubation in the dark on a rotary shaker at 300 rpm and RT luminescence was measured using Tecan® Spark10M plate reader, 1 sec/well as detection time. Upon co-cultivation of target and reporter cells in a ratio 5:1 (FIG. 12A black dots) for 20 h the graphs show a dose-dependent activation of Anti-P329G-Fab-CD28ATD-CD28CSD-CD3zSSD expressing Jurkat NFAT reporter CAR-T cells beginning with 0.01 µg/ml of TNC A2B10 with P329G LALA mutation. If the control antibody DP47/vk3 IgG with P329G LALA mutation (FIGS. 12A and C grey dots) was used, no activation of Anti-P329G-Fab-CD28ATD-CD28CSD-CD3zSSD expressing Jurkat NFAT reporter CAR-T cells was detectable. Each point represents the mean value of technical triplicates. All values are depicted as baseline corrected. Standard deviation is indicated by error bars.

FIG. 12B, represents data of Anti-P329G-Fab-CD28ATD-CD28CSD-CD3zSSD expressing Jurkat NFAT reporter CAR-T cells co-cultivated with target cells and 1 µg/ml of TNC A2B10 antibody compared to different control conditions.

Anti-P329G-Fab-CD28ATD-CD28CSD-CD3zSSD expressing Jurkat NFAT reporter CAR-T cells incubated with target cells but without antibody (FIG. 12B black square) as well as Jurkat NFAT cells incubated with target cells and 1 µg/ml of TNC A2B10 antibody (FIG. 12B white dots) show no detectable luminescence signal. Whereas Jurkat NFAT cells co-cultured with target cells and 1 µg/ml of TNC A2B10 plated in CD3 coated wells, show a clear luminescence signal.

Further Anti-P329G-CD28ATD-CD28CSD-CD3zSSD Fab expressing Jurkat NFAT reporter CAR-T cells incubated with target cells and either 1 µg/ml of TNC A2B10 or 1 µg/ml DP47/vk3 antibody, in CD3 coated wells, show a high luminescence signal. Each point represents the mean value of technical triplicates. Standard deviation is indicated by error bars.

Example 8

Described herein is the assessment of specificity of HLA-A2/WT1-peptide-binders 5E11 (SEQ ID NOs: 102 and 103) and 33H09 (SEQ ID NOs: 100 and 101) by means of flow cytometry with T2 cells pulsed with RMF-peptide or VLD-peptide. Prior to incubation with the HLA-A2/WT1-peptide-binding antibodies, T2 cells were pulsed with the respective peptide at $10^{-5}$ M for 2 hours at 37° C., or left unpulsed. Binding of the respective IgG to cell aliquots of 100000 cells, each, at different concentrations of the antibody in question was allowed for 1 h on ice, followed by two washing steps with PBS, and assessed via anti-huFc-detection (anti-human F(ab)2_AF647 from Jackson ImmunoResearch) at a concentration of 90 nM in flow cytometry on a Fortessa analyzer (BD Biosciences). Both binders 5E11 and 33H09 give clear concentration-dependent binding signal on RMF-pepide-pulsed, but not on VLD-pepide-pulsed T2 cells (FIGS. 13A and B). According to this flow cytometry-based assessment, both antibody candidates appear to bind specifically to RMF-peptide-pulsed, but not to VLD-peptide-pulsed T2 cells.

Example 9

Described herein is a Jurkat NFAT reporter CAR-T cell assay using peptide-pulsed T2 cells as target cells in order to assess the specificity of HLA-A2/WT1-peptide-binders 33F05 (SEQ ID NOs: 96 and 97), 11D06 (SEQ ID NOs: 98 and 99), 33H09 (SEQ ID NOs: 100 and 101) and 5E11 (SEQ ID NOs: 102 and 103). As reporter cells, a sorted pool of Anti-P329G-ds-Fab-CD28ATD-CD28CSD-CD3zSSD expressing Jurkat NFAT reporter CAR-T cells were used. The HLA-A2/WT1-peptide-binders with P329G LALA mutation were used as IgG. Prior to incubation with the HLA-A2/WT1-peptide-binding antibodies and the reporter cells, T2 cells were pulsed with the respective peptide at $10^{-5}$ M for 2 hours at 37° C., or left unpulsed. Target cells and reporter cells were plated in 5:1 E:T ratio (10.000 effector cells per 2000 target cells per well) in triplicates in a 384-well white flat clear bottom plate (Greiner-bio-one). As a next step serial dilutions of the IgGs in question were prepared in growth medium. Incubation of reporter cells, T2 cells and IgGs was allowed for 16 hours at 37° C., followed by addition of 6 µl per well of ONE-Glo™ luciferase substrate (Promega) and direct measurement of luminescence using a TECAN infinite M1000Pro plate reader.

The resulting graphs (FIG. 14A to FIG. 14D) show a dose-dependent activation of anti-P329G-ds-Fab-CD28ATD-CD28CSD-CD3zS SD expressing Jurkat NFAT reporter CAR-T cells. Importantly, this activation appears selectively on RMF-peptide-pulsed T2 cells only for binders 11D06 and 33H09, but unspecifically on RMF- and VLD-peptide-pulsed T2 cells for binders 33F05 and 5E11, indicating the unselective nature of T cell activation for these latter two antibodies.

Example 10

Described herein is a Jurkat NFAT reporter CAR-T cell assay using peptide-pulsed T2 cells as target cells in order to assess the specificity of variants of HLA-A2/WT1-peptide-binder 11D06/D43. As reporter cells, a sorted pool of Anti-P329G-ds-Fab-CD28ATD-CD28CSD-CD3zSSD expressing Jurkat NFAT reporter CAR-T cells were used. The HLA-A2/WT1-peptide-binders with P329G LALA mutation were used as IgG. Prior to incubation with the HLA-A2/WT1-peptide-binding antibodies and the reporter cells, T2 cells were pulsed with the RMF peptide at $10^{-5}$ M for 2 hours at 37° C., or left unpulsed. Target cells and reporter cells were plated in 5:1 E:T ratio (10.000 effector cells per 2000 target cells per well) in triplicates in a 384-well white flat clear bottom plate (Greiner-bio-one). As a next step serial dilutions of the IgGs in question were prepared in growth medium. Incubation of reporter cells, T2 cells and IgGs was allowed for 16 hours at 37° C., followed by addition of 6 µl per well of ONE-Glo™ luciferase substrate (Promega) and direct measurement of luminescence using a TECAN infinite M1000Pro plate reader.

The resulting graphs (FIG. 15A to FIG. 15F) show dose-dependent activation of anti-P329G-ds-Fab-CD28ATD-CD28CSD-CD3zS SD expressing Jurkat NFAT reporter CAR-T cells. All antibody variants show clear specificity and activation on RMF-pulsed T2 cells over no activation on unpulsed T2 cells, however none of the antibody variants is superior to the parental binder 11D06/D43.

Example 11

Described herein is a Jurkat NFAT reporter CAR-T cell assay with a sorted pool of anti-P329G-ds-Fab-CD28ATD-CD28CSD-CD3zSSD expressing Jurkat NFAT CAR-T cells as reporter cells. The reporter cells bind the HLA-A2/WT1-peptide binders in IgG format with P329G LALA mutation, which in turn do recognize the tested HLA-A2/WT1 peptides (RMF or VLD, respectively) to different degrees.

The four different antibodies in question (33F05 (SEQ ID NOs: 96 and 97), 11D06 (SEQ ID NOs: 98 and 99), 33H09 (SEQ ID NOs: 100 and 101) and 5E11 (SEQ ID NOs: 102 and 103), respectively) were present at 10 nM. Prior to co-incubation with the Jurkat NFAT reporter cells and the IgGs, T2 cells were pulsed with RMF- or VLD-peptide, respectively, like described in Example 9, or left without peptide. Jurkat NFAT reporter cells and target cells were coincubated for 6 hours at 37° C. at an E:T-ratio of 5:1 with 10000 to 2000 cells in 20 μl per well of a 384-well plate (white flat clear bottom 384 well plate (Greiner bio-one)) and an IgG concentration of 10 nM, followed by addition of 6 μl per well of ONE-Glo™ luciferase substrate (Promega) and direct measurement of luminescence using a TECAN infinite M1000Pro plate reader. The activation of CAR-NFAT-signaling from triplicate measurements of the respective experimental settings is expressed as column graph (FIG. 16) with error bars indicating standard deviations. Comparison of signals on RMF-peptide (target) vs. signal on VLD-peptide (off-target) helps to assess specificity of activation of the respective binder. Signal strength on T2 cells without peptide indicates unspecific binding for candidate binders 35F05 and 05E11. Candidate binders 33H09 and 11D06 prove specific and selective for HLA-A2/WT1-peptide RMF, only, since the signal on off-target peptide VLD is low, especially with regard to the assessed background ("T2 w/o peptide", effector cells "without T2" and effector and target cell co-incubation "without addition of IgG").

Exemplary Sequences

TABLE 2

Anti-P329G-ds-scFv amino acid sequences:

| Construct | Amino acid sequence | SEQ ID NO |
| --- | --- | --- |
| Anti-P329G CDR H1 Kabat | RYWMN | 1 |
| Anti-P329G CDR H2 Kabat | EITPDSSTINYTPSLKD | 2 |
| Anti-P329G CDR H3 Kabat | PYDYGAWFAS | 3 |
| Anti-P329G CDR L1 Kabat | RSSTGAVTTSNYAN | 4 |
| Anti-P329G CDR L2 Kabat | GTNKRAP | 5 |
| Anti-P329G CDR L3 Kabat | ALWYSNHWV | 6 |
| Anti-P329G-ds-scFv-CD28ATD-CD28CSD-CD3zSSD fusion pETR17096 | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQIEDEAIY FCALWYSNHWVFGCGTKLTVLGGGGSFWVLVVVGGV LACYSLLVTVAFIIFWVRSKRSRLLHSDYMNMTPRRPG PTRKHYQPYAPPRDFAAYRSRVKFSRSADAPAYQQGQ NQLYNELNLGRREEYDVLDKRRGRDPEMGGKPRRKNP QEGLYNELQKDKMAEAYSEIGMKGERRRGKGHDGLY QGLSTATKDTYDALHMQALPPR | 7 |
| Anti-P329G-dsVH | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSA | 8 |
| Anti-P329G-ds VL | QAVVTQESALTTSPGETVTLTCRSSTGAVTTSNYANWV QEKPDHLFTGLIGGTNKRAPGVPARFSGSLIGDKAALTI TGAQIEDEAIYFCALWYSNHWVFGCGTKLTVL | 9 |
| Anti-P329G-ds-scFv | EVKLLESGGGLVQPGGSLKLSCAASGFDFSRYWMNWV RQAPGKCLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQIEDEAIY FCALWYSNHWVFGCGTKLTVL | 10 |
| CD28ATD | FWVLVVVGGVLACYSLLVTVAFIIFWV | 11 |
| CD28CSD | RSKRSRLLHSDYMNMTPRRPGPTRKHYQPYAPPRDFA AYRS | 12 |

TABLE 2-continued

Anti-P329G-ds-scFv amino acid sequences:

| Construct | Amino acid sequence | SEQ ID NO |
|---|---|---|
| CD3zSSD | RVKFSRSADAPAYQQGQNQLYNELNLGRREEYDVLDK RRGRDPEMGGKPRRKNPQEGLYNELQKDKMAEAYSEI GMKGERRRGKGHDGLYQGLSTATKDTYDALHMQALP PR | 13 |
| CD28ATD-CD28CSD-CD3zSSD | FWVLVVVGGVLACYSLLVTVAFIIFWVRSKRSRLLHSD YMNMTPRRPGPTRKHYQPYAPPRDFAAYRSRVKFSRS ADAPAYQQGQNQLYNELNLGRREEYDVLDKRRGRDP EMGGKPRRKNPQEGLYNELQKDKMAEAYSEIGMKGE RRRGKGHDGLYQGLSTATKDTYDALHMQALPPR | 14 |
| eGFP | VSKGEELFTGVVPILVELDGDVNGHKFSVSGEGEGDAT YGKLTLKFICTTGKLPVPWPTLVTTLTYGVQCFSRYPD HMKQHDFFKSAMPEGYVQERTIFFKDDGNYKTRAEVK FEGDTLVNRIELKGIDFKEDGNILGHKLEYNYNSHNVYI MADKQKNGIKVNFKIRHNIEDGSVQLADHYQQNTPIG DGPVLLPDNHYLSTQSALSKDPNEKRDHMVLLEFVTA AGITLGMDELYK | 15 |
| (G4S)4 linker | GGGGSGGGGSGGGGSGGGGS | 16 |
| G4S linker | GGGGS | 17 |
| T2A linker | GEGRGSLLTCGDVEENPGP | 18 |

TABLE 3 anti-P329G-ds-scFv DNA sequences:

| Construct | DNA sequence | SEQ ID NO |
|---|---|---|
| Anti-P329G-ds-scFv-CD28ATD-CD28CSD-CD3zSSD fusion pETR17096 | ATGGGATGGAGCTGTATCATCCTCTTCTTGGTAGCAA CAGCTACCGGTGTGCATTCCGAGGTGAAGCTGCTGG AGAGCGGCGGCGGCCTGGTGCAGCCCGGCGGCAGCC TGAAGCTGAGCTGCGCCGCCAGCGGCTTCGACTTCA GCAGGTACTGGATGAACTGGGTGAGGCAGGCCCCCG GCAAGTGTCTGGAGTGGATCGGCGAGATCACCCCCG ACAGCAGCACCATCAACTACACCCCCAGCCTGAAGG ACAAGTTCATCATCAGCAGGGACAACGCCAAGAACA CCCTGTACCTGCAGATGATCAAGGTGAGGAGCGAGG ACACCGCCCTGTACTACTGCGTGAGGCCCTACGACT ACGGCGCCTGGTTCGCCAGCTGGGGCCAGGGCACCC TGGTGACCGTGAGCGCCGGAGGGGGCGGAAGTGGTG GCGGGGGAAGCGGCGGGGGTGGCAGCGGAGGGGGC GGATCTCAGGCCGTGGTGACCCAGGAGAGCGCCCTG ACCACCAGCCCCGGCGAGACCGTGACCCTGACCTGC AGGAGCAGCACCGGCGCCGTGACCACCAGCAACTAC GCCAACTGGGTGCAGGAGAAGCCCGACCACCTGTTC ACCGGCCTGATCGGCGGCACCAACAAGAGGGCCCCC GGCGTGCCCGCCAGGTTCAGCGGCAGCCTGATCGGC GACAAGGCCGCCCTGACCATCACCGGCGCCCAGACC GAGGACGAGGCCATCTACTTCTGCGCCCTGTGGTAC AGCAACCACTGGGTGTTCGGCTGTGGCACCAAGCTG ACCGTGCTGGGAGGGGGCGGATCCTTCTGGGTGCTG GTGGTGGTGGGCGGCGTGCTGGCCTGCTACAGCCTG CTGGTGACCGTGGCCTTCATCATCTTCTGGGTGAGGA GCAAGAGGAGCAGGCTGCTGCACAGCGACTACATGA ACATGACCCCCAGGAGGCCCGGCCCCACCAGGAAGC ACTACCAGCCCTACGCCCCCCCCAGGGACTTCGCCG CCTACAGGAGCAGGGTGAAGTTCAGCAGGAGCGCCG ACGCCCCCGCCTACCAGCAGGGCCAGAACCAGCTGT ATAACGAGCTGAACCTGGGCAGGAGGGAGGAGTAC GACGTGCTGGACAAGAGGAGGGGCAGGGACCCCGA GATGGGCGGCAAGCCCAGGAGGAAGAACCCCCAGG AGGGCCTGTATAACGAGCTGCAGAAGGACAAGATGG CCGAGGCCTACAGCGAGATCGGCATGAAGGGCGAG AGGAGGAGGGGCAAGGGCCACGACGGCCTGTACCA GGGCCTGAGCACCGCCACCAAGGACACCTACGACGC CCTGCACATGCAGGCCCTGCCCCCCAGG | 19 |
| Anti-P329G-ds VH | GAGGTGAAGCTGCTGGAGAGCGGCGGCGGCCTGGTG CAGCCCGGCGGCAGCCTGAAGCTGAGCTGCGCCGCC | 20 |

TABLE 3-continued anti-P329G-ds-scFv DNA sequences:

| Construct | DNA sequence | SEQ ID NO |
|---|---|---|
| | AGCGGCTTCGACTTCAGCAGGTACTGGATGAACTGG<br>GTGAGGCAGGCCCCCGGCAAGTGTCTGGAGTGGATC<br>GGCGAGATCACCCCCGACAGCAGCACCATCAACTAC<br>ACCCCCAGCCTGAAGGACAAGTTCATCATCAGCAGG<br>GACAACGCCAAGAACACCCTGTACCTGCAGATGATC<br>AAGGTGAGGAGCGAGGACACCGCCCTGTACTACTGC<br>GTGAGGCCCTACGACTACGGCGCCTGGTTCGCCAGC<br>TGGGGCCAGGGCACCCTGGTGACCGTGAGCGCC | |
| Anti-P329G-ds VL | CAGGCCGTGGTGACCCAGGAGAGCGCCCTGACCACC<br>AGCCCCGGCGAGACCGTGACCCTGACCTGCAGGAGC<br>AGCACCGGCGCCGTGACCACCAGCAACTACGCCAAC<br>TGGGTGCAGGAGAAGCCCGACCACCTGTTCACCGGC<br>CTGATCGGCGGCACCAACAAGAGGGCCCCCGGCGTG<br>CCCGCCAGGTTCAGCGGCAGCCTGATCGGCGACAAG<br>GCCGCCCTGACCATCACCGGCGCCCAGACCGAGGAC<br>GAGGCCATCTACTTCTGCGCCCTGTGGTACAGCAACC<br>ACTGGGTGTTCGGCTGTGGCACCAAGCTGACCGTGC<br>TG | 21 |
| Anti-P329G-ds-scFv | ATGGGATGGAGCTGTATCATCCTCTTCTTGGTAGCAA<br>CAGCTACCGGTGTGCATTCCGAGGTGAAGCTGCTGG<br>AGAGCGGCGGCGCCCTGGTGCAGCCCGGCGGCAGCC<br>TGAAGCTGAGCTGCGCCGCCAGCGGCTTCGACTTCA<br>GCAGGTACTGGATGAACTGGGTGAGGCAGGCCCCCG<br>GCAAGTGTCTGGAGTGGATCGGCGAGATCACCCCCG<br>ACAGCAGCACCATCAACTACACCCCCAGCCTGAAGG<br>ACAAGTTCATCATCAGCAGGGACAACGCCAAGAACA<br>CCCTGTACCTGCAGATGATCAAGGTGAGGAGCGAGG<br>ACACCGCCCTGTACTACTGCGTGAGGCCCTACGACT<br>ACGGCGCCTGGTTCGCCAGCTGGGGCCAGGGCACCC<br>TGGTGACCGTGAGCGCCGGAGGGGGCGGAAGTGGTG<br>GCGGGGGAAGCGGCGGGGGTGGCAGCGGAGGGGGC<br>GGATCTCAGGCCGTGGTGACCCAGGAGAGCGCCCTG<br>ACCACCAGCCCCGGCGAGACCGTGACCCTGACCTGC<br>AGGAGCAGCACCGGCGCCGTGACCACCAGCAACTAC<br>GCCAACTGGGTGCAGGAGAAGCCCGACCACCTGTTC<br>ACCGGCCTGATCGGCGGCACCAACAAGAGGGCCCCC<br>GGCGTGCCCGCCAGGTTCAGCGGCAGCCTGATCGGC<br>GACAAGGCCGCCCTGACCATCACCGGCGCCCAGACC<br>GAGGACGAGGCCATCTACTTCTGCGCCCTGTGGTAC<br>AGCAACCACTGGGTGTTCGGCTGTGGCACCAAGCTG<br>ACCGTGC | 22 |
| IRES EV71, internal ribosomal entry side | CCCGAAGTAACTTAGAAGCTGTAAATCAACGATCAA<br>TAGCAGGTGTGGCACACCAGTCATACCTTGATCAAG<br>CACTTCTGTTTCCCCGGACTGAGTATCAATAGGCTGC<br>TCGCGCGGCTGAAGGAGAAAACGTTCGTTACCCGAC<br>CAACTACTTCGAGAAGCTTAGTACCACCATGAACGA<br>GGCAGGGTGTTTCGCTCAGCACAACCCCAGTGTAGA<br>TCAGGCTGATGAGTCACTGCAACCCCCATGGGCGAC<br>CATGGCAGTGGCTGCGTTGGCGGCCTGCCCATGGAG<br>AAATCCATGGGACGCTCTAATTCTGACATGGTGTGA<br>AGTGCCTATTGAGCTAACTGGTAGTCCTCCGGCCCCT<br>GATTGCGGCTAATCCTAACTGCGGAGCACATGCTCA<br>CAAACCAGTGGGTGGTGTGTCGTAACGGGCAACTCT<br>GCAGCGGAACCGACTACTTTGGGTGTCCGTGTTTCCT<br>TTTATTCCTATATTGGCTGCTTATGGTGACAATCAAA<br>AAGTTGTTACCATATAGCTATTGGATTGGCCATCCGG<br>TGTGCAACAGGGCAACTGTTTACCTATTTATTGGTTT<br>TGTACCATTATCACTGAAGTCTGTGATCACTCTCAAA<br>TTCATTTTGACCCTCAACACAATCAAAC | 23 |
| CD28ATD | TTTTGGGTGCTGGTGGTGGTTGGTGGAGTCCTGGCTT<br>GCTATAGCTTGCTAGTAACAGTGGCCTTTATTATTTT<br>CTGGGTG | 24 |
| CD28CSD | AGGAGTAAGAGGAGCAGGCTCCTGCACAGTGACTAC<br>ATGAACATGACTCCCCGCCGCCCCGGGCCCACCCGC<br>AAGCATTACCAGCCCTATGCCCCACCACGCGACTTC<br>GCAGCCTATCGCTCC | 25 |
| CD3zSSD | AGAGTGAAGTTCAGCAGGAGCGCAGACGCCCCCGCG<br>TACCAGCAGGGCCAGAACCAGCTCTATAACGAGCTC<br>AATCTAGGACGAAGAGAGGAGTACGATGTTTTGGAC<br>AAGAGACGTGGCCGGGACCCTGAGATGGGGGGAAA | 26 |

TABLE 3-continued anti-P329G-ds-scFv DNA sequences:

| Construct | DNA sequence | SEQ ID NO |
|---|---|---|
| | GCCGAGAAGGAAGAACCCTCAGGAAGGCCTGTACA<br>ATGAACTGCAGAAAGATAAGATGGCGGAGGCCTACA<br>GTGAGATTGGGATGAAAGGCGAGCGCCGGAGGGGC<br>AAGGGGCACGATGGCCTTTACCAGGGTCTCAGTACA<br>GCCACCAAGGACACCTACGACGCCCTTCACATGCAG<br>GCCCTGCCCCCTCGC | |
| CD28ATD-CD28CSD-<br>CD3zSSD | TTCTGGGTGCTGGTGGTGGTGGGCGGCGTGCTGGCCT<br>GCTACAGCCTGCTGGTGACCGTGGCCTTCATCATCTT<br>CTGGGTGAGGAGCAAGAGGAGCAGGCTGCTGCACA<br>GCGACTACATGAACATGACCCCCAGGAGGCCCGGCC<br>CCACCAGGAAGCACTACCAGCCCTACGCCCCCCCCA<br>GGGACTTCGCCGCCTACAGGAGCAGGGTGAAGTTCA<br>GCAGGAGCGCCGACGCCCCCGCCTACCAGCAGGGCC<br>AGAACCAGCTGTATAACGAGCTGAACCTGGGCAGGA<br>GGGAGGAGTACGACGTGCTGGACAAGAGGAGGGGC<br>AGGGACCCCGAGATGGGCGGCAAGCCCAGGAGGAA<br>GAACCCCCAGGAGGGCCTGTATAACGAGCTGCAGAA<br>GGACAAGATGGCCGAGGCCTACAGCGAGATCGGCAT<br>GAAGGGCGAGAGGAGGAGGGGCAAGGGCCACGACG<br>GCCTGTACCAGGGCCTGAGCACCGCCACCAAGGACA<br>CCTACGACGCCCTGCACATGCAGGCCCTGCCCCCCA<br>GG | 27 |
| T2A element | TCCGGAGAGGGCAGAGGAAGTCTTCTAACATGCGGT<br>GACGTGGAGGAGAATCCCGGCCCTAGG | 28 |
| eGFP | GTGAGCAAGGGCGAGGAGCTGTTCACCGGGGTGGTG<br>CCCATCCTGGTCGAGCTGGACGGCGACGTAAACGGC<br>CACAAGTTCAGCGTGTCCGGCGAGGGCGAGGGCGAT<br>GCCACCTACGGCAAGCTGACCCTGAAGTTCATCTGC<br>ACCACCGGCAAGCTGCCCGTGCCCTGGCCCACCCTC<br>GTGACCACCCTGACCTACGGCGTGCAGTGCTTCAGC<br>CGCTACCCCGACCACATGAAGCAGCACGACTTCTTC<br>AAGTCCGCCATGCCCGAAGGCTACGTCCAGGAGCGC<br>ACCATCTTCTTCAAGGACGACGGCAACTACAAGACC<br>CGCGCCGAGGTGAAGTTCGAGGGCGACACCCTGGTG<br>AACCGCATCGAGCTGAAGGGCATCGACTTCAAGGAG<br>GACGGCAACATCCTGGGGCACAAGCTGGAGTACAAC<br>TACAACAGCCACAACGTCTATATCATGGCCGACAAG<br>CAGAAGAACGGCATCAAGGTGAACTTCAAGATCCGC<br>CACAACATCGAGGACGGCAGCGTGCAGCTCGCCGAC<br>CACTACCAGCAGAACACCCCCATCGGCGACGGCCCC<br>GTGCTGCTGCCCGACAACCACTACCTGAGCACCCAG<br>TCCGCCCTGAGCAAAGACCCCAACGAGAAGCGCGAT<br>CACATGGTCCTGCTGGAGTTCGTGACCGCCGCCGGG<br>ATCACTCTCGGCATGGACGAGCTGTACAAGTGA | 29 |
| Anti-P329G-ds-scFv-<br>CD28ATD-CD28CSD-<br>CD3zSSD-<br>eGFP fusion pETR17096 | ATGGGATGGAGCTGTATCATCCTCTTCTTGGTAGCAA<br>CAGCTACCGGTGTGCATTCCGAGGTGAAGCTGCTGG<br>AGAGCGGCGGCGGCCTGGTGCAGCCCGGCGGCAGCC<br>TGAAGCTGAGCTGCGCCGCCAGCGGCTTCGACTTCA<br>GCAGGTACTGGATGAACTGGGTGAGGCAGGCCCCCG<br>GCAAGTGTCTGGAGTGGATCGGCGAGATCACCCCCG<br>ACAGCAGCACCATCAACTACACCCCCAGCCTGAAGG<br>ACAAGTTCATCATCAGCAGGGACAACGCCAAGAACA<br>CCCTGTACCTGCAGATGATCAAGGTGAGGAGCGAGG<br>ACACCGCCCTGTACTACTGCGTGAGGGCCCTACGACT<br>ACGGCGCCTGGTTCGCCAGCTGGGGCCAGGGCACCC<br>TGGTGACCGTGAGCGCCGGAGGGGGCGGAAGTGGTG<br>GCGGGGGAAGCGGCGGGGGTGGCAGCGAGGGGGC<br>GGATCTCAGGCCGTGGTGACCCAGGAGAGCGCCCTG<br>ACCACCAGCCCCGGCGAGACCGTGACCCTGACCTGC<br>AGGAGCAGCACCGGCGCCGTGACCACCAGCAACTAC<br>GCCAACTGGGTGCAGGAGAAGCCCGACCACCTGTTC<br>ACCGGCCTGATCGGCGGCACCAACAAGAGGGCCCCC<br>GGCGTGCCCGCCAGGTTCAGCGGCAGCCTGATCGGC<br>GACAAGGCCGCCCTGACCATCACCGGCGCCCAGACC<br>GAGGACGAGGCCATCTACTTCTGCGCCCTGTGGTAC<br>AGCAACCACTGGGTGTTCGGCTGTGGCACCAAGCTG<br>ACCGTGCTGGGAGGGGGCGGATCCTTCTGGGTGCTG<br>GTGGTGGTGGGCGGCGTGCTGGCCTGCTACAGCCTG<br>CTGGTGACCGTGGCCTTCATCATCTTCTGGGTGAGGA<br>GCAAGAGGAGCAGGCTGCTGCACAGCGACTACATGA<br>ACATGACCCCCAGGAGGCCCGGCCCCACCAGGAAGC<br>ACTACCAGCCCTACGCCCCCCCCAGGGACTTCGCCG | 30 |

TABLE 3-continued anti-P329G-ds-scFv DNA sequences:

| Construct | DNA sequence | SEQ ID NO |
|---|---|---|
| | CCTACAGGAGCAGGGTGAAGTTCAGCAGGAGCGCCG<br>ACGCCCCCGCCTACCAGCAGGGCCAGAACCAGCTGT<br>ATAACGAGCTGAACCTGGGCAGGAGGGAGGAGTAC<br>GACGTGCTGGACAAGAGGAGGGGCAGGGACCCCGA<br>GATGGGCGGCAAGCCCAGGAGGAAGAACCCCCAGG<br>AGGGCCTGTATAACGAGCTGCAGAAGGACAAGATGG<br>CCGAGGCCTACAGCGAGATCGGCATGAAGGGCGAG<br>AGGAGGAGGGGCAAGGGCCACGACGGCCTGTACCA<br>GGGCCTGAGCACCGCCACCAAGGACACCTACGACGC<br>CCTGCACATGCAGGCCCTGCCCCCCAGGTCCGGAGA<br>GGGCAGAGGAAGTCTTCTAACATGCGGTGACGTGGA<br>GGAGAATCCCGGCCCTAGGGTGAGCAAGGGCGAGG<br>AGCTGTTCACCGGGGTGGTGCCCATCCTGGTCGAGCT<br>GGACGGCGACGTAAACGGCCACAAGTTCAGCGTGTC<br>CGGCGAGGGCGAGGGCGATGCCACCTACGGCAAGCT<br>GACCCTGAAGTTCATCTGCACCACCGGCAAGCTGCC<br>CGTGCCCTGGCCCACCCTCGTGACCACCCTGACCTAC<br>GGCGTGCAGTGCTTCAGCCGCTACCCCGACCACATG<br>AAGCAGCACGACTTCTTCAAGTCCGCCATGCCCGAA<br>GGCTACGTCCAGGAGCGCACCATCTTCTTCAAGGAC<br>GACGGCAACTACAAGACCCGCGCCGAGGTGAAGTTC<br>GAGGGCGACACCCTGGTGAACCGCATCGAGCTGAAG<br>GGCATCGACTTCAAGGAGGACGGCAACATCCTGGGG<br>CACAAGCTGGAGTACAACTACAACAGCCACAACGTC<br>TATATCATGGCCGACAAGCAGAAGAACGGCATCAAG<br>GTGAACTTCAAGATCCGCCACAACATCGAGGACGGC<br>AGCGTGCAGCTCGCCGACCACTACCAGCAGAACACC<br>CCCATCGGCGACGGCCCCGTGCTGCTGCCCGACAAC<br>CACTACCTGAGCACCCAGTCCGCCCTGAGCAAAGAC<br>CCCAACGAGAAGCGCGATCACATGGTCCTGCTGGAG<br>TTCGTGACCGCCGCCGGGATCACTCTCGGCATGGAC<br>GAGCTGTACAAGTGA | |

TABLE 4

Anti-P329G-scFv amino acid sequences:

| Construct | Amino acid sequence | SEQ ID NO |
|---|---|---|
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-scFv-<br>CD28ATD-CD28CSD-<br>CD3zSSD fusion | EVKLLESGGGLVQPGGSLKLSCAASGFDFSRYWMNWV<br>RQAPGKGLEWIGEITPDSSTINYTPSLKDKFIISRDNAKN<br>TLYLQMIKVRSEDTALYYCVRPYDYGAWFASWGQGT<br>LVTVSAGGGGSGGGGSGGGGSGGGGSQAVVTQESALT<br>TSPGETVTLTCRSSTGAVTTSNYANWVQEKPDHLFTGL<br>IGGTNKRAPGVPARFSGSLIGDKAALTITGAQTEDEAIY<br>FCALWYSNHWVFGGGTKLTVLGGGGSFWVLVVVGGV<br>LACYSLLVTVAFIIFWVRSKRSRLLHSDYMNMTPRRPG<br>PTRKHYQPYAPPRDFAAYRSRVKFSRSADAPAYQQGQ<br>NQLYNELNLGRREEYDVLDKRRGRDPEMGGKPRRKNP<br>QEGLYNELQKDKMAEAYSEIGMKGERRRGKGHDGLY<br>QGLSTATKDTYDALHMQALPPR | 31 |
| Anti-P329G VH | EVKLLESGGGLVQPGGSLKLSCAASGFDFSRYWMNWV<br>RQAPGKGLEWIGEITPDSSTINYTPSLKDKFIISRDNAKN<br>TLYLQMIKVRSEDTALYYCVRPYDYGAWFASWGQGT<br>LVTVSA | 32 |
| Anti-P329G VL | QAVVTQESALTTSPGETVTLTCRSSTGAVTTSNYANWV<br>QEKPDHLFTGLIGGTNKRAPGVPARFSGSLIGDKAALTI<br>TGAQTEDEAIYFCALWYSNHWVFGGGTKLTVL | 33 |

TABLE 4-continued

Anti-P329G-scFv amino acid sequences:

| Construct | Amino acid sequence | SEQ ID NO |
|---|---|---|
| Anti-P329G-scFv | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSAGGGGSGGGGSGGGGSGGGGSQAVVTQESALT TSPGETVTLTCRSSTGAVTTSNYANWVQEKPDHLFTGL IGGTNKRAPGVPARFSGSLIGDKAALTITGAQTEDEAIY FCALWYSNHWVFGGGTKLTVL | 34 |
| CD28ATD | see Table 2 | 11 |
| CD28CSD | see Table 2 | 12 |
| CD3zSSD | see Table 2 | 13 |
| CD28ATD-CD28CDS-CD3zSSD | see Table 2 | 14 |
| eGFP | see Table 2 | 15 |
| (G4S)4 linker | see Table 2 | 16 |
| G4S linker | see Table 2 | 17 |
| T2A linker | see Table 2 | 18 |

TABLE 5

Anti-P329G-scFv DNA sequences:

| Construct | DNA sequence | SEQ ID NO |
|---|---|---|
| Anti-P329G-scFv-CD28ATD-CD28CSD-CD3zSSD fusion | ATGGGATGGAGCTGTATCATCCTCTTCTTGGTAGCAA CAGCTACCGGTGTGCATTCCGAGGTGAAGCTGCTGG AGAGCGGCGGCGGCCTGGTGCAGCCCGGCGGCAGCC TGAAGCTGAGCTGCGCCGCCAGCGGCTTCGACTTCA GCAGGTACTGGATGAACTGGGTGAGGCAGGCCCCCG GCAAGGGTCTGGAGTGGATCGGCGAGATCACCCCCG ACAGCAGCACCATCAACTACACCCCCAGCCTGAAGG ACAAGTTCATCATCAGCAGGGACAACGCCAAGAACA CCCTGTACCTGCAGATGATCAAGGTGAGGAGCGAGG ACACCGCCCTGTACTACTGCGTGAGGCCCTACGACT ACGGCGCCTGGTTCGCCAGCTGGGGCCAGGGCACCC TGGTGACCGTGAGCGCCGGAGGGGGCGGAAGTGGTG GCGGGGGAAGCGGCGGGGGTGGCAGCGGAGGGGGC GGATCTCAGGCCGTGGTGACCCAGGAGAGCGCCCTG ACCACCAGCCCCGGCGAGACCGTGACCCTGACCTGC AGGAGCAGCACCGGCGCCGTGACCACCAGCAACTAC GCCAACTGGGTGCAGGAGAAGCCCGACCACCTGTTC ACCGGCCTGATCGGCGGCACCAACAAGAGGGCCCCC GGCGTGCCCGCCAGGTTCAGCGGCAGCCTGATCGGC GACAAGGCCGCCCTGACCATCACCGGCGCCCAGACC GAGGACGAGGCCATCTACTTCTGCGCCCTGTGGTAC AGCAACCACTGGGTGTTCGGCGGTGGCACCAAGCTG ACCGTGCTGGGAGGGGGCGGATCCTTCTGGGTGCTG GTGGTGGTGGGCGGCGTGCTGGCCTGCTACAGCCTG CTGGTGACCGTGGCCTTCATCATCTTCTGGGTGAGGA GCAAGAGGAGCAGGCTGCTGCACAGCGACTACATGA ACATGACCCCCAGGAGGCCCGGCCCCACCAGGAAGC ACTACCAGCCCTACGCCCCCCCCAGGGACTTCGCCG CCTACAGGAGCAGGGTGAAGTTCAGCAGGAGCGCCG ACGCCCCCGCCTACCAGCAGGGCCAGAACCAGCTGT ATAACGAGCTGAACCTGGGCAGGAGGGAGGAGTAC GACGTGCTGGACAAGAGGAGGGGCAGGGACCCCGA GATGGGCGGCAAGCCCAGGAGGAAGAACCCCCAGG AGGGCCTGTATAACGAGCTGCAGAAGGACAAGATGG CCGAGGCCTACAGCGAGATCGGCATGAAGGGCGAG AGGAGGAGGGGCAAGGGCCACGACGGCCTGTACCA GGGCCTGAGCACCGCCACCAAGGACACCTACGACGC CCTGCACATGCAGGCCCTGCCCCCCAGG | 35 |
| Anti-P329G VH | GAGGTGAAGCTGCTGGAGAGCGGCGGCGGCCTGGTG CAGCCCGGCGGCAGCCTGAAGCTGAGCTGCGCCGCC AGCGGCTTCGACTTCAGCAGGTACTGGATGAACTGG | 36 |

TABLE 5-continued

Anti-P329G-scFv DNA sequences:

| Construct | DNA sequence | SEQ ID NO |
|---|---|---|
| | GTGAGGCAGGCCCCCGGCAAGGGTCTGGAGTGGATC<br>GGCGAGATCACCCCCGACAGCAGCACCATCAACTAC<br>ACCCCCAGCCTGAAGGACAAGTTCATCATCAGCAGG<br>GACAACGCCAAGAACACCCTGTACCTGCAGATGATC<br>AAGGTGAGGAGCGAGGACACCGCCCTGTACTACTGC<br>GTGAGGCCCTACGACTACGGCGCCTGGTTCGCCAGC<br>TGGGGCCAGGGCACCCTGGTGACCGTGAGCGCC | |
| Anti-P329G VL | CAGGCCGTGGTGACCCAGGAGAGCGCCCTGACCACC<br>AGCCCCGGCGAGACCGTGACCCTGACCTGCAGGAGC<br>AGCACCGGCGCCGTGACCACCAGCAACTACGCCAAC<br>TGGGTGCAGGAGAAGCCCGACCACCTGTTCACCGGC<br>CTGATCGGCGGCACCAACAAGAGGGCCCCCGGCGTG<br>CCCGCCAGGTTCAGCGGCAGCCTGATCGGCGACAAG<br>GCCGCCCTGACCATCACCGGCGCCCAGACCGAGGAC<br>GAGGCCATCTACTTCTGCGCCCTGTGGTACAGCAACC<br>ACTGGGTGTTCGGCGGTGGCACCAAGCTGACCGTGGC<br>TG | 37 |
| CD28ATD | see Table 3 | 24 |
| CD28CSD | see Table 3 | 25 |
| CD3zSSD | see Table 3 | 26 |
| CD28ATD-CD28CSD-<br>CD3zSSD | see Table 3 | 27 |
| T2A element | see Table 3 | 28 |
| eGFP | see Table 3 | 29 |
| Anti-P329G-scFv-<br>CD28ATD-CD28CSD-<br>CD3zSSD-<br>eGFP fusion | ATGGGATGGAGCTGTATCATCCTCTTCTTGGTAGCAA<br>CAGCTACCGGTGTGCATTCCGAGGTGAAGCTGCTGG<br>AGAGCGGCGGCGGCCTGGTGCAGCCCGGCGGCAGCC<br>TGAAGCTGAGCTGCGCCGCCAGCGGCTTCGACTTCA<br>GCAGGTACTGGATGAACTGGGTGAGGCAGGCCCCCG<br>GCAAGGGTCTGGAGTGGATCGGCGAGATCACCCCCG<br>ACAGCAGCACCATCAACTACACCCCCAGCCTGAAGG<br>ACAAGTTCATCATCAGCAGGGACAACGCCAAGAACA<br>CCCTGTACCTGCAGATGATCAAGGTGAGGAGCGAGG<br>ACACCGCCCTGTACTACTGCGTGAGGCCCTACGACT<br>ACGGCGCCTGGTTCGCCAGCTGGGGCCAGGGCACCC<br>TGGTGACCGTGAGCGCCGAGGGGGCGGAAGTGGTG<br>GCGGGGGAAGCGGCGGGGGTGGCAGCGGAGGGGGC<br>GGATCTCAGGCCGTGGTGACCCAGGAGAGCGCCCTG<br>ACCACCAGCCCCGGCGAGACCGTGACCCTGACCTGC<br>AGGAGCAGCACCGGCGCCGTGACCACCAGCAACTAC<br>GCCAACTGGGTGCAGGAGAAGCCCGACCACCTGTTC<br>ACCGGCCTGATCGGCGGCACCAACAAGAGGGCCCCC<br>GGCGTGCCCGCCAGGTTCAGCGGCAGCCTGATCGGC<br>GACAAGGCCGCCCTGACCATCACCGGCGCCCAGACC<br>GAGGACGAGGCCATCTACTTCTGCGCCCTGTGGTAC<br>AGCAACCACTGGGTGTTCGGCGGTGGCACCAAGCTG<br>ACCGTGCTGGGAGGGGCGGATCCTTCTGGGTGCTG<br>GTGGTGGTGGGCGGCGTGCTGGCCTGCTACAGCCTG<br>CTGGTGACCGTGGCCTTCATCATCTTCTGGGTGAGGA<br>GCAAGAGGAGCAGGCTGCTGCACAGCGACTACATGA<br>ACATGACCCCCAGGAGGCCCGGCCCCACCAGGAAGC<br>ACTACCAGCCCTACGCCCCCCCCAGGGACTTCGCCG<br>CCTACAGGAGCAGGGTGAAGTTCAGCAGGAGCGCCG<br>ACGCCCCCGCCTACCAGCAGGGCCAGAACCAGCTGT<br>ATAACGAGCTGAACCTGGGCAGGAGGGAGGAGTAC<br>GACGTGCTGGACAAGAGGAGGGGCAGGGACCCCGA<br>GATGGGCGGCAAGCCCAGGAGGAAGAACCCCCAGG<br>AGGGCCTGTATAACGAGCTGCAGAAGGACAAGATGG<br>CCGAGGCCTACAGCGAGATCGGCATGAAGGGCGAG<br>AGGAGGAGGGGCAAGGGCCACGACGGCCTGTACCA<br>GGGCCTGAGCACCGCCACCAAGGACACCTACGACGC<br>CCTGCACATGCAGGCCCTGCCCCCAGGTCCGGAGA<br>GGGCAGAGGAAGTCTTCTAACATGCGGTGACGTGGA<br>GGAGAATCCCGGCCCTAGGGTGAGCAAGGGCGAGG<br>AGCTGTTCACCGGGGTGGTGCCCATCCTGGTCGAGCT<br>GGACGGCGACGTAAACGGCCACAAGTTCAGCGTGTC<br>CGGCGAGGGCGAGGGCGATGCCACCTACGGCAAGCT<br>GACCCTGAAGTTCATCTGCACCACCGGCAAGCTGCC | 38 |

TABLE 5-continued

| Anti-P329G-scFv DNA sequences: | | |
|---|---|---|
| Construct | DNA sequence | SEQ ID NO |
| | CGTGCCCTGGCCCACCCTCGTGACCACCCTGACCTAC<br>GGCGTGCAGTGCTTCAGCCGCTACCCCGACCACATG<br>AAGCAGCACGACTTCTTCAAGTCCGCCATGCCCGAA<br>GGCTACGTCCAGGAGCGCACCATCTTCTTCAAGGAC<br>GACGGCAACTACAAGACCCGCGCCGAGGTGAAGTTC<br>GAGGGCGACACCCTGGTGAACCGCATCGAGCTGAAG<br>GGCATCGACTTCAAGGAGGACGGCAACATCCTGGGG<br>CACAAGCTGGAGTACAACTACAACAGCCACAACGTC<br>TATATCATGGCCGACAAGCAGAAGAACGGCATCAAG<br>GTGAACTTCAAGATCCGCCACAACATCGAGGACGGC<br>AGCGTGCAGCTCGCCGACCACTACCAGCAGAACACC<br>CCCATCGGCGACGGCCCCGTGCTGCTGCCCGACAAC<br>CACTACCTGAGCACCCAGTCCGCCCTGAGCAAAGAC<br>CCCAACGAGAAGCGCGATCACATGGTCCTGCTGGAG<br>TTCGTGACCGCCGCCGGGATCACTCTCGGCATGGAC<br>GAGCTGTACAAGTGA | |

TABLE 6

| Anti-P329G-ds-Fab amino acid sequences | | |
|---|---|---|
| Construct | Amino acid sequence | SEQ ID NO |
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-ds-Fab-heavy chain-CD28ATD-CD28CSD-CD3zSSD fusion pETR17100 | EVKLLESGGGLVQPGGSLKLSCAASGFDFSRYWMNWV<br>RQAPGKCLEWIGEITPDSSTINYTPSLKDKFIISRDNAKN<br>TLYLQMIKVRSEDTALYYCVRPYDYGAWFASWGQGT<br>LVTVSAASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCGGGGS<br>FWVLVVVGGVLACYSLLVTVAFIIFWVRSKRSRLLHSD<br>YMNMTPRRPGPTRKHYQPYAPPRDFAAYRSRVKFSRS<br>ADAPAYQQGQNQLYNELNLGRREEYDVLDKRRGRDP<br>EMGGKPRRKNPQEGLYNELQKDKMAEAYSEIGMKGE<br>RRRGKGHDGLYQGLSTATKDTYDALHMQALPPR | 39 |
| Anti-P329G-ds-Fab heavy chain | EVKLLESGGGLVQPGGSLKLSCAASGFDFSRYWMNWV<br>RQAPGKCLEWIGEITPDSSTINYTPSLKDKFIISRDNAKN<br>TLYLQMIKVRSEDTALYYCVRPYDYGAWFASWGQGT<br>LVTVSAASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSC | 40 |
| Anti-P329G-ds-Fab light chain | QAVVTQESALTTSPGETVTLTCRSSTGAVTTSNYANWV<br>QEKPDHLFTGLIGGTNKRAPGVPARFSGSLIGDKAALTI<br>TGAQIEDEAIYFCALWYSNHWVFGCGTKLTVLRTVAA<br>PSVFIFPPSDEQLKSGTASVVCLLNNFYPREAKVQWKV<br>DNALQSGNSQESVTEQDSKDSTYSLSSTLTLSKADYEK<br>HKVYACEVTHQGLSSPVTKSFNRGEC | 41 |
| Anti-P329G-ds VL | see Table 2 | 9 |
| CL | RTVAAPSVFIFPPSDEQLKSGTASVVCLLNNFYPREAKV<br>QWKVDNALQSGNSQESVTEQDSKDSTYSLSSTLTLSKA<br>DYEKHKVYACEVTHQGLSSPVTKSFNRGEC | 42 |

TABLE 6-continued

Anti-P329G-ds-Fab amino acid sequences

| Construct | Amino acid sequence | SEQ ID NO |
|---|---|---|
| Anti-P329G-ds VH | see Table 2 | 8 |
| CH1 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC | 43 |
| CD28ATD-CD28CSD-CD3zSSD | see Table 2 | 14 |

TABLE 7

Anti-P329G-ds-Fab DNA sequences:

| Construct | DNA Sequenz | SEQ ID NO |
|---|---|---|
| Anti-P329G-ds-Fab-heavy chain-CD28ATD-CD28CSD-CD3zSSD fusion pETR17100 | ATGGGATGGAGCTGTATCATCCTCTTCTTGGTAGCAA CAGCTACGGGTGTGCATTCCCAGGCCGTGGTGACCC AGGAGAGCGCCCTGACCACCCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA CCGGCGCCCAGACCGAGGACGAGGCCATCTACTTCT GCGCCCTGTGGTACAGCAACCACTGGGTGTTCGGCT GTGGCACCAAGCTGACCGTGCTGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG AAGGTGGATAACGCCCTCCAATCGGGTAACTCCCAG GAGAGTGTCACAGAGCAGGACAGCAAGGACAGCAC CTACAGCCTCAGCAGCACCCTGACGCTGAGCAAAGC AGACTACGAGAAACACAAAGTCTACGCCTGCGAAGT CACCCATCAGGGCCTGAGCTCGCCCGTCACAAAGAG CTTCAACAGGGGAGAGTGTTAGGAATTCCCCGAAGT AACTTAGAAGCTGTAAATCAACGATCAATAGCAGGT GTGGCACACCAGTCATACCTTGATCAAGCACTTCTGT TTCCCCGGACTGAGTATCAATAGGCTGCTCGCGCGG CTGAAGGAGAAAACGTTCGTTACCCGACCAACTACT TCGAGAAGCTTAGTACCACCATGAACGAGGCAGGGT GTTTCGCTCAGCACAACCCCAGTGTAGATCAGGCTG ATGAGTCACTGCAACCCCCATGGGCGACCATGGCAG TGGCTGCGTTGGCGGCCTGCCCATGGAGAAATCCAT GGGACGCTCTAATTCTGACATGGTGTGAAGTGCCTAT TGAGCTAACTGGTAGTCCTCCGGCCCCTGATTGCGGC TAATCCTAACTGCGGAGCACATGCTCACAAACCAGT GGGTGGTGTGTCGTAACGGGCAACTCTGCAGCGGAA CCGACTACTTTGGGTGTCCGTGTTTCCTTTTATTCCTA TATTGGCTGCTTATGGTGACAATCAAAAAGTTGTTAC CATATAGCTATTGGATTGGCCATCCGGTGTGCAACA GGGCAACTGTTTACCTATTTATTGGTTTTGTACCATT ATCACTGAAGTCTGTGATCACTCTCAAATTCATTTTG ACCCTCAACACAATCAAACGCCACCATGGGATGGAG CTGTATCATCCTCTTCTTGGTAGCAACAGCTACCGGT GTGCACTCCGAGGTGAAGCTGCTGGAGAGCGGCGGC GGCCTGGTGCAGCCCGGCGGCAGCCTGAAGCTGAGC TGCGCCGCCAGCGGCTTCGACTTCAGCAGGTACTGG ATGAACTGGGTGAGGCAGGCCCCCGGCAAGTGTCTG GAGTGGATCGGCGAGATCACCCCCGACAGCAGCACC ATCAACTACACCCCCAGCCTGAAGGACAAGTTCATC ATCAGCAGGGACAACGCCAAGAACACCCTGTACCTG CAGATGATCAAGGTGAGGAGCGAGGACACCGCCCTG TACTACTGCGTGAGGCCCTACGACTACGGCGCCTGG TTCGCCAGCTGGGGCCAGGGCACCCTGGTGACCGTG AGCGCCGCTAGCACCAAGGGCCCCTCCGTGTTCCCC CTGGCCCCCAGCAGCAAGAGCACCAGCGGCGGCACA GCCGCTCTGGGCTGCCTGGTCAAGGACTACTTCCCCG AGCCCGTGACCGTGTCCTGGAACAGCGGAGCCCTGA CCTCCGGCGTGCACACCTTCCCCGCCGTGCTGCAGAG TTCTGGCCTGTATAGCCTGAGCAGCGTGGTCACCGTG CCTTCTAGCAGCCTGGGCACCCAGACCTACATCTGCA ACGTGAACCACAAGCCCAGCAACACCAAGGTGGACA | 44 |

TABLE 7-continued

Anti-P329G-ds-Fab DNA sequences:

| Construct | DNA Sequenz | SEQ ID NO |
|---|---|---|
| | AGAAGGTGGAGCCCAAGAGCTGCGGAGGGGCGGA<br>TCCTTCTGGGTGCTGGTGGTGGTGGGCGGCGTGCTGG<br>CCTGCTACAGCCTGCTGGTGACCGTGGCCTTCATCAT<br>CTTCTGGGTGAGGAGCAAGAGGAGCAGGCTGCTGCA<br>CAGCGACTACATGAACATGACCCCCAGGAGGCCCGG<br>CCCCACCAGGAAGCACTACCAGCCCTACGCCCCCCC<br>CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CCAGG | |
| Anti-P329G-ds VL | see Table 3 | 21 |
| CL | CGTACGGTGGCTGCACCATCTGTCTTCATCTTCCCGC<br>CATCTGATGAGCAGTTGAAATCTGGAACTGCCTCTGT<br>TGTGTGCCTGCTGAATAACTTCTATCCCAGAGAGGCC<br>AAAGTACAGTGGAAGGTGGATAACGCCCTCCAATCG<br>GGTAACTCCCAGGAGAGTGTCACAGAGCAGGACAGC<br>AAGGACAGCACCTACAGCCTCAGCAGCACCCTGACG<br>CTGAGCAAAGCAGACTACGAGAAACACAAAGTCTAC<br>GCCTGCGAAGTCACCCATCAGGGCCTGAGCTCGCCC<br>GTCACAAAGAGCTTCAACAGGGGAGAGTGTTAG | 45 |
| Anti-P329G-ds VH | see Table 3 | 20 |
| CH1 | GCTAGCACCAAGGGCCCCTCCGTGTTCCCCCTGGCCC<br>CCAGCAGCAAGAGCACCAGCGGCGGCACAGCCGCTC<br>TGGGCTGCCTGGTCAAGGACTACTTCCCCGAGCCCGT<br>GACCGTGTCCTGGAACAGCGGAGCCCTGACCTCCGG<br>CGTGCACACCTTCCCCGCCGTGCTGCAGAGTTCTGGC<br>CTGTATAGCCTGAGCAGCGTGGTCACCGTGCCTTCTA<br>GCAGCCTGGGCACCCAGACCTACATCTGCAACGTGA<br>ACCACAAGCCCAGCAACACCAAGGTGGACAAGAAG<br>GTGGAGCCCAAGAGCTGC | 46 |
| CD28ATD-CD28CSD-<br>CD3zSSD | see Table 3 | 27 |
| Anti-P329G-ds-Fab-<br>heavy chain-CD28ATD-<br>CD28CSD-<br>CD3ZSSD-<br>eGFP fusion pETR17100 | ATGGGATGGAGCTGTATCATCCTCTTCTTGGTAGCAA<br>CAGCTACGGGTGTGCATTCCCAGGCCGTGGTGACCC<br>AGGAGAGCGCCCTGACCACCAGCCCCGGCGAGACCG<br>TGACCCTGACCTGCAGGAGCAGCACCGGCGCCGTGA<br>CCACCAGCAACTACGCCAACTGGGTGCAGGAGAAGC<br>CCGACCACCTGTTCACCGGCCTGATCGGCGGCACCA<br>ACAAGAGGGCCCCCGGCGTGCCCGCCAGGTTCAGCG<br>GCAGCCTGATCGGCGACAAGGCCGCCCTGACCATCA<br>CCGGCGCCCAGACCGAGGACGAGGCCATCTACTTCT<br>GCGCCCTGTGGTACAGCAACCACTGGGTGTTCGGCT<br>GTGGCACCAAGCTGACCGTGCTGCGTACGGTGGCTG<br>CACCATCTGTCTTCATCTTCCCGCCATCTGATGAGCA<br>GTTGAAATCTGGAACTGCCTCTGTTGTGTGCCTGCTG<br>AATAACTTCTATCCCAGAGAGGCCAAAGTACAGTGG<br>AAGGTGGATAACGCCCTCCAATCGGGTAACTCCCAG<br>GAGAGTGTCACAGAGCAGGACAGCAAGGACAGCAC<br>CTACAGCCTCAGCAGCACCCTGACGCTGAGCAAAGC<br>AGACTACGAGAAACACAAAGTCTACGCCTGCGAAGT<br>CACCCATCAGGGCCTGAGCTCGCCCGTCACAAAGAG<br>CTTCAACAGGGGAGAGTGTTAGGAATTCCCCGAAGT<br>AACTTAGAAGCTGTAAATCAACGATCAATAGCAGGT<br>GTGGCACACCAGTCATACCTTGATCAAGCACTTCTGT<br>TTCCCCGGACTGAGTATCAATAGGCTGCTCGCGCGG<br>CTGAAGGAGAAAACGTTCGTTACCCGACCAACTACT<br>TCGAGAAGCTTAGTACCACCATGAACGAGGCAGGGT<br>GTTTCGCTCAGCACAACCCCAGTGTAGATCAGGCTG<br>ATGAGTCACTGCAACCCCCATGGGCGACCATGGCAG<br>TGGCTGCGTTGGCGGCCTGCCCATGGAGAAATCCAT<br>GGGACGCTCTAATTCTGACATGGTGTGAAGTGCCTAT<br>TGAGCTAACTGGTAGTCCTCCGGCCCCTGATTGCGGC<br>TAATCCTAACTGCGGAGCACATGCTCACAAACCAGT | 47 |

TABLE 7-continued

Anti-P329G-ds-Fab DNA sequences:

| Construct | DNA Sequenz | SEQ ID NO |
|---|---|---|
| | GGGTGGTGTGTCGTAACGGGCAACTCTGCAGCGGAA<br>CCGACTACTTTGGGTGTCCGTGTTTCCTTTTATTCCTA<br>TATTGGCTGCTTATGGTGACAATCAAAAAGTTGTTAC<br>CATATAGCTATTGGATTGGCCATCCGGTGTGCAACA<br>GGGCAACTGTTTACCTATTTATTGGTTTTGTACCATT<br>ATCACTGAAGTCTGTGATCACTCTCAAATTCATTTTG<br>ACCCTCAACACAATCAAACGCCACCATGGGATGGAG<br>CTGTATCATCCTCTTCTTGGTAGCAACAGCTACCGGT<br>GTGCACTCCGAGGTGAAGCTGCTGGAGAGCGGCGGC<br>GGCCTGGTGCAGCCCGGCGGCAGCCTGAAGCTGAGC<br>TGCGCCGCCAGCGGCTTCGACTTCAGCAGGTACTGG<br>ATGAACTGGGTGAGGCAGGCCCCCGGCAAGTGTCTG<br>GAGTGGATCGGCGAGATCACCCCCGACAGCAGCACC<br>ATCAACTACACCCCCAGCCTGAAGGACAAGTTCATC<br>ATCAGCAGGGACAACGCCAAGAACACCCTGTACCTG<br>CAGATGATCAAGGTGAGGAGCGAGGACACCGCCCTG<br>TACTACTGCGTGAGGCCCTACGACTACGGCGCCTGG<br>TTCGCCAGCTGGGGCCAGGGCACCCTGGTGACCGTG<br>AGCGCCGCTAGCACCAAGGGCCCCTCCGTGTTCCCC<br>CTGGCCCCCAGCAGCAAGAGCACCAGCGGCGGCACA<br>GCCGCTCTGGGCTGCCTGGTCAAGGACTACTTCCCCG<br>AGCCCGTGACCGTGTCCTGGAACAGCGGAGCCCTGA<br>CCTCCGGCGTGCACACCTTCCCCGCCGTGCTGCAGAG<br>TTCTGGCCTGTATAGCCTGAGCAGCGTGGTCACCGTG<br>CCTTCTAGCAGCCTGGGCACCCAGACCTACATCTGCA<br>ACGTGAACCACAAGCCCAGCAACACCAAGGTGGACA<br>AGAAGGTGGAGCCCAAGAGCTGCGGAGGGGGCGGA<br>TCCTTCTGGGTGCTGGTGGTGGTGGGCGGCGTGCTGG<br>CCTGCTACAGCCTGCTGGTGACCGTGGCCTTCATCAT<br>CTTCTGGGTGAGGAGCAAGAGGAGCAGGCTGCTGCA<br>CAGCGACTACATGAACATGACCCCCAGGAGGCCCGG<br>CCCCACCAGGAAGCACTACCAGCCCTACGCCCCCCC<br>CAGGGACTTCGCCGCCTACAGGAGCAGGGTGAAGTT<br>CAGCAGGAGCGCCGACGCCCCCGCCTACCAGCAGGG<br>CCAGAACCAGCTGTATAACGAGCTGAACCTGGGCAG<br>GAGGGAGGAGTACGACGTGCTGGACAAGAGGAGGG<br>GCAGGGACCCCGAGATGGGCGGCAAGCCCAGGAGG<br>AAGAACCCCCAGGAGGGCCTGTATAACGAGCTGCAG<br>AAGGACAAGATGGCCGAGGCCTACAGCGAGATCGG<br>CATGAAGGGCGAGAGGAGGAGGGGCAAGGGCCACG<br>ACGGCCTGTACCAGGGCCTGAGCACCGCCACCAAGG<br>ACACCTACGACGCCCTGCACATGCAGGCCCTGCCCC<br>CCAGGTCCGGAGAGGGCAGAGGAAGTCTTCTAACAT<br>GCGGTGACGTGGAGGAGAATCCCGGCCCTAGGGTGA<br>GCAAGGGCGAGGAGCTGTTCACCGGGGTGGTGCCCA<br>TCCTGGTCGAGCTGGACGGCGACGTAAACGGCCACA<br>AGTTCAGCGTGTCCGGCGAGGGCGAGGGCGATGCCA<br>CCTACGGCAAGCTGACCCTGAAGTTCATCTGCACCA<br>CCGGCAAGCTGCCCGTGCCCTGGCCCACCCTCGTGA<br>CCACCCTGACCTACGGCGTGCAGTGCTTCAGCCGCTA<br>CCCCGACCACATGAAGCAGCACGACTTCTTCAAGTC<br>CGCCATGCCCGAAGGCTACGTCCAGGAGCGCACCAT<br>CTTCTTCAAGGACGACGGCAACTACAAGACCCGCGC<br>CGAGGTGAAGTTCGAGGGCGACACCCTGGTGAACCG<br>CATCGAGCTGAAGGGCATCGACTTCAAGGAGGACGG<br>CAACATCCTGGGGCACAAGCTGGAGTACAACTACAA<br>CAGCCACAACGTCTATATCATGGCCGACAAGCAGAA<br>GAACGGCATCAAGGTGAACTTCAAGATCCGCCACAA<br>CATCGAGGACGGCAGCGTGCAGCTCGCCGACCACTA<br>CCAGCAGAACACCCCCATCGGCGACGGCCCCGTGCT<br>GCTGCCCGACAACCACTACCTGAGCACCCAGTCCGC<br>CCTGAGCAAAGACCCCAACGAGAAGCGCGATCACAT<br>GGTCCTGCTGGAGTTCGTGACCGCCGCCGGGATCAC<br>TCTCGGCATGGACGAGCTGTACAAGTGA | |

TABLE 8

Anti-P329G-Fab amino acid sequences:

| Construct | Amino acid sequence | SEQ ID NO |
|---|---|---|
| Anti-P329G CDR H1 Kabat | see Table 2 | 1 |
| Anti-P329G CDR H2 Kabat | see Table 2 | 2 |
| Anti-P329G CDR H3 Kabat | see Table 2 | 3 |
| Anti-P329G CDR L1 Kabat | see Table 2 | 4 |
| Anti-P329G CDR L2 Kabat | see Table 2 | 5 |
| Anti-P329G CDR L3 Kabat | see Table 2 | 6 |
| Anti-P329G-Fab-heavy chain-CD28ATD-CD28CSD-CD3zSSD fusion pETR17594 | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCGGGGS FWVLVVVGGVLACYSLLVTVAFIIFWVRSKRSRLLHSD YMNMTPRRPGPTRKHYQPYAPPRDFAAYRSRVKFSRS ADAPAYQQGQNQLYNELNLGRREEYDVLDKRRGRDP EMGGKPRRKNPQEGLYNELQKDKMAEAYSEIGMKGE RRRGKGHDGLYQGLSTATKDTYDALHMQALPPR | 48 |
| Anti-P329G-Fab heavy chain | EVKLLESGGGLVQPGGSLKLSCAASGFDFSRYWMNWV RQAPGKGLEWIGEITPDSSTINYTPSLKDKFIISRDNAKN TLYLQMIKVRSEDTALYYCVRPYDYGAWFASWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSC | 49 |
| Anti-P329G-Fab light chain | QAVVTQESALTTSPGETVTLTCRSSTGAVTTSNYANWV QEKPDHLFTGLIGGTNKRAPGVPARFSGSLIGDKAALTI TGAQTEDEAIYFCALWYSNHWVFGGGTKLTVLRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC | 50 |
| Anti-P329G VL | see Table 4 | 33 |
| CL | see Table 6 | 42 |
| Anti-P329G VH | see Table 4 | 32 |
| CH1 | see Table 6 | 43 |
| CD28ATD-CD28CSD-CD3zSSD | see Table 2 | 14 |

TABLE 9

Anti-P329G-Fab DNA sequences:

| Construct | DNA Sequenz | SEQ ID NO |
|---|---|---|
| Anti-P329G-Fab-heavy chain-CD28ATD-CD28CSD-CD3zSSD fusion pETR17594 | ATGGGATGGAGCTGTATCATCCTCTTCTTGGTAGCAA CAGCTACGGGTGTGCATTCCCAGGCCGTGGTGACCC AGGAGAGCGCCCTGACCACCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA CCGGCGCCCAGACCGAGGACGAGGCCATCTACTTCT GCGCCCTGTGGTACAGCAACCACTGGGTGTTCGGCG GTGGCACCAAGCTGACCGTGCTGCGTACGGTGGCTG CACCATCTGTCTTCATCTTCCCGCCATCTGATGAGCA GTTGAAATCTGGAACTGCCTCTGTTGTGTGCCTGCTG AATAACTTCTATCCCAGAGAGGCCAAAGTACAGTGG AAGGTGGATAACGCCCTCCAATCGGGTAACTCCCAG GAGAGTGTCACAGAGCAGGACAGCAAGGACAGCAC CTACAGCCTCAGCAGCACCCTGACGCTGAGCAAAGC AGACTACGAGAAACACAAAGTCTACGCCTGCGAAGT | 51 |

TABLE 9-continued

Anti-P329G-Fab DNA sequences:

| Construct | DNA Sequenz | SEQ ID NO |
|---|---|---|
| | CACCCATCAGGGCCTGAGCTCGCCCGTCACAAAGAG CTTCAACAGGGGAGAGTGTTAGGAATTCCCCGAAGT AACTTAGAAGCTGTAAATCAACGATCAATAGCAGGT GTGGCACACCAGTCATACCTTGATCAAGCACTTCTGT TTCCCCGGACTGAGTATCAATAGGCTGCTCGCGCGG CTGAAGGAGAAAACGTTCGTTACCCGACCAACTACT TCGAGAAGCTTAGTACCACCATGAACGAGGCAGGGT GTTTCGCTCAGCACAACCCCAGTGTAGATCAGGCTG ATGAGTCACTGCAACCCCCATGGGCGACCATGGCAG TGGCTGCGTTGGCGGCCTGCCCATGGAGAAATCCAT GGGACGCTCTAATTCTGACATGGTGTGAAGTGCCTAT TGAGCTAACTGGTAGTCCTCCGGCCCCTGATTGCGGC TAATCCTAACTGCGGAGCACATGCTCACAAACCAGT GGGTGGTGTGTCGTAACGGGCAACTCTGCAGCGGAA CCGACTACTTTGGGTGTCCGTGTTTCCTTTTATTCCTA TATTGGCTGCTTATGGTGACAATCAAAAAGTTGTTAC CATATAGCTATTGGATTGGCCATCCGGTGTGCAACA GGGCAACTGTTTACCTATTTATTGGTTTTGTACCATT ATCACTGAAGTCTGTGATCACTCTCAAATTCATTTTG ACCCTCAACACAATCAAACGCCACCATGGGATGGAG CTGTATCATCCTCTTCTTGGTAGCAACAGCTACCGGT GTGCACTCCGAGGTGAAGCTGCTGGAGAGCGGCGGC GGCCTGGTGCAGCCCGGCGGCAGCCTGAAGCTGAGC TGCGCCGCCAGCGGCTTCGACTTCAGCAGGTACTGG ATGAACTGGGTGAGGCAGGCCCCCGGCAAGGGTCTG GAGTGGATCGGCGAGATCACCCCCGACAGCAGCACC ATCAACTACACCCCCAGCCTGAAGGACAAGTTCATC ATCAGCAGGGACAACGCCAAGAACACCCTGTACCTG CAGATGATCAAGGTGAGGAGCGAGGACACCGCCCTG TACTACTGCGTGAGGCCCTACGACTACGGCGCCTGG TTCGCCAGCTGGGGCCAGGGCACCCTGGTGACCGTG AGCGCCGCTAGCACCAAGGGCCCCTCCGTGTTCCCC CTGGCCCCCAGCAGCAAGAGCACCAGCGGCGGCACA GCCGCTCTGGGCTGCCTGGTCAAGGACTACTTCCCCG AGCCCGTGACCGTGTCCTGGAACAGCGGAGCCCTGA CCTCCGGCGTGCACACCTTCCCCGCCGTGCTGCAGAG TTCTGGCCTGTATAGCCTGAGCAGCGTGGTCACCGTG CCTTCTAGCAGCCTGGGCACCCAGACCTACATCTGCA ACGTGAACCACAAGCCCAGCAACACCAAGGTGGACA AGAAGGTGGAGCCCAAGAGCTGCGGAGGGGCGGA TCCTTCTGGGTGCTGGTGGTGGTGGCGGCGTGCTGG CCTGCTACAGCCTGCTGGTGACCGTGGCCTTCATCAT CTTCTGGGTGAGGAGCAAGAGGAGCAGGCTGCTGCA CAGCGACTACATGAACATGACCCCCAGGAGGCCCGG CCCCACCAGGAAGCACTACCAGCCCTACGCCCCCCC CAGGGACTTCGCCGCCTACAGGAGCAGGGTGAAGTT CAGCAGGAGCGCCGACGCCCCCGCCTACCAGCAGGG CCAGAACCAGCTGTATAACGAGCTGAACCTGGGCAG GAGGGAGGAGTACGACGTGCTGGACAAGAGGAGGG GCAGGGACCCCGAGATGGGCGGCAAGCCCAGGAGG AAGAACCCCCAGGAGGGCCTGTATAACGAGCTGCAG AAGGACAAGATGGCCGAGGCCTACAGCGAGATCGG CATGAAGGGCGAGAGGAGGAGGGGCAAGGGCCACG ACGGCCTGTACCAGGGCCTGAGCACCGCCACCAAGG ACACCTACGACGCCCTGCACATGCAGGCCCTGCCCC CAGG | |
| Anti-P329G VL | see Table 5 | 37 |
| CL | see Table 7 | 45 |
| Anti-P329G VH | see Table 5 | 36 |
| CH1 | see Table 7 | 46 |
| CD28ATD-CD28CSD-CD3zSSD | see Table 3 | 27 |
| Anti-P329G-Fab-heavy chain-CD28ATD-CD28CSD-CD3zSSD-eGFP fusion pETR17594 | ATGGGATGGAGCTGTATCATCCTCTTCTTGGTAGCAA CAGCTACGGGTGTGCATTCCCAGGCCGTGGTGACCC AGGAGAGCGCCCTGACCACCAGCCCCGGCGAGACCG TGACCCTGACCTGCAGGAGCAGCACCGGCGCCGTGA CCACCAGCAACTACGCCAACTGGGTGCAGGAGAAGC CCGACCACCTGTTCACCGGCCTGATCGGCGGCACCA ACAAGAGGGCCCCCGGCGTGCCCGCCAGGTTCAGCG GCAGCCTGATCGGCGACAAGGCCGCCCTGACCATCA | 52 |

TABLE 9-continued

Anti-P329G-Fab DNA sequences:

| Construct | DNA Sequenz | SEQ ID NO |
|---|---|---|
| | CCGGCGCCCAGACCGAGGACGAGGCCATCTACTTCT | |
| | GCGCCCTGTGGTACAGCAACCACTGGGTGTTCGGCG | |
| | GTGGCACCAAGCTGACCGTGCTGCGTACGGTGGCTG | |
| | CACCATCTGTCTTCATCTTCCCGCCATCTGATGAGCA | |
| | GTTGAAATCTGGAACTGCCTCTGTTGTGTGCCTGCTG | |
| | AATAACTTCTATCCCAGAGAGGCCAAAGTACAGTGG | |
| | AAGGTGGATAACGCCCTCCAATCGGGTAACTCCCAG | |
| | GAGAGTGTCACAGAGCAGGACAGCAAGGACAGCAC | |
| | CTACAGCCTCAGCAGCACCCTGACGCTGAGCAAAGC | |
| | AGACTACGAGAAACACAAAGTCTACGCCTGCGAAGT | |
| | CACCCATCAGGGCCTGAGCTCGCCCGTCACAAAGAG | |
| | CTTCAACAGGGGAGAGTGTTAGGAATTCCCCGAAGT | |
| | AACTTAGAAGCTGTAAATCAACGATCAATAGCAGGT | |
| | GTGGCACACCAGTCATACCTTGATCAAGCACTTCTGT | |
| | TTCCCCGGACTGAGTATCAATAGGCTGCTCGCGCGG | |
| | CTGAAGGAGAAAACGTTCGTTACCCGACCAACTACT | |
| | TCGAGAAGCTTAGTACCACCATGAACGAGGCAGGGT | |
| | GTTTCGCTCAGCACAACCCCAGTGTAGATCAGGCTG | |
| | ATGAGTCACTGCAACCCCCATGGGCGACCATGGCAG | |
| | TGGCTGCGTTGGCGGCCTGCCCATGGAGAAATCCAT | |
| | GGGACGCTCTAATTCTGACATGGTGTGAAGTGCCTAT | |
| | TGAGCTAACTGGTAGTCCTCCGGCCCTGATTGCGGC | |
| | TAATCCTAACTGCGGAGCACATGCTCACAAACCAGT | |
| | GGGTGGTGTGTCGTAACGGGCAACTCTGCAGCGGAA | |
| | CCGACTACTTTGGGTGTCCGTGTTTCCTTTTATTCCTA | |
| | TATTGGCTGCTTATGGTGACAATCAAAAAGTTGTTAC | |
| | CATATAGCTATTGGATTGGCCATCCGGTGTGCAACA | |
| | GGGCAACTGTTTACCTATTTATTGGTTTTGTACCATT | |
| | ATCACTGAAGTCTGTGATCACTCTCAAATTCATTTTG | |
| | ACCCTCAACACAATCAAACGCCACCATGGGATGGAG | |
| | CTGTATCATCCTCTTCTTGGTAGCAACAGCTACCGGT | |
| | GTGCACTCCGAGGTGAAGCTGCTGGAGAGCGGCGGC | |
| | GGCCTGGTGCAGCCCGGCGGCAGCCTGAAGCTGAGC | |
| | TGCGCCGCCAGCGGCTTCGACTTCAGCAGGTACTGG | |
| | ATGAACTGGGTGAGGCAGGCCCCCGGCAAGGGTCTG | |
| | GAGTGGATCGGCGAGATCACCCCCGACAGCAGCACC | |
| | ATCAACTACACCCCCAGCCTGAAGGACAAGTTCATC | |
| | ATCAGCAGGGACAACGCCAAGAACACCCTGTACCTG | |
| | CAGATGATCAAGGTGAGGAGCGAGGACACCGCCCTG | |
| | TACTACTGCGTGAGGGCCCTACGACTACGGCGCCTGG | |
| | TTCGCCAGCTGGGGCCAGGGCACCCTGGTGACCGTG | |
| | AGCGCCGCTAGCACCAAGGGCCCCTCCGTGTTCCCC | |
| | CTGGCCCCCAGCAGCAAGAGCACCAGCGGCGGCACA | |
| | GCCGCTCTGGGCTGCCTGGTCAAGGACTACTTCCCCG | |
| | AGCCCGTGACCGTGTCCTGGAACAGCGGGAGCCCTGA | |
| | CCTCCGGCGTGCACACCTTCCCCGCCGTGCTGCAGAG | |
| | TTCTGGCCTGTATAGCCTGAGCAGCGTGGTCACCGTG | |
| | CCTTCTAGCAGCCTGGGCACCCAGACCTACATCTGCA | |
| | ACGTGAACCACAAGCCCAGCAACACCAAGGTGGACA | |
| | AGAAGGTGGAGCCCAAGAGCTGCGGAGGGGCGGA | |
| | TCCTTCTGGGTGCTGGTGGTGGTGGGCGGCGTGCTGG | |
| | CCTGCTACAGCCTGCTGGTGACCGTGGCCTTCATCAT | |
| | CTTCTGGGTGAGGAGCAAGAGGAGCAGGCTGCTGCA | |
| | CAGCGACTACATGAACATGACCCCCAGGAGGCCCGG | |
| | CCCCACCAGGAAGCACTACCAGCCCTACGCCCCCCC | |
| | CAGGGACTTCGCCGCCTACAGGAGCAGGGTGAAGTT | |
| | CAGCAGGAGCGCCGACGCCCCCGCCTACCAGCAGGG | |
| | CCAGAACCAGCTGTATAACGAGCTGAACCTGGGCAG | |
| | GAGGGAGGAGTACGACGTGCTGGACAAGAGGAGGG | |
| | GCAGGGACCCCGAGATGGGCGGCAAGCCCAGGAGG | |
| | AAGAACCCCCAGGAGGGCCTGTATAACGAGCTGCAG | |
| | AAGGACAAGATGGCCGAGGCCTACAGCGAGATCGG | |
| | CATGAAGGGCGAGAGGAGGAGGGGCAAGGGCCACG | |
| | ACGGCCTGTACCAGGGCCTGAGCACCGCCACCAAGG | |
| | ACACCTACGACGCCCTGCACATGCAGGCCCTGCCCC | |
| | CCAGGTCCGGAGAGGGCAGAGGAAGTCTTCTAACAT | |
| | GCGGTGACGTGGAGGAGAATCCCGGCCCTAGGGTGA | |
| | GCAAGGGCGAGGAGCTGTTCACCGGGGTGGTGCCCA | |
| | TCCTGGTCGAGCTGGACGGCGACGTAAACGGCCACA | |
| | AGTTCAGCGTGTCCGGCGAGGGCGAGGGCGATGCCA | |
| | CCTACGGCAAGCTGACCCTGAAGTTCATCTGCACCA | |
| | CCGGCAAGCTGCCCGTGCCCTGGCCCACCCTCGTGA | |
| | CCACCCTGACCTACGGCGTGCAGTGCTTCAGCCGCTA | |
| | CCCCGACCACATGAAGCAGCACGACTTCTTCAAGTC | |
| | CGCCATGCCCGAAGGCTACGTCCAGGAGCGCACCAT | |
| | CTTCTTCAAGGACGACGGCAACTACAAGACCCGCGC | |

TABLE 9-continued

Anti-P329G-Fab DNA sequences:

| Construct | DNA Sequenz | SEQ ID NO |
|---|---|---|
| | CGAGGTGAAGTTCGAGGGCGACACCCTGGTGAACCG<br>CATCGAGCTGAAGGGCATCGACTTCAAGGAGGACGG<br>CAACATCCTGGGGCACAAGCTGGAGTACAACTACAA<br>CAGCCACAACGTCTATATCATGGCCGACAAGCAGAA<br>GAACGGCATCAAGGTGAACTTCAAGATCCGCCACAA<br>CATCGAGGACGGCAGCGTGCAGCTCGCCGACCACTA<br>CCAGCAGAACACCCCCATCGGCGACGGCCCCGTGCT<br>GCTGCCCGACAACCACTACCTGAGCACCCAGTCCGC<br>CCTGAGCAAAGACCCCAACGAGAAGCGCGATCACAT<br>GGTCCTGCTGGAGTTCGTGACCGCCGCCGGGATCAC<br>TCTCGGCATGGACGAGCTGTACAAGTGA | |

TABLE 10

Anti-AAA-scFv amino acid sequences

| Construct | Amino acid sequence | SEQ ID NO |
|---|---|---|
| Anti-AAA CDR H1 Kabat | SYGMS | 53 |
| Anti-AAA CDR H2 Kabat | SSGGSY | 54 |
| Anti-AAA CDR H3 Kabat | LGMITTGYAMDY | 55 |
| Anti-AAA CDR L1 Kabat | RSSQTIVHSTGHTYLE | 56 |
| Anti-AAA CDR L2 Kabat | KVSNRFS | 57 |
| Anti-AAA CDR L3 Kabat | FQGSHVPYT | 58 |
| Anti-AAA-scFv-CD28ATD-<br>CD28CSD-<br>CD3zSSD fusion | MNFGLSLVFLALILKGVQCEVQLVESGGDLVKPGGSLK<br>LSCAASGFTFSSYGMSWVRQTPDKRLEWVATISSGGSY<br>IYYPDSVKGRFTISRDNAKNTLYLQMSSLKSEDTAMYY<br>CARLGMITTGYAMDYWGQGTSVTVSSGGGGSGGGGS<br>GGGGSGGGGSDVLMTQTPLSLPVSLGDQASISCRSSQTI<br>VHSTGHTYLEWFLQKPGQSPKLLIYKVSNRFSGVPDRF<br>SGSGSGTDFTLKISRVEAEDLGVYYCFQGSHVPYTFGG<br>GTKLEIKGGGGSFWVLVVVGGVLACYSLLVTVAFIIFW<br>VRSKRSRLLHSDYMNMTPRRPGPTRKHYQPYAPPRDF<br>AAYRSRVKFSRSADAPAYQQGQNQLYNELNLGRREEY<br>DVLDKRRGRDPEMGGKPRRKNPQEGLYNELQKDKMA<br>EAYSEIGMKGERRRGKGHDGLYQGLSTATKDTYDALH<br>MQALPPR | 59 |
| Anti-AAA-scFv | MNFGLSLVFLALILKGVQCEVQLVESGGDLVKPGGSLK<br>LSCAASGFTFSSYGMSWVRQTPDKRLEWVATISSGGSY<br>IYYPDSVKGRFTISRDNAKNTLYLQMSSLKSEDTAMYY<br>CARLGMITTGYAMDYWGQGTSVTVSSGGGGSGGGGS<br>GGGGSGGGGSDVLMTQTPLSLPVSLGDQASISCRSSQTI<br>VHSTGHTYLEWFLQKPGQSPKLLIYKVSNRFSGVPDRF<br>SGSGSGTDFTLKISRVEAEDLGVYYCFQGSHVPYTFGG<br>GTKLEIK | 60 |
| Anti-AAA VH | MNFGLSLVFLALILKGVQCEVQLVESGGDLVKPGGSLK<br>LSCAASGFTFSSYGMSWVRQTPDKRLEWVATISSGGSY<br>IYYPDSVKGRFTISRDNAKNTLYLQMSSLKSEDTAMYY<br>CARLGMITTGYAMDYWGQGTSVTVSS | 61 |
| Anti-AAA VL | DVLMTQTPLSLPVSLGDQASISCRSSQTIVHSTGHTYLE<br>WFLQKPGQSPKLLIYKVSNRFSGVPDRFSGSGSGTDFTL<br>KISRVEAEDLGVYYCFQGSHVPYTFGGGTKLEIK | 62 |

TABLE 11

Anti-AAA-Fab amino acid sequences

| Construct | Protein Sequence | SEQ ID NO |
|---|---|---|
| Anti-AAA CDR H1 Kabat | see Table 10 | 53 |
| Anti-AAA CDR H2 Kabat | see Table 10 | 54 |
| Anti-AAA CDR H3 Kabat | see Table 10 | 55 |
| Anti-AAA CDR L1 Kabat | see Table 10 | 56 |
| Anti-AAA CDR L2 Kabat | see Table 10 | 57 |
| Anti-AAA CDR L3 Kabat | see Table 10 | 58 |
| Anti-AAA-Fab-heavy chain-CD28ATD-CD28CSD-CD3zSSD fusion | MNFGLSLVFLALILKGVQCEVQLVESGGDLVKPGGSLK LSCAASGFTFSSYGMSWVRQTPDKRLEWVATISSGGSY IYYPDSVKGRFTISRDNAKNTLYLQMSSLKSEDTAMYY CARLGMITTGYAMDYWGQGTSVTVSSASTKGPSVFPL APSSKSTSGGTAALGCLVKDYFPEPVTVSWNSGALTSG VHTFPAVLQSSGLYSLSSVVTVPSSSLGTQTYICNVNHK PSNTKVDKKVEPKSCGGGGSFWVLVVVGGVLACYSLL VTVAFIIFWVRSKRSRLLHSDYMNMTPRRPGPTRKHYQ PYAPPRDFAAYRSRVKFSRSADAPAYQQGQNQLYNEL NLGRREEYDVLDKRRGRDPEMGGKPRRKNPQEGLYNE LQKDKMAEAYSEIGMKGERRRGKGHDGLYQGLSTAT KDTYDALHMQALPPR | 63 |
| Anti-AAA-Fab heavy chain | MNFGLSLVFLALILKGVQCEVQLVESGGDLVKPGGSLK LSCAASGFTFSSYGMSWVRQTPDKRLEWVATISSGGSY IYYPDSVKGRFTISRDNAKNTLYLQMSSLKSEDTAMYY CARLGMITTGYAMDYWGQGTSVTVSSASTKGPSVFPL APSSKSTSGGTAALGCLVKDYFPEPVTVSWNSGALTSG VHTFPAVLQSSGLYSLSSVVTVPSSSLGTQTYICNVNHK PSNTKVDKKVEPKSC | 64 |
| Anti-AAA-Fab light chain | DVLMTQTPLSLPVSLGDQASISCRSSQTIVHSTGHTYLE WFLQKPGQSPKLLIYKVSNRFSGVPDRFSGSGSGTDFTL KISRVEAEDLGVYYCFQGSHVPYTFGGGTKLEIKRTVA APSVFIFPPSDEQLKSGTASVVCLLNNFYPREAKVQWK VDNALQSGNSQESVTEQDSKDSTYSLSSTLTLSKADYE KHKVYACEVTHQGLSSPVTKSFNRGEC | 65 |
| Anti-AAA VL | see Table 10 | 62 |
| CL | see Table 6 | 42 |
| Anti-AAA VH | see Table 10 | 61 |
| CH1 | see Table 6 | 43 |

TABLE 12

| Construct | Amino acid sequence | SEQ ID NO |
|---|---|---|
| Human CD3z | MKWKALFTAAILQAQLPITEAQSFGLLDPKLCYLLDGI LFIYGVILTALFLRVKFSRSADAPAYQQGQNQLYNELN LGRREEYDVLDKRRGRDPEMGGKPQRRKNPQEGLYNE LQKDKMAEAYSEIGMKGERRRGKGHDGLYQGLSTAT KDTYDALHMQALPPR | 66 |
| Human CD3z | ATGAAGTGGAAGGCGCTTTTCACCGCGGCCATCCTG CAGGCACAGTTGCCGATTACAGAGGCACAGAGCTTT GGCCTGCTGGATCCCAAACTCTGCTACCTGCTGGATG GAATCCTCTTCATCTATGGTGTCATTCTCACTGCCTT GTTCCTGAGAGTGAAGTTCAGCAGGAGCGCAGAGCC CCCCGCGTACCAGCAGGGCCAGAACCAGCTCTATAA CGAGCTCAATCTAGGACGAAGAGAGGAGTACGATGT TTTGGACAAGAGACGTGGCCGGGACCCTGAGATGGG GGGAAAGCCGAGAAGGAAGAACCCTCAGGAAGGCC TGTACAATGAACTGCAGAAAGATAAGATGGCGGAGG CCTACAGTGAGATTGGGATGAAAGGCGAGCGCCGGA GGGGCAAGGGGCACGATGGCCTTTACCAGGGTCTCA GTACAGCCACCAAGGACACCTACGACGCCCTTCACA TGCAGGCCCTGCCCCCTCGCTAA | 67 |

TABLE 12-continued

| Construct | Amino acid sequence | SEQ ID NO |
|---|---|---|
| Murine CD3z | MKWKVSVLACILHVRFPGAEAQSFGLLDPKLCYLLDGI LFIYGVIITALYLRAKFSRSAETAANLQDPNQLYNELNL GRREEYDVLEKKRARDPEMGGKQQRRRNPQEGVYNA LQKDKMAEAYSEIGTKGERRRGKGHDGLYQGLSTATK DTYDALHMQTLAPR | 68 |
| Murine CD3z | ATGAAGTGGAAAGTGTCTGTTCTCGCCTGCATCCTCC ACGTGCGGTTCCCAGGAGCAGAGGCACAGAGCTTTG GTCTGCTGGATCCCAAACTCTGCTACTTGCTAGATGG AATCCTCTTCATCTACGGAGTCATCATCACAGCCCTG TACCTGAGAGCAAAATTCAGCAGGAGTGCAGAGACT GCTGCCAACCTGCAGGACCCCAACCAGCTCTACAAT GAGCTCAATCTAGGGCGAAGAGAGGAATATGACGTC TTGGAGAAGAAGCGGGCTCGGGATCCAGAGATGGG AGGCAAACAGCAGAGGAGGAGGAACCCCCAGGAAG GCGTATACAATGCACTGCAGAAAGACAAGATGGCAG AAGCCTACAGTGAGATCGGCACAAAAGGCGAGAGG CGGAGAGGCAAGGGGCACGATGGCCTTTACCAGGGT CTCAGCACTGCCACCAAGGACACCTATGATGCCCTG CATATGCAGACCCTGGCCCCTCGCTAA | 69 |
| Human CD28 | ATGCTGCGCCTGCTGCTGGCGCTGAACCTGTTTCCGA GCATTCAGGTGACCGGCAACAAAATTCTGGTGAAAC AGAGCCCGATGCTGGTGGCGTATGATAACGCGGTGA ACCTGAGCTGCAAATATAGCTATAACCTGTTTAGCCG CGAATTTCGCGCGAGCCTGCATAAAGGCCTGGATAG CGCGGTGGAAGTGTGCGTGGTGTATGGCAACTATAG CCAGCAGCTGCAGGTGTATAGCAAAACCGGCTTTAA CTGCGATGGCAAACTGGGCAACGAAAGCGTGACCTT TTATCTGCAGAACCTGTATGTGAACCAGACCGATATT TATTTTTGCAAAATTGAAGTGATGTATCCGCCGCCGT ATCTGGATAACGAAAAAAGCAACGGCACCATTATTC ATGTGAAAGGCAAACATCTGTGCCCGAGCCCGCTGT TTCCGGGCCCGAGCAAACCGTTTTGGGTGCTGGTGGT GGTGGGCGGCGTGCTGGCGTGCTATAGCCTGCTGGT GACCGTGGCGTTTATTATTTTTTGGGTGCGCAGCAAA CGCAGCCGCCTGCTGCATAGCGATTATATGAACATG ACCCCGCGCCGCCCGGGCCCGACCCGCAAACATTAT CAGCCGTATGCGCCGCCGCGCGATTTTGCGGCGTATC GCAGC | 70 66 |
| Human CD28 | MLRLLLALNLFPSIQVTGNKILVKQSPMLVAYDNAVNL SCKYSYNLFSREFRASLHKGLDSAVEVCVVYGNYSQQ LQVYSKTGFNCDGKLGNESVTFYLQNLYVNQTDIYFC KIEVMYPPPYLDNEKSNGTIIHVKGKHLCPSPLFPGPSK PFWVLVVVGGVLACYSLLVTVAFIIFWVRSKRSRLLHS DYMNMTPRRPGPTRKHYQPYAPPRDFAAYRS | 71 |
| Murine CD28 | ATGACCCTGCGCCTGCTGTTTCTGGCGCTGAACTTTT TTAGCGTGCAGGTGACCGAAAACAAAATTCTGGTGA AACAGAGCCCGCTGCTGGTGGTGGATAGCAACGAAG TGAGCCTGAGCTGCCGCTATAGCTATAACCTGCTGGC GAAAGAATTTCGCGCGAGCCTGTATAAAGGCGTGAA CAGCGATGTGGAAGTGTGCGTGGGCAACGGCAACTT TACCTATCAGCCGCAGTTTCGCAGCAACGCGGAATTT AACTGCGATGGCGATTTTGATAACGAAACCGTGACC TTTCGCCTGTGGAACCTGCATGTGAACCATACCGATA TTTATTTTTGCAAAATTGAATTTATGTATCCGCCGCC GTATCTGGATAACGAACGCAGCAACGGCACCATTAT TCATATTAAAGAAAAACATCTGTGCCATACCCAGAG CAGCCCGAAACTGTTTTGGGCGCTGGTGGTGGTGGC GGGCGTGCTGTTTTGCTATGGCCTGCTGGTGACCGTG GCGCTGTGCGTGATTTGGACCAACAGCCGCCGCAAC CGCCTGCTGCAGAGCGATTATATGAACATGACCCCG CGCCGCCCGGGCCTGACCCGCAAACCGTATCAGCCG TATGCGCCGGCGCGCGATTTTGCGGCGTATCGCCCG | 72 |
| Murine CD28 | MTLRLLFLALNFFSVQVIENKILVKQSPLLVVDSNEVSL SCRYSYNLLAKEFRASLYKGVNSDVEVCVGNGNFTYQ PQFRSNAEFNCDGDFDNETVTFRLWNLHVNHTDIYFCK IEFMYPPPYLDNERSNGTIIHIKEKHLCHTQSSPKLFWAL VVVAGVLFCYGLLVTVALCVIWTNSRRNRLLQSDYMN MTPRRPGLTRKPYQPYAPARDFAAYRP | 73 |
| CD28 YMNM | YMNM | 74 |
| CD28 PYAP | PYAP | 75 |

TABLE 12-continued

| Construct | Amino acid sequence | SEQ ID NO |
|---|---|---|
| Signal peptide | ATMGWSCIILFLVATATGVHS | 76 |
| Signal peptide DNA sequence | ATGGGATGGAGCTGTATCATCCTCTTCTTGGTAGCAACAGCTACCGGTGTGCACTCC | 77 |
| Anti-CD20 (GA101) heavy chain | QVQLVQSGAEVKKPGSSVKVSCKASGYAFSYSWINWVRQAPGQGLEWMGRIFPGDGDTDYNGKFKGRVTITADKSTSTAYMELSSLRSEDTAVYYCARNVFDGYWLVYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 78 |
| Anti-CD20 (GA101) light chain | DIVMTQTPLSLPVTPGEPASISCRSSKSLLHSNGITYLYWYLQKPGQSPQLLIYQMSNLVSGVPDRFSGSGSGTDFTLKISRVEAEDVGVYYCAQNLELPYTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 79 |
| Anti-FAP(4B9)PGLALA heavy chain | EVQLLESGGGLVQPGGSLRLSCAASGFTFSSYAMSWVRQAPGKGLEWVSAIIGSGASTYYADSVKGRFTISRDNSKNTLYLQMNSLRAEDTAVYYCAKGWFGGFNYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 80 |
| Anti-FAP(4B9)light chain | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 81 |
| Anti-CEA(A5B7)PGLALA heavy chain | EVQLVESGGGLVQPGRSLRLSCAASGFTVSSYWMHWVRQAPGKGLEWVGFIRNKANGGTTEYAASVKGRFTISRDDSKNTLYLQMNSLRAEDTAVYYCARDRGLRFYFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 82 |
| Anti-CEA(A5B7)light chain | QAVLTQPASLSASPGASASLTCTLRRGINVGAYSIYWYQQKPGSPPQYLLRYKSDSDKQQGSGVSSRFSASKDASANAGILLISGLQSEDEADYYCMIWHSGASAVFGGGTKLTVLRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 83 |
| Anti-CEA(T84.66LCHA) PGLALA heavy chain | QVQLVQSGAEVKKPGSSVKVSCKASGFNIKDTYMHWVRQAPGQGLEWMGRIDPANGNSKYVPKFQGRVTITADTSTSTAYMELSSLRSEDTAVYYCAPFGYYVSDYAMAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQ | 84 |

TABLE 12-continued

| Construct | Amino acid sequence | SEQ ID NO |
|---|---|---|
| | YNSTYRVVSVLTVLHQDWLNGKEYKCKVSNKALGAPI EKTISKAKGQPREPQVYTLPPSRDELTKNQVSLTCLVK GFYPSDIAVEWESNGQPENNYKTTPPVLDSDGSFFLYS KLTVDKSRWQQGNVFSCSVMHEALHNHYTQKSLSLSP GK | |
| Anti-CEA(T84.66LCHA) light chain | EIVLTQSPATLSLSPGERATLSCRAGESVDIFGVGFLHW YQQKPGQAPRLLIYRASNRATGIPARFSGSGSGTDFTLT ISSLEPEDFAVYYCQQTNEDPYTFGQGTKLEIKRTVAAP SVFIFPPSDEQLKSGTASVVCLLNNFYPREAKVQWKVD NALQSGNSQESVTEQDSKDSTYSLSSTLTLSKADYEKH KVYACEVTHQGLSSPVTKSFNRGEC | 85 |
| Anti-CEA (CH1A1A98/992F1) PGLALA heavy chain | QVQLVQSGAEVKKPGASVKVSCKASGYTFTEFGMNW VRQAPGQGLEWMGWINTKTGEATYVEEFKGRVTFTTD TSTSTAYMELRSLRSDDTAVYYCARWDFAYYVEAMD YWGQGTTVTVSSASTKGPSVFPLAPSSKSTSGGTAALG CLVKDYFPEPVTVSWNSGALTSGVHTFPAVLQSSGLYS LSSVVTVPSSSLGTQTYICNVNHKPSNTKVDKKVEPKS CDKTHTCPPCPAPEAAGGPSVFLFPPKPKDTLMISRTPE VTCVVVDVSHEDPEVKFNWYVDGVEVHNAKTKPREE QYNSTYRVVSVLTVLHQDWLNGKEYKCKVSNKALGA PIEKTISKAKGQPREPQVCTLPPSRDELTKNQVSLSCAV KGFYPSDIAVEWESNGQPENNYKTTPPVLDSDGSFFLV SKLTVDKSRWQQGNVFSCSVMHEALHNHYTQKSLSLS PGK | 86 |
| Anti-CEA (CH1A1A98/992F1) light chain | DIQMTQSPSSLSASVGDRVTITCKASAAVGTYVAWYQ QKPGKAPKLLIYSASYRKRGVPSRFSGSGSGTDFTLTISS LQPEDFATYYCHQYYTYPLFTFGQGTKLEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| Anti-CEA(hMN14) PGLALA heavy chain | EVQLVESGGGVVQPGRSLRLSCSASGFDFTTYWMSWV RQAPGKGLEWIGEIHPDSSTINYAPSLKDRFTISRDNAK NTLFLQMDSLRPEDTGVYFCASLYFGFPWFAYWGQGT PVTVSSASTKGPSVFPLAPSSKSTSGGTAALGCLVKDYF PEPVTVSWNSGALTSGVHTFPAVLQSSGLYSLSSVVTV PSSSLGTQTYICNVNHKPSNTKVDKKVEPKSCDKTHTC PPCPAPEAAGGPSVFLFPPKPKDTLMISRTPEVTCVVVD VSHEDPEVKFNWYVDGVEVHNAKTKPREEQYNSTYR VVSVLTVLHQDWLNGKEYKCKVSNKALGAPIEKTISK AKGQPREPQVYTLPPSRDELTKNQVSLTCLVKGFYPSDI AVEWESNGQPENNYKTTPPVLDSDGSFFLYSKLTVDKS RWQQGNVFSCSVMHEALHNHYTQKSLSLSPGK | 88 |
| Anti-CEA(hMN14) light chain | DIQLTQSPSSLSASVGDRVTITCKASQDVGTSVAWYQQ KPGKAPKLLIYWTSTRHTGVPSRFSGSGSGTDFTFTISSL QPEDIATYYCQQYSLYRSFGQGTKVEIKRTVAAPSVFIF PPSDEQLKSGTASVVCLLNNFYPREAKVQWKVDNALQ SGNSQESVIEQDSKDSTYSLSSTLTLSKADYEKHKVYA CEVTHQGLSSPVTKSFNRGEC | 89 |
| Anti-TNC(2B10) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARLYGYAYYGAFDYW GQGTTVTVSSASTKGPSVFPLAPSSKSTSGGTAALGCLV KDYFPEPVTVSWNSGALTSGVHTFPAVLQSSGLYSLSS VVTVPSSSLGTQTYICNVNHKPSNTKVDKKVEPKSCDK THTCPPCPAPEAAGGPSVFLFPPKPKDTLMISRTPEVTC VVVDVSHEDPEVKFNWYVDGVEVHNAKTKPREEQYN STYRVVSVLTVLHQDWLNGKEYKCKVSNKALGAPIEK TISKAKGQPREPQVCTLPPSRDELTKNQVSLSCAVKGF YPSDIAVEWESNGQPENNYKTTPPVLDSDGSFFLVSKL TVDKSRWQQGNVFSCSVMHEALHNHYTQKSLSLSPGK | 90 |
| Anti-TNC(2B10) light chain | DIQMTQSPSSLSASVGDRVTITCRASQGIRNDLGWYQQ KPGKAPKRLIYAASSLQSGVPSRFSGSGSGTEFTLTISSL QPEDFATYYCLQNGLQPATFGQGTKVEIKRTVAAPSVF IFPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 91 |
| Anti-HER2(PER)PG LALA heavy chain 1 | EVQLVESGGGLVQPGGSLRLSCAASGFTFTDYTMDWV RQAPGKGLEWVADVNPNSGGSIYNQRFKGRFTLSVDR SKNTLYLQMNSLRAEDTAVYYCARNLGPSFYFDYWG QGTLVTVSSASTKGPSVFPLAPSSKSTSGGTAALGCLVK | 92 |

TABLE 12-continued

| Construct | Amino acid sequence | SEQ ID NO |
|---|---|---|
| | DYFPEPVTVSWNSGALTSGVHTFPAVLQSSGLYSLSSV VTVPSSSLGTQTYICNVNHKPSNTKVDKKVEPKSCDKT HTCPPCPAPEAAGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALGAPIEKT ISKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | |
| Anti-HER2(PER) light chain 1 | DIQMTQSPSSLSASVGDRVTITCKASQDVSIGVAWYQQ KPGKAPKLLIYSASYRYTGVPSRFSGSGSGTDFTLTISSL QPEDFATYYCQQYYIYPYTFGQGTKVEIKRTVAAPSVFI FPPSDEQLKSGTASVVCLLNNFYPREAKVQWKVDNAL QSGNSQESVIFQDSKDSTYSLSSTLTLSKADYEKHKVY ACEVTHQGLSSPVTKSFNRGEC | 93 |
| Anti-HER2(PER)PG LALA heavy chain 2 | EVQLVESGGGLVQPGGSLRLSCAASGFTFTDYTMDWV RQAPGKGLEWVADVNPNSGGSIYNQRFKGRFTLSVDR SKNTLYLQMNSLRAEDTAVYYCARNLGPSFYFDYWG QGTLVTVSSASTKGPSVFPLAPSSKSTSGGTAALGCLVK DYFPEPVTVSWNSGALTSGVHTFPAVLQSSGLYSLSSV VTVPSSSLGTQTYICNVNHKPSNTKVDKKVEPKSCDKT HTCPPCPAPEAAGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALGAPIEKT ISKAKGQPREPQVYTLPPSRDELTKNQVSLTCLVKGFYP SDIAVEWESNGQPENNYKTTPPVLDSDGSFFLYSKLTV DKSRWQQGNVFSCSVMHEALHNHYTQKSLSLSPGK | 94 |
| Anti-HER2(PER) light chain 2 | DIQMTQSPSSLSASVGDRVTITCKASQDVSIGVAWYQQ KPGKAPKLLIYSASYRYTGVPSRFSGSGSGTDFTLTISSL QPEDFATYYCQQYYIYPYTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 95 |
| Anti-WT1(33F05) PGLALA heavy chain | QVQLQESGPGLVKPSETLSLTCTVSGGSINSYYWSWIR QPPGKGLEWIGYIYYSGSTNYNPSLKSRVTISVDTSKNQ FSLKLSSVTAADTAVYYCARSYYEAFDYWGQGTLVTV SSSLGTQTYICNVNHKPSNTKVDKKVEPKSCDKTHTCP PCPAPEAAGGPSVFLFPPKPKDTLMISRTPEVTCVVVDV SHEDPEVKFNWYVDGVEVHNAKTKPREEQYNSTYRV VSVLTVLHQDWLNGKEYKCKVSNKALGAPIEKTISKA KGQPREPQVCTLPPSRDELTKNQVSLSCAVKGFYPSDIA VEWESNGQPENNYKTTPPVLDSDGSFFLVSKLTVDKSR WQQGNVFSCSVMHEALHNHYTQKSLSLSPGK | 96 |
| Anti-WT1(33F05) ight chain | SSELTQDPAVSVALGQTVRITCQGDSLRSYYASWYQQ KPGQAPVLVIYGKNNRPSGIPDRFSGSSSGNTASLTITG AQAEDEADYYCNSPDMNGNAVFGGGTKLTVLRTVAA PSVFIFPPSDEQLKSGTASVVCLLNNFYPREAKVQWKV DNALQSGNSQESVTEQDSKDSTYSLSSTLTLSKADYEK HKVYACEVTHQGLSSPVTKSFNRGEC | 97 |
| Anti-WT1(11D06) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARSIELWWGGFDYWGQ GTTVTVSSSLGTQTYICNVNHKPSNTKVDKKVEPKSCD KTHTCPPCPAPEAAGGPSVFLFPPKPKDTLMISRTPEVT CVVVDVSHEDPEVKFNWYVDGVEVHNAKTKPREEQY NSTYRVVSVLTVLHQDWLNGKEYKCKVSNKALGAPIE KTISKAKGQPREPQVCTLPPSRDELTKNQVSLSCAVKG FYPSDIAVEWESNGQPENNYKTTPPVLDSDGSFFLVSKL TVDKSRWQQGNVFSCSVMHEALHNHYTQKSLSLSPGK | 98 |
| Anti-WT1(11D06) light chain | DIQMTQSPSTLSASVGDRVTITCRASQSISSWLAWYQQ KPGKAPKLLIYDASSLESGVPSRFSGSGSGTEFTLTIGSL QPDDFATYYCQQYEDYTTFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 99 |
| Anti-WT1(33H09) PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARGSYDLFSLDYWGQG TTVTVSSSLGTQTYICNVNHKPSNTKVDKKVEPKSCDK THTCPPCPAPEAAGGPSVFLFPPKPKDTLMISRTPEVTC VVVDVSHEDPEVKFNWYVDGVEVHNAKTKPREEQYN | 100 |

TABLE 12-continued

| Construct | Amino acid sequence | SEQ ID NO |
|---|---|---|
| | STYRVVSVLTVLHQDWLNGKEYKCKVSNKALGAPIEK TISKAKGQPREPQVCTLPPSRDELTKNQVSLSCAVKGF YPSDIAVEWESNGQPENNYKTTPPVLDSDGSFFLVSKL TVDKSRWQQGNVFSCSVMHEALHNHYTQKSLSLSPGK | |
| Anti-WT1(33H09)light chain | DIQMTQSPSTLSASVGDRVTITCRASQSISSWLAWYQQ KPGKAPKLLIYDASSLESGVPSRFSGSGSGTEFTLTISSL QPDDFATYYCQQYYDGITFGQGTKVEIKRTVAAPSVFI FPPSDEQLKSGTASVVCLLNNFYPREAKVQWKVDNAL QSGNSQESVTEQDSKDSTYSLSSTLTLSKADYEKHKVY ACEVTHQGLSSPVTKSFNRGEC | 101 |
| Anti-WT1(5E11)PGLALA heavy chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCARSSYDLYSFDYWGQG TTVTVSSSLGTQTYICNVNHKPSNTKVDKKVEPKSCDK THTCPPCPAPEAAGGPSVFLFPPKPKDTLMISRTPEVTC VVVDVSHEDPEVKFNWYVDGVEVHNAKTKPREEQYN STYRVVSVLTVLHQDWLNGKEYKCKVSNKALGAPIEK TISKAKGQPREPQVCTLPPSRDELTKNQVSLSCAVKGF YPSDIAVEWESNGQPENNYKTTPPVLDSDGSFFLVSKL TVDKSRWQQGNVFSCSVMHEALHNHYTQKSLSLSPGK | 102 |
| Anti-WT1(5E11)light chain | DIQMTQSPSTLSASVGDRVTITCRASQSISSWLAWYQQ KPGKAPKLLIYDASSLESGVPSRFSGSGSGTEFTLTISSL QPDDFATYYCQQYSFPPMITFGQGTKVEIKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC | 103 |
| Anti-CD3 HCDR1 Kabat | TYAMN | 104 |
| Anti-CD3 HCDR2 Kabat | RIRSKYNNYATYYADSVKG | 105 |
| Anti-CD3 HCDR3 Kabat | HGNFGNSYVSWFAY | 106 |
| Anti-CD3 LCDR1 Kabat | GSSTGAVTTSNYAN | 107 |
| Anti-CD3 LCDR2 Kabat | GTNKRAP | 108 |
| Anti-CD3 LCDR3 Kabat | ALWYSNLWV | 109 |

The invention claimed is:

1. A method for assessing the specificity of a Fab fragment comprising the steps of:
   a) providing an antigen binding molecule comprising an antigen binding domain and a recognition domain, wherein the antigen binding domain comprises the Fab fragment, wherein the Fab fragment is specific for a target antigen;
   b) contacting the antigen binding molecule with a target cell comprising the target antigen on the surface;
   c) contacting the antigen binding molecule with a chimeric antigen receptor (CAR) expressing reporter T (CAR-T) cell wherein the reporter CAR-T cell comprises:
      i. a CAR capable of specific binding to the recognition domain wherein the CAR is operationally coupled to a response element;
      ii. a reporter gene under the control of the response element; and
   d) determining T cell activation by determining the expression of the reporter gene to establish the specificity of the Fab fragment;
   wherein the recognition domain is an Fc domain.

2. The method of claim 1, wherein the Fc domain is a mutated Fc domain, wherein the mutated Fc domain comprises at least one amino acid substitution compared to the non-mutated parent Fc domain, wherein the CAR is capable of specific binding to the mutated Fc domain but not capable of specific binding to the non-mutated parent Fc domain.

3. The method of claim 2, wherein the mutated Fc domain comprises at least one amino acid mutation at a position selected from the group consisting of L234, L235, I253, H310, P331, P329 and H435 according to EU numbering, in particular wherein the amino acid mutation is L234A, L235A, I253A, N297A, H310A, P329G and/or H435A.

4. The method of claim 2, wherein the mutated Fc domain comprises the amino acid mutation P329G according to EU numbering.

5. The method of claim 1, wherein the Fab fragment is derived from a phage display library screening.

6. The method according to claim 1, wherein activation of the response element leads to expression of the reporter gene.

7. The method according to claim 1, wherein the reporter gene is coding for green fluorescent protein (GFP) or luciferase.

8. The method according to claim 1, wherein the target antigen is selected from the group consisting of CD20, CEA, HER2, TYRP, EGFR, MCSP, STEAP1, WT1 and FolR1, or a fragment thereof.

9. The method according to claim 1, wherein high level of expression of the reporter gene in the presence of the target cell and low level of expression of the reporter gene in the absence of the target cell is indicative for high specificity of the FAB fragment.

10. The method according to claim 1, wherein high level of expression of the reporter gene in the presence of the target cell and low level of expression of the reporter gene in the absence of the target cell is indicative for high specificity of a T cell bispecific (TCB) antibody comprising the FAB fragment.

11. A method for generating a T cell bispecific (TCB) antibody, wherein the TCB antibody comprises a first antigen binding moiety specific for a target antigen and a second antigen binding moiety capable of specific binding to a T cell activating receptor, wherein the first antigen binding moiety is a Fab fragment selected according to the method of claim 1.

12. The method of claim 2, wherein the mutated Fc domain comprises the amino acid mutation P329G according to EU numbering.

13. The method of claim 1, wherein the target cell is a cancer cell.

* * * * *

SEQUENCE LISTING

```
<160> NUMBER OF SEQ ID NOS: 109

<210> SEQ ID NO 1
<211> LENGTH: 5
<212> TYPE: PRT
<213> ORGANISM: Artificial sequence
<220> FEATURE:
<223> OTHER INFORMATION: Anti-P329G CDR H1 Kabat

<400> SEQUENCE: 1

Arg Tyr Trp Met Asn
1               5

<210> SEQ ID NO 2
<211> LENGTH: 17
<212> TYPE: PRT
<213> ORGANISM: Artificial sequence
<220> FEATURE:
<223> OTHER INFORMATION: Anti-P329G CDR H2 Kabat

<400> SEQUENCE: 2

Glu Ile Thr Pro Asp Ser Ser Thr Ile Asn Tyr Thr Pro Ser Leu Lys
1               5                   10                  15

Asp
```

<210> SEQ ID NO 3
<211> LENGTH: 10
<212> TYPE: PRT
<213> ORGANISM: Artificial sequence
<220> FEATURE:
<223> OTHER INFORMATION: Anti-P329G CDR H3 Kabat

<400> SEQUENCE: 3

Pro Tyr Asp Tyr Gly Ala Trp Phe Ala Ser
1               5                   10

<210> SEQ ID NO 4
<211> LENGTH: 14
<212> TYPE: PRT
<213> ORGANISM: Artificial sequence
<220> FEATURE:
<223> OTHER INFORMATION: Anti-P329G CDR L1 Kabat

<400> SEQUENCE: 4

Arg Ser Ser Thr Gly Ala Val Thr Thr Ser Asn Tyr Ala Asn
1               5                   10

<210> SEQ ID NO 5
<211> LENGTH: 7
<212> TYPE: PRT
<213> ORGANISM: Artificial sequence
<220> FEATURE:
<223> OTHER INFORMATION: Anti-P329G CDR L2 Kabat

<400> SEQUENCE: 5

Gly Thr Asn Lys Arg Ala Pro
1               5

<210> SEQ ID NO 6
<211> LENGTH: 9
<212> TYPE: PRT
<213> ORGANISM: Artificial sequence
<220> FEATURE:
<223> OTHER INFORMATION: Anti-P329G CDR L3 Kabat

<400> SEQUENCE: 6

Ala Leu Trp Tyr Ser Asn His Trp Val
1               5

<210> SEQ ID NO 7
<211> LENGTH: 433
<212> TYPE: PRT
<213> ORGANISM: Artificial sequence
<220> FEATURE:
<223> OTHER INFORMATION: Anti-P329G-ds-scFv-CD28ATM-CD28CSD-CD3zSSD
      fusion pETR17096

<400> SEQUENCE: 7

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys

```
                85                  90                  95
Val Arg Pro Tyr Asp Tyr Gly Ala Trp Phe Ala Ser Trp Gly Gln Gly
            100                 105                 110

Thr Leu Val Thr Val Ser Ala Gly Gly Gly Ser Gly Gly Gly Gly
            115                 120                 125

Ser Gly Gly Gly Ser Gly Gly Gly Ser Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Lys Arg Ala Pro Gly Val Pro Ala Arg Phe Ser Gly Ser Leu Ile
            195                 200                 205

Gly Asp Lys Ala Ala Leu Thr Ile Thr Gly Ala Gln Thr Glu Asp Glu
            210                 215                 220

Ala Ile Tyr Phe Cys Ala Leu Trp Tyr Ser Asn His Trp Val Phe Gly
225                 230                 235                 240

Cys Gly Thr Lys Leu Thr Val Leu Gly Gly Gly Ser Phe Trp Val
            245                 250                 255

Leu Val Val Val Gly Val Leu Ala Cys Tyr Ser Leu Leu Val Thr
            260                 265                 270

Val Ala Phe Ile Ile Phe Trp Val Arg Ser Lys Arg Ser Arg Leu Leu
            275                 280                 285

His Ser Asp Tyr Met Asn Met Thr Pro Arg Arg Pro Gly Pro Thr Arg
    290                 295                 300

Lys His Tyr Gln Pro Tyr Ala Pro Pro Arg Asp Phe Ala Ala Tyr Arg
305                 310                 315                 320

Ser Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
            355                 360                 365

Lys Pro Arg Arg Lys Asn Pro Gln Glu Gly Leu Tyr Asn Glu Leu Gln
            370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 8
<211> LENGTH: 119
<212> TYPE: PRT
<213> ORGANISM: Artificial sequence
<220> FEATURE:
<223> OTHER INFORMATION: Anti-P329G-ds VH

<400> SEQUENCE: 8

Glu Val Lys Leu Leu Glu Ser Gly Gly Gly Leu Val Gln Pro Gly Gly
1               5                   10                  15
```

-continued

```
Ser Leu Lys Leu Ser Cys Ala Ala Ser Gly Phe Asp Phe Ser Arg Tyr
         20                  25                  30

Trp Met Asn Trp Val Arg Gln Ala Pro Gly Lys Cys Leu Glu Trp Ile
         35                  40                  45

Gly Glu Ile Thr Pro Asp Ser Ser Thr Ile Asn Tyr Thr Pro Ser Leu
 50                  55                  60

Lys Asp Lys Phe Ile Ile Ser Arg Asp Asn Ala Lys Asn Thr Leu Tyr
 65                  70                  75                  80

Leu Gln Met Ile Lys Val Arg Ser Glu Asp Thr Ala Leu Tyr Tyr Cys
             85                  90                  95

Val Arg Pro Tyr Asp Tyr Gly Ala Trp Phe Ala Ser Trp Gly Gln Gly
             100                 105                 110

Thr Leu Val Thr Val Ser Ala
         115
```

<210> SEQ ID NO 9
<211> LENGTH: 109
<212> TYPE: PRT
<213> ORGANISM: Artificial sequence
<220> FEATURE:
<223> OTHER INFORMATION: Anti-P329G-ds VL

<400> SEQUENCE: 9

```
Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Val Thr Thr Ser
             20                  25                  30

Asn Tyr Ala Asn Trp Val Gln Glu Lys Pro Asp His Leu Phe Thr Gly
         35                  40                  45

Leu Ile Gly Gly Thr Asn Lys Arg Ala Pro Gly Val Pro Ala Arg Phe
     50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
             85                  90                  95

His Trp Val Phe Gly Cys Gly Thr Lys Leu Thr Val Leu
             100                 105
```

<210> SEQ ID NO 10
<211> LENGTH: 248
<212> TYPE: PRT
<213> ORGANISM: Artificial sequence
<220> FEATURE:
<223> OTHER INFORMATION: Anti-P329G-ds-scFv

<400> SEQUENCE: 10

```
Glu Val Lys Leu Leu Glu Ser Gly Gly Gly Leu Val Gln Pro Gly Gly
 1               5                  10                  15

Ser Leu Lys Leu Ser Cys Ala Ala Ser Gly Phe Asp Phe Ser Arg Tyr
             20                  25                  30

Trp Met Asn Trp Val Arg Gln Ala Pro Gly Lys Cys Leu Glu Trp Ile
         35                  40                  45

Gly Glu Ile Thr Pro Asp Ser Ser Thr Ile Asn Tyr Thr Pro Ser Leu
     50                  55                  60

Lys Asp Lys Phe Ile Ile Ser Arg Asp Asn Ala Lys Asn Thr Leu Tyr
 65                  70                  75                  80

Leu Gln Met Ile Lys Val Arg Ser Glu Asp Thr Ala Leu Tyr Tyr Cys
```

```
                    85                  90                  95
Val Arg Pro Tyr Asp Tyr Gly Ala Trp Phe Ala Ser Trp Gly Gln Gly
                100                 105                 110

Thr Leu Val Thr Val Ser Ala Gly Gly Gly Gly Ser Gly Gly Gly Gly
            115                 120                 125

Ser Gly Gly Gly Gly Ser Gly Gly Gly Ser Gln Ala Val Val Thr
    130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
                180                 185                 190

Asn Lys Arg Ala Pro Gly Val Pro Ala Arg Phe Ser Gly Ser Leu Ile
                195                 200                 205

Gly Asp Lys Ala Ala Leu Thr Ile Thr Gly Ala Gln Thr Glu Asp Glu
                210                 215                 220

Ala Ile Tyr Phe Cys Ala Leu Trp Tyr Ser Asn His Trp Val Phe Gly
225                 230                 235                 240

Cys Gly Thr Lys Leu Thr Val Leu
                245

<210> SEQ ID NO 11
<211> LENGTH: 27
<212> TYPE: PRT
<213> ORGANISM: Artificial sequence
<220> FEATURE:
<223> OTHER INFORMATION: CD28ATM

<400> SEQUENCE: 11

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 12
<211> LENGTH: 41
<212> TYPE: PRT
<213> ORGANISM: Artificial sequence
<220> FEATURE:
<223> OTHER INFORMATION: CD28CSD

<400> SEQUENCE: 12

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 13
<211> LENGTH: 112
<212> TYPE: PRT
<213> ORGANISM: Artificial sequence
<220> FEATURE:
<223> OTHER INFORMATION: CD3zSSD

<400> SEQUENCE: 13

Arg Val Lys Phe Ser Arg Ser Ala Asp Ala Pro Ala Tyr Gln Gln Gly
1               5                   10                  15
```

```
Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 14
<211> LENGTH: 180
<212> TYPE: PRT
<213> ORGANISM: Artificial sequence
<220> FEATURE:
<223> OTHER INFORMATION: CD28ATM-CD28-CD3z

<400> SEQUENCE: 14

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
50                  55                  60

Ala Tyr Arg Ser Arg Val Lys Phe Ser Arg Ser Ala Asp Ala Pro Ala
65                  70                  75                  80

Tyr Gln Gln Gly Gln Asn Gln Leu Tyr Asn Glu Leu Asn Leu Gly Arg
                85                  90                  95

Arg Glu Glu Tyr Asp Val Leu Asp Lys Arg Arg Gly Arg Asp Pro Glu
            100                 105                 110

Met Gly Gly Lys Pro Arg Arg Lys Asn Pro Gln Glu Gly Leu Tyr Asn
        115                 120                 125

Glu Leu Gln Lys Asp Lys Met Ala Glu Ala Tyr Ser Glu Ile Gly Met
130                 135                 140

Lys Gly Glu Arg Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180
```

<210> SEQ ID NO 15
<211> LENGTH: 238
<212> TYPE: PRT
<213> ORGANISM: Artificial sequence
<220> FEATURE:
<223> OTHER INFORMATION: eGFP

<400> SEQUENCE: 15

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
```

```
                20                  25                  30
Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Leu
 50                  55                  60

Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 16
<211> LENGTH: 20
<212> TYPE: PRT
<213> ORGANISM: Artificial sequence
<220> FEATURE:
<223> OTHER INFORMATION: (G4S)4 linker

<400> SEQUENCE: 16

Gly Gly Gly Gly Ser Gly Gly Gly Gly Ser Gly Gly Gly Gly Ser Gly
 1               5                  10                  15

Gly Gly Gly Ser
        20

<210> SEQ ID NO 17
<211> LENGTH: 5
<212> TYPE: PRT
<213> ORGANISM: Artificial sequence
<220> FEATURE:
<223> OTHER INFORMATION: G4S linker

<400> SEQUENCE: 17

Gly Gly Gly Gly Ser
 1               5

<210> SEQ ID NO 18
<211> LENGTH: 19
<212> TYPE: PRT
<213> ORGANISM: Artificial sequence
<220> FEATURE:
<223> OTHER INFORMATION: T2A linker

<400> SEQUENCE: 18
```

Gly Glu Gly Arg Gly Ser Leu Leu Thr Cys Gly Asp Val Glu Glu Asn
1               5                   10                  15

Pro Gly Pro

<210> SEQ ID NO 19
<211> LENGTH: 1356
<212> TYPE: DNA
<213> ORGANISM: Artificial sequence
<220> FEATURE:
<223> OTHER INFORMATION: Anti-P329G-ds-scFv-CD28ATM-CD28CSD-CD3zSSD
      fusion pETR17096

<400> SEQUENCE: 19

```
atgggatgga gctgtatcat cctcttcttg gtagcaacag ctaccggtgt gcattccgag      60
gtgaagctgc tggagagcgg cggcggcctg gtgcagcccg gcggcagcct gaagctgagc     120
tgcgccgcca gcggcttcga cttcagcagg tactggatga actgggtgag caggcccccc     180
ggcaagtgtc tggagtggat cggcgagatc acccccgaca gcagccacat caactacacc     240
cccagcctga aggacaagtt catcatcagc agggacaacg ccaagaacac cctgtacctg     300
cagatgatca ggtgaggag cgaggacacc gccctgtact actgcgtgag gccctacgac     360
tacggcgcct ggttcgccag ctggggccag ggcaccctgg tgaccgtgag cgccggaggg     420
ggcggaagtg gtggcggggg aagcggcggg ggtggcagcg aggggggcgg atctcaggcc     480
gtggtgaccc aggagagcgc cctgaccacc agccccggcg agaccgtgac cctgacctgc     540
aggagcagca ccgcgccgt gaccaccagc aactacgcca actgggtgca ggagaagccc     600
gaccacctgt tcaccggcct gatcggcggc accaacaaga gggcccccgg cgtgcccgcc     660
aggttcagcg gcagcctgat cggcgacaag gccgccctga ccatcaccgg cgcccagacc     720
gaggacgagg ccatctactt ctgcgccctg tggtacagca ccactgggt gttcggctgt     780
ggcaccaagc tgaccgtgct gggagggggc ggatccttct gggtgctggt ggtggtgggc     840
ggcgtgctgg cctgctacag cctgctggtg accgtggcct tcatcatctt ctgggtgagg     900
agcaagagga gcaggctgct gcacagcgac tacatgaaca tgaccccag gaggcccggc     960
cccaccagga agcactacca gccctacgcc ccccccaggg acttcgccgc ctacaggagc    1020
agggtgaagt tcagcaggag cgccgacgcc cccgcctacc agcagggcca gaaccagctg    1080
tataacgagc tgaacctggg caggagggag gagtacgacg tgctggacaa gagggagggc    1140
agggaccccg agatgggcgg caagcccagg aggaagaacc ccaggagggg cctgtataac    1200
gagctgcaga aggacaagat ggccgaggcc tacagcgaga tcggcatgaa gggcgagagg    1260
aggaggggca agggccacga cggcctgtac cagggcctga gcaccgccac caaggacacc    1320
tacgacgccc tgcacatgca ggccctgccc cccagg                              1356
```

<210> SEQ ID NO 20
<211> LENGTH: 357
<212> TYPE: DNA
<213> ORGANISM: Artificial sequence
<220> FEATURE:
<223> OTHER INFORMATION: Anti-P329G-ds VH

<400> SEQUENCE: 20

```
gaggtgaagc tgctggagag cggcggcggc ctggtgcagc ccggcggcag cctgaagctg      60
agctgcgccg ccagcggctt cgacttcagc aggtactgga tgaactgggt gaggcaggcc     120
cccggcaagt gtctggagtg gatcggcgag atcacccccg acagcagcca catcaactac     180
```

```
acccccagcc tgaaggacaa gttcatcatc agcagggaca acgccaagaa caccctgtac    240
ctgcagatga tcaaggtgag gagcgaggac accgccctgt actactgcgt gaggccctac    300
gactacggcg cctggttcgc cagctggggc cagggcaccc tggtgaccgt gagcgcc       357

<210> SEQ ID NO 21
<211> LENGTH: 327
<212> TYPE: DNA
<213> ORGANISM: Artificial sequence
<220> FEATURE:
<223> OTHER INFORMATION: Anti-P329G-ds VL

<400> SEQUENCE: 21
caggccgtgg tgacccagga gagcgccctg accaccagcc ccggcgagac cgtgaccctg     60
acctgcagga gcagcaccgg cgccgtgacc accagcaact acgccaactg ggtgcaggag    120
aagcccgacc acctgttcac cggcctgatc ggcggcacca acaagagggc ccccggcgtg    180
cccgccaggt tcagcggcag cctgatcggc gacaaggccg ccctgaccat caccggcgcc    240
cagaccgagg acgaggccat ctacttctgc gccctgtggt acagcaacca ctgggtgttc    300
ggctgtggca ccaagctgac cgtgctg                                        327

<210> SEQ ID NO 22
<211> LENGTH: 799
<212> TYPE: DNA
<213> ORGANISM: Artificial sequence
<220> FEATURE:
<223> OTHER INFORMATION: Anti-P329G-ds-scFv

<400> SEQUENCE: 22
atgggatgga gctgtatcat cctcttcttg gtagcaacag ctaccggtgt gcattccgag     60
gtgaagctgc tggagagcgg cggcggcctg gtgcagcccg gcggcagcct gaagctgagc    120
tgcgccgcca gcggcttcga cttcagcagg tactggatga actgggtgag gcaggccccc    180
ggcaagtgtc tggagtggat cggcgagatc accccgaca gcagcaccat caactacacc    240
cccagcctga aggacaagtt catcatcagc agggacaacg ccaagaacac cctgtacctg    300
cagatgatca aggtgaggag cgaggacacc gccctgtact actgcgtgag gccctacgac    360
tacggcgcct ggttcgccag ctggggccag ggcaccctgg tgaccgtgag cgccggaggg    420
ggcggaagtg gtggcggggg aagcggcggg ggtggcagcg gaggggcgg atctcaggcc    480 gtggtgaccc aggagagcgc cctgaccacc agccccggcg agaccgtgac cctgacctgc    540
aggagcagca ccggcgccgt gaccaccagc aactacgcca actgggtgca ggagaagccc    600
gaccacctgt tcaccggcct gatcggcggc accaacaaga gggcccccgg cgtgcccgcc    660
aggttcagcg gcagcctgat cggcgacaag gccgccctga ccatcaccgg cgcccagacc    720
gaggacgagg ccatctactt ctgcgccctg tggtacagca accactgggt gttcggctgt    780
ggcaccaagc tgaccgtgc                                                  799

<210> SEQ ID NO 23
<211> LENGTH: 647
<212> TYPE: DNA
<213> ORGANISM: Artificial sequence
<220> FEATURE:
<223> OTHER INFORMATION: IRES EV71, internal ribosomal entry side

<400> SEQUENCE: 23
cccgaagtaa cttagaagct gtaaatcaac gatcaatagc aggtgtggca caccagtcat     60
accttgatca agcacttctg tttccccgga ctgagtatca ataggctgct cgcgcggctg    120
```

| | |
|---|---|
| aaggagaaaa cgttcgttac ccgaccaact acttcgagaa gcttagtacc accatgaacg | 180 |
| aggcagggtg tttcgctcag cacaacccca gtgtagatca ggctgatgag tcactgcaac | 240 |
| ccccatgggc gaccatggca gtggctgcgt tggcggcctg cccatggaga atccatggg | 300 |
| acgctctaat tctgacatgg tgtgaagtgc ctattgagct aactggtagt cctccggccc | 360 |
| ctgattgcgg ctaatcctaa ctgcggagca catgctcaca aaccagtggg tggtgtgtcg | 420 |
| taacgggcaa ctctgcagcg gaaccgacta ctttgggtgt ccgtgtttcc ttttattcct | 480 |
| atattggctg cttatggtga caatcaaaaa gttgttacca tatagctatt ggattggcca | 540 |
| tccggtgtgc aacagggcaa ctgtttacct atttattggt tttgtaccat tatcactgaa | 600 |
| gtctgtgatc actctcaaat tcattttgac cctcaacaca atcaaac | 647 |

<210> SEQ ID NO 24
<211> LENGTH: 81
<212> TYPE: DNA
<213> ORGANISM: Artificial sequence
<220> FEATURE:
<223> OTHER INFORMATION: CD28ATM

<400> SEQUENCE: 24

| | |
|---|---|
| ttttgggtgc tggtggtggt tggtggagtc ctggcttgct atagcttgct agtaacagtg | 60 |
| gcctttatta ttttctgggt g | 81 |

<210> SEQ ID NO 25
<211> LENGTH: 123
<212> TYPE: DNA
<213> ORGANISM: Artificial sequence
<220> FEATURE:
<223> OTHER INFORMATION: CD28CSD

<400> SEQUENCE: 25

| | |
|---|---|
| aggagtaaga ggagcaggct cctgcacagt gactacatga acatgactcc ccgccgcccc | 60 |
| gggcccaccc gcaagcatta ccagccctat gccccaccac gcgacttcgc agcctatcgc | 120 |
| tcc | 123 |

<210> SEQ ID NO 26
<211> LENGTH: 336
<212> TYPE: DNA
<213> ORGANISM: Artificial sequence
<220> FEATURE:
<223> OTHER INFORMATION: CD3z SSD

<400> SEQUENCE: 26

| | |
|---|---|
| agagtgaagt tcagcaggag cgcagacgcc cccgcgtacc agcagggcca gaaccagctc | 60 |
| tataacgagc tcaatctagg acgaagagag gagtacgatg ttttggacaa gagacgtggc | 120 |
| cgggaccctg agatgggggg aaagccgaga aggaagaacc ctcaggaagg cctgtacaat | 180 |
| gaactgcaga agataagat ggcggaggcc tacagtgaga ttgggatgaa aggcgagcgc | 240 |
| cggaggggca aggggcacga tggcctttac cagggtctca gtacagccac caaggacacc | 300 |
| tacgacgccc ttcacatgca ggccctgccc cctcgc | 336 |

<210> SEQ ID NO 27
<211> LENGTH: 540
<212> TYPE: DNA
<213> ORGANISM: Artificial sequence
<220> FEATURE:
<223> OTHER INFORMATION: CD28ATM-CD28-CD3z

<400> SEQUENCE: 27

```
ttctgggtgc tggtggtggt gggcggcgtg ctggcctgct acagcctgct ggtgaccgtg    60
gccttcatca tcttctgggt gaggagcaag aggagcaggc tgctgcacag cgactacatg   120
aacatgaccc ccaggaggcc cggcccacc aggaagcact accagcccta cgccccccc    180
agggacttcg ccgcctacag gagcagggtg aagttcagca ggagcgccga cgccccgcc   240
taccagcagg gccagaacca gctgtataac gagctgaacc tgggcaggag ggaggagtac   300
gacgtgctgg acaagaggag gggcagggac cccgagatgg gcggcaagcc caggaggaag   360
aaccccagg agggcctgta taacgagctg cagaaggaca gatggccga ggcctacagc    420
gagatcggca tgaagggcga gaggaggagg ggcaagggcc acgacggcct gtaccagggc   480
ctgagcaccg ccaccaagga cacctacgac gccctgcaca tgcaggccct gccccccagg   540
```

<210> SEQ ID NO 28
<211> LENGTH: 63
<212> TYPE: DNA
<213> ORGANISM: Artificial sequence
<220> FEATURE:
<223> OTHER INFORMATION: T2A element

<400> SEQUENCE: 28

```
tccggagagg gcagaggaag tcttctaaca tgcggtgacg tggaggagaa tcccggccct    60
agg                                                                  63
```

<210> SEQ ID NO 29
<211> LENGTH: 717
<212> TYPE: DNA
<213> ORGANISM: Artificial sequence
<220> FEATURE:
<223> OTHER INFORMATION: eGFP

<400> SEQUENCE: 29

```
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggtga acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660
ctggagttcg tgaccgccgc cgggatcact ctcggcatgg acgagctgta caagtga      717
```

<210> SEQ ID NO 30
<211> LENGTH: 2136
<212> TYPE: DNA
<213> ORGANISM: Artificial sequence
<220> FEATURE:
<223> OTHER INFORMATION: Anti-P329G-ds-scFv-CD28ATM-CD28CSD-CD3zSSD-eGFP
      fusion pETR17096

<400> SEQUENCE: 30

```
atgggatgga gctgtatcat cctcttcttg gtagcaacag ctaccggtgt gcattccgag    60
gtgaagctgc tggagagcgg cggcggcctg gtgcagcccg gcggcagcct gaagctgagc   120
tgcgccgcca gcggcttcga cttcagcagg tactggatga actgggtgag gcaggccccc   180
ggcaagtgtc tggagtggat cggcgagatc accccccgaca gcagcaccat caactacacc   240
cccagcctga aggacaagtt catcatcagc agggacaacg ccaagaacac cctgtacctg   300
cagatgatca aggtgaggag cgaggacacc gccctgtact actgcgtgag gccctacgac   360
tacggcgcct ggttcgccag ctggggccag ggcaccctgg tgaccgtgag cgccggaggg   420
ggcggaagtg gtggcggggg aagcggcggg ggtggcagcg agggggcgg atctcaggcc    480
gtggtgaccc aggagagcgc cctgaccacc agccccggcg agaccgtgac cctgacctgc   540
aggagcagca ccgcgccgt gaccaccagc aactacgcca actgggtgca ggagaagccc   600
gaccacctgt tcaccggcct gatcggcggc accaacaaga gggcccccgg cgtgcccgcc   660
aggttcagcg gcagcctgat cggcgacaag gccgccctga ccatcaccgg cgcccagacc   720
gaggacgagg ccatctactt ctgcgccctg tggtacagca ccactgggt gttcggctgt   780
ggcaccaagc tgaccgtgct ggaggggggc ggatccttct gggtgctggt ggtggtgggc   840
ggcgtgctgg cctgctacag cctgctggtg accgtggcct tcatcatctt ctgggtgagg   900
agcaagagga gcaggctgct gcacagcgac tacatgaaca tgaccccccag gaggccggc    960
cccaccagga agcactacca gccctacgcc cccccaggg acttcgccgc ctacagagc    1020
agggtgaagt tcagcaggag cgccgacgcc cccgcctacc agcagggcca gaaccagctg   1080
tataacgagc tgaacctggg caggaggag gagtacgacg tgctggacaa gaggaggggc   1140
agggaccccg agatgggcgg caagcccagg aggaagaacc cccaggaggg cctgtataac   1200
gagctgcaga aggacaagat ggccgaggcc tacagcgaga tcggcatgaa gggcgagagg   1260
aggaggggca agggccacga cggcctgtac cagggcctga gcaccgccac caaggacacc   1320
tacgacgccc tgcacatgca ggccctgccc ccaggtccgg agagggcag aggaagtctt   1380
ctaacatgcg gtgacgtgga ggagaatccc ggccctaggg tgagcaaggg cgaggagctg   1440
ttcaccgggg tggtgcccat cctggtcgag ctggacggcg acgtaaacgg ccacaagttc   1500
agcgtgtccg gcgagggcga gggcgatgcc acctacggca agctgaccct gaagttcatc   1560
tgcaccaccg gcaagctgcc cgtgccctgg cccaccctcg tgaccaccct gacctacggc   1620
gtgcagtgct tcagccgcta ccccgaccac atgaagcagc acgacttctt caagtccgcc   1680
atgcccgaag gctacgtcca ggagcgcacc atcttcttca aggacgacgg caactacaag   1740
acccgcgccg aggtgaagtt cgagggcgac accctggtga accgcatcga gctgaagggc   1800
atcgacttca aggaggacgg caacatcctg gggcacaagc tggagtacaa ctacaacagc   1860
cacaacgtct atatcatggc cgacaagcag aagaacggca tcaaggtgaa cttcaagatc   1920
cgccacaaca tcgaggacgg cagcgtgcag ctcgccgacc actaccagca gaacaccccc   1980
atcggcgacg gccccgtgct gctgcccgac aaccactacc tgagcaccca gtccgccctg   2040
agcaaagacc ccaacgagaa gcgcgatcac atggtcctgc tggagttcgt gaccgccgcc   2100
gggatcactc tcggcatgga cgagctgtac aagtga                              2136
```

<210> SEQ ID NO 31
<211> LENGTH: 433
<212> TYPE: PRT
<213> ORGANISM: Artificial sequence
<220> FEATURE:
<223> OTHER INFORMATION: Anti-P329G-scFv- CD28ATM-CD28CSD-CD3zSSD fusion

<400> SEQUENCE: 31

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Gly Gly Gly Ser Gly Gly Gly Gly
            115                 120                 125

Ser Gly Gly Gly Gly Ser Gly Gly Gly Gly Ser Gln Ala Val Val Thr
130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Lys Arg Ala Pro Gly Val Pro Ala Arg Phe Ser Gly Ser Leu Ile
        195                 200                 205

Gly Asp Lys Ala Ala Leu Thr Ile Thr Gly Ala Gln Thr Glu Asp Glu
    210                 215                 220

Ala Ile Tyr Phe Cys Ala Leu Trp Tyr Ser Asn His Trp Val Phe Gly
225                 230                 235                 240

Gly Gly Thr Lys Leu Thr Val Leu Gly Gly Gly Ser Phe Trp Val
                245                 250                 255

Leu Val Val Gly Val Leu Ala Cys Tyr Ser Leu Leu Val Thr
            260                 265                 270

Val Ala Phe Ile Ile Phe Trp Val Arg Ser Lys Arg Ser Arg Leu Leu
        275                 280                 285

His Ser Asp Tyr Met Asn Met Thr Pro Arg Arg Pro Gly Pro Thr Arg
    290                 295                 300

Lys His Tyr Gln Pro Tyr Ala Pro Pro Arg Asp Phe Ala Ala Tyr Arg
305                 310                 315                 320

Ser Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
        355                 360                 365

Lys Pro Arg Arg Lys Asn Pro Gln Glu Gly Leu Tyr Asn Glu Leu Gln
    370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
```

Ala Thr Lys Asp Thr Tyr Asp Ala Leu His Met Gln Ala Leu Pro Pro
            420                 425                 430

Arg

<210> SEQ ID NO 32
<211> LENGTH: 119
<212> TYPE: PRT
<213> ORGANISM: Artificial sequence
<220> FEATURE:
<223> OTHER INFORMATION: Anti-P329G VH

<400> SEQUENCE: 32

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala
        115

<210> SEQ ID NO 33
<211> LENGTH: 109
<212> TYPE: PRT
<213> ORGANISM: Artificial sequence
<220> FEATURE:
<223> OTHER INFORMATION: Anti-P329G VL

<400> SEQUENCE: 33

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 34
<211> LENGTH: 248
<212> TYPE: PRT
<213> ORGANISM: Artificial sequence
<220> FEATURE:
<223> OTHER INFORMATION: Anti-P329G-scFv

<400> SEQUENCE: 34

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Gly Gly Gly Ser Gly Gly Gly
        115                 120                 125

Ser Gly Gly Gly Ser Gly Gly Gly Ser Gln Ala Val Val Thr
130                 135                 140

Gln Glu Ser Ala Leu Thr Thr Ser Pro Gly Glu Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Glu Lys Pro Asp His Leu Phe Thr Gly Leu Ile Gly Gly Thr
            180                 185                 190

Asn Lys Arg Ala Pro Gly Val Pro Ala Arg Phe Ser Gly Ser Leu Ile
        195                 200                 205

Gly Asp Lys Ala Ala Leu Thr Ile Thr Gly Ala Gln Thr Glu Asp Glu
    210                 215                 220

Ala Ile Tyr Phe Cys Ala Leu Trp Tyr Ser Asn His Trp Val Phe Gly
225                 230                 235                 240

Gly Gly Thr Lys Leu Thr Val Leu
                245

<210> SEQ ID NO 35
<211> LENGTH: 1356
<212> TYPE: DNA
<213> ORGANISM: Artificial sequence
<220> FEATURE:
<223> OTHER INFORMATION: Anti-P329G-scFv-CD28ATM-CD28CSD-CD3zSSD fusion

<400> SEQUENCE: 35

```
atgggatgga gctgtatcat cctcttcttg gtagcaacag ctaccggtgt gcattccgag      60
gtgaagctgc tggagagcgg cggcggcctg gtgcagcccg gcggcagcct gaagctgagc     120
tgcgccgcca gcggcttcga cttcagcagg tactggatga actgggtgag gcaggccccc     180
ggcaagggtc tggagtggat cggcgagatc accccgaca gcagcaccat caactacacc     240
cccagcctga aggacaagtt catcatcagc agggacaacg ccaagaacac cctgtacctg     300
cagatgatca aggtgaggag cgaggacacc gccctgtact actgcgtgag gccctacgac     360
tacggcgcct ggttcgccag ctggggccag ggcaccctgg tgaccgtgag cgccggaggg     420
ggcggaagtg gtggcggggg aagcggcggg ggtggcagcg gaggggcgg atctcaggcc     480
gtggtgaccc aggagagcgc cctgaccacc agccccggcg agaccgtgac cctgacctgc     540
```

```
aggagcagca ccggcgccgt gaccaccagc aactacgcca actgggtgca ggagaagccc      600
gaccacctgt tcaccggcct gatcggcggc accaacaaga gggcccccgg cgtgcccgcc      660
aggttcagcg gcagcctgat cggcgacaag gccgccctga ccatcaccgg cgcccagacc      720
gaggacgagg ccatctactt ctgcgccctg tggtacagca ccactgggt gttcggcggt       780 ggcaccaagc tgaccgtgct ggggaggggc ggatccttct gggtgctggt ggtggtgggc      840
ggcgtgctgg cctgctacag cctgctggtg accgtggcct tcatcatctt ctgggtgagg      900
agcaagagga gcaggctgct gcacagcgac tacatgaaca tgacccccag gaggcccggc      960
cccaccagga agcactacca gccctacgcc cccccagggg acttcgccgc ctacaggagc     1020
agggtgaagt tcagcaggag cgccgacgcc cccgcctacc agcagggcca gaaccagctg     1080
tataacgagc tgaacctggg caggaggagg agtacgacg tgctggacaa gaggaggggc     1140
agggaccccg agatgggcgg caagcccagg aggaagaacc cccaggaggg cctgtataac     1200
gagctgcaga aggacaagat ggccgaggcc tacagcgaga tcggcatgaa gggcgagagg     1260
aggaggggca agggccacga cggcctgtac cagggcctga gcaccgccac caaggacacc     1320
tacgacgccc tgcacatgca ggccctgccc cccagg                               1356

<210> SEQ ID NO 36
<211> LENGTH: 357
<212> TYPE: DNA
<213> ORGANISM: Artificial sequence
<220> FEATURE:
<223> OTHER INFORMATION: Anti-P329G VH

<400> SEQUENCE: 36
gaggtgaagc tgctggagag cggcggcggc ctggtgcagc ccggcggcag cctgaagctg       60
agctgcgccg ccagcggctt cgacttcagc aggtactgga tgaactgggt gaggcaggcc      120
cccggcaagg gtctggagtg gatcggcgag atcacccccg acagcagcac catcaactac      180 accccccagcc tgaaggacaa gttcatcatc agcagggaca cgccaagaa cacccctgtac      240 ctgcagatga tcaaggtgag gagcgaggac accgccctgt actactgcgt gaggccctac      300
gactacggcg cctggttcgc cagctgggc cagggcaccc tggtgaccgt gagcgcc          357

<210> SEQ ID NO 37
<211> LENGTH: 327
<212> TYPE: DNA
<213> ORGANISM: Artificial sequence
<220> FEATURE:
<223> OTHER INFORMATION: Anti-P329G VL

<400> SEQUENCE: 37
caggccgtgg tgacccagga gagcgccctg accaccagcc ccggcgagac cgtgaccctg       60
acctgcagga gcagcaccgg cgccgtgacc accagcaact acgccaactg ggtgcaggag      120
aagcccgacc acctgttcac cggcctgatc ggcggcacca acaagagggc cccccggcgtg     180 cccgccaggt tcagcggcag cctgatcggc gacaaggccg ccctgaccat caccggcgcc      240
cagaccgagg acgaggccat ctacttctgc gccctgtggt acagcaacca ctgggtgttc      300
ggcggtggca ccaagctgac cgtgctg                                          327

<210> SEQ ID NO 38
<211> LENGTH: 2136
<212> TYPE: DNA
<213> ORGANISM: Artificial sequence
<220> FEATURE:
<223> OTHER INFORMATION: Anti-P329G-scFv-CD28ATM-CD28CSD-CD3zSSD-eGFP
``` fusion

<400> SEQUENCE: 38

```
atgggatgga gctgtatcat cctcttcttg gtagcaacag ctaccggtgt gcattccgag    60
gtgaagctgc tggagagcgg cggcggcctg gtgcagcccg gcggcagcct gaagctgagc   120
tgcgccgcca gcggcttcga cttcagcagg tactggatga actgggtgag gcaggccccc   180
ggcaagggtc tggagtggat cggcgagatc accccgaca gcagcaccat caactacacc   240
cccagcctga aggacaagtt catcatcagc agggacaacg ccaagaacac cctgtacctg   300
cagatgatca aggtgaggag cgaggacacc gccctgtact actgcgtgag gccctacgac   360
tacggcgcct ggttcgccag ctggggccag ggcaccctgg tgaccgtgag cgccggaggg   420
ggcggaagtg gtggcggggg aagcggcggg ggtggcagcg gaggggcgg atctcaggcc   480
gtggtgaccc aggagagcgc cctgaccacc agccccggcg agaccgtgac cctgacctgc   540
aggagcagca ccggcgccgt gaccaccagc aactacgcca actgggtgca ggagaagccc   600
gaccacctgt tcaccggcct gatcggcggc accaacaaga gggcccccgg cgtgcccgcc   660
aggttcagcg gcagcctgat cggcgacaag gccgccctga ccatcaccgg cgcccagacc   720
gaggacgagg ccatctactt ctgcgccctg tggtacagca accactgggt gttcggcggt   780
ggcaccaagc tgaccgtgct gggaggggc ggatccttct gggtgctggt ggtggtgggc   840
ggcgtgctgg cctgctacag cctgctggtg accgtggcct tcatcatctt ctgggtgagg   900
agcaagagga gcaggctgct gcacagcgac tacatgaaca tgaccccag gaggccggc   960
cccaccagga agcactacca gccctacgcc ccccccaggg acttcgccgc ctacaggagc  1020
agggtgaagt tcagcaggag cgccgacgcc cccgcctacc agcagggcca gaaccagctg  1080
tataacgagc tgaacctggg caggagggag gagtacgacg tgctggacaa gaggaggggc  1140
agggaccccg agatgggcgg caagcccagg aggaagaacc cccaggaggg cctgtataac  1200
gagctgcaga aggacaagat ggccgaggcc tacagcgaga tcggcatgaa gggcgagagg  1260
aggagggca agggccacga cggcctgtac cagggcctga gcaccgccac caaggacacc  1320
tacgacgccc tgcacatgca ggccctgccc ccaggtccg agagggcag aggaagtctt  1380
ctaacatgcg gtgacgtgga ggagaatccc ggccctaggg tgagcaaggg cgaggagctg  1440
ttcaccgggg tggtgcccat cctggtcgag ctggacggcg acgtaaacgg ccacaagttc  1500
agcgtgtccg gcgagggcga gggcgatgcc acctacggca agctgaccct gaagttcatc  1560
tgcaccaccg gcaagctgcc cgtgccctgg cccaccctcg tgaccaccct gacctacggc  1620
gtgcagtgct tcagccgcta ccccgaccac atgaagcagc acgacttctt caagtccgcc  1680
atgcccgaag gctacgtcca ggagcgcacc atcttcttca aggacgacgg caactacaag  1740
acccgcgccg aggtgaagtt cgagggcgac accctggtga accgcatcga gctgaagggc  1800
atcgacttca aggaggacgg caacatcctg gggcacaagc tggagtacaa ctacaacagc  1860
cacaacgtct atatcatggc cgacaagcag aagaacggca tcaaggtgaa cttcaagatc  1920
cgccacaaca tcgaggacgg cagcgtgcag ctcgccgacc actaccagca gaacacccc  1980
atcggcgacg gccccgtgct gctgcccgac aaccactacc tgagcaccca gtccgccctg  2040
agcaaagacc ccaacgagaa gcgcgatcac atggtcctgc tggagttcgt gaccgccgcc  2100
gggatcactc tcggcatgga cgagctgtac aagtga                           2136
```

<210> SEQ ID NO 39
<211> LENGTH: 407

<212> TYPE: PRT
<213> ORGANISM: Artificial sequence
<220> FEATURE:
<223> OTHER INFORMATION: Anti-P329G-ds-Fab- heavy chain-CD28ATM-CD28CSD-
    CD3zSSD fusion pETR17100

<400> SEQUENCE: 39

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Phe Trp Val Leu Val Val Val Gly Gly Val Leu Ala Cys
225                 230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
        275                 280                 285

Asp Phe Ala Ala Tyr Arg Ser Arg Val Lys Phe Ser Arg Ser Ala Asp
    290                 295                 300

Ala Pro Ala Tyr Gln Gln Gly Gln Asn Gln Leu Tyr Asn Glu Leu Asn
305                 310                 315                 320

Leu Gly Arg Arg Glu Glu Tyr Asp Val Leu Asp Lys Arg Arg Gly Arg
                325                 330                 335

Asp Pro Glu Met Gly Gly Lys Pro Arg Arg Lys Asn Pro Gln Glu Gly
            340                 345                 350

Leu Tyr Asn Glu Leu Gln Lys Asp Lys Met Ala Glu Ala Tyr Ser Glu
        355                 360                 365

Ile Gly Met Lys Gly Glu Arg Arg Arg Gly Lys Gly His Asp Gly Leu
    370                 375                 380

Tyr Gln Gly Leu Ser Thr Ala Thr Lys Asp Thr Tyr Asp Ala Leu His
385                 390                 395                 400

Met Gln Ala Leu Pro Pro Arg
            405

<210> SEQ ID NO 40
<211> LENGTH: 222
<212> TYPE: PRT
<213> ORGANISM: Artificial sequence
<220> FEATURE:
<223> OTHER INFORMATION: Anti-P329G-ds-Fab heavy chain

<400> SEQUENCE: 40

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Cys Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220

<210> SEQ ID NO 41
<211> LENGTH: 216
<212> TYPE: PRT
<213> ORGANISM: Artificial sequence
<220> FEATURE:
<223> OTHER INFORMATION: Anti P329G-ds-Fab light chain

<400> SEQUENCE: 41

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                 85                  90                  95

His Trp Val Phe Gly Cys Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 42
<211> LENGTH: 107
<212> TYPE: PRT
<213> ORGANISM: Artificial sequence
<220> FEATURE:
<223> OTHER INFORMATION: CL

<400> SEQUENCE: 42

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 43
<211> LENGTH: 103
<212> TYPE: PRT
<213> ORGANISM: Artificial sequence
<220> FEATURE:
<223> OTHER INFORMATION: CH1

<400> SEQUENCE: 43

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100

<210> SEQ ID NO 44
<211> LENGTH: 2645
<212> TYPE: DNA
<213> ORGANISM: Artificial sequence
<220> FEATURE:
<223> OTHER INFORMATION: Anti-P329G-ds-Fab-heavy chain-CD28ATM-CD28CSD-
      CD3zSSD fusion pETR17100

<400> SEQUENCE: 44
atgggatgga gctgtatcat cctcttcttg gtagcaacag ctacgggtgt gcattcccag      60
gccgtggtga cccaggagag cgccctgacc accagccccg cgagaccgt gaccctgacc     120 tgcaggagca gcaccggcgc cgtgaccacc agcaactacg ccaactgggt gcaggagaag    180
cccgaccacc tgttcaccgg cctgatcggc ggcaccaaca gagggcccc cggcgtgccc     240 gccaggttca gcggcagcct gatcggcgac aaggccgccc tgaccatcac cggcgcccag    300
accgaggacg aggccatcta cttctgcgcc ctgtggtaca gcaaccactg ggtgttcggc    360
tgtggcacca gctgaccgt gctgcgtacg gtggctgcac catctgtctt catcttcccg     420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag acagcacct acagcctcag cagcaccctg    600
acgctgagca agcagacta cgagaaacac aaagtctacg cctgcgaagt cacccatcag    660
ggcctgagct cgcccgtcac aaagagcttc aacaggggag agtgttagga attccccgaa    720
gtaacttaga agctgtaaat caacgatcaa tagcaggtgt ggcacaccag tcataccttg    780
atcaagcact tctgtttccc cggactgagt atcaataggc tgctcgcgcg gctgaaggag    840
aaaacgttcg ttacccgacc aactacttcg agaagcttag taccaccatg aacgaggcag    900
ggtgtttcgc tcagcacaac cccagtgtag atcaggctga tgagtcactg caacccccat    960
gggcgaccat ggcagtggct gcgttggcgg cctgcccatg gagaaatcca tgggacgctc    1020
taattctgac atggtgtgaa gtgcctattg agctaactgg tagtcctccg gcccctgatt    1080
gcggctaatc ctaactgcgg agcacatgct cacaaaccag tgggtggtgt gtcgtaacgg    1140
gcaactctgc agcggaaccg actactttgg tgtccgtgt ttcctttat tcctatattg      1200 gctgcttatg gtgacaatca aaagttgtt accatatagc tattggattg ccatccggt      1260 gtgcaacagg gcaactgttt acctatttat tggttttgta ccattatcac tgaagtctgt    1320
gatcactctc aaattcattt tgaccctcaa cacaatcaaa cgccaccatg gatggagct     1380 gtatcatcct cttcttggta gcaacagcta ccggtgtgca ctccgaggtg aagctgctgg    1440
agagcggcgg cggcctggtg cagcccggcg gcagcctgaa gctgagctgc cgccagcg     1500 gcttcgactt cagcaggtac tggatgaact gggtgaggca ggccccggc aagtgtctgg     1560 agtggatcgg cgagatcacc cccgacagca gcaccatcaa ctacacccc agcctgaagg    1620

```
acaagttcat catcagcagg gacaacgcca agaacaccct gtacctgcag atgatcaagg    1680
tgaggagcga ggacaccgcc ctgtactact gcgtgaggcc ctacgactac ggcgcctggt    1740
tcgccagctg gggccagggc accctggtga ccgtgagcgc cgctagcacc aagggcccct    1800
ccgtgttccc cctggccccc agcagcaaga gcaccagcgg cggcacagcc gctctgggct    1860
gcctggtcaa ggactacttc cccgagcccg tgaccgtgtc ctggaacagc ggagccctga    1920
cctccggcgt gcacaccttc ccgccgtgc tgcagagttc tggcctgtat agcctgagca     1980
gcgtggtcac cgtgccttct agcagcctgg gcacccagac ctacatctgc aacgtgaacc    2040
acaagcccag caacaccaag gtggacaaga aggtggagcc caagagctgc ggaggggcg     2100 gatccttctg ggtgctggtg gtggtgggcg gcgtgctggc ctgctacagc ctgctggtga    2160
ccgtggcctt catcatcttc tgggtgagga caagaggag caggctgctg cacagcgact     2220
acatgaacat gaccccagg aggcccggcc ccaccaggaa gcactaccag ccctacgccc      2280 ccccaggga cttcgccgcc tacaggacag ggtgaagtt cagcaggagc gccgacgccc      2340
ccgcctacca gcagggccag aaccagctgt ataacgagct gaacctgggc aggagggagg    2400
agtacgacgt gctggacaag aggaggggca gggaccccga gatgggcggc aagcccagga    2460
ggaagaaccc ccaggagggc ctgtataacg agctgcagaa ggacaagatg gccgaggcct    2520
acagcgagat cggcatgaag ggcgagagga ggaggggcaa gggccacgac ggcctgtacc    2580
agggcctgag caccgccacc aaggacacct acgacgccct gcacatgcag gccctgcccc    2640
ccagg                                                               2645

<210> SEQ ID NO 45
<211> LENGTH: 324
<212> TYPE: DNA
<213> ORGANISM: Artificial sequence
<220> FEATURE:
<223> OTHER INFORMATION: CL

<400> SEQUENCE: 45
cgtacggtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                          324

<210> SEQ ID NO 46
<211> LENGTH: 309
<212> TYPE: DNA
<213> ORGANISM: Artificial sequence
<220> FEATURE:
<223> OTHER INFORMATION: CH1

<400> SEQUENCE: 46
gctagcacca agggcccctc cgtgttcccc ctggccccca gcagcaagag caccagcggc     60
ggcacagccg ctctgggctg cctggtcaag gactacttcc ccgagcccgt gaccgtgtcc    120
tggaacagcg gagccctgac ctccggcgtg cacaccttcc cgccgtgct gcagagttct      180 ggcctgtata gcctgagcag cgtggtcacc gtgccttcta gcagcctggg cacccagacc    240
tacatctgca acgtgaacca caagcccagc aacaccaagg tggacaagaa ggtggagccc    300
```

|  |  |
|---|---:|
| aagagctgc | 309 |

<210> SEQ ID NO 47
<211> LENGTH: 3425
<212> TYPE: DNA
<213> ORGANISM: Artificial sequence
<220> FEATURE:
<223> OTHER INFORMATION: Anti-P329G-ds-Fab-heavy chain-CD28TM-CD28CSD-
CD3ZSSD-eGFP fusion pETR17100

<400> SEQUENCE: 47

|  |  |
|---|---:|
| atgggatgga gctgtatcat cctcttcttg gtagcaacag ctacgggtgt gcattcccag | 60 |
| gccgtggtga cccaggagag cgccctgacc accagcccg gcgagaccgt gaccctgacc | 120 |
| tgcaggagca gcaccggcgc cgtgaccacc agcaactacg ccaactgggt gcaggagaag | 180 |
| cccgaccacc tgttcaccgg cctgatcggc ggcaccaaca gagggcccc cggcgtgccc | 240 |
| gccaggttca gcggcagcct gatcggcgac aaggccgccc tgaccatcac cggcgcccag | 300 |
| accgaggacg aggccatcta cttctgcgcc ctgtggtaca gcaaccactg ggtgttcggc | 360 |
| tgtggcacca agctgaccgt gctgcgtacg gtggctgcac catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag acagcacct acagcctcag cagcaccctg | 600 |
| acgctgagca aagcagacta cgagaaacac aaagtctacg cctgcgaagt cacccatcag | 660 |
| ggcctgagct cgcccgtcac aaagagcttc aacaggggag agtgttagga attccccgaa | 720 |
| gtaacttaga agctgtaaat caacgatcaa tagcaggtgt ggcacaccag tcataccttg | 780 |
| atcaagcact tctgtttccc cggactgagt atcaataggc tgctcgcgcg gctgaaggag | 840 |
| aaaacgttcg ttacccgacc aactacttcg agaagcttag taccaccatg aacgaggcag | 900 |
| ggtgtttcgc tcagcacaac cccagtgtag atcaggctga tgagtcactg caaccccat | 960 |
| gggcgaccat ggcagtggct gcgttggcgg cctgcccatg gagaaatcca tgggacgctc | 1020 |
| taattctgac atggtgtgaa gtgcctattg agctaactgg tagtcctccg gcccctgatt | 1080 |
| gcggctaatc ctaactgcgg agcacatgct cacaaaccag tgggtggtgt gtcgtaacgg | 1140 |
| gcaactctgc agcggaaccg actactttgg gtgtccgtgt tccttttat tcctatattg | 1200 |
| gctgcttatg tgacaatca aaaagttgtt accatatagc tattggattg gccatccggt | 1260 |
| gtgcaacagg gcaactgttt acctatttat tggttttgta ccattatcac tgaagtctgt | 1320 |
| gatcactctc aaattcattt tgaccctcaa cacaatcaaa cgccaccatg ggatggagct | 1380 |
| gtatcatcct cttcttggta gcaacagcta ccggtgtgca ctccgaggtg aagctgctgg | 1440 |
| agagcggcgg cggcctggtg cagcccggcg gcagcctgaa gctgagctgc gccgccagcg | 1500 |
| gcttcgactt cagcaggtac tggatgaact gggtgaggca ggcccccggc aagtgtctgg | 1560 |
| agtggatcgg cgagatcacc cccgacagca gcaccatcaa ctacacccc agcctgaagg | 1620 |
| acaagttcat catcagcagg gacaacgcca agaacaccct gtacctgcag atgatcaagg | 1680 |
| tgaggagcga ggacaccgcc ctgtactact gcgtgaggcc ctacgactac ggcgcctggt | 1740 |
| tcgccagctg gggccagggc acctggtga cgtgagcgc cgctagcacc aagggccct | 1800 |
| ccgtgttccc cctggccccc agcagcaaga gcaccagcgg cggcacagcc gctctgggct | 1860 |
| gcctggtcaa ggactacttc cccgagcccg tgaccgtgtc ctggaacagc ggagccctga | 1920 |
| cctccggcgt gcacaccttc cccgccgtgc tgcagagttc tggcctgtat agcctgagca | 1980 |

-continued

```
gcgtggtcac cgtgccttct agcagcctgg gcacccagac ctacatctgc aacgtgaacc   2040
acaagcccag caacaccaag gtggacaaga aggtggagcc caagagctgc ggaggggggcg   2100 gatccttctg ggtgctggtg gtggtgggcg cgtgctggc ctgctacagc ctgctggtga    2160
ccgtggcctt catcatcttc tgggtgagga gcaagaggag caggctgctg cacagcgact   2220
acatgaacat gacccccagg aggcccggcc ccaccaggaa gcactaccag ccctacgccc   2280
cccccaggga cttcgccgcc tacaggagca gggtgaagtt cagcaggagc gccgacgccc   2340
ccgcctacca gcagggccag aaccagctgt ataacgagct gaacctgggc aggagggagg   2400
agtacgacgt gctggacaag aggaggggca gggaccccga gatgggcggc aagcccagga   2460
ggaagaaccc ccaggagggc ctgtataacg agctgcagaa ggacaagatg gccgaggcct   2520
acagcgagat cggcatgaag ggcgagagga ggagggggcaa gggccacgac ggcctgtacc   2580
agggcctgag caccgccacc aaggacacct acgacgccct gcacatgcag gccctgcccc   2640
ccaggtccgg agagggcaga ggaagtcttc taacatgcgg tgacgtggag gagaatcccg   2700
gccctagggt gagcaagggc gaggagctgt tcaccggggt ggtgcccatc ctggtcgagc   2760
tggacggcga cgtaaacggc cacaagttca gcgtgtccgg cgagggcgag ggcgatgcca   2820
cctacggcaa gctgaccctg aagttcatct gcaccaccgg caagctgccc gtgccctggc   2880
ccaccctcgt gaccaccctg acctacggcg tgcagtgctt cagccgctac cccgaccaca   2940
tgaagcagca cgacttcttc aagtccgcca tgcccgaagg ctacgtccag gagcgcacca   3000
tcttcttcaa ggacgacggc aactacaaga cccgcgccga ggtgaagttc gagggcgaca   3060
ccctggtgaa ccgcatcgag ctgaagggca tcgacttcaa ggaggacggc aacatcctgg   3120
ggcacaagct ggagtacaac tacaacagcc acaacgtcta tatcatggcc gacaagcaga   3180
agaacggcat caaggtgaac ttcaagatcc gccacaacat cgaggacggc agcgtgcagc   3240
tcgccgacca ctaccagcag aaccccccca tcggcgacgg ccccgtgctg ctgcccgaca   3300
accactacct gagcacccag tccgcccctga gcaaagaccc caacgagaag cgcgatcaca   3360
tggtcctgct ggagttcgtg accgccgccg ggatcactct cggcatggac gagctgtaca   3420
agtga                                                                3425
```

<210> SEQ ID NO 48
<211> LENGTH: 407
<212> TYPE: PRT
<213> ORGANISM: Artificial sequence
<220> FEATURE:
<223> OTHER INFORMATION: Anti-P329G-Fab-heavy chain-CD28ATM-CD28CSD-
       CD3zSSD fusion pETR17594

<400> SEQUENCE: 48

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Thr Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95
```

```
Val Arg Pro Tyr Asp Tyr Gly Ala Trp Phe Ala Ser Trp Gly Gln Gly
            100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Gly Gly
210                 215                 220

Gly Gly Ser Phe Trp Val Leu Val Val Gly Gly Val Leu Ala Cys
225                 230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
            275                 280                 285

Asp Phe Ala Ala Tyr Arg Ser Arg Val Lys Phe Ser Arg Ser Ala Asp
290                 295                 300

Ala Pro Ala Tyr Gln Gln Gly Gln Asn Gln Leu Tyr Asn Glu Leu Asn
305                 310                 315                 320

Leu Gly Arg Arg Glu Glu Tyr Asp Val Leu Asp Lys Arg Arg Gly Arg
                325                 330                 335

Asp Pro Glu Met Gly Gly Lys Pro Arg Arg Lys Asn Pro Gln Glu Gly
            340                 345                 350

Leu Tyr Asn Glu Leu Gln Lys Asp Lys Met Ala Glu Ala Tyr Ser Glu
            355                 360                 365

Ile Gly Met Lys Gly Glu Arg Arg Arg Gly Lys Gly His Asp Gly Leu
            370                 375                 380

Tyr Gln Gly Leu Ser Thr Ala Thr Lys Asp Thr Tyr Asp Ala Leu His
385                 390                 395                 400

Met Gln Ala Leu Pro Pro Arg
                405

<210> SEQ ID NO 49
<211> LENGTH: 222
<212> TYPE: PRT
<213> ORGANISM: Artificial sequence
<220> FEATURE:
<223> OTHER INFORMATION: Anti-P329G-Fab heavy chain

<400> SEQUENCE: 49

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
            35                  40                  45
```

```
Gly Glu Ile Thr Pro Asp Ser Ser Thr Ile Asn Tyr Thr Pro Ser Leu
 50                  55                  60
Lys Asp Lys Phe Ile Ile Ser Arg Asp Asn Ala Lys Asn Thr Leu Tyr
 65                  70                  75                  80
Leu Gln Met Ile Lys Val Arg Ser Glu Asp Thr Ala Leu Tyr Tyr Cys
                 85                  90                  95
Val Arg Pro Tyr Asp Tyr Gly Ala Trp Phe Ala Ser Trp Gly Gln Gly
            100                 105                 110
Thr Leu Val Thr Val Ser Ala Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys
210                 215                 220

<210> SEQ ID NO 50
<211> LENGTH: 216
<212> TYPE: PRT
<213> ORGANISM: Artificial sequence
<220> FEATURE:
<223> OTHER INFORMATION: Anti-P329G-Fab light chain

<400> SEQUENCE: 50

Gln Ala Val Val Thr Gln Glu Ser Ala Leu Thr Thr Ser Pro Gly Glu
 1               5                  10                  15
Thr Val Thr Leu Thr Cys Arg Ser Ser Thr Gly Ala Val Thr Thr Ser
                20                  25                  30
Asn Tyr Ala Asn Trp Val Gln Glu Lys Pro Asp His Leu Phe Thr Gly
             35                  40                  45
Leu Ile Gly Gly Thr Asn Lys Arg Ala Pro Gly Val Pro Ala Arg Phe
 50                  55                  60
Ser Gly Ser Leu Ile Gly Asp Lys Ala Ala Leu Thr Ile Thr Gly Ala
 65                  70                  75                  80
Gln Thr Glu Asp Glu Ala Ile Tyr Phe Cys Ala Leu Trp Tyr Ser Asn
                 85                  90                  95
His Trp Val Phe Gly Gly Gly Thr Lys Leu Thr Val Leu Arg Thr Val
            100                 105                 110
Ala Ala Pro Ser Val Phe Ile Phe Pro Pro Ser Asp Glu Gln Leu Lys
        115                 120                 125
Ser Gly Thr Ala Ser Val Val Cys Leu Leu Asn Asn Phe Tyr Pro Arg
130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
            180                 185                 190
```

Val Tyr Ala Cys Glu Val Thr His Gln Gly Leu Ser Ser Pro Val Thr
            195                 200                 205

Lys Ser Phe Asn Arg Gly Glu Cys
    210                 215

<210> SEQ ID NO 51
<211> LENGTH: 2645
<212> TYPE: DNA
<213> ORGANISM: Artificial sequence
<220> FEATURE:
<223> OTHER INFORMATION: Anti-P329G-Fab-heavy chain-CD28ATM-CD28CSD-
      CD3zSSD fusion pETR17594

<400> SEQUENCE: 51

| | |
|---|---|
| atgggatgga gctgtatcat cctcttcttg gtagcaacag ctacgggtgt gcattcccag | 60 |
| gccgtggtga cccaggagag cgccctgacc accagcccg gcgagaccgt gaccctgacc | 120 |
| tgcaggagca gcaccggcgc cgtgaccacc agcaactacg ccaactgggt gcaggagaag | 180 |
| cccgaccacc tgttcaccgg cctgatcggc ggcaccaaca gagggcccc cggcgtgccc | 240 |
| gccaggttca gcggcagcct gatcggcgac aaggccgccc tgaccatcac cggcgcccag | 300 |
| accgaggacg aggccatcta cttctgcgcc ctgtggtaca gcaaccactg ggtgttcggc | 360 |
| ggtggcacca agctgaccgt gctgcgtacg gtggctgcac atctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca agcagactac gagaaacac aaagtctacg cctgcgaagt cacccatcag | 660 |
| ggcctgagct cgcccgtcac aaagagcttc aacaggggag agtgttagga attccccgaa | 720 |
| gtaacttaga agctgtaaat caacgatcaa tagcaggtgt ggcacaccag tcataccttg | 780 |
| atcaagcact tctgtttccc cggactgagt atcaataggc tgctcgcgcg gctgaaggag | 840 |
| aaaacgttcg ttacccgacc aactacttcg agaagcttag taccaccatg aacgaggcag | 900 |
| ggtgtttcgc tcagcacaac cccagtgtag atcaggctga tgagtcactg caaccccccat | 960 |
| gggcgaccat ggcagtggct gcgttggcgg cctgcccatg gagaaatcca tgggacgctc | 1020 |
| taattctgac atggtgtgaa gtgcctattg agctaactgg tagtcctccg gcccctgatt | 1080 |
| gcggctaatc ctaactgcgg agcacatgct cacaaaccag tgggtggtgt gtcgtaacgg | 1140 |
| gcaactctgc agcggaaccg actactttgg gtgtccgtgt tccttttat tcctatattg | 1200 |
| gctgcttatg tgacaatca aaagttgtt accatatagc tattggattg gccatccggt | 1260 |
| gtgcaacagg gcaactgttt acctatttat tggttttgta ccattatcac tgaagtctgt | 1320 |
| gatcactctc aaattcattt tgaccctcaa cacaatcaaa cgccaccatg ggatggagct | 1380 |
| gtatcatcct cttcttggta gcaacagcta ccggtgtgca ctccgaggtg aagctgctgg | 1440 |
| agagcggcgg cggcctggtg cagcccggcg gcagcctgaa gctgagctgc cgccagcg | 1500 |
| gcttcgactt cagcaggtac tggatgaact gggtgaggca ggccccggc aagggtctgg | 1560 |
| agtggatcgg cgagatcacc cccgacagca gcaccatcaa ctacacccc agcctgaagg | 1620 |
| acaagttcat catcagcagg gacaacgcca agaacaccct gtacctgcag atgatcaagg | 1680 |
| tgaggagcga ggacaccgcc ctgtactact gcgtgaggcc ctacgactac ggcgcctggt | 1740 |
| tcgccagctg gggccagggc acctggtga ccgtgagcgc cgctagcacc aagggcccct | 1800 |
| ccgtgttccc cctggccccc agcagcaaga gcaccagcgg cggcacagcc gctctgggct | 1860 |

```
gcctggtcaa ggactacttc cccgagcccg tgaccgtgtc ctggaacagc ggagccctga   1920
cctccggcgt gcacaccttc cccgccgtgc tgcagagttc tggcctgtat agcctgagca   1980
gcgtggtcac cgtgccttct agcagcctgg gcacccagac ctacatctgc aacgtgaacc   2040
acaagcccag caacaccaag gtggacaaga aggtggagcc caagagctgc gaggggggcg   2100
gatccttctg ggtgctggtg gtggtgggcg gcgtgctggc ctgctacagc ctgctggtga   2160
ccgtggcctt catcatcttc tgggtgagga gcaagaggag caggctgctg cacagcgact   2220
acatgaacat gaccccagg aggcccggcc ccaccaggaa gcactaccag ccctacgccc   2280
cccccaggga cttcgccgcc tacaggagca gggtgaagtt cagcaggagc gccgacgccc   2340
ccgcctacca gcagggccag aaccagctgt ataacgagct gaacctgggc aggagggagg   2400
agtacgacgt gctggacaag aggaggggca gggaccccga gatgggcggc aagcccagga   2460
ggaagaaccc ccaggagggc ctgtataacg agctgcagaa ggacaagatg gccgaggcct   2520
acagcgagat cggcatgaag ggcgagagga ggagggcaa gggccacgac ggcctgtacc   2580
agggcctgag caccgccacc aaggacacct acgacgccct gcacatgcag gccctgcccc   2640
ccagg                                                              2645
```

<210> SEQ ID NO 52
<211> LENGTH: 3425
<212> TYPE: DNA
<213> ORGANISM: Artificial sequence
<220> FEATURE:
<223> OTHER INFORMATION: Anti-P329G-Fab-heavy chain-CD28ATM-CD28CSD-
      CD3zSSD-eGFP fusion pETR17594

<400> SEQUENCE: 52

```
atgggatgga gctgtatcat cctcttcttg gtagcaacag ctacgggtgt gcattcccag     60
gccgtggtga cccaggagag cgccctgacc accagccccg gcgagaccgt gaccctgacc    120
tgcaggagca gcaccggcgc cgtgaccacc agcaactacg ccaactgggt gcaggagaag    180
cccgaccacc tgttcaccgg cctgatcggc ggcaccaaca gagggcccc cggcgtgccc    240 gccaggttca gcggcagcct gatcggcgac aaggccgccc tgaccatcac cggcgcccag    300
accgaggacg aggccatcta cttctgcgcc ctgtggtaca gcaaccactg ggtgttcggc    360
ggtggcacca gctgaccgt gctgcgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacaggggag agtgttagga attccccgaa    720
gtaacttaga agctgtaaat caacgatcaa tagcaggtgt ggcacaccag tcataccttg    780
atcaagcact tctgtttccc cggactgagt atcaataggc tgctcgcgcg gctgaaggag    840
aaaacgttcg ttacccgacc aactacttcg agaagcttag taccaccatg aacgaggcag    900
ggtgtttcgc tcagcacaac cccagtgtag atcaggctga tgagtcactg caacccccat    960
gggcgaccat ggcagtggct gcgttggcgg cctgcccatg gagaaatcca tgggacgctc   1020
taattctgac atggtgtgaa gtgcctattg agctaactgg tagtcctccg gcccctgatt   1080
gcggctaatc ctaactgcgg agcacatgct cacaaaccag tgggtggtgt gtcgtaacgg   1140
gcaactctgc agcggaaccg actactttgg ggtgtccgtgt ttccttttat tcctatattg   1200
```

```
gctgcttatg gtgacaatca aaaagttgtt accatatagc tattggattg ccatccggt   1260
gtgcaacagg gcaactgttt acctatttat tggttttgta ccattatcac tgaagtctgt   1320
gatcactctc aaattcattt tgaccctcaa cacaatcaaa cgccaccatg ggatggagct   1380
gtatcatcct cttcttggta gcaacagcta ccggtgtgca ctccgaggtg aagctgctgg   1440
agagcggcgg cggcctggtg cagcccggcg gcagcctgaa gctgagctgc gccgccagcg   1500
gcttcgactt cagcaggtac tggatgaact gggtgaggca ggcccccggc aagggtctgg   1560
agtggatcgg cgagatcacc cccgacagca gcaccatcaa ctacaccccc agcctgaagg   1620
acaagttcat catcagcagg gacaacgcca agaacaccct gtacctgcag atgatcaagg   1680
tgaggagcga ggacaccgcc ctgtactact gcgtgaggcc ctacgactac ggcgcctggt   1740
tcgccagctg gggccagggc accctggtga ccgtgagcgc cgctagcacc aagggcccct   1800
ccgtgttccc cctggccccc agcagcaaga gcaccagcgg cggcacagcc gctctgggct   1860
gcctggtcaa ggactacttc cccgagcccg tgaccgtgtc ctggaacagc ggagccctga   1920
cctccggcgt gcacaccttc cccgccgtgc tgcagagttc tggcctgtat agcctgagca   1980
gcgtggtcac cgtgccttct agcagcctgg gcacccagac ctacatctgc aacgtgaacc   2040
acaagcccag caacaccaag gtggacaaga aggtggagcc caagagctgc ggaggggcg   2100
gatccttctg ggtgctggtg gtggtgggcg gcgtgctggc ctgctacagc ctgctggtga   2160
ccgtggcctt catcatcttc tgggtgagga caagaggag caggctgctg cacagcgact   2220
acatgaacat gacccccagg aggcccggcc ccaccaggaa gcactaccag ccctacgccc   2280
cccccaggga cttcgccgcc tacaggagca gggtgaagtt cagcaggagc gccgacgccc   2340
ccgcctacca gcagggccag aaccagctgt ataacgagct gaacctgggc aggagggagg   2400
agtacgacgt gctggacaag aggaggggca gggaccccga tgggcggc aagcccagga   2460
ggaagaaccc ccaggagggc ctgtataacg agctgcagaa ggacaagatg gccgaggcct   2520
acagcgagat cggcatgaag ggcgagagga gagggcaa gggccacgac ggcctgtacc   2580
agggcctgag caccgccacc aaggacacct acgacgccct gcacatgcag gccctgcccc   2640
ccagtccgg agagggcaga ggaagtcttc taacatgcgg tgacgtggag gagaatcccg   2700
gcctagggt gagcaaggc gaggagctgt tcaccggggt ggtgcccatc ctggtcgagc   2760
tggacggcga cgtaaacggc cacaagttca gcgtgtccgg cgagggcgag ggcgatgcca   2820
cctacggcaa gctgaccctg aagttcatct gcaccaccgg caagctgccc gtgccctggc   2880
ccaccctcgt gaccaccctg acctacggcg tgcagtgctt cagccgctac cccgaccaca   2940
tgaagcagca cgacttcttc aagtccgcca tgcccgaagg ctacgtccag gagcgcacca   3000
tcttcttcaa ggacgacggc aactacaaga cccgcgccga ggtgaagttc gagggcgaca   3060
ccctggtgaa ccgcatcgag ctgaagggca tcgacttcaa ggaggacggc aacatcctgg   3120
ggcacaagct ggagtacaac tacaacagcc acaacgtcta tatcatggcc gacaagcaga   3180
agaacggcat caaggtgaac ttcaagatcc gccacaacat cgaggacggc agcgtgcagc   3240
tcgccgacca ctaccagcag aacaccccca tcggcgacgg ccccgtgctg ctgcccgaca   3300
accactacct gagcacccag tccgccctga gcaaagaccc caacgagaag cgcgatcaca   3360
tggtcctgct ggagttcgtg accgccgccg ggatcactct cggcatggac gagctgtaca   3420
agtga                                                               3425

<210> SEQ ID NO 53
<211> LENGTH: 5
```

```
<212> TYPE: PRT
<213> ORGANISM: Artificial sequence
<220> FEATURE:
<223> OTHER INFORMATION: Anti-AAA CDR H1 Kabat

<400> SEQUENCE: 53

Ser Tyr Gly Met Ser
1               5

<210> SEQ ID NO 54
<211> LENGTH: 6
<212> TYPE: PRT
<213> ORGANISM: Artificial sequence
<220> FEATURE:
<223> OTHER INFORMATION: Anti-AAA CDR H2 Kabat

<400> SEQUENCE: 54

Ser Ser Gly Gly Ser Tyr
1               5

<210> SEQ ID NO 55
<211> LENGTH: 12
<212> TYPE: PRT
<213> ORGANISM: Artificial sequence
<220> FEATURE:
<223> OTHER INFORMATION: Anti-AAA CDR H3 Kabat

<400> SEQUENCE: 55

Leu Gly Met Ile Thr Thr Gly Tyr Ala Met Asp Tyr
1               5                   10

<210> SEQ ID NO 56
<211> LENGTH: 16
<212> TYPE: PRT
<213> ORGANISM: Artificial sequence
<220> FEATURE:
<223> OTHER INFORMATION: Anti-AAA CDR L1 Kabat

<400> SEQUENCE: 56

Arg Ser Ser Gln Thr Ile Val His Ser Thr Gly His Thr Tyr Leu Glu
1               5                   10                  15

<210> SEQ ID NO 57
<211> LENGTH: 7
<212> TYPE: PRT
<213> ORGANISM: Artificial sequence
<220> FEATURE:
<223> OTHER INFORMATION: Anti-AAA CDR L2 Kabat

<400> SEQUENCE: 57

Lys Val Ser Asn Arg Phe Ser
1               5

<210> SEQ ID NO 58
<211> LENGTH: 9
<212> TYPE: PRT
<213> ORGANISM: Artificial sequence
<220> FEATURE:
<223> OTHER INFORMATION: Anti-AAA CDR L3 Kabat

<400> SEQUENCE: 58

Phe Gln Gly Ser His Val Pro Tyr Thr
1               5

<210> SEQ ID NO 59
<211> LENGTH: 457
<212> TYPE: PRT
```

<213> ORGANISM: Artificial sequence
<220> FEATURE:
<223> OTHER INFORMATION: Anti-AAA-scFv-CD28ATM-CD28CSD-CD3zSSD fusion

<400> SEQUENCE: 59

```
Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Ser Gly Gly Gly Gly Ser
145                 150                 155                 160

Asp Val Leu Met Thr Gln Thr Pro Leu Ser Leu Pro Val Ser Leu Gly
                165                 170                 175

Asp Gln Ala Ser Ile Ser Cys Arg Ser Ser Gln Thr Ile Val His Ser
            180                 185                 190

Thr Gly His Thr Tyr Leu Glu Trp Phe Leu Gln Lys Pro Gly Gln Ser
        195                 200                 205

Pro Lys Leu Leu Ile Tyr Lys Val Ser Asn Arg Phe Ser Gly Val Pro
    210                 215                 220

Asp Arg Phe Ser Gly Ser Gly Ser Gly Thr Asp Phe Thr Leu Lys Ile
225                 230                 235                 240

Ser Arg Val Glu Ala Glu Asp Leu Gly Val Tyr Tyr Cys Phe Gln Gly
                245                 250                 255

Ser His Val Pro Tyr Thr Phe Gly Gly Gly Thr Lys Leu Glu Ile Lys
            260                 265                 270

Gly Gly Gly Gly Ser Phe Trp Val Leu Val Val Gly Gly Val Leu
        275                 280                 285

Ala Cys Tyr Ser Leu Leu Val Thr Val Ala Phe Ile Ile Phe Trp Val
290                 295                 300

Arg Ser Lys Arg Ser Arg Leu Leu His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
```

```
385                 390                 395                 400
Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
                420                 425                 430

Gly Leu Tyr Gln Gly Leu Ser Thr Ala Thr Lys Asp Thr Tyr Asp Ala
                435                 440                 445

Leu His Met Gln Ala Leu Pro Pro Arg
            450                 455

<210> SEQ ID NO 60
<211> LENGTH: 272
<212> TYPE: PRT
<213> ORGANISM: Artificial sequence
<220> FEATURE:
<223> OTHER INFORMATION: Anti-AAA-scFv

<400> SEQUENCE: 60

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Gly Gly Gly Gly
    130                 135                 140

Ser Gly Gly Gly Gly Ser Gly Gly Gly Ser Gly Gly Gly Gly Ser
145                 150                 155                 160

Asp Val Leu Met Thr Gln Thr Pro Leu Ser Leu Pro Val Ser Leu Gly
                165                 170                 175

Asp Gln Ala Ser Ile Ser Cys Arg Ser Ser Gln Thr Ile Val His Ser
            180                 185                 190

Thr Gly His Thr Tyr Leu Glu Trp Phe Leu Gln Lys Pro Gly Gln Ser
        195                 200                 205

Pro Lys Leu Leu Ile Tyr Lys Val Ser Asn Arg Phe Ser Gly Val Pro
    210                 215                 220

Asp Arg Phe Ser Gly Ser Gly Ser Gly Thr Asp Phe Thr Leu Lys Ile
225                 230                 235                 240

Ser Arg Val Glu Ala Glu Asp Leu Gly Val Tyr Tyr Cys Phe Gln Gly
                245                 250                 255

Ser His Val Pro Tyr Thr Phe Gly Gly Gly Thr Lys Leu Glu Ile Lys
            260                 265                 270

<210> SEQ ID NO 61
<211> LENGTH: 140
<212> TYPE: PRT
```

```
<213> ORGANISM: Artificial sequence
<220> FEATURE:
<223> OTHER INFORMATION: Anti-AAA VH

<400> SEQUENCE: 61

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser
    130                 135                 140

<210> SEQ ID NO 62
<211> LENGTH: 112
<212> TYPE: PRT
<213> ORGANISM: Artificial sequence
<220> FEATURE:
<223> OTHER INFORMATION: Anti-AAA VL

<400> SEQUENCE: 62

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Thr Gly His Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 63
<211> LENGTH: 428
<212> TYPE: PRT
<213> ORGANISM: Artificial sequence
<220> FEATURE:
<223> OTHER INFORMATION: Anti-AAA-Fab-heavy chain-CD28ATM-CD28CSD-
      CD3zSSD fusion

<400> SEQUENCE: 63

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
```

```
            20                  25                  30
Pro Gly Gly Ser Leu Lys Leu Ser Cys Ala Ala Ser Gly Phe Thr Phe
            35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Gly Gly Gly Gly Ser Phe Trp Val Leu Val Val Val Gly
                245                 250                 255

Gly Val Leu Ala Cys Tyr Ser Leu Leu Val Thr Val Ala Phe Ile Ile
                260                 265                 270

Phe Trp Val Arg Ser Lys Arg Ser Arg Leu Leu His Ser Asp Tyr Met
            275                 280                 285

Asn Met Thr Pro Arg Arg Pro Gly Pro Thr Arg Lys His Tyr Gln Pro
        290                 295                 300

Tyr Ala Pro Pro Arg Asp Phe Ala Ala Tyr Arg Ser Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
            340                 345                 350

Lys Arg Arg Gly Arg Asp Pro Glu Met Gly Gly Lys Pro Arg Arg Lys
        355                 360                 365

Asn Pro Gln Glu Gly Leu Tyr Asn Glu Leu Gln Lys Asp Lys Met Ala
        370                 375                 380

Glu Ala Tyr Ser Glu Ile Gly Met Lys Gly Glu Arg Arg Arg Gly Lys
385                 390                 395                 400

Gly His Asp Gly Leu Tyr Gln Gly Leu Ser Thr Ala Thr Lys Asp Thr
                405                 410                 415

Tyr Asp Ala Leu His Met Gln Ala Leu Pro Pro Arg
            420                 425

<210> SEQ ID NO 64
```

```
<211> LENGTH: 243
<212> TYPE: PRT
<213> ORGANISM: Artificial sequence
<220> FEATURE:
<223> OTHER INFORMATION: Anti-AAA-Fab heavy chain

<400> SEQUENCE: 64
```

Met Asn Phe Gly Leu Ser Leu Val Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Gly Met Ser Trp Val Arg Gln Thr Pro Asp Lys Arg Leu
    50                  55                  60

Glu Trp Val Ala Thr Ile Ser Ser Gly Gly Ser Tyr Ile Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys

```
<210> SEQ ID NO 65
<211> LENGTH: 219
<212> TYPE: PRT
<213> ORGANISM: Artificial sequence
<220> FEATURE:
<223> OTHER INFORMATION: Anti-AAA-Fab light chain

<400> SEQUENCE: 65
```

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Thr Gly His Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
              85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 66
<211> LENGTH: 164
<212> TYPE: PRT
<213> ORGANISM: Homo sapiens

<400> SEQUENCE: 66

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 67
<211> LENGTH: 492
<212> TYPE: DNA
<213> ORGANISM: Homo sapiens

<400> SEQUENCE: 67
atgaagtgga aggcgctttt caccgcggcc atcctgcagg cacagttgcc gattacagag      60
gcacagagct ttggcctgct ggatcccaaa ctctgctacc tgctggatgg aatcctcttc     120

```
atctatggtg tcattctcac tgccttgttc ctgagagtga agttcagcag gagcgcagag    180 cccccgcgt accagcaggg ccagaaccag ctctataacg agctcaatct aggacgaaga     240
gaggagtacg atgttttgga caagagacgt ggccgggacc ctgagatggg gggaaagccg    300
agaaggaaga accctcagga aggcctgtac aatgaactgc agaaagataa gatggcggag    360
gcctacagtg agattgggat gaaaggcgag cgccggaggg gcaaggggca cgatggcctt    420
taccagggtc tcagtacagc caccaaggac acctacgacg cccttcacat gcaggccctg    480 cccctcgct aa                                                         492
```

<210> SEQ ID NO 68
<211> LENGTH: 164
<212> TYPE: PRT
<213> ORGANISM: Mus musculus

<400> SEQUENCE: 68

```
Met Lys Trp Lys Val Ser Val Leu Ala Cys Ile Leu His Val Arg Phe
1               5                   10                  15

Pro Gly Ala Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Ile Thr Ala
        35                  40                  45

Leu Tyr Leu Arg Ala Lys Phe Ser Arg Ser Ala Glu Thr Ala Ala Asn
    50                  55                  60

Leu Gln Asp Pro Asn Gln Leu Tyr Asn Glu Leu Asn Leu Gly Arg Arg
65                  70                  75                  80

Glu Glu Tyr Asp Val Leu Glu Lys Lys Arg Ala Arg Asp Pro Glu Met
                85                  90                  95

Gly Gly Lys Gln Gln Arg Arg Asn Pro Gln Glu Gly Val Tyr Asn
            100                 105                 110

Ala Leu Gln Lys Asp Lys Met Ala Glu Ala Tyr Ser Glu Ile Gly Thr
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Thr
145                 150                 155                 160

Leu Ala Pro Arg
```

<210> SEQ ID NO 69
<211> LENGTH: 495
<212> TYPE: DNA
<213> ORGANISM: Mus musculus

<400> SEQUENCE: 69

```
atgaagtgga aagtgtctgt tctcgcctgc atcctccacg tgcggttccc aggagcagag    60
gcacagagct tggtctgct ggatcccaaa ctctgctact tgctagatgg aatcctcttc    120
atctacggag tcatcatcac agccctgtac ctgagagcaa aattcagcag gagtgcagag    180
actgctgcca acctgcagga ccccaaccag ctctacaatg agctcaatct agggcgaaga    240
gaggaatatg acgtcttgga gaagaagcgg gctcgggatc cagagatggg aggcaaacag    300
cagaggagga ggaaccccca ggaaggcgta caatgcac tgcagaaaga caagatggca    360
gaagcctaca gtgagatcgg cacaaaaggc gagaggcgga gaggcaaggg gcacgatggc    420
ctttaccagg gtctcagcac tgccaccaag gacacctatg atgccctgca tatgcagacc    480
```

```
ctggcccctc gctaa                                                495
```

<210> SEQ ID NO 70
<211> LENGTH: 660
<212> TYPE: DNA
<213> ORGANISM: Homo sapiens

<400> SEQUENCE: 70

```
atgctgcgcc tgctgctggc gctgaacctg tttccgagca ttcaggtgac cggcaacaaa    60
attctggtga acagagccc gatgctggtg gcgtatgata cgcggtgaa cctgagctgc     120
aaatatagct ataacctgtt tagccgcgaa tttcgcgcga gcctgcataa aggcctggat    180
agcgcggtgg aagtgtgcgt ggtgtatggc aactatagcc agcagctgca ggtgtatagc    240
aaaaccggct ttaactgcga tggcaaactg ggcaacgaaa gcgtgacctt ttatctgcag    300
aacctgtatg tgaaccagac cgatatttat ttttgcaaaa ttgaagtgat gtatccgccg    360
ccgtatctgg ataacgaaaa agcaacggc accattattc atgtgaaagg caaacatctg    420
tgcccgagcc cgctgtttcc gggcccgagc aaaccgtttt gggtgctggt ggtggtgggc    480
ggcgtgctgg cgtgctatag cctgctggtg accgtggcgt ttattatttt ttgggtgcgc    540
agcaaacgca gccgcctgct gcatagcgat tatatgaaca tgaccccgcg ccgcccgggc    600
ccgacccgca acattatca gccgtatgcg ccgccgcgcg attttgcggc gtatcgcagc    660
```

<210> SEQ ID NO 71
<211> LENGTH: 220
<212> TYPE: PRT
<213> ORGANISM: Homo sapiens

<400> SEQUENCE: 71

```
Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205
```

```
Tyr Ala Pro Pro Arg Asp Phe Ala Ala Tyr Arg Ser
    210                 215                 220
```

<210> SEQ ID NO 72
<211> LENGTH: 654
<212> TYPE: DNA
<213> ORGANISM: Mus musculus

<400> SEQUENCE: 72

```
atgaccctgc gcctgctgtt tctggcgctg aacttttta gcgtgcaggt gaccgaaaac      60
aaaattctgg tgaaacagag cccgctgctg gtggtggata gcaacgaagt gagcctgagc     120
tgccgctata gctataacct gctggcgaaa gaatttcgcg cgagcctgta taaaggcgtg     180
aacagcgatg tggaagtgtg cgtgggcaac ggcaacttta cctatcagcc gcagtttcgc     240
agcaacgcgg aatttaactg cgatggcgat tttgataacg aaaccgtgac ctttcgcctg     300
tggaacctgc atgtgaacca taccgatatt tattttgca aaattgaatt tatgtatccg      360
ccgccgtatc tggataacga acgcagcaac ggcaccatta ttcatattaa agaaaaacat     420
ctgtgccata cccagagcag cccgaaactg ttttgggcgc tggtggtggt ggcgggcgtg     480
ctgttttgct atggcctgct ggtgaccgtg gcgctgtgcg tgatttggac caacagccgc     540
cgcaaccgcc tgctgcagag cgattatatg aacatgaccc cgcgccgccc gggcctgacc     600
cgcaaaccgt atcagccgta tgcgccggcg cgcgattttg cggcgtatcg cccg           654
```

<210> SEQ ID NO 73
<211> LENGTH: 218
<212> TYPE: PRT
<213> ORGANISM: Mus musculus

<400> SEQUENCE: 73

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
        195                 200                 205
```

-continued

Pro Ala Arg Asp Phe Ala Ala Tyr Arg Pro
    210                 215

<210> SEQ ID NO 74
<211> LENGTH: 4
<212> TYPE: PRT
<213> ORGANISM: Artificial sequence
<220> FEATURE:
<223> OTHER INFORMATION: CD28 YMNM

<400> SEQUENCE: 74

Tyr Met Asn Met
1

<210> SEQ ID NO 75
<211> LENGTH: 4
<212> TYPE: PRT
<213> ORGANISM: Artificial sequence
<220> FEATURE:
<223> OTHER INFORMATION: CD28 PYAP

<400> SEQUENCE: 75

Pro Tyr Ala Pro
1

<210> SEQ ID NO 76
<211> LENGTH: 21
<212> TYPE: PRT
<213> ORGANISM: Artificial sequence
<220> FEATURE:
<223> OTHER INFORMATION: Signal peptide

<400> SEQUENCE: 76

Ala Thr Met Gly Trp Ser Cys Ile Ile Leu Phe Leu Val Ala Thr Ala
1               5                   10                  15

Thr Gly Val His Ser
            20

<210> SEQ ID NO 77
<211> LENGTH: 57
<212> TYPE: DNA
<213> ORGANISM: Artificial sequence
<220> FEATURE:
<223> OTHER INFORMATION: Signal peptide DNA sequence

<400> SEQUENCE: 77
atgggatgga gctgtatcat cctcttcttg gtagcaacag ctaccggtgt gcactcc        57

<210> SEQ ID NO 78
<211> LENGTH: 449
<212> TYPE: PRT
<213> ORGANISM: Artificial sequence
<220> FEATURE:
<223> OTHER INFORMATION: Anti-CD20 (GA101) heavy chain

<400> SEQUENCE: 78

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 79
<211> LENGTH: 219
<212> TYPE: PRT

<213> ORGANISM: Artificial sequence
<220> FEATURE:
<223> OTHER INFORMATION: Anti-CD20 (GA101) light chain

<400> SEQUENCE: 79

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 80
<211> LENGTH: 447
<212> TYPE: PRT
<213> ORGANISM: Artificial sequence
<220> FEATURE:
<223> OTHER INFORMATION: Anti-FAP(4B9) PGLALA heavy chain

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 81
<211> LENGTH: 215
<212> TYPE: PRT
<213> ORGANISM: Artificial sequence
<220> FEATURE:
<223> OTHER INFORMATION: Anti-FAP(4B9) light chain

<400> SEQUENCE: 81

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30
```

Tyr Leu Ala Trp Tyr Gln Gln Lys Pro Gly Gln Ala Pro Arg Leu Leu
            35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 82
<211> LENGTH: 451
<212> TYPE: PRT
<213> ORGANISM: Artificial sequence
<220> FEATURE:
<223> OTHER INFORMATION: Anti-CEA (A5B7) PGLALA heavy chain

<400> SEQUENCE: 82

Glu Val Gln Leu Val Glu Ser Gly Gly Gly Leu Val Gln Pro Gly Arg
 1                   5                  10                  15

Ser Leu Arg Leu Ser Cys Ala Ala Ser Gly Phe Thr Val Ser Ser Tyr
             20                  25                  30

Trp Met His Trp Val Arg Gln Ala Pro Gly Lys Gly Leu Glu Trp Val
            35                  40                  45

Gly Phe Ile Arg Asn Lys Ala Asn Gly Gly Thr Thr Glu Tyr Ala Ala
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Arg Gly Leu Arg Phe Tyr Phe Asp Tyr Trp Gly
                100                 105                 110

Gln Gly Thr Thr Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

```
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 83
<211> LENGTH: 223
<212> TYPE: PRT
<213> ORGANISM: Artificial sequence
<220> FEATURE:
<223> OTHER INFORMATION: Anti-CEA (A5B7) light chain

<400> SEQUENCE: 83

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80
```

```
Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Arg Thr Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220

<210> SEQ ID NO 84
<211> LENGTH: 451
<212> TYPE: PRT
<213> ORGANISM: Artificial sequence
<220> FEATURE:
<223> OTHER INFORMATION: Anti-CEA (T84.66LCHA) PGLALA heavy chain

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 85
<211> LENGTH: 218
<212> TYPE: PRT
<213> ORGANISM: Artificial sequence
<220> FEATURE:
<223> OTHER INFORMATION: Anti-CEA (T84.66LCHA) light chain

<400> SEQUENCE: 85

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215
```

<210> SEQ ID NO 86
<211> LENGTH: 451
<212> TYPE: PRT
<213> ORGANISM: Artificial sequence
<220> FEATURE:
<223> OTHER INFORMATION: Anti-CEA (CH1A1A98/992F1) PGLALA heavy chain

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
                20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

```
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 87
<211> LENGTH: 215
<212> TYPE: PRT
<213> ORGANISM: Artificial sequence
<220> FEATURE:
<223> OTHER INFORMATION: Anti-CEA (CH1A1A98/992F1) light chain

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 88
<211> LENGTH: 449
<212> TYPE: PRT
<213> ORGANISM: Artificial sequence
<220> FEATURE:
<223> OTHER INFORMATION: Anti-CEA (hMN14) PGLALA heavy chain

<400> SEQUENCE: 88

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445
Lys

<210> SEQ ID NO 89
<211> LENGTH: 213
<212> TYPE: PRT
<213> ORGANISM: Artificial sequence
<220> FEATURE:
<223> OTHER INFORMATION: Anti-CEA (hMN14) light chain

<400> SEQUENCE: 89

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
                20                  25                  30

Val Ala Trp Tyr Gln Gln Lys Pro Gly Lys Ala Pro Lys Leu Leu Ile
            35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210
```

-continued

<210> SEQ ID NO 90
<211> LENGTH: 451
<212> TYPE: PRT
<213> ORGANISM: Artificial sequence
<220> FEATURE:
<223> OTHER INFORMATION: Anti-TNC (2B10) PGLALA heavy chain

<400> SEQUENCE: 90

```
Gln Val Gln Leu Val Gln Ser Gly Ala Glu Val Lys Lys Pro Gly Ser
1               5                   10                  15

Ser Val Lys Val Ser Cys Lys Ala Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
```

```
                    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Val Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly Lys
    450

<210> SEQ ID NO 91
<211> LENGTH: 214
<212> TYPE: PRT
<213> ORGANISM: Artificial sequence
<220> FEATURE:
<223> OTHER INFORMATION: Anti-TNC (2B10) light chain

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 92
<211> LENGTH: 449
<212> TYPE: PRT
<213> ORGANISM: Artificial sequence
<220> FEATURE:
<223> OTHER INFORMATION: Anti-HER2 (PER) PG LALA heavy chain 1

<400> SEQUENCE: 92
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Ser Ile Tyr Asn Gln Arg Phe
    50                  55                  60

Lys Gly Arg Phe Thr Leu Ser Val Asp Arg Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

-continued

```
                    420                 425                 430
Ala Leu His Asn His Tyr Thr Gln Lys Ser Leu Ser Leu Ser Pro Gly
            435                 440                 445
Lys

<210> SEQ ID NO 93
<211> LENGTH: 214
<212> TYPE: PRT
<213> ORGANISM: Artificial sequence
<220> FEATURE:
<223> OTHER INFORMATION: Anti-HER2 (PER) light chain 1

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 449
<212> TYPE: PRT
<213> ORGANISM: Artificial sequence
<220> FEATURE:
<223> OTHER INFORMATION: Anti-HER2 (PER) PG LALA heavy chain 2

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
```

50                  55                  60
Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 95
<211> LENGTH: 214

<212> TYPE: PRT
<213> ORGANISM: Artificial sequence
<220> FEATURE:
<223> OTHER INFORMATION: Anti-HER2 (PER) light chain 2

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 96
<211> LENGTH: 372
<212> TYPE: PRT
<213> ORGANISM: Artificial sequence
<220> FEATURE:
<223> OTHER INFORMATION: Anti-WT1 (33F05) PGLALA heavy chain

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Tyr Tyr Glu Ala Phe Asp Tyr Trp Gly Gln Gly Thr Leu Val
            100                 105                 110

```
Thr Val Ser Ser Ser Leu Gly Thr Gln Thr Tyr Ile Cys Asn Val Asn
            115                 120                 125

His Lys Pro Ser Asn Thr Lys Val Asp Lys Lys Val Glu Pro Lys Ser
        130                 135                 140

Cys Asp Lys Thr His Thr Cys Pro Pro Cys Pro Ala Pro Glu Ala Ala
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Gly Ala Pro
                245                 250                 255

Ile Glu Lys Thr Ile Ser Lys Ala Lys Gly Gln Pro Arg Glu Pro Gln
            260                 265                 270

Val Cys Thr Leu Pro Pro Ser Arg Asp Glu Leu Thr Lys Asn Gln Val
        275                 280                 285

Ser Leu Ser Cys Ala Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Val Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 97
<211> LENGTH: 214
<212> TYPE: PRT
<213> ORGANISM: Artificial sequence
<220> FEATURE:
<223> OTHER INFORMATION: Anti-WT1 (33F05) light chain

<400> SEQUENCE: 97

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Pro Asp Met Asn Gly Asn Ala
                85                  90                  95
```

```
Val Phe Gly Gly Gly Thr Lys Leu Thr Val Leu Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 98
<211> LENGTH: 376
<212> TYPE: PRT
<213> ORGANISM: Artificial sequence
<220> FEATURE:
<223> OTHER INFORMATION: Anti-WT1 (11D06) PGLALA heavy chain

<400> SEQUENCE: 98

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Glu Leu Trp Trp Gly Gly Phe Asp Tyr Trp Gly Gln
            100                 105                 110

Gly Thr Thr Val Thr Val Ser Ser Leu Gly Thr Gln Thr Tyr Ile
        115                 120                 125

Cys Asn Val Asn His Lys Pro Ser Asn Thr Lys Val Asp Lys Lys Val
130                 135                 140

Glu Pro Lys Ser Cys Asp Lys Thr His Thr Cys Pro Pro Cys Pro Ala
145                 150                 155                 160

Pro Glu Ala Ala Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240
```

-continued

```
Asp Trp Leu Asn Gly Lys Glu Tyr Lys Cys Lys Val Ser Asn Lys Ala
            245                 250                 255
Leu Gly Ala Pro Ile Glu Lys Thr Ile Ser Lys Ala Lys Gly Gln Pro
        260                 265                 270
Arg Glu Pro Gln Val Cys Thr Leu Pro Pro Ser Arg Asp Glu Leu Thr
    275                 280                 285
Lys Asn Gln Val Ser Leu Ser Cys Ala Val Lys Gly Phe Tyr Pro Ser
290                 295                 300
Asp Ile Ala Val Glu Trp Glu Ser Asn Gly Gln Pro Glu Asn Asn Tyr
305                 310                 315                 320
Lys Thr Thr Pro Pro Val Leu Asp Ser Asp Gly Ser Phe Phe Leu Val
            325                 330                 335
Ser Lys Leu Thr Val Asp Lys Ser Arg Trp Gln Gln Gly Asn Val Phe
        340                 345                 350
Ser Cys Ser Val Met His Glu Ala Leu His Asn His Tyr Thr Gln Lys
    355                 360                 365
Ser Leu Ser Leu Ser Pro Gly Lys
    370                 375
```

<210> SEQ ID NO 99
<211> LENGTH: 213
<212> TYPE: PRT
<213> ORGANISM: Artificial sequence
<220> FEATURE:
<223> OTHER INFORMATION: Anti-WT1 (11D06) light chain

<400> SEQUENCE: 99

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
    50                  55                  60
Ser Gly Ser Gly Thr Glu Phe Thr Leu Thr Ile Gly Ser Leu Gln Pro
65                  70                  75                  80
Asp Asp Phe Ala Thr Tyr Tyr Cys Gln Gln Tyr Glu Asp Tyr Thr Thr
                85                  90                  95
Phe Gly Gln Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 100
<211> LENGTH: 375
<212> TYPE: PRT
<213> ORGANISM: Artificial sequence
<220> FEATURE:
<223> OTHER INFORMATION: Anti-WT1 (33H09) PGLALA heavy chain

<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Asp Leu Phe Ser Leu Asp Tyr Trp Gly Gln Gly
            100                 105                 110

Thr Thr Val Thr Val Ser Ser Leu Gly Thr Gln Thr Tyr Ile Cys
        115                 120                 125

Asn Val Asn His Lys Pro Ser Asn Thr Lys Val Asp Lys Lys Val Glu
    130                 135                 140

Pro Lys Ser Cys Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Gly Ala Pro Ile Glu Lys Thr Ile Ser Lys Ala Lys Gly Gln Pro Arg
            260                 265                 270

Glu Pro Gln Val Cys Thr Leu Pro Pro Ser Arg Asp Glu Leu Thr Lys
        275                 280                 285

Asn Gln Val Ser Leu Ser Cys Ala Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Val Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 101
<211> LENGTH: 213
<212> TYPE: PRT
<213> ORGANISM: Artificial sequence
<220> FEATURE:
<223> OTHER INFORMATION: Anti-WT1 (33H09) light chain

<400> SEQUENCE: 101

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Asp Gly Ile Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 102
<211> LENGTH: 375
<212> TYPE: PRT
<213> ORGANISM: Artificial sequence
<220> FEATURE:
<223> OTHER INFORMATION: Anti-WT1 (5E11) PGLALA heavy chain

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr

```
            65                  70                  75                  80
Met Glu Leu Ser Ser Leu Arg Ser Glu Asp Thr Ala Val Tyr Tyr Cys
                    85                  90                  95

Ala Arg Ser Ser Tyr Asp Leu Tyr Ser Phe Asp Tyr Trp Gly Gln Gly
                100                 105                 110

Thr Thr Val Thr Val Ser Ser Leu Gly Thr Gln Thr Tyr Ile Cys
                115                 120                 125

Asn Val Asn His Lys Pro Ser Asn Thr Lys Val Asp Lys Lys Val Glu
            130                 135                 140

Pro Lys Ser Cys Asp Lys Thr His Thr Cys Pro Pro Cys Pro Ala Pro
145                 150                 155                 160

Glu Ala Ala Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
                180                 185                 190

Asp Val Ser His Glu Asp Pro Glu Val Lys Phe Asn Trp Tyr Val Asp
            195                 200                 205

Gly Val Glu Val His Asn Ala Lys Thr Lys Pro Arg Glu Glu Gln Tyr
        210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Gly Ala Pro Ile Glu Lys Thr Ile Ser Lys Ala Lys Gly Gln Pro Arg
                260                 265                 270

Glu Pro Gln Val Cys Thr Leu Pro Pro Ser Arg Asp Glu Leu Thr Lys
            275                 280                 285

Asn Gln Val Ser Leu Ser Cys Ala Val Lys Gly Phe Tyr Pro Ser Asp
        290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Val Ser
                325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
            355                 360                 365

Leu Ser Leu Ser Pro Gly Lys
        370                 375

<210> SEQ ID NO 103
<211> LENGTH: 215
<212> TYPE: PRT
<213> ORGANISM: Artificial sequence
<220> FEATURE:
<223> OTHER INFORMATION: Anti-WT1 (5E11) light chain

<400> SEQUENCE: 103

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
```

```
                50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ser Phe Pro Pro Met
                 85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 104
<211> LENGTH: 5
<212> TYPE: PRT
<213> ORGANISM: Artificial sequence
<220> FEATURE:
<223> OTHER INFORMATION: Anti-CD3 HCDR1 Kabat

<400> SEQUENCE: 104

Thr Tyr Ala Met Asn
 1               5

<210> SEQ ID NO 105
<211> LENGTH: 19
<212> TYPE: PRT
<213> ORGANISM: Artificial sequence
<220> FEATURE:
<223> OTHER INFORMATION: Anti-CD3 HCDR2 Kabat

<400> SEQUENCE: 105

Arg Ile Arg Ser Lys Tyr Asn Asn Tyr Ala Thr Tyr Tyr Ala Asp Ser
 1               5                  10                  15

Val Lys Gly

<210> SEQ ID NO 106
<211> LENGTH: 14
<212> TYPE: PRT
<213> ORGANISM: Artificial sequence
<220> FEATURE:
<223> OTHER INFORMATION: Anti-CD3 HCDR3 Kabat

<400> SEQUENCE: 106

His Gly Asn Phe Gly Asn Ser Tyr Val Ser Trp Phe Ala Tyr
 1               5                  10

<210> SEQ ID NO 107
<211> LENGTH: 14
<212> TYPE: PRT
<213> ORGANISM: Artificial sequence
<220> FEATURE:
```

```
<223> OTHER INFORMATION: Anti-CD3 LCDR1 Kabat

<400> SEQUENCE: 107

Gly Ser Ser Thr Gly Ala Val Thr Thr Ser Asn Tyr Ala Asn
1               5                   10

<210> SEQ ID NO 108
<211> LENGTH: 7
<212> TYPE: PRT
<213> ORGANISM: Artificial sequence
<220> FEATURE:
<223> OTHER INFORMATION: Anti-CD3 LCDR2 Kabat

<400> SEQUENCE: 108

Gly Thr Asn Lys Arg Ala Pro
1               5

<210> SEQ ID NO 109
<211> LENGTH: 9
<212> TYPE: PRT
<213> ORGANISM: Artificial sequence
<220> FEATURE:
<223> OTHER INFORMATION: Anti-CD3 LCDR3 Kabat

<400> SEQUENCE: 109

Ala Leu Trp Tyr Ser Asn Leu Trp Val
1               5
```